US008735131B2

(12) United States Patent
Hashizume et al.

(10) Patent No.: US 8,735,131 B2
(45) Date of Patent: May 27, 2014

(54) METHOD FOR DESIGNING MUTANT PROTEIN DEAMIDASE

(75) Inventors: Ryota Hashizume, Uji (JP); Bunzo Mikami, Uji (JP); Hirotaka Matsubara, Kakamigahara (JP); Akiko Matsunaga, Kakamigahara (JP); Shotaro Yamaguchi, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 312 days.

(21) Appl. No.: 13/062,798

(22) PCT Filed: Aug. 12, 2009

(86) PCT No.: PCT/JP2009/003870
§ 371 (c)(1),
(2), (4) Date: Mar. 8, 2011

(87) PCT Pub. No.: WO2010/029685
PCT Pub. Date: Mar. 18, 2010

(65) Prior Publication Data
US 2011/0165605 A1    Jul. 7, 2011

(30) Foreign Application Priority Data
Sep. 9, 2008   (JP) ................ 2008-230559

(51) Int. Cl.
C12P 21/00 (2006.01)
C12N 15/00 (2006.01)
C12N 9/78 (2006.01)

(52) U.S. Cl.
USPC ................. 435/227; 435/440; 435/69.1

(58) Field of Classification Search
USPC .............................. 435/440, 69.1
See application file for complete search history.

(56) References Cited

U.S. PATENT DOCUMENTS 6,251,651 B1 * 6/2001 Yamaguchi et al. .......... 435/228

FOREIGN PATENT DOCUMENTS

| EP | 0976829 A2 | 2/2000 |
| EP | 1106696 A1 | 6/2001 |
| JP | 2000-50887 A | 2/2000 |
| JP | 2001-218590 A | 8/2001 |
| JP | 2002-306178 A | 10/2002 |
| JP | 2004-505606 A | 2/2004 |
| JP | 2004-97099 A1 | 4/2004 |
| WO | WO-01/42453 A1 | 6/2001 |
| WO | WO-03/040361 A1 | 5/2003 |
| WO | WO-2008/138900 A2 | 11/2008 |

OTHER PUBLICATIONS

Kikuchi et al., Appl. Microbiol. Biotechnol. 78:67-74, published on-line on Dec. 6, 2007.*
Vaintraub, I. A. et al., "Protein deamidases from germinating seeds," Physiol. Plantarum 1996 96, pp. 662-666.
Ueshima T., "3.2.6 Modification of food functions, Use of transglutaminase" Sangyo-yo kouso (Industrial Enzymes), 1995 pp. 40-42.
Kikuchi, M et. al., "Peptidoglutaminase. Enzymes for Selective Deamidation of γ-Amide of Peptide-Bound Glutamine," Biochemistry 10, pp. 1222-1229.
International Search Report dated Sep. 29, 2009, issued for PCT/JP2009/003870.
C. Derst et al., "Engineering the substrate specificity of *Escherichia coli* asparaginase II. Selective reduction of glutaminase activity by amino acid replacements at position 248," Protein Science, Cambridge University Press, vol. 9, No. 10, Oct. 1, 2000, pp. 2009-2017.
Y. Liu, "Site-directed Mutagenesis of Essential Residues Involved in the Mechanism of Bacterial Glycosylasparaginase," Journal of Biological Chemistry, vol. 273, No. 16, Apr. 17, 1998, pp. 9688-9694.
G. Brown et al., "Functional and Structural Characterization of Four Glutaminases from *Escherichia coli* and *Bacillus subtilis*," Biochemistry, vol. 47, No. 21, May 1, 2008, pp. 5724-5735.
S. Yamaguchi et al., "Protein-glutaminase from *Chryseobacterium proteolyticum*, an enzyme that deamidates glutaminyl residues in proteins. Purification, characterization and gene cloning," European Journal of Biochemistry, vol. 268, No. 5, Mar. 1, 2001, pp. 1410-1421.
Supplementary European Search Report dated Nov. 29, 2012, issued for the corresponding European patent application No. 09812834.1.
Office Action issued on Dec. 19, 2013 in JP2010-528603.

* cited by examiner

*Primary Examiner* — Delia Ramirez
(74) *Attorney, Agent, or Firm* — Edwards Wildman Palmer LLP; James E. Armstrong, IV; Edmund J. Koundakjian

(57) ABSTRACT

An object is to provide a novel method for improving an enzyme capable of deamidating a protein. A mutant protein deamidase is designed by the following steps: (A) identifying one or more amino acid in an amino acid sequence for a protein deamidase which corresponds to the amino acid at position 35, 38 to 43, 45, 46, 49, 79 to 84, 103 to 106, 117, 142, 143, 146, 166, or 185 in the amino acid sequence set forth in SEQ ID NO: 2; and (B) constructing a mutant amino acid sequence of the protein deamidase by substituting the one or more amino acid identified in step (A) with another amino acid or other amino acids or by deleting the one or more amino acid identified in step (A).

13 Claims, 4 Drawing Sheets

SEQUENCE LISTING

<160> NUMBER OF SEQ ID NOS: 8

<210> SEQ ID NO 1
<211> LENGTH: 795
<212> TYPE: DNA
<213> ORGANISM: Chryseobacterium proteolyticum

<400> SEQUENCE: 1

```
ttggcgagtg taattcctga tgtagctaca ttaaattctt tattcaatca aataaagaat     60
cagtcttgcg gtacctctac ggcgtcctca ccatgcatca cattcagata tcctgtagac    120
ggatgttatg caagagccca taagatgaga caaatcttaa tgaacaacgg ctatgactgt    180
gaaaaacaat ttgtatacgg aaacctaaag gcatcaacag gaacttgctg tgtggcgtgg    240
agctaccacg ttgcaatatt ggtaagctat aaaaatgctt ccggagtaac ggaaaaaaga    300
attattgatc cttcactatt ttcaagcggt cctgtaacag atacagcatg gagaaacgct    360
tgcgttaaca cctcttgcgg atctgcatcc gtttcctctt atgctaatac tgcaggaaat    420
gtttattaca gaagtcctag taattcttac ctgtatgaca acaatctgat caataccaac    480
tgtgtactga ctaaattttc actgctttcc ggatgttctc cttcacctgc accggatgta    540
tccagctgtg gatttaatt aattgataat tttacagcac ctgctcattt acagaatcag    600
caggtgctgt tatataataa tactattttt atgaaagtat ggacattact attatttttt    660
tgtatgataa catcctgctc cggtagttcg ggttcacaga atttaacctg gtacaaaaat    720
gcaacaatca gtcagattac ggaagacccc gatcatcccg gggattttat gcgtatctct    780
attggaatca gcgcg                                                     795
```

<210> SEQ ID NO 2
<211> LENGTH: 185
<212> TYPE: PRT
<213> ORGANISM: Chryseobacterium proteolyticum

<400> SEQUENCE: 2

```
Leu Ala Ser Val Ile Pro Asp Val Ala Thr Leu Asn Ser Leu Phe Asn
1               5                   10                  15

Gln Ile Lys Asn Gln Ser Cys Gly Thr Ser Thr Ala Ser Ser Pro Cys
            20                  25                  30

Ile Thr Phe Arg Tyr Pro Val Asp Gly Cys Tyr Ala Arg Ala His Lys
        35                  40                  45

Met Arg Gln Ile Leu Met Asn Asn Gly Tyr Asp Cys Glu Lys Gln Phe
    50                  55                  60
```

```
Val Tyr Gly Asn Leu Lys Ala Ser Thr Gly Thr Cys Cys Val Ala Trp
 65                  70                  75                  80

Ser Tyr His Val Ala Ile Leu Val Ser Tyr Lys Asn Ala Ser Gly Val
                 85                  90                  95

Thr Glu Lys Arg Ile Ile Asp Pro Ser Leu Phe Ser Ser Gly Pro Val
            100                 105                 110

Thr Asp Thr Ala Trp Arg Asn Ala Cys Val Asn Thr Ser Cys Gly Ser
        115                 120                 125

Ala Ser Val Ser Ser Tyr Ala Asn Thr Ala Gly Asn Val Tyr Tyr Arg
    130                 135                 140

Ser Pro Ser Asn Ser Tyr Leu Tyr Asp Asn Asn Leu Ile Asn Thr Asn
145                 150                 155                 160

Cys Val Leu Thr Lys Phe Ser Leu Leu Ser Gly Cys Ser Pro Ser Pro
                165                 170                 175

Ala Pro Asp Val Ser Ser Cys Gly Phe
            180                 185

<210> SEQ ID NO 3
<211> LENGTH: 1137
<212> TYPE: DNA
<213> ORGANISM: Chryseobacterium proteolyticum

<400> SEQUENCE: 3
gattccaacg ggaatcagga aatcaacgga aaggaaaaac taagtgtaaa tgattctaag      60
ctgaaagatt tcggaaagac tgtaccggta gggatagacg aagaaaacgg aatgataaag     120
gtgtcattta tgttaactgc gcaattctat gaaattaagc cgaccaaaga aaatgagcag     180
tatatcggaa tgcttagaca ggctgttaag aatgaatctc ctgtacacat tttcttaaag     240
cctaatagca atgaaatagg aaaagtggag tctgcaagtc cggaagacgt aagatatttt     300
aaaacgatcc tgacaaaaga agtaaaaggg caaaccaata aattggcgag tgtaattcct     360
gatgtagcta cattaaattc tttattcaat caaataaaga atcagtcttg cggtacctct     420
acggcgtcct caccatgcat cacattcaga tatcctgtag acggatgtta tgcaagagcc     480
cataagatga gacaaatctt aatgaacaac ggctatgact gtgaaaaaca atttgtatac     540
ggaaacctaa aggcatcaac aggaacttgc tgtgtggcgt ggagctacca cgttgcaata     600
ttggtaagct ataaaaatgc ttccggagta acggaaaaaa gaattattga tccttcacta     660
ttttcaagcg gtcctgtaac agatacagca tggagaaacg cttgcgttaa cacctcttgc     720
ggatctgcat ccgtttcctc ttatgctaat actgcaggaa atgtttatta cagaagtcct     780
agtaattctt acctgtatga caacaatctg atcaatacca actgtgtact gactaaattt     840
tcactgcttt ccggatgttc tccttcacct gcaccggatg tatccagctg tggattttaa     900
ttaattgata attttacagc acctgctcat ttacagaatc agcaggtgct gttatataat     960
aatactattt ttatgaaagt atggacatta ctattatttt tttgtatgat aacatcctgc    1020
tccggtagtt cgggttcaca gaatttaacc tggtacaaaa atgcaacaat cagtcagatt    1080
acggaagacc ccgatcatcc cggggatttt atgcgtatct ctattggaat cagcgcg       1137

<210> SEQ ID NO 4
<211> LENGTH: 299
<212> TYPE: PRT
<213> ORGANISM: Chryseobacterium proteolyticum

<400> SEQUENCE: 4

Asp Ser Asn Gly Asn Gln Glu Ile Asn Gly Lys Glu Lys Leu Ser Val
```

```
                1               5                   10                  15
Asn Asp Ser Lys Leu Lys Asp Phe Gly Lys Thr Val Pro Val Gly Ile
                                20                  25                  30

Asp Glu Glu Asn Gly Met Ile Lys Val Ser Phe Met Leu Thr Ala Gln
                35                      40                      45

Phe Tyr Glu Ile Lys Pro Thr Lys Glu Asn Glu Gln Tyr Ile Gly Met
         50                     55                      60

Leu Arg Gln Ala Val Lys Asn Glu Ser Pro Val His Ile Phe Leu Lys
65                      70                      75                      80

Pro Asn Ser Asn Glu Ile Gly Lys Val Glu Ser Ala Ser Pro Glu Asp
                85                      90                      95

Val Arg Tyr Phe Lys Thr Ile Leu Thr Lys Glu Val Lys Gly Gln Thr
                100                     105                     110

Asn Lys Leu Ala Ser Val Ile Pro Asp Val Ala Thr Leu Asn Ser Leu
                115                     120                     125

Phe Asn Gln Ile Lys Asn Gln Ser Cys Gly Thr Ser Thr Ala Ser Ser
        130                     135                     140

Pro Cys Ile Thr Phe Arg Tyr Pro Val Asp Gly Cys Tyr Ala Arg Ala
145                     150                     155                     160

His Lys Met Arg Gln Ile Leu Met Asn Asn Gly Tyr Asp Cys Glu Lys
                165                     170                     175

Gln Phe Val Tyr Gly Asn Leu Lys Ala Ser Thr Gly Thr Cys Cys Val
                180                     185                     190

Ala Trp Ser Tyr His Val Ala Ile Leu Val Ser Tyr Lys Asn Ala Ser
                195                     200                     205

Gly Val Thr Glu Lys Arg Ile Ile Asp Pro Ser Leu Phe Ser Ser Gly
        210                     215                     220

Pro Val Thr Asp Thr Ala Trp Arg Asn Ala Cys Val Asn Thr Ser Cys
225                     230                     235                     240

Gly Ser Ala Ser Val Ser Ser Tyr Ala Asn Thr Ala Gly Asn Val Tyr
                245                     250                     255

Tyr Arg Ser Pro Ser Asn Ser Tyr Leu Tyr Asp Asn Asn Leu Ile Asn
                260                     265                     270

Thr Asn Cys Val Leu Thr Lys Phe Ser Leu Leu Ser Gly Cys Ser Pro
        275                     280                     285

Ser Pro Ala Pro Asp Val Ser Ser Cys Gly Phe
        290                     295

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cgtgccatat ggattccaac gggaatcagg                                       30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ctcgctcgag aaatccacag ctggatacat                                       30
```

```
<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
tgtgtggcgt ggagctctca cgttgcaata ttg                            33

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
gcgtggagct accacgatgc aatattggta agc                            33
```

METHOD FOR DESIGNING MUTANT PROTEIN DEAMIDASE

TECHNICAL FIELD

The present invention relates to a method for designing a mutant enzyme that deamidates a protein, a method for preparing such a mutant enzyme, a mutant enzyme, and the like.

BACKGROUND ART

A protein deamidase is an enzyme that hydrolyzes amide groups of glutamine and asparagine in a protein to convert to glutamic acid and asparaginic acid and isolates ammonia. A protein deamidase is applicable to various uses such as improvement in functionalities of a protein (solubility, emulsification characteristics, foam characteristics, gelation characteristics, etc.), improvement in extension of dough of wheat gluten, reduction of wheat allergen induction, improvement in efficiency of protein extraction from agricultural products, and improvement in calcium solubility in a protein solution, and is an enzyme having high industrial applicability.

Protein deamidases exist widely in the natural world. As the most known protein deamidase, a protein-glutaminase derived from a microorganism is exemplified (Patent documents 1 and 2). As a protein deamidase derived from plants, existence of an enzyme that deamidates a glutamine residue in a protein from wheat in germination, kidney beans, pumpkin seeds has been reported (Non-patent document 1). Existence of protein deamidases has been widely known in the natural world including living organisms as well, and, for example, a transglutaminase derived from actinomyces that has been broadly used as an enzyme for food processing in recent years catalyzes a crosslinking reaction between a glutamine residue and a lysine residue in a protein, but deamidates a glutamine residue in a protein when primary amine such as lysine is not present in a reaction system (Non-patent document 2). Existence of a peptide glutaminase that is an enzyme deamidating a glutamine residue in a peptide in a fungus body of a bacterium (*Bacillus circulans*) has been reported for other microorganisms (Non-patent document 3).

When a protein deamidase is used, a substrate and a concentration of an enzyme, a reaction temperature, a reaction time, and the like are adjusted according to its application in the same manner as the other enzymes. However, only adjustment of such enzyme reaction conditions may cause the case that a desired product cannot be produced or the case that an expected yield cannot be obtained, and thus, the requirement of modifying properties of a protein deamidase has arisen. Furthermore, although preservation stability is important when a protein deamidase is used as an industrial enzyme preparation, an enzyme is generally low in stability to oxygen, and thus, addition of a stabilizing agent or wrapping in a degassed state is required to maintain sufficient preservation stability, which has led to cost increase.

In order to modify properties of a protein deamidase, in general, it is necessary that a mutant of a protein deamidase is prepared, and its activity, substrate specificity, and the like are evaluated to identify an excellent mutant, but these processes required a large amount of labor.

Patent document 1: Japanese Patent Application Laid-Open (JP-A) No. 2000-50887
Patent document 2: JP-A No. 2001-218590
Patent document 3: JP-A No. 2004-97099
Non-patent document 1: Vaintraub, Kotova, L. V. & Shaha, R. (1996) Protein deamidases from germinating seeds. Physiol. Plantarum. 96, 662-666
Non-patent document 2: "Industrial Enzymes" (1995) Takayuki Uwajima, MARUZEN CO., LTD., 3.2.6 Modification of food functions "Use of transglutaminase" pp. 40-42
Non-patent document 3: Kikuchi, M., Hayashida, H., Nakano, E. & Sakaguchi K. (1971) Peptidoglutaminase. Enzymes for selective deamidation of γ-amido of peptide-bound glutamine. Biochemistry 10, 1222-1229

DISCLOSURE OF THE INVENTION

Problems to be Solved by the Invention

An object of the present invention is to provide a novel method of improving an enzyme that deamidates a protein. Another object of the present invention is to provide a mutant enzyme having improved action properties and stability. Change of the action properties makes it possible to reduce an amount used of an enzyme, shorten a reaction time, expand applications, and so on. On the other hand, improvement in stability makes it possible to provide an enzyme preparation having high preservation stability.

Means for Solving the Problems

As a result of intensive studies in view of the above problems, the present inventors obtained an important finding regarding recognition of a substrate in the protein-glutaminase derived from the *Chryseobacterium proteolyticum* 9670 strain (FERM BP-7351) and an important finding regarding the active site and the proximity thereof by fully using a technique of an X-ray crystal structure analysis. That is, the inventors succeeded in crystallization of the mature form and the pro-enzyme for the protein-glutaminase and also obtaining their conformational information, which revealed an active site and a substrate pocket. According to the above findings, an amino acid supposed to relate to recognition of a substrate was specified. An amino acid in the active site was also revealed and an amino acid residue in the proximity, which is supposed to give an effect on an electronic state of a side chain in an amino acid being the active center was also revealed. What is more, as a result of trying modification of properties of an enzyme based on the result of the structure analysis, the inventors succeeded in modification of substrate specificity and improvement in stability.

The present invention is mainly based on the above described achievements, and provides the following method for designing a mutant enzyme, and the like,

[1] A method for designing a mutant enzyme including the following steps:

(1) specifying one or more amino acids selected from the following group, namely, consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, an amino acid corresponding to the amino acid at position 117 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2, in an amino acid sequence for a protein deamidase (an enzyme to be mutated); and (2) constructing an amino acid sequence having substitution of the amino acid(s) specified in the step (1) by another amino acid(s) or deletion of the amino acid(s) specified in the step (1) using the amino acid sequence for the enzyme to be mutated as a base sequence.

[2] The method for designing a mutant enzyme according to [1], wherein the step (1) specifies one or more amino acids selected from the group consisting of an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 43 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2.

[3] The method for designing a mutant enzyme according to [1], wherein the step (1) specifies an amino acid corresponding to the amino acid at position 82 in the amino acid sequence set forth in SEQ ID NO: 2.

[4] The method for designing a mutant enzyme according to [1], wherein the step (1) specifies one or more amino acids selected from the group consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, and an amino acid corresponding to the amino acid at position 117 in the amino acid sequence set forth in SEQ ID NO: 2.

[5] The method for designing a mutant enzyme according to [1], wherein the step (1) specifies an amino acid corresponding to the amino acid at position 84 in the amino acid sequence set forth in SEQ ID NO: 2.

[6] The method for designing a mutant enzyme according to any one of [1] to [5], wherein the specification of an amino acid(s) in the step (1) is performed by comparison between the amino acid sequence of the enzyme to be mutated and the amino acid sequence set forth in SEQ ID NO: 2 and/or comparison between the conformation of the enzyme to be mutated and a conformation of an enzyme having the amino acid sequence set forth in SEQ ID NO: 2.

[7] The method for designing a mutant enzyme according to any one of [1] to [6], wherein the amino acid(s) specified in the step (1) is/are substituted by an amino acid(s) having a different charge state.

[8] The method for designing a mutant enzyme according to any one of [1] to [7], wherein the enzyme to be mutated is a wild-type enzyme.

[9] The method for designing a mutant enzyme according to any one of [1] to [8], wherein the enzyme to be mutated is a protein deamidase derived from a microorganism.

[10] The method for designing a mutant enzyme according to [9], wherein the enzyme to be mutated is a protein-glutaminase derived from the Genus *Chryseobacterium*.

[11] The method for designing a mutant enzyme according to [9], wherein the enzyme to be mutated is a protein-glutaminase derived from *Chryseobacterium proteolyticum*.

[12] The method for designing a mutant enzyme according to any one of [1] to [11], wherein the amino acid sequence of the enzyme to be mutated has 70% or more of an identity to the amino acid sequence set forth in SEQ ID NO: 2.

[13] A method for designing a mutant enzyme including the following steps:
(1) performing a structure analysis of a pro-enzyme of a protein deamidase (an enzyme to be mutated) to specify one or more amino acids which relate to substrate specificity or oxidation stability; and
(2) constructing an amino acid sequence having substitution of the amino acid(s) specified in the step (1) by another amino acid(s) or having deletion of the amino acid(s) specified in the step (1) using the amino acid sequence for the enzyme to be mutated as a base sequence.

[14] A method for preparing a mutant enzyme, including the following steps:
(1) preparing a nucleic acid coding for an amino acid sequence constructed in the designing method according to any one of [1] to [13];
(2) expressing the nucleic acid; and
(3) recovering the expressed product.

[15] A mutant enzyme containing an amino acid sequence having, in an amino acid sequence for a protein deamidase (an enzyme to be mutated), substitution of amino acids of the following group by another amino acids or having deletion of the amino acids of the following group, namely, consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, an amino acid corresponding to the amino acid at position 117 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2, in an amino acid sequence for a protein deamidase (an enzyme to be mutated).

[16] The mutant enzyme according to [15], wherein the substituted or deleted amino acid(s) is/are one or more amino acids selected from the following group, namely, consisting of an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 43 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2.

[17] The mutant enzyme according to [15], wherein the substituted or deleted amino acid is an amino acid corresponding to the amino acid at position 82 in the amino acid sequence set forth in SEQ ID NO: 2.

[18] The mutant enzyme according to [15], wherein the substituted or deleted amino acid(s) is/are one or more amino acids selected from the following group, namely, consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, and an amino acid corresponding to the amino acid at position 117 in the amino acid sequence set forth in SEQ ID NO: 2.

[19] The mutant enzyme according to [15], wherein the substituted or deleted amino acid is an amino acid corresponding to the amino acid at position 84 in the amino acid sequence set forth in SEQ ID NO: 2.

[20] The mutant enzyme according to any one of [15] to [19], wherein the enzyme to be mutated is a wild-type enzyme,

[21] The mutant enzyme according to any one of [15] to [20], wherein the enzyme to be mutated is a protein deamidase derived from a microorganism.

[22] The mutant enzyme according to [21], wherein the enzyme to be mutated is a protein-glutaminase derived from the Genus *Chryseobacterium*.

[23] The mutant enzyme according to [21], wherein the enzyme to be mutated is a protein-glutaminase derived from *Chryseobacterium proteolyticum*,

[24] The mutant enzyme according to any one of [15] to [23], wherein the amino acid sequence of the enzyme to be mutated has 70% or more of an identity to the amino acid sequence set forth in SEQ ID NO: 2.

[25] The mutant enzyme according to any one of [16], [17], and [20] to [23], wherein action properties to a substrate protein are changed as compared to the enzyme to be mutated.

[26] The mutant enzyme according to any one of [18] to [23], wherein stability to hydrogen peroxide is improved as compared to the enzyme to be mutated.

[27] A gene coding for the mutant enzyme according to any one of [15] to [26].

[28] A recombinant DNA having the gene according to [27].

[29] A microorganism having the recombinant DNA according to [28].

DESCRIPTION OF EMBODIMENTS

1. Method for Designing Mutant Enzyme

Figure 1:
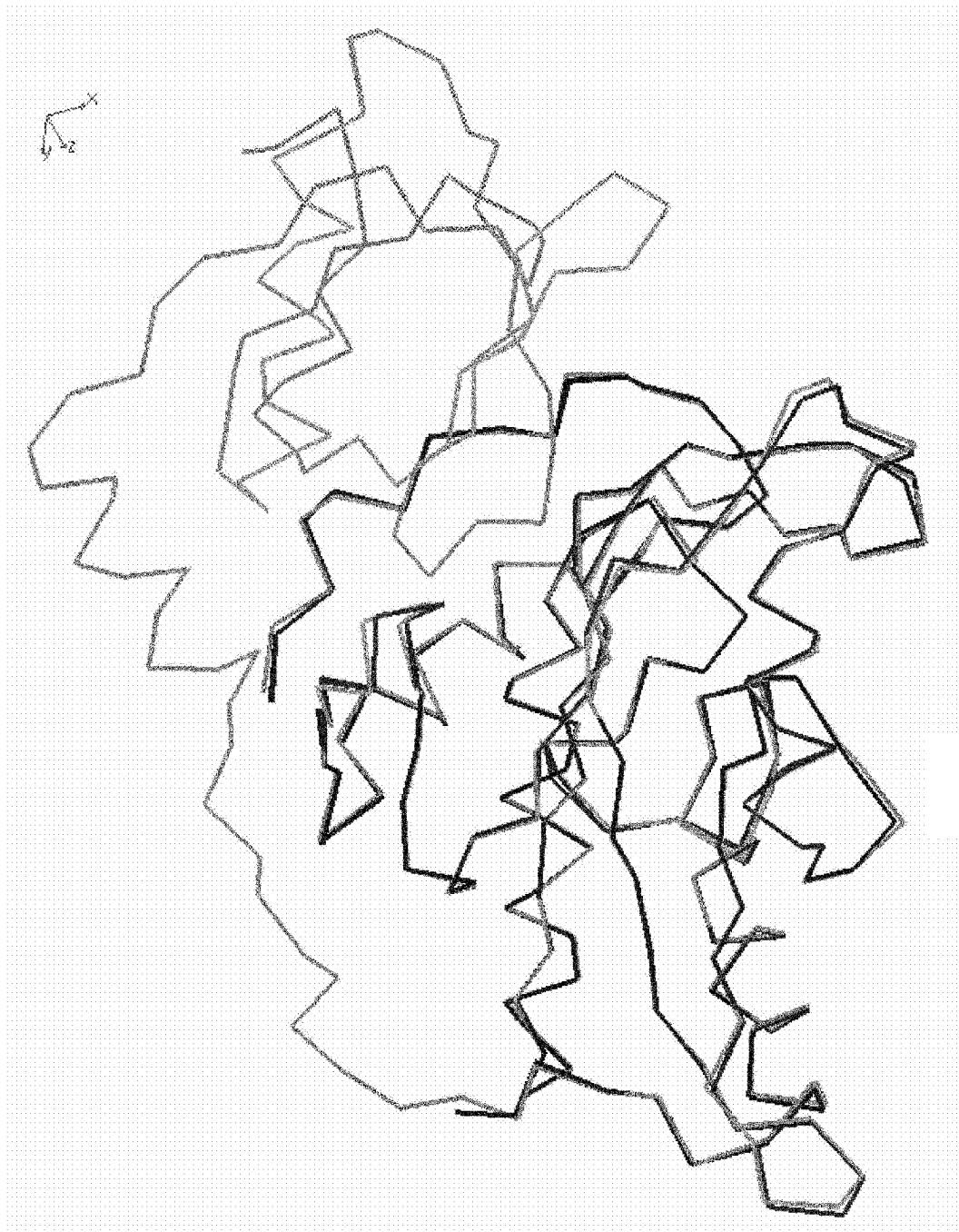
FIG. 1 shows a view of overlapping a carbons of a mature form (thick line) and a pro-enzyme (light line) of a protein-glutaminase derived from the *Chryseobacterium proteolyticum* 9670 strain.

A first aspect of the present invention provides a method for designing a mutant enzyme based on an enzyme that deamidates a protein. According to the designing method of the present invention, an enzyme different from the enzyme before mutation can be obtained in view of action properties and/or stability. In other words, the designing method of the present invention is used as a technique of changing action properties and stability of an enzyme. Specifically, the designing method of the invention can be used for the purpose of, for example, changing activity and/or substrate specificity to an individual protein substrate of a protein deamidase. Furthermore specifically, the designing method of the invention can be used for the purpose of, for example, improving stability of a protein deamidase. If specificity to an individual protein substrate can be changed, a protein that has been supposed to have low reactivity so far can also be deamidated with a less amount of an enzyme, that is, decrease of an amount used can be expected. In addition, if different substrate specificity can be given, such an enzyme can be applied to novel applications, On the other hand, if oxidation stability can be improved, effects such as improvement in handiness in use of an enzyme or steps of transportation and preservation are provided.

A protein-glutaminase, which is one of protein deamidases, acts on a glutamine residue in a protein and converts it into glutamic acid. Utilizing this property, a protein-glutaminase can be applied to various uses such as improvement in functionalities of a protein (solubility, emulsification characteristics, foam characteristics, gelation characteristics, etc.), improvement in extension of dough of wheat gluten, reduction of wheat allergen induction, improvement in efficiency of protein extraction from agricultural products, and improvement in calcium solubility in a protein solution, and is an enzyme having high industrial applicability. If reactivity to an amide group in a substrate can be changed, for example, improvement in general versatility, and reduction of an enzyme amount used (amount added) can be intended, which at the same time makes it possible to apply the present enzyme to new fields.

The "action properties" in the specification is used as a term including properties that relate to hydrolyzing an amide group of glutamine or asparagine in a protein or a peptide and converting to a glutamic acid residue or an asparaginic acid residue respectively to release ammonia, as otherwise specifically explained. The "action properties" can be evaluated by a relative activity obtained by measuring a free ammonia amount under constant conditions of a substrate concentration, a reaction temperature, and the like, in a test system using a protein or a peptide as a substrate, as described below.

(1) A protein or a peptide are dissolved or dispersed in a 176 mM phosphate buffer solution (pH 6.0) at 1% concentration, and the solution is reacted with a protein deamidase at 37° C.

(2) After a certain time, the concentration of free ammonia in the reaction solution is determined by Ammonia Test Wako (Wako Pure Chemical Industries, Ltd.) to measure an increase amount of ammonia per unit of time and unit of an enzyme.

In addition, the "action properties" may be evaluated by comparing Km values, Kcat values, and the like, which are obtained in a test system using a protein or a peptide as a substrate.

"Oxidation stability" in the present invention indicates stability that relates to the above described action properties (that is, activity of hydrolyzing an amide group of glutamine or asparagine in a protein or a peptide and converting to a glutamic acid residue or an asparaginic acid residue respectively to release ammonia) in the presence of oxides, as otherwise specifically explained. Oxidation stability can be obtained in the following method, for example.

(1) A certain concentration of a substrate (e.g., 10 mM Cbz-Gln-Gly) is dissolved in a 176 mM phosphate buffer solution (pH 6.0) containing 0.45 to 0.9% of hydrogen peroxide and the solution is reacted with a protein deamidase at 37° C.

(2) After a certain time, a concentration of free ammonia in the reaction solution is determined by Ammonia Test Wako (Wako Pure Chemical Industries, Ltd.) to measure an increase amount of ammonia. The ammonia increase amount in the presence of hydrogen peroxide is expressed assuming an ammonia increase amount in the absence of hydrogen peroxide as 100%.

The method for designing a mutant enzyme of the present invention includes, roughly in parts, two steps, that is, a step of specifying an amino acid to be mutated (step (1)), and a step of constructing an amino acid sequence having mutation of the specified amino acid (step (2)). The details of each step will be explained below. Note that an enzyme that is used as a base for designing a mutant enzyme (an enzyme that is subjected to mutation) is referred to as "an enzyme to be mutated" in the specification.

Step (1)

In the step (1), one or more amino acids that are subjected to mutation (hereinafter also referred to as "amino acids to be mutated") are specified in an amino acid sequence of a protein deamidase (an enzyme to be mutated). An amino acid to be mutated in the present invention is selected from the following group, namely, consisting of an amino acid corresponding to the amino acid at position 35 in the amino acid sequence set forth in SEQ ID NO; 2, an amino acid corresponding to the amino acid at position 38 in the amino acid sequence set forth in SEQ ID NO: 2, an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO; 2, an amino acid corresponding to the amino acid at position 42 in the amino acid sequence set forth in SEQ ID NO; 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, an amino acid corresponding to the amino acid at position 117 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2, In addition, as a result of analyzing conformations of a mature form (composed of the amino acid sequence set forth in SEQ ID NO: 2) and a pro-enzyme (composed of the amino acid sequence set forth in SEQ ID NO: 4) for the protein-glutaminase derived from the *Chryseobacterium proteolyticum* 9670 strain, these amino acids to be mutated are amino acids that were suggested to relate to recognition of a substrate, and/or amino acids that are the active center, and present close to the active center and revealed to give an effect on the amino acids being the active center. When these amino acids are mutated, changing action properties (in particular, substrate specificity) and/or oxidation stability of an enzyme can be expected.

Herein, the term "corresponding" when used for an amino acid residue in the present specification means contributing equally to exhibition of functions among proteins (enzymes) being compared, and particularly means that contributions to substrate specificities are equal. For example, when an amino acid sequence for comparison to the base amino acid sequence (that is, the amino acid sequence set forth in SEQ ID NO: 2) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank (at the World Wide Web (www) pdbj.org/index_j.html).

One example of a method for determination of a protein conformation by the X-ray crystal structure analysis will be shown below, (1) A protein is crystallized. Crystallization is essential to determine a conformation, and in addition, crystallization is industrially useful as a purification method of a protein at high purity and a stable preservation method of a protein at high density. Note that a protein to which a substrate as a ligand or its analogous compound is bound may be used for crystallization.

(2) The prepared crystal is irradiated with X ray to collect diffraction data. There are many cases that a protein crystal is damaged due to X ray irradiation and the diffraction ability is deteriorated. In such cases, a low-temperature measurement technique of rapidly cooling the crystal to about −173° C. and collecting diffraction data in the state has been recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structural precision is performed using a program such as X-PLOR made by MSI Co. to complete the structure analysis.

When a crystal structure of an analogous protein to a desired protein is known, it can be determined in a molecular substitution method using the atomic coordinate of the known protein. Molecular substitution and structural precision can be performed using a program such as CNS_SOLVE ver.11.

The present inventors tried crystallization of a mature form of a protein-glutaminase purified from a culture liquid of the *Chryseobacterium proteolyticum* 9670 strain and crystallization of a pro-enzyme of a protein-glutaminase purified from a culture liquid of a recombinant *Escherichia coli* and succeeded in obtaining the conformations of the both. Note that the atomic coordinates of the conformation of the pro-enzyme of the protein-glutaminase will be shown in the end of the specification. In addition, the amino acid sequence of the mature form of the protein-glutaminase is set forth in the SEQ ID NO: 2 in the sequence listing, a base sequence of a gene that codes for the amino acid sequence of the mature form of the protein-glutaminase is set forth in SEQ ID NO: 1, the amino acid sequence of the pro-enzyme of the protein-glutaminase is set forth in SEQ ID NO: 4 in the sequence listing, and a base sequence of a gene that codes for the amino acid sequence of the pro-enzyme of the protein-glutaminase is set forth in SEQ ID NO: 3, respectively.

Figure 2:
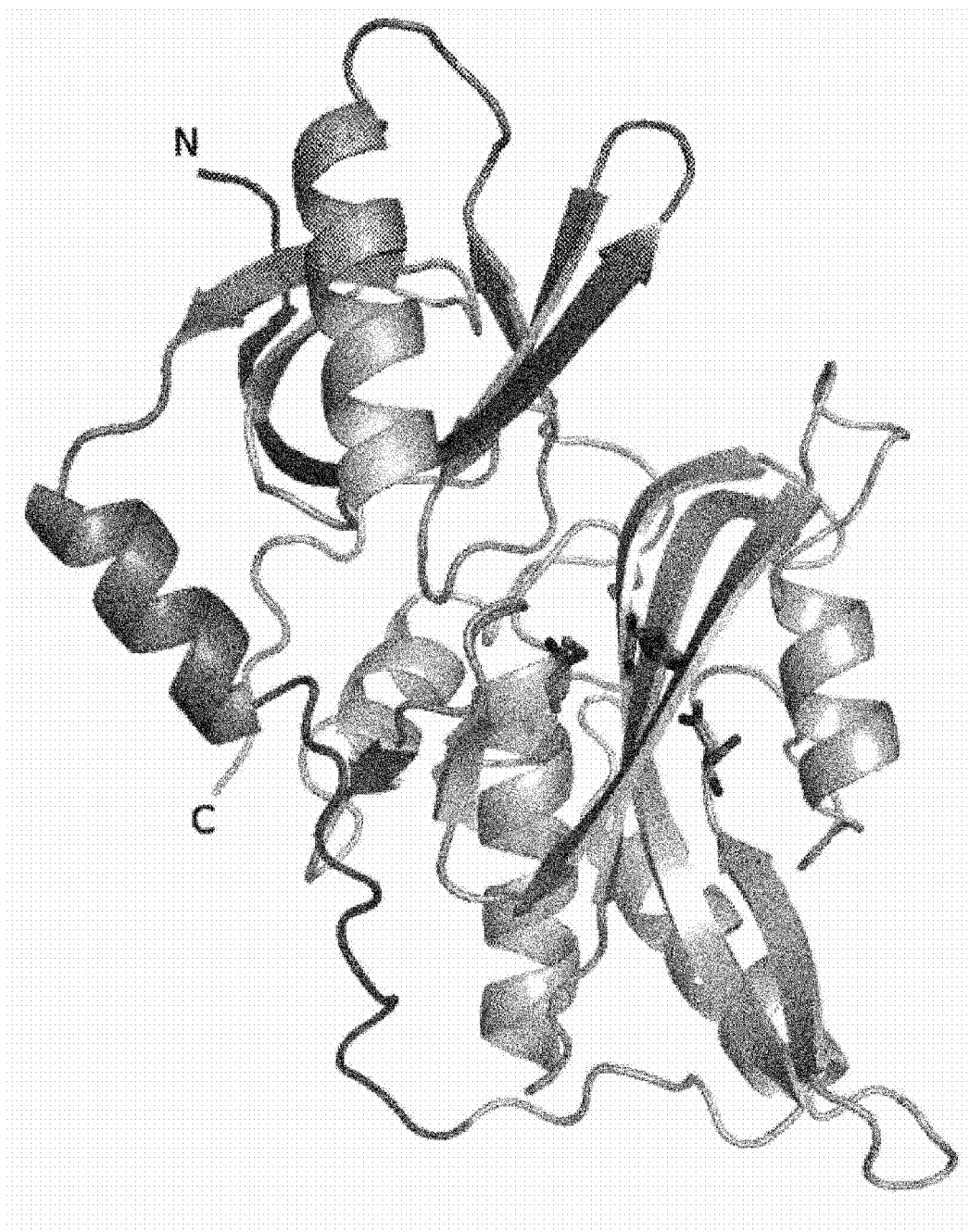
FIG. 2 shows a view of a higher structure of a pro-enzyme of a protein-glutaminase derived from the *Chryseobacterium proteolyticum* 9670 strain expressed in a ribbon model, α-helices and β-sheets are respectively shown in spirals and arrows.
Figure 3:
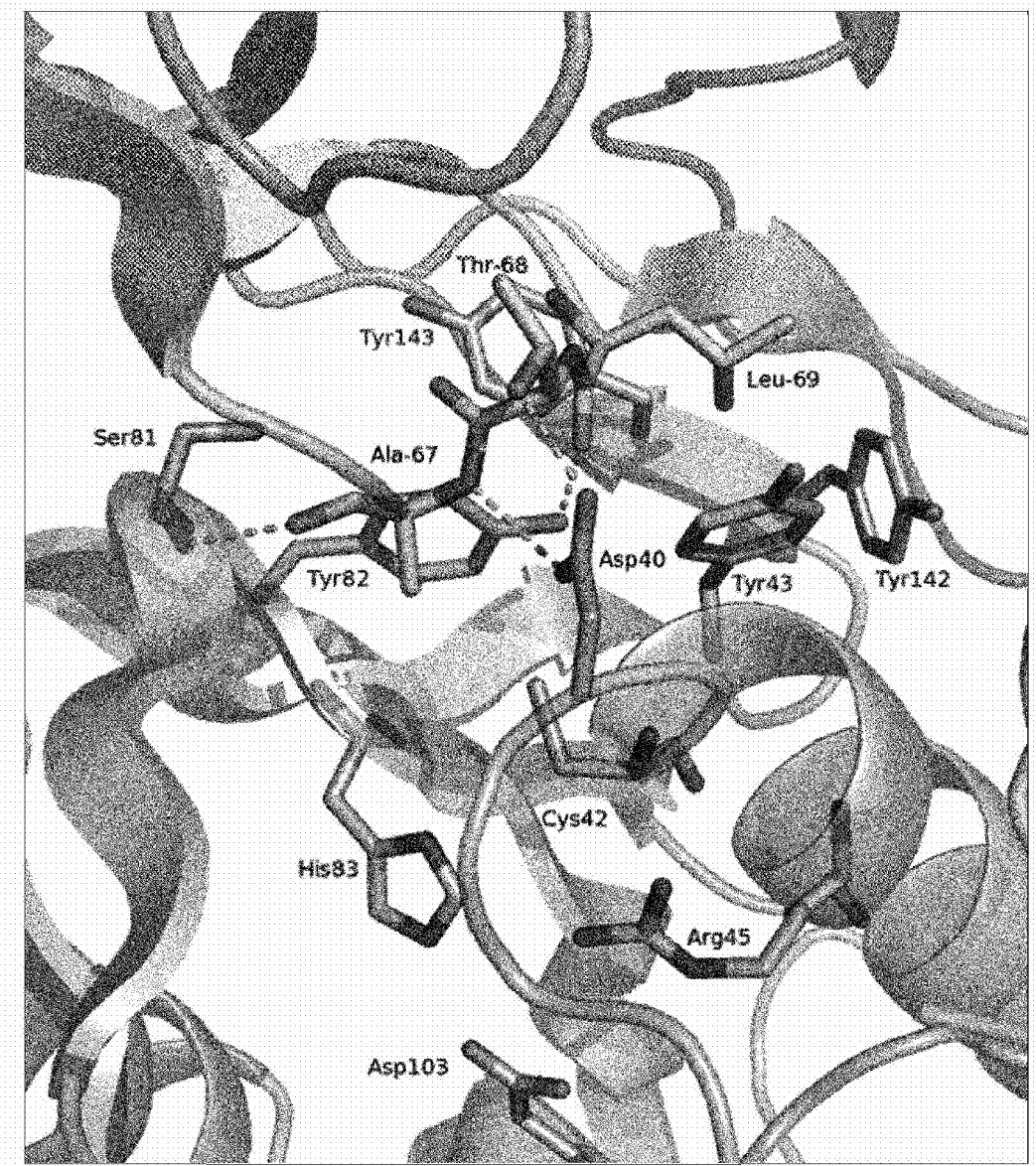
FIG. 3 shows a view of enlarging an area around the active center Cys42 and a substrate bonding region in a pro-enzyme of a protein-glutaminase derived from the *Chryseobacterium proteolyticum* 9670 strain.
Figure 4:
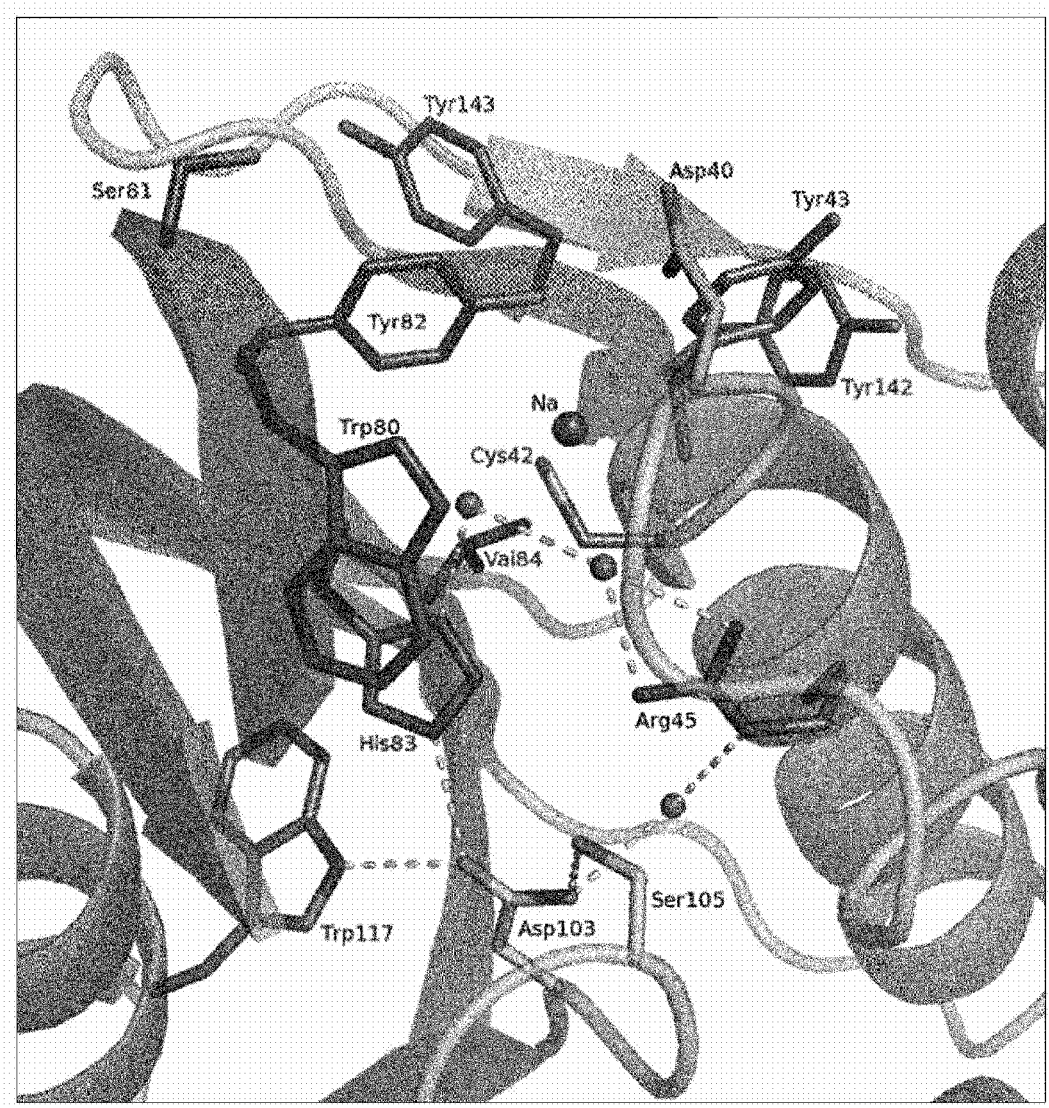
FIG. 4 shows a view of enlarging an amino acid region that is supposed to give an effect on the active center in a pro-enzyme of a protein-glutaminase derived from the *Chryseobacterium proteolyticum* 9670 strain.

As shown in examples described later, it was revealed that a mature form molecule of the protein-glutaminase derived from the *Chryseobacterium proteolyticum* 9670 strain is in a hexagonal P6$_5$22 shape with 62.306×62.306×185.532 Å, and a pro-enzyme molecule is in an orthorhombic P2$_1$2$_1$2$_1$ shape with 56.644×103.290×132.510 Å (see Tables 1 and 2 described later). FIG. 1 shows a view of overlapping a carbons of the mature form (thick line) and the pro-enzyme (light line) of the protein-glutaminase, and FIG. 2 shows a view of a higher structure of the pro-enzyme of the protein-glutaminase expressed in a ribbon model. α-helices and β-sheets are respectively shown in spirals and arrows. FIG. 3 shows a view of enlarging an area around the active center Cys42 and a substrate bonding region in the pro-enzyme, and FIG. 4 shows a view of enlarging an amino acid region that is supposed to give an effect on the active center.

When modification of substrate specificity is intended, an amino acid to be mutated is preferably selected from the group consisting of an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 43 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2. As a result of analyzing the conformation of the pro-enzyme of the protein-glutaminase derived from the *Chryseobacterium proteolyticum* 9670 strain, these amino acids to be mutated are amino acids suggested to be associated with substrate specificity, and include those arranged on a surface around a cleft, and those arranged close to amino acids being the active center.

Among the above amino acids, the tyrosine residue at position 82 is arranged close to an amino acid (Ala-(minus) position 67 etc.) in a pro-region that is closely attached to cysteine (position 42) being the active center, located at the active pocket entrance, and is expected to form a hydrogen bond with a substrate, and thus, it was considered to act as an important role for substrate recognition. Then, when a mutant obtained by substitution of the amino acid by another amino acid was prepared to examine the properties, it was confirmed that the amino acid acts as an important role for substrate specificity (see section of examples). Accordingly, in a further preferable embodiment of the present invention, an amino acid corresponding to the amino acid (amino acid at position 82) is to be the amino acid to be mutated.

On the other hand, when improvement in oxidation stability is intended, an amino acid to be mutated is preferably selected from the group consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, and an amino acid corresponding to the amino acid at position 117 in the amino acid sequence set forth in SEQ ID NO: 2. As a result of analyzing the conformations of the mature form and the pro-enzyme of the protein-glutaminase derived from the *Chryseobacterium proteolyticum* 9670 strain, these amino acids to be mutated are amino acids suggested to be associated with oxidation stability, and include those relating to interactions of catalytic residues (Cys42, His83, Asp103) and structure preservation.

Among the above described amino acids, the amino acid at position 84 is arranged in a position close to the cysteine (position 42) being the active center and giving an effect on a dissociative state of a thiol group of cysteine in a conformational analysis of the protein-glutaminase derived from the *Chryseobacterium proteolyticum* 9670 strain, and thus, it was expected to act as an important role for easiness of oxidation of the active center cysteine. Then, when a mutant obtained by substitution of the amino acid by another amino acid was prepared to examine the properties, it was confirmed that the amino acid acts as an important role for oxidation stability (see section of examples). Accordingly, in a further preferable embodiment of the present invention, an amino acid corresponding to the amino acid (amino acid at position 84) is to be the amino acid to be mutated.

A kind, a derivation, and the like of an enzyme to be mutated in the present invention are not particularly limited as long as it is an enzyme that hydrolyzes an amide group in a protein. Examples of the enzyme to be mutated include enzymes deamidating glutamine residues in a protein, which have been reported in wheat, kidney beans, and pumpkin seeds, transglutaminases derived from mammals, fish, or microorganisms such as actinomyces, and peptide glutaminases of bacteria (*Bacillus circulans*). Preferably, a protein deamidase derived from microorganisms, more preferably, a protein-glutaminase derived from the *Chryseobacterium proteolyticum* 9670 strain is used as the enzyme to be mutated.

It is preferred to use an enzyme composed of an amino acid sequence having a high identity to the amino acid sequence set forth in SEQ ID NO: 2 as the enzyme to be mutated. For its reasons, such an enzyme can be expected to achieve effective modification and facilitates specification of the amino acid to be mutated. Specifically, an enzyme composed of an amino acid sequence having 70% or more of an identity to the amino acid sequence set forth in SEQ ID NO: 2 is preferably used as the enzyme to be mutated. Generally, the identity herein is more preferable if it is higher. For example, an enzyme composed of an amino acid sequence having 80% or more of an identity, preferably 90% or more of an identity, more preferably 95% or more of an identity is used as the enzyme to be mutated.

Herein, the identity (%) of two amino acid sequences can be determined in the following procedure, for example. Firstly, two sequences are aligned so that optimal comparison can be made (for example, gaps may be introduced into the first sequence to optimize an alignment with the second sequence). When a molecule (amino acid residue) at a specific position in the first sequence is the same as a molecule at a corresponding position in the second sequence, the molecules at the positions are referred to as being identical. An identity of two sequences is a function of the number of the same positions in common to the two sequences (that is, identity (%)=number of the same positions/total number of positions× 100), and the number of gaps required in optimization of an alignment and sizes thereof are preferably taken into consideration.

Comparison and determination of an identity of two sequences are feasible using a mathematical algorithm. A specific example of the mathematical algorithm that can be used in comparison of sequences includes the algorithm described in Karlin and Altschul (1990) Proc. Natl. Acad. Sci. USA 87:2264-68 and modified in Karlin and Altschul (1993) Proc. Natl. Acad. Sci. USA 90:5873-77, but is not limited thereto. Such an algorithm is incorporated in the NBLAST program and the XBLAST program (version 2.0) described in Altschul et al. (1990) J. Mol. Biol. 215:403-10. In order to obtain an amino acid sequence homologous to a certain amino acid sequence, for example, BLAST polypeptide search may be performed in the XBLAST program using score=50 and wordlength=3. In order to obtain a gap alignment for comparison, Gapped BLAST described in Altschul et al. (1997) Amino Acids Research 25(17):3389-3402 is available. When BLAST and Gapped BLAST are used, a default parameter of a corresponding program (e.g., XBLAST and NBLAST) can be used. Specifically, see the World Wide Web (www) at ncbi.nlm.nih.gov. An example of other mathematical algorithms available for comparison of sequences includes the algorithm described in Myers and Miller (1988) Comput Appl Biosci. 4:11-17. Such an algorithm is incorporated in the ALIGN program available in, for example, the GENESTREAM networked server (IGH Montpellier, France) or the ISREC server. When the ALIGN program is used for comparison of amino acid sequences, for example, the PAM120 weight residue table is used, and a gap length penalty=12 and a gap penalty=4 can be used.

An identity of two amino acid sequences can be determined in use of the GAP program in the GCG software package with Blossom 62 matrix or PAM250 matrix, using gap weight=12, 10, 8, 6, or 4, and gap length weight=2, 3, or 4. Further, a homology of two nucleic acid sequences can be determined in use of the GAP program in the GCG software package (available at the World Wide Web (www) gcg.com), using gap weight=50 and gap length weight=3.

An enzyme to be mutated is typically a wild-type enzyme (enzyme found in nature). However, the fact does not hinder using an enzyme that has already undergone any of mutation and modification as the enzyme to be mutated. As described above, the present invention can be used for the purpose of further improvement in characteristics of an enzyme.

Step (2)

In step (2), an amino acid sequence having substitution of the amino acid specified in the step (1) by another amino acid or deletion of the amino acid specified in the step (1) is constructed using the amino acid sequence for the enzyme to be mutated as a base sequence. A kind of the amino acid after substitution is not particularly limited. Therefore, either of conservative amino acid substitution or nonconservative amino acid substitution may be adopted. The "conservative amino acid substitution" herein refers to substituting a certain amino acid residue by an amino acid residue having a side chain with the same properties. Amino acid residues are classified into some families according to their side chains, such as basic side chains (e.g., lysine, arginine, and histidine), acidic side chains (e.g., asparaginic acid, and glutamic acid), uncharged polar side chains (e.g., asparagine, glutamine, serine, threonine, tyrosine, and cysteine), nonpolar side chains (e.g., glycine, alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, and tryptophan). The conservative amino acid substitution is preferably substitution between amino acid residues in the same family. In one preferable embodiment, a specified amino acid is substituted by an amino acid having a different charge state. According to such substitution, significant modification of properties can be expected.

2. Method for Preparing Mutant Enzyme

A second aspect of the present invention relates a method for preparing a mutant enzyme. The preparation method of the invention includes the following steps: (1) a step of preparing a nucleic acid coding for the amino acid sequence constructed in the designing method of the present invention; (2) expressing the nucleic acid; and (3) recovering the expressed product.

In step (1), necessary mutation (that is, substitution or deletion of an amino acid at a specific position in a protein that is an expressed product) is added to a gene coding for an enzyme to be mutated based on the amino acid sequence constructed in the designing method of the present invention to obtain a nucleic acid (gene) coding for a mutant enzyme. A large number of methods for position specific base sequence substitution have been known in the present technical field (for example, see Molecular Cloning, Third Edition, Cold Spring Harbor Laboratory Press, New York), and among those methods, a suitable method can be selected to be used.

A method of position specific amino acid saturation mutation can be adopted as the method of position specific mutation introduction. The method of position specific amino acid saturation mutation is a "semi-rational, semi-random" technique of assuming a position which relates to a desired function based on a conformation of a protein and introducing amino acid saturation mutation (J. Mol. Biol. 331, 585-592 (2003)). For example, use of a kit such as Quick change (Stratagene Corporation) and Overlap extension PCR (Nucleic Acid Res. 16, 7351-7367 (1988)) makes it possible to introduce position specific amino acid saturation mutation. A Taq polymerase and the like can be used for a DNA polymerase used in PCR. Provided that a DNA polymerase having high precision such as KOD-PLUS-(TOYOBO CO., LTD.) or Pfu turbo (Stratagene Corporation) is preferably used.

On the other hand, random mutation is inserted in enzyme genes and substrate specificities of expressed products of respective mutants (altered genes) are compared to select a gene having preferable substrate specificity, which also makes it possible to prepare a gene coding for a mutant enzyme. When such random mutation is introduced, firstly, mutation is randomly introduced into a target gene region using, for example, error-prone PCR and a mutant enzyme gene library is constructed. Then, enzyme activity and substrate specificity are used as indices to select a clone from the obtained library.

In the step (2), the gene prepared in the step (1) is expressed. Then, a mutant enzyme that is the expressed product is recovered in the following step (3). In general, a suitable host-vector system is used to perform from expression of the gene to recovery of the expressed product (mutant enzyme), but a cell-free synthesis system may be used. Note that, for the details of a method for preparing a mutant enzyme using a host-vector system, corresponding description mentioned later (section such as 4. Nucleic acid coding for mutant enzyme) is cited by reference.

Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disrupter that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make various amino acids combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

3. Mutant Enzyme

According to the above described preparation method, a mutant enzyme having changed action properties to a protein and a peptide, or a mutant enzyme having changed oxidation stability can be obtained. Thus, a further aspect of the present invention provides a mutant enzyme. The mutant enzyme of a preferable embodiment is improved in action properties to a protein that has hardly acted with an enzyme to be mutated. Further, the mutant enzyme of another preferable embodiment is improved in stability in the presence of hydrogen peroxide more than an enzyme to be mutated.

The mutant enzyme of the present invention is composed of an amino acid sequence having, in an amino acid sequence for an enzyme hydrolyzing an amide group of a protein (an enzyme to be mutated), substitution of one or more amino acids selected from the following group by another amino acids or having deletion of the one or more amino acids selected from the following group, namely, consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, an amino acid corresponding to the amino acid at position 117 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2.

Preferably, when modification of substrate specificity is intended, the substituted or deleted amino acid(s) is/are one or more amino acids selected from the following group, namely, consisting of an amino acid corresponding to the amino acid at position 39 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 43 in the amino acid sequence set forth in SEQ ID NO: 2, an amino acid corresponding to the amino acid at position 79 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 142 in the amino acid sequence set forth in SEQ ID NO: 2, an amino acid corresponding to the amino acid at position 143 in the amino acid sequence set forth in SEQ ID NO: 2, an amino acid corresponding to the amino acid at position 146 in the amino acid sequence set forth in SEQ ID NO: 2, an amino acid corresponding to the amino acid at position 166 in the amino acid sequence set forth in SEQ ID NO: 2, and an amino acid corresponding to the amino acid at position 185 in the amino acid sequence set forth in SEQ ID NO: 2. On the other hand in the amino acid sequence set forth in SEQ ID NO: 2, when improvement in oxidation stability is intended in the amino acid sequence set forth in SEQ ID NO: 2, the substituted or deleted amino acid(s) is/are one or more amino acids selected from the following group in the amino acid sequence set forth in SEQ ID NO: 2, namely in the amino acid sequence set forth in SEQ ID NO: 2, consisting of an amino acid corresponding to the amino acid at position 35 in the amino acid sequence set forth in SEQ ID NO: 2, an amino acid corresponding to the amino acid at position 38 in the amino acid sequence set forth in SEQ ID NO: 2, an amino acid corresponding to the amino acid at position 40 in the amino acid sequence set forth in SEQ ID NO: 2, an amino acid corresponding to the amino acid at position 41 in the amino acid sequence set forth in SEQ ID NO: 2, an amino acid corresponding to the amino acid at position 42 in the amino acid sequence set forth in SEQ ID NO: 2, an amino acid corresponding to the amino acid at position 43 in the amino acid sequence set forth in SEQ ID NO: 2, an amino acid corresponding to the amino acid at position 45 in the amino acid sequence set forth in SEQ ID NO: 2, an amino acid corresponding to the amino acid at position 46 in the amino acid sequence set forth in SEQ ID NO: 2, an amino acid corresponding to the amino acid at position 49 in the amino acid sequence set forth in SEQ ID NO: 2, an amino acid corresponding to the amino acid at position 80 in the amino acid sequence set forth in SEQ ID NO: 2, an amino acid corresponding to the amino acid at position 81 in the amino acid sequence set forth in SEQ ID NO: 2, an amino acid corresponding to the amino acid at position 82 in the amino acid sequence set forth in SEQ ID NO: 2, an amino acid corresponding to the amino acid at position 83 in the amino acid sequence set forth in SEQ ID NO: 2, an amino acid corresponding to the amino acid at position 84 in the amino acid sequence set forth in SEQ ID NO: 2, an amino acid corresponding to the amino acid at position 103 in the amino acid sequence set forth in SEQ ID NO: 2, an amino acid corresponding to the amino acid at position 104 in the amino acid sequence set forth in SEQ ID NO: 2, an amino acid corresponding to the amino acid at position 105 in the amino acid sequence set forth in SEQ ID NO: 2, an amino acid corresponding to the amino acid at position 106 in the amino acid sequence set forth in SEQ ID NO: 2, and an amino acid corresponding to the amino acid at position 117 in the amino acid sequence set forth in SEQ ID NO: 2.

The substituted or deleted amino acid(s) is/are more preferably an amino acid(s) corresponding to the amino acid at position 82 and/or position 84 in the amino acid sequence set forth in SEQ ID NO: 2.

A kind, a derivation, and the like of an enzyme to be mutated are the same as the case of the first aspect described above, and repeated explanation is thus omitted. In addition, specific examples of the enzyme to be mutated include an enzyme made of the amino acid sequence set forth in SEQ ID NO: 2 (protein-glutaminase derived from *Chryseobacterium proteolyticum* 9670 strain), an enzyme having the amino acid sequence shown in Patent document 1 (protein-glutaminase derived from *Chryseobacterium gleum* JCM2410 strain), and an enzyme having the amino acid sequence shown in Patent document 3 (transglutaminase derived from *Streptomyces mobaraensis* S-8112 strain).

The mutant enzyme of the present invention is characterized in having an amino acid sequence having mutation (substitution or deletion of amino acids) at a specific position in the amino acid sequence of the enzyme before mutation (that is, the enzyme to be mutated), and mutation or modification of a part of amino acids may be performed also at a position other than the position of the mutation. The present invention thus also provides a protein different in an amino acid sequence in a part (hereinafter also referred to as a "homologous protein") as compared to the mutant enzyme having the amino acid sequence subjected to the mutation although the protein has equal functions. "Different in an amino acid sequence in a part" refers to occurrence of mutation (change) in an amino acid sequence typically by deletion or substitution of 1 to several amino acids that constitute the amino acid sequence, or addition or insertion of 1 to several amino acids, alternatively combinations thereof. Difference in an amino acid sequence can be allowed as long as a property that relates to hydrolysis of an amide group of a protein does not significantly decrease (preferably to the extent that the property is practically retained). As long as this condition is satisfied, a position different in an amino acid sequence is not limited, and differences may occur at a plural number of positions. Herein the plural number means, for example, the number corresponding to about less than 30% of the whole amino acids, preferably the number corresponding to about less than 20%, more preferably the number corresponding to about less than 10%, further more preferably the number corresponding to about less than 5%, and the most preferably the number corresponding to about less than 1%. That is, the homologous protein has an identity of, for example, about 70% or more to any of amino acid sequences of the above described mutant enzymes, preferably about 80% or more, more preferably about 90% or more, further more preferably about 95% or more, and the most preferably about 99% or more.

A mutant enzyme can be used in any application requiring hydrolysis of an amide group of a protein. For example, the mutant enzyme can be used in improvement in functionalities of a protein (solubility, emulsification characteristics, foam characteristics, gelation characteristics, etc.), improvement in extension of dough of wheat gluten, reduction of wheat allergen induction, improvement in efficiency of protein extraction from agricultural products, and improvement in calcium solubility in a protein solution. An amount used of the mutant enzyme is suitably set so as to exert effects of a purpose. Furthermore, a mutant enzyme having improved preservation stability provides an effect such as improvement in handiness in use of the enzyme or steps of transportation and preservation.

4. Nucleic Acid Coding for Mutant Enzyme, etc.

The present invention further provides a nucleic acid relating to the mutant enzyme of the invention. That is, provided are a gene coding for the mutant enzyme, a nucleic acid that can be used as a probe for identifying a nucleic acid coding for the mutant enzyme, and a nucleic acid that can be used as a primer for amplifying or mutating a nucleic acid coding for the mutant enzyme.

The gene coding for a mutant enzyme is typically used in preparation of the mutant enzyme. According to a genetic engineering preparation method using the gene coding for a mutant enzyme, a mutant enzyme in a more uniform state can be obtained. Further, the method can be a preferable method also in the case of preparing a large amount of a mutant enzyme. Note that uses of the gene coding for a mutant enzyme are not limited to preparation of a mutant enzyme. For example, the nucleic acid can also be used as a tool for an experiment intended for clarification of action mechanisms of a mutant enzyme or a tool for designing or preparing a further mutant of an enzyme.

The "gene coding for a mutant enzyme" herein refers to a nucleic acid capable of obtaining the mutant enzyme when it is expressed, and includes, as a matter of course of a nucleic acid having a base sequence corresponding to the amino acid sequence of the mutant enzyme, also a nucleic acid obtained by adding a sequence that does not code for an amino acid sequence to such a nucleic acid. Degeneracy of a codon is also considered.

The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a base sequence in a part (hereinafter also referred to as a "homologous nucleic acid", and a base sequence defining a homologous nucleic acid is also referred to as a "homologous base sequence") as compared to the base sequence of the gene coding for the mutant enzyme of the invention, although functions of a protein coded by the nucleic acid are equal. An example of the homologous nucleic acid includes a DNA composed of a base sequence containing substitution, deletion, insertion, addition or inversion of 1 to several bases on the basis of the base sequence of the nucleic acid coding for the mutant enzyme of the present invention and coding for a protein having activity of hydrolyzing an amide group in a protein. Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site directed mutation introduction method (Molecular Cloning, Third Edition, Chapter 13, Cold Spring Harbor Laboratory Press, New York), and random mutation introduction method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having a base sequence complementary to the base sequence of the gene coding for the mutant enzyme of the invention. Another embodiment of the present invention provides a nucleic acid having a base sequence with an identity of at least about 60%, 70%, 80%, 90%, 95%, 99%, or 99.9% to the base sequence of the gene coding for the mutant enzyme of the invention or a base sequence complementary to the base sequence.

Another embodiment of the present invention relates to a nucleic acid having a base sequence hybridizing to a base sequence complementary to the base sequence of the gene coding for the mutant enzyme of the invention or its homologous base sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 μg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 μg/ml of modified salmon sperm DNA, and a 50 mM phosphate buffer (pH 7.5) as a hybridization liquid.

Another embodiment of the present invention provides a nucleic acid (nucleic acid fragment) having a part of the base sequence of the gene coding for the mutant enzyme of the invention or a base sequence complementary to the base sequence.

Such a nucleic acid fragment can be used in detection, identification, and/or amplification of a nucleic acid having the base sequence of the gene coding for the mutant enzyme of the present invention. For example, the nucleic acid fragment is designed so as to at least contain a part being hybridized to a sequential nucleotide moiety (for example, about 10 to about 100 bases length, preferably about 20 to about 100 bases length, more preferably about 30 to about 100 bases length) in the base sequence of the gene coding for the mutant enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a mutant enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed in a standard recombinant DNA technique (for example, a known method of using a restriction enzyme and a DNA ligase, which can be referred in Molecular Cloning, Third Edition, L84, Cold Spring Harbor Laboratory Press, New York).

A bacterial cell such as *Escherichia coli* is preferably used as a host cell from the viewpoint of easiness of handiness, but a host cell capable of duplicating a recombinant DNA and expressing a gene of a mutant enzyme can be used. As typical examples of preferable hosts include *Escherichia coli* BL21 (DE3)pLysS when a T7 type promoter is used, and *Escherichia coli* JM109 when a T7 type promoter is not used.

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, electroporation (Potter, H. et al., Proc. Natl. Acad. Sci. U.S.A. 81, 7161-7165 (1984)), and lipofectin (Feigner, P. L. et al., Proc. Natl. Acad. Sci. U.S.A. 84, 7413-7417 (1984)).

The microorganism of the present invention can be used for producing the mutant enzyme of the invention. That is, another aspect of the invention provides a method for producing the mutant enzyme of the invention using the microorganism. The production method of the invention includes at least a step of culturing the microorganism under the condition of producing the mutant enzyme of the invention. In addition to the step, a step of recovering (separating and purifying) a produced protein is generally carried out.

Culture of the microorganism (transformant) according to the present invention may be followed by a general method. A carbon source used as a medium may be a carbon compound consumable by microorganisms, and examples such as glucose, sucrose, lactose, maltose, molasses, and pyruvic acid are used. A nitrogen source may be a usable nitrogen compound, and examples such as peptone, meat extract, yeast extract, a casein hydrolyzed product, and soybean cake alkali extract are used. Other than these examples, salts such as phosphate, carbonate, sulfate, magnesium, calcium, potassium, iron, manganese, and zinc, specific amino acids, specific vitamins, and the like are used according to necessity.

On the other hand, a culture temperature can be set within the range from 30° C. to 40° C. (preferably around at 37° C.). A culture time can be set considering cultivation characteristics of a transformant to be cultured, production characteristics of a mutant enzyme, and the like. A pH of a medium is adjusted within a range wherein a transformant grows and an enzyme is produced. A pH of a medium is preferably set to about 6.0 to 9.0 (preferably around at pH 7.0).

A culture liquid containing fungus forms which produce a mutant enzyme can be used as it is, or as an enzyme solution after undergoing concentration, removal of impurities, and the like, and in general, the mutant enzyme is once recovered from the culture liquid or the fungus forms. When the produced mutant enzyme is a secretory protein, it can be recovered from the culture liquid, and in the other cases, the mutant enzyme can be recovered from the fungus forms. When recovered from a culture liquid, for example, insoluble matters are removed by filtration or centrifugation of a culture supernatant, and then, separation and purification are carried out in combination with vacuum concentration, membrane concentration, salting out using ammonium sulfate or sodium sulfate, a fractional precipitation method by methanol, ethanol, or acetone, etc., dialysis, heat treatment, isoelectric treatment, various chromatographies such as gel filtration, adsorption chromatography, ion exchange chromatography, and affinity chromatography (e.g., gel filtration by Sephadex gel (Pharmacia Biotech Inc.) etc., DEAE sepharose CL-6B (Pharmacia Biotech Inc.), octyl sepharose CL-6B (Pharmacia Biotech Inc.), CM sepharose CL-6B (Pharmacia Biotech Inc.)) to thus obtain a purified product of a mutant enzyme. On the other hand, when a mutant enzyme is recovered from fungus forms, the fungus forms are removed by filtration, centrifugation, or the like of the culture liquid, followed by destructing the fungus forms in a mechanical method such as a pressure treatment or sonication, or an enzymatic method by lysozyme, etc., thereafter carrying out separation and purification in the same manner as described above to thus obtain a purified product of a mutant enzyme.

The purified enzyme obtained as described above can be provided after powdering by, for example, freeze dry, vacuum dry, or spray dry. In this case, the purified enzyme may be previously dissolved in a phosphate buffer solution, a triethanolamine buffer solution, a tris-hydrochloride buffer solution, or a GOOD's buffer solution. A phosphate buffer solution or a triethanolamine buffer solution can be preferably used. In addition, an example of the GOOD's buffer solution herein includes PIPES, MES or MOPS. Hereinafter, the present invention will be more specifically described with reference to examples, but the invention is not limited to these examples.

EXAMPLES

1. X-Ray Crystal Structure Analysis of Mature Form of Protein-Glutaminase (1) Preparation of Mature Form of Protein-Glutaminase A mature form of a protein-glutaminase derived from the *Chryseobacterium proteolyticum* 9670 strain was prepared according to the method previously reported (Yamaguchi, S., Jeens D. J. & Archer, D. B. (2001) Protein-glutaminase from *Chryseobacterium proteolyticum*, an enzyme that deamidates glutaminyl residues in proteins. Purification, characterization and gene cloning. Eur. J. Biochem., 268, 1410-1421).

(2) Crystallization

Crystallization of the mature form of the protein-glutaminase was carried out in the following procedure. Firstly, the mature form of the protein-glutaminase was screened in a sitting drop vapor diffusion method using a 24-hole plate manufactured by Hampton Research Co. Stood still at 20° C., crystals were observed in three wells after a few days. The most preferable condition was adopted among them and a preferable crystal was obtained with 10 µl of a hanging drop made of 5 µl of an enzyme liquid (40 mg/ml) and 5 µl of a reservoir solution (1.0 M ammonium phosphate, 0.1 M sodium citrate, pH 5.6), using a hanging drop vapor diffusion method. Prior to the X ray analysis, the crystal was treated with a reservoir solution containing 30% of glycerol, and then instantly cooled with liquid nitrogen (−173° C.).

(3) X Ray Analysis

X ray diffraction data was collected using synchrotron radiation BL-38B1 of SPring-8 (Hyogo prefecture) at the temperature of liquid nitrogen and processed using HKL2000 program. X ray diffraction data of 1.15 Å resolution was collected and a crystallographic parameter was determined. A space group was $P6_522$ and lattice constants were a=62.306 Å, b=62.306 Å, and c=185.582 Å.

(4) Determination of Three-Dimensional Structure

The three-dimensional structure was determined at a resolution of 1.15 Å in a heavy atom isomorphous replacement method of soaking a crystal in 2 mM Na[AuCl$_4$] for 5 minutes, introducing a gold atom and utilizing this abnormal dispersion to determine a phase. SEHLXD and SHELXC programs were used for the phase determination, WinCoot was used for modeling, and Refmac5 and SHELXL were used for structural precision. Data collection and statistic data of precision are shown in Table 1.

TABLE 1

| Crystal | Mature form of protein-glutaminase (Au heavy atom substitution) | Mature form of protein-glutaminase |
|---|---|---|
| <Data measurement> | | |
| Space group | $P6_5 2 2$ | $P6_5 2 2$ |
| Lattice constant (Å, °) | 62.455, 62.455, 185.841 $\alpha = 90\ \beta = 90\ \gamma = 120$ | 62.306, 62,306, 185.532 $\alpha = 90\ \beta = 90\ \gamma = 120$ |
| Wavelength (Å) | 1.00 | 0.90 |
| Resolutionon (Å) | 50-2.32 (2.36-2.32) | 50-1.15 (1.19-1.15) |
| Measurement reflection | 130380 | 1008233 |
| Unique reflection | 17536 | 76489 |
| Rmerge | 0.043 (0.058) | 0.058 (0.385) |
| Data perfection (%) | 99.5 (95.6) | 99.8 (99.8) |
| Equipment | SPring-8 BL38B1 | SPring-8 BL38B1 |
| Detector | JUPITER 210 CCD | R-Axis V |

TABLE 1-continued

| Crystal | Mature form of protein-glutaminase (Au heavy atom substitution) | Mature form of protein-glutaminase |
|---|---|---|
| Structural determination | | Heavy atom isomorphous replacement method |
| <Structural precision> | | |
| Resolution (Å) | | 10-1.15 |
| Use reflection | | 72390 |
| Rcryst/Rfree | | 0.0979/0.1359 |
| r.m.s.d bond | | 0.030Å |
| r.m.s.d angle | | 0.032Å |
| Residues/water/Na+/glycerol | | 185/448/1/1 |

2. X Ray Crystal Structure Analysis of Pro-Enzyme of Protein-Glutaminase (1) Preparation of Expression Plasmid of Pro-Enzyme of Protein-Glutaminase in *Escherichia coli*

A gene coding for a pro-enzyme of a protein-glutaminase derived from the *Chryseobacterium proteolyticum* 9670 strain (GenBank Accession No AB046594) was amplified in PCR as follows. Using a chromosome DNA of the *Chryseobacterium proteolyticum* 9670 strain isolated in a method by Sambrook, et al, (Molecular Cloning: a laboratory manual, 2$^{nd}$ Edition, Cold Spring harbor Laboratory Press, 1989) as a template for PCR, oligonucleotides set forth in SEQ ID NO: 5 and SEQ ID NO: 6 were synthesized to form a primer. The PCR reaction was performed 30 cycles of 94° C./2 minutes, 94° C./15 seconds –70° C./30 seconds –68° C./70 seconds, using the KOD plus system (TOYOBO CO., LTD.). The obtained PCR fragment was treated with restriction enzymes, NdeI and XhoI, and then connected to a plasmid pET20(b) (Novagen Co.) which was cut with the both enzymes in the same manner to obtain an expression plasmid pETPG1. It was confirmed that the obtained PCR fragment correctly codes for the pro-enzyme of the protein-glutaminase by determining the base sequence.

```
                                          SEQ ID NO: 5
5'-CGTGCCATATGGATTCCAACGGGAATCAGG-3' (The underline indicates the restriction enzyme NdeI recognition site)

SEQ ID NO: 6
5'-CTCGCTCGAGAAATCCACAGCTGGATACAT-3' (The underline indicates the restriction enzyme XhoI recogntion site)
```

(2) Expression of Pro-Enzyme of Protein-Glutaminase in *Escherichia coli*

The above described expression plasmid was introduced in *Escherichia coli* BL21(DE3) (Novagen Co.) by genetic transformation. The obtained transformant was inoculated in a LB medium (800 ml×2) containing 100 μ/ml of ampicillin and shaken at 37° C. Isopropyl thiogalactoside (IPTG) was added at the time when a turbidity of 600 nm reached 0.6 to 0.8 so as to have a final concentration of 0.5 mM, and the culture liquid was further cultured at 18° C. for 15 hours. Fungus forms were collected from the culture liquid by centrifugation, and suspended in a buffer solution (20 mM sodium phosphate (pH 6.3), 0.5 M NaCl, 10 mM imidazole).

(3) Purification of Pro-Enzyme of Recombinant Protein-Glutaminase

The suspension obtained in (2) was treated by sonication at 200 μA for 20 minutes in ice water and then provided in centrifugation at 14000 rpm, at 4° C. for 30 minutes to obtain a crude extraction. The crude extraction was provided in Ni-NTA affinity chromatography (Qiagen Co.) and eluted with 20 mM sodium phosphate/300 mM imidazole (pH 7.0). The obtained eluted protein was provided in TALON affinity chromatography (Clontech Co.) and eluted with 20 mM sodium phosphate/300 mM imidazole (pH 7.0) in the same manner to obtain a pro-enzyme of a protein-glutaminase. The buffer was exchanged using 0.1 M sodium phosphate (pH 6.1), and at the same time, this purified product was concentrated to about 27.5 mg/ml.

(4) Crystallization

Crystallization of the pro-enzyme of the protein-glutaminase was carried out in the following procedure. Firstly, the pro-enzyme of the protein-glutaminase was screened in a sitting drop vapor diffusion method using two 24-hole plates by PEG/Ion Screen manufactured by Hampton Research Co. Stood still at 20° C., crystals were observed in 22 wells after a few days. The most preferable crystal among them was obtained from 4 μl of a sitting drop made of 2 μl of an enzyme liquid (27 mg/ml) and 2 of a reservoir solution (20% PEG3350, 0.2 M ammonium citrate, pH 5.1). Prior to the X ray analysis, the crystal was treated with a reservoir solution containing 20% of methyl pentadiol and then instantly cooled with liquid nitrogen (−173° C.).

(5) X Ray Analysis

X ray diffraction data was collected using synchrotron radiation BL-38B1 of SPring-8 (Hyogo prefecture) at the temperature of liquid nitrogen and processed using HKL2000 program. X ray diffraction data of 1.73 Å resolution was collected and a crystallographic parameter was determined. A space group was $P2_12_12_1$ and lattice constants were a=56.644 Å, b=103.290 Å, and c=132.510 Å.

(6) Determination of Three-Dimensional Structure

The three-dimensional structure was determined at a resolution of 1.73 Å in a molecular replacement method using the atomic coordinates of the protein-glutaminase, which were solved above. Phaser was used for phase determination, Win-Coot was used for modeling, and Refmac5 was used for structural precision. Data collection and statistic data of precision are shown in Table 2.

TABLE 2

| Crystal | Pro-enzyme of protein-glutaminase |
|---|---|
| <Data collection> | |
| Space group | $P2_12_12_1$ |
| Lattice constant (Å, o) | 56.644, 103.290, 132.510 |
| | α = 90 β = 90 γ = 90 |
| X ray wavelength | 1.0 |
| Resolution (Å) | 1.73 (1.79-1.73) |
| Measurement reflection | 533046 |
| Unique reflection | 80701 |
| Rmerge | 0.056 (0.314) |
| Data perfection (%) | 98.2 (90.9) |
| Equipment | Spring-8 BL38b1 |
| Detector | JUPITER 210 CCD |
| <Structural precision> | |
| Resolution (Å) | 81.379-1.728 |
| Use reflection | 76594 |

TABLE 2-continued

| Crystal | Pro-enzyme of protein-glutaminase |
|---|---|
| Rcryst/Rfree | 0.183/0.209 |
| r.m.s.d bond | 0.012Å |
| r.m.s.d angle | 1.492° |

Models of the three-dimensional structures of the obtained mature form (thick line) and pro-enzyme (light line) of the protein-glutaminase derived from the *Chryseobacterium proteolyticum* 9670 strain are shown in FIG. 1 (figure in which a carbons are overlapped). A ribbon model of a higher structure of the pro-enzyme is shown in FIG. 2. Note that data of atomic coordinates of the pro-enzyme is shown in the end of the specification. FIG. 3 is a view of enlarging an area around the active center Cys42 and a substrate bonding region in the pro-enzyme, and FIG. 4 is a view of enlarging an amino acid region that is supposed to give an effect on the active center.

3. Preparation of Protein-Glutaminase Mutant Tyr82Ser

On the ground of being arranged on a surface around a cleft or close to an amino acid being the active center from the three-dimensional structure of the pro-enzyme of the protein-glutaminase derived from the *Chryseobacterium proteolyticum* 9670 strain, which was obtained in 2., as an amino acid that can give an effect on substrate specificity, the amino acid at position 39, the amino acid at position 40, the amino acid at position 41, the amino acid at position 43, the amino acid at position 79, the amino acid at position 80, the amino acid at position 81, the amino acid at position 82, the amino acid at position 142, the amino acid at position 143, the amino acid at position 146, the amino acid at position 166, and the amino acid at position 185 were specified. Among them, the tyrosine residue at position 82 is arranged close to an amino acid (Ala-(minus) position 67 etc.) in a pro-region that is closely attached to the active center cysteine (position 42), and thus, it was considered to act as an important role for substrate recognition (FIG. 3). Four tyrosine residues (positions 43, 82, 142, and 143) present in an entrance of a cleft connected to the active center have a function of attracting a protein molecule due to their hydrophobicity, and the tyrosine residue at position 82 is located at an active pocket entrance, which is expected to form a hydrogen bond with a substrate (FIG. 3). Based on this supposition, the amino acid (Tyr82) was replaced by another amino acid, for instance, an amino acid having hydrophilicity and small steric hindrance, and the effect was verified.

(1) Expression of Pro-Enzyme of Protein-Glutaminase Mutant Tyr82Ser

Based on the sequence of the gene coding for the pro-enzyme of the protein-glutaminase derived from the *Chryseobacterium proteolyticum* 9670 strain, a primer for replacing Tyr82 to serine was synthesized. A forward primer for mutation set forth in SEQ ID NO: 7 and a reverse primer corresponding thereto were synthesized and prepared to have a concentration of 100 ng/µl. The expression plasmid pETPG1 of the pro-enzyme of the protein-glutaminase derived from the *Chryseobacterium proteolyticum* 9670 strain was used as a template and a PCR reaction was performed using the Quickchange PCR system (Stratagene Corporation). 1 µl (20 ng/µl) of pETPG1, 5 µl of a 10×PCR buffer solution (added to DNA polymerase described later), 1.0 µl (2.5 mM each) of dNTP, 1.25 µl each of a mutant primer set (forward and reverse primers), 39 µl of sterile water, 1 µl (2.5 U) of Pfu Turbo Hotstart DNA polymerase (Stratagene Corporation) were prepared, 17 cycles of 95° C./30 seconds (mutation) –60° C./1 minute (annealing) –68° C./4.7 minutes (elongation) were preformed, and amplification at 68° C./5 minutes was finally carried out. The obtained PCR product was confirmed with 1% agarose gel electrophoresis, the residual PCR product was treated with the restriction enzyme Dpn I to decompose the methylated template plasmid and transformed to *Escherichia coli* competent cell DH5α strain. A plasmid DNA was isolated from the obtained ampicillin resistant transformant and the base sequence was confirmed to obtain a target mutant gene. A plasmid having the target mutant gene was introduced into the expression host, *Escherichia coli* BL21(DE3) strain, and the pro-enzyme of the protein-glutaminase mutant Tyr82Ser was expressed and purified in the same manner as in 2.(2) and (3).

SEQ ID No: 7
5'-TGTGTGGCGTGGAGC<u>TCT</u>CACGTTGCAATATTG-3'

(The underline codes for a substituted amino acid)

(2) Purification of Mature Form of Protein-Glutaminase Mutant Tyr82Ser

Next, in order to remove the pro-region, trypsin (Sigma Co.) of 9.32 U/mg protein was added to react at 30° C. for 4 hours. The reaction solution was provided in TALON affinity chromatography to remove protease in an unadsorbed fraction, and then eluted with 20 mM sodium phosphate/300 mM imidazole (pH 7.0). The eluted fraction was dialyzed with a 20 mM sodium citrate buffer solution at pH 4.9, and provided in MonoS cation exchange chromatography (GE Healthcare Bio-Sciences Ltd.). The adsorbed protein was eluted with 0.5 M of a NaCl gradient, thereby purifying the mature form of the protein-glutaminase mutant Tyr82Ser having activity.

4. Substrate Specificity of Protein-Glutaminase Mutant Tyr82Ser

Specificity to various proteins of the mature form of the protein-glutaminase mutant Tyr82Ser prepared in 3. was examined. 0.3 µg/4 µl of the mature form of the protein-glutaminase mutant Tyr82Ser was added to 196 µl of a 20 mM phosphate buffer solution (pH 6.0) containing 0.2% each of α-lactalbumin (Sigma Co.), β-lactoglobulin (Sigma Co.), separated soybean protein (Fuji Pro F, FUJI OIL CO., LTD.), wheat gluten (Viten, ROQUETTE Co.) and casein (Wako Pure Chemical Industries, Ltd.), and reacted at 37° C. for 10 to 200 minutes. Thereto was added trichloroacetic acid so as to have a final concentration of 0.2 M, the reaction was stopped, and then, a quantity of free ammonium was determined by the ammonium test, Wako (Wako Pure Chemical Industries, Ltd.). A mature form of mutant protein-glutaminase was used in the same amount as a control. An amount of free ammonium per unit of time was found, and the amount of free ammonium for each protein was expressed as a relative value, assuming the free ammonia amount to the α-lactalbumin amount as 100%, The result is shown in Table 3.

TABLE 3

| | Relative activity (%) | | Ratio |
|---|---|---|---|
| | Wild-type | Y82S | (Y82S/Wild-type) |
| α-lactalbumin | 100 | 100 | 1.0 |
| β-lactoglobulin | 61 | 309 | 5.0 |

TABLE 3-continued

| | Relative activity (%) | | Ratio |
|---|---|---|---|
| | Wild-type | Y82S | (Y82S/Wild-type) |
| Separated soybean protein | 127 | 531 | 4.2 |
| Wheat gluten | 2619 | 4274 | 1.6 |
| Casein | 1016 | 701 | 0.7 |

It was found that, as compared to a wild-type protein-glutaminase, the protein-glutaminase mutant Tyr82Ser can act more easily on β-lactoglobulin, separated soybean protein, and wheat gluten, on the other hand, reactivity to casein decreased. As described above, action properties to various proteins was able to be changed due to introduction of mutation. According to the above results, it was confirmed that mutation of Tyr82 is effective to modification of substrate specificity. In addition, improvement in action properties makes it possible to reduce an enzyme amount used. What is more, expansion of applications can also be expected.

5. Preparation of Protein-Glutaminase Mutant Val84Asp

The three-dimensional structures of the mature form and the pro-enzyme of the protein-glutaminase derived from the *Chryseobacterium proteolyticum* 9670 strain were analyzed, and as a result, as amino acids associated with interaction among catalytic residues (Cys42, His83, Asp103) and structure preservation, and capable of giving an effect on oxidation stability, the amino acid at position 35, the amino acid at position 38, the amino acid at position 40, the amino acid at position 41, the amino acid at position 42, the amino acid at position 43, the amino acid at position 45, the amino acid at position 46, the amino acid at position 49, the amino acid at position 80, the amino acid at position 81, the amino acid at position 82, the amino acid at position 83, the amino acid at position 84, the amino acid at position 103, the amino acid at position 104, the amino acid at position 105, the amino acid at position 106, and the amino acid at position 117 were specified. Among them, the amino acid at position 84 is close to the active center cysteine (position 42) and arranged in a position giving an effect on a dissociative state of a thiol group in the cysteine (FIG. 4), and thus, it was considered to act as an important role for easiness of oxidation of the active center cysteine. Based on this supposition, the amino acid (Val84) was replaced by another amino acid, for instance, an amino acid having negative charge, in the procedure below, and the effect was verified.

Based on the sequence of the gene that codes for the pro-enzyme of the protein-glutaminase derived from the *Chryseobacterium proteolyticum* 9670 strain, a primer for replacing Val84 to asparaginic acid was synthesized. A forward primer for mutation set forth in SEQ ID NO: 8, and a corresponding reverse primer thereto were synthesized, and the pro-enzyme of the protein-glutaminase mutant Val84Asp was expressed and purified in the same method of 3. (1) below. Furthermore, the mature form of the protein-glutaminase mutant Val84Asp having activity was purified in the same method of 3. (2).

SEQ ID NO: 8
5'-GCGTGGAGCTACCAC<u>GAT</u>GCAATATTGGTAAGC-3'

(The underline codes for a substituted amino acid)

6. Oxidation Stability of Protein-Glutaminase Mutant Val84Asp

In order to examine oxidation stability of the protein-glutaminase mutant Val84Asp prepared in 5., stability in the presence of hydrogen peroxide was examined. To a substrate liquid of a 10 mM Z-Gln-Gly (PEPTIDE INSTITUTE, INC.)/100 mM phosphate buffer solution (pH 6.0) containing 0.45% or 0.9% of hydrogen peroxide, 0.809 µg of the mature form of the protein-glutaminase mutant Val84Asp was added and reacted at 37° C. for 20 minutes. Thereto was added trichloroacetic acid so as to have a final concentration of 0.2 M, the reaction was stopped, and then, a quantity of free ammonium was determined with the ammonium test, Wako (Wako Pure Chemical Industries, Ltd.). 0.121 µg of a mature form of a wild-type protein-glutaminase was used as a control. An amount of free ammonium per unit of time was found, and the amount of free ammonium at each hydrogen peroxide concentration was expressed as a relative value to be a residual activity, assuming an amount of free ammonia in the absence of hydrogen peroxide as 100%. The result is shown in Table 4.

TABLE 4

| $H_2O_2$ concentration | Residual activity (%) | |
|---|---|---|
| (%) | Wild Type | V84D |
| 0 | 100 | 100 |
| 0.45 | 1.7 | 50.5 |
| 0.9 | 1.8 | 32.3 |

As described above, it was found that the protein-glutaminase mutant Val84Asp was significantly improved in stability in the presence of hydrogen peroxide as compared to the wild-type protein-glutaminase. As described above, oxidation stability was able to be improved due to introduction of mutation. Thus, it was confirmed that mutation of Val84 is effective to improvement in oxidation stability. Additionally, improvement in oxidation stability makes it possible to omit a stabilizing agent or reduce an amount used of the stabilizing agent. Also, handiness is more facilitated in production steps (particularly in a wrapping step)

INDUSTRIAL APPLICABILITY

The designing method and the preparation method of the present invention are used for modification of an enzyme capable of deamidating a protein. According to a mutant enzyme improved in action properties, for example, it makes possible to reduce an amount used of an enzyme, shorten a reaction time, expand applications (application to a substrate on which enzymes could not act, etc), and so on. Further, according to a mutant enzyme improved in oxidation stability, for example, it makes possible to omit a stabilizing agent for maintaining reservation stability or reduce an amount used of the stabilizing agent, simplify production steps (e.g., it becomes unnecessary to wrap in an degassed state), and so on. On the other hand, according to use of the designing method and the preparation method of the present invention, it can be expected to provide a mutant enzyme capable of applying to novel applications, which could not be assumed with wild-type enzymes. That is, the present invention can contribute to expansion of applications of an enzyme that deamidates a protein and improvement in usability.

The invention is not limited by the above described embodiments and examples of the invention at all. Various modifications are included in the invention within the range that a person skilled in the art can easily conceived of, without deviating from the description of the scope, of patent claims.

Contents of treatises, laid-open patent publications, and patent publications specified in this specification are all incorporated herewith by their references.

Atomic coordinates of the conformation of the pro-enzyme of the protein-glutaminase derived from the *Chryseobacterium proteolyticum* 9670 strain are shown below.

```
HEADER    ----               XX-XXX-9- xxxx
COMPND    ---
REMARK 3
REMARK 3   REFINEMENT.
REMARK 3     PROGRAM       :REFMAC 5.2.0019
REMARK 3     AUTHORS       :MURSHUDOV, VAGIN, DODSON
REMARK 3
REMARK 3    REFINEMENT TARGET: MAXIMUM LIKELIHOOD
REMARK 3
REMARK 3   DATA USED IN REFINEMENT.
REMARK 3    RESOLUTION RANGE HIGH (ANGSTROMS):    1.73
REMARK 3    RESOLUTION RANGE LOW (ANGSTROMS):    81.38
REMARK 3    DATA CUTOFF       (SIGMA(F)): NONE
REMARK 3    COMPLETENESS FOR RANGE   (%): 98.17
REMARK 3    NUMBER OF REFLECTIONS        : 76594
REMARK 3
REMARK 3   FIT TO DATA USED IN REFINEMENT.
REMARK 3    CROSS-VALIDATION METHOD     :THROUGHOUT
REMARK 3    FREE R VALUE TEST SET SELECTION :RANDOM
REMARK 3    R VALUE   (WORKING + TEST SET): 0.18371
REMARK 3    R VALUE        (WORKING SET): 0.18241
REMARK 3    FREE R VALUE           :0.20864
REMARK 3    FREE R VALUE TEST SET SIZE (%): 5.0
REMARK 3    FREE R VALUE TEST SET COUNT   : 4037
REMARK 3
REMARK 3   FIT IN THE HIGHEST RESOLUTION BIN.
REMARK 3    TOTAL NUMBER OF BINS USED      :   20
REMARK 3    BIN RESOLUTION RANGE HIGH     :  1.728
REMARK 3    BIN RESOLUTION RANGE LOW      :  1.773
REMARK 3    REFLECTION IN BIN   (WORKING SET):    5068
REMARK 3    BIN COMPLETENESS(WORKING + TEST) (%):     88.97
REMARK 3    BIN R VALUE       (WORKING SET):   0.242
REMARK 3    BIN FREE R VALUE SET COUNT      :   279
REMARK 3    BIN FREE R VALUE            :   0.250
REMARK 3
REMARK 3   NUMBER OF NON-HYDROGEN ATOMS USED IN REFINEMENT.
REMARK 3    ALL ATOMS        :  5470
REMARK 3
REMARK 3   B VALUES.
REMARK 3    FROM WILSON PLOT       (A**2):NULL
REMARK 3    MEAN B VALUE     (OVERALL, A**2): 27.925
REMARK 3    OVERALL ANISOTROPIC B VALUE.
REMARK 3    B11 (A**2):   1.76
REMARK 3    B22 (A**2):  -1.28
REMARK 3    B33 (A**2):  -0.49
REMARK 3    B12 (A**2):   0.00
REMARK 3    B13 (A**2):   0.00
REMARK 3    B23 (A**2):   0.00
REMARK 3
REMARK 3   ESTIMATED OVERALL COORDINATE ERROR.
REMARK 3    ESU BASED ON R VALUE        (A):  0.102
REMARK 3    ESU BASED ON FREE R VALUE    (A):  0.099
REMARK 3    ESU BASED ON MAXIMUM LIKELIHOOD  (A):  0.065
REMARK 3   ESU FOR B VALUES BASED ON MAXIMUM LIKELIHOOD (A**2): 1.954
REMARK 3
REMARK 3   CORRELATION COEFFICIENTS.
REMARK 3    CORRELATION COEFFICIENT FO-FC     : 0.962
REMARK 3    CORRELATION COEFFICIENT FO-FC FREE: 0.950
REMARK 3
REMARK 3   RMS DEVIATIONS FROM IDEAL VALUES COUNT RMS WEIGHT
REMARK 3   BOND LENGTHS REFINED ATOMS  (A): 4850; 0.012; 0.022
REMARK 3   BOND ANGLES REFINED ATOMS (DEGREES): 6697; 1.497; 1.967
REMARK 3   TORSION ANGLES, PERIOD 1 (DEGREES): 693; 11.741; 5.000
REMARK 3   TORSION ANGLES, PERIOD 2 (DEGREES): 196; 38.364; 25.000
REMARK 3   TORSION ANGLES, PERIOD 3 (DEGREES): 852; 14.504; 15.000
REMARK 3   TORSION ANGLES, PERIOD 4 (DEGREES): 18; 12.593; 15.000
REMARK 3   CHIRAL-CENTER RESTRAINTS (A**3): 762; 0.126; 0.200
REMARK 3   GENERAL, PLANES REFINED ATOMS (A): 3722; 0.006; 0.020
REMARK 3   NON-BONDED CONTACTS REFINED ATOMS (A): 2619; 0.200; 0.200
REMARK 3   NON-BONDED TORSION REFINED ATOMS (A): 3434; 0.308; 0.200
REMARK 3   H-BOND (X...Y) REFINED ATOMS (A): 731; 0.145; 0.200
REMARK 3   SYMMETRY VDW REFINED ATOMS  (A): 105; 0.204; 0.200
```

-continued

| | | | | | | | | | |
|---|---|---|---|---|---|---|---|---|---|
| REMARK | 3 | SYMMETRY H-BOND REFINED ATOMS (A): 34; 0.333; 0.200 | | | | | | | |
| REMARK | 3 | | | | | | | | |
| REMARK | 3 | ISOTROPIC THERMAL FACTOR RESTRAINTS. COUNT RMS WEIGHT | | | | | | | |
| REMARK | 3 | MAIN-CHAIN BOND REFINED ATOMS (A**2): 3105; 0.841; 1.500 | | | | | | | |
| REMARK | 3 | MAIN-CHAIN ANGLE REFINED ATOMS (A**2): 5034; 1.391; 2.000 | | | | | | | |
| REMARK | 3 | SIDE-CHAIN BOND REFINED ATOMS (A**2): 1950; 1.832; 3.000 | | | | | | | |
| REMARK | 3 | SIDE-CHAIN ANGLE REFINED ATOMS (A**2): 1598; 2.746; 4.500 | | | | | | | |
| REMARK | 3 | | | | | | | | |
| REMARK | 3 | NCS RESTRAINTS STATISTICS | | | | | | | |
| REMARK | 3 | NUMBER OF NCS GROUPS: NULL | | | | | | | |
| REMARK | 3 | | | | | | | | |
| REMARK | 3 | | | | | | | | |
| REMARK | 3 | TLS DETAILS | | | | | | | |
| REMARK | 3 | NUMBER OF TLS GROUPS: NULL | | | | | | | |
| REMARK | 3 | | | | | | | | |
| REMARK | 3 | | | | | | | | |
| REMARK | 3 | BULK SOLVENT MODELLING. | | | | | | | |
| REMARK | 3 | METHOD USED: MASK | | | | | | | |
| REMARK | 3 | PARAMETERS FOR MASK CALCULATION | | | | | | | |
| REMARK | 3 | VDW PROBE RADIUS : 1.20 | | | | | | | |
| REMARK | 3 | ION PROBE RADIUS : 0.80 | | | | | | | |
| REMARK | 3 | SHRINKAGE RADIUS : 0.80 | | | | | | | |
| REMARK | 3 | | | | | | | | |
| REMARK | 3 | OTHER REFINEMENT REMARKS: | | | | | | | |
| REMARK | 3 | HYDROGENS HAVE BEEN ADDED IN THE RIDING POSITIONS | | | | | | | |
| REMARK | 3 | | | | | | | | |
| SSBOND | 1 CYS X 158 | CYS X 167 | | | | | | | |
| SSBOND | 2 CYS X 211 | CYS X 307 | | | | | | | |
| SSBOND | 3 CYS X 212 | CYS X 261 | | | | | | | |
| SSBOND | 4 CYS X 296 | CYS X 318 | | | | | | | |
| SSBOND | 5 CYS C 211 | CYS C 307 | | | | | | | |
| SSBOND | 6 CYS C 212 | CYS C 261 | | | | | | | |
| SSBOND | 7 CYS C 296 | CYS C 318 | | | | | | | |
| SSBOND | 8 CYS C 158 | CYS C 167 | | | | | | | |
| CISPEP | 1 LYS X 43 | ASP X 44 | 0.00 | | | | | | |
| CISPEP | 2 ASN X 57 | GLY X 58 | 0.00 | | | | | | |
| CISPEP | 3 LYS X 135 | LEU X 136 | 0.00 | | | | | | |
| CISPEP | 4 SER X 165 | PRO X 166 | 0.00 | | | | | | |
| CISPEP | 5 PRO X 173 | VAL X 174 | 0.00 | | | | | | |
| CISPEP | 6 ASP X 175 | GLY X 176 | 0.00 | | | | | | |
| CISPEP | 7 SER X 308 | PRO X 309 | 0.00 | | | | | | |
| CISPEP | 8 SER X 310 | PRO X 311 | 0.00 | | | | | | |
| CISPEP | 9 ASN C 79 | GLU C 80 | 0.00 | | | | | | |
| CISPEP | 10 SER C 165 | PRO C 166 | 0.00 | | | | | | |
| CISPEP | 11 PRO C 173 | VAL C 174 | 0.00 | | | | | | |
| CISPEP | 12 SER C 308 | PRO C 309 | 0.00 | | | | | | |
| CISPEP | 13 SER C 310 | PRO C 311 | 0.00 | | | | | | |
| CRYST1 | 56.644 103.290 132.510 90.00 90.00 90.00 P 21 21 21 | | | | | | | | |
| SCALE1 | 0.017654 | 0.000000 | 0.000000 | 0.00000 | | | | | |
| SCALE2 | 0.000000 | 0.009681 | 0.000000 | 0.00000 | | | | | |
| SCALE3 | 0.000000 | 0.000000 | 0.007547 | 0.00000 | | | | | |
| ATOM | 1 | N | ASP | X | −96 | −12.592 | 0.198 | −54.520 | 1.00 | 58.56 | N |
| ATOM | 2 | CA | ASP | X | −96 | −12.881 | −1.265 | −54.427 | 1.00 | 58.40 | C |
| ATOM | 3 | CB | ASP | X | −96 | −12.225 | −2.029 | −55.590 | 1.00 | 58.69 | C |
| ATOM | 4 | CG | ASP | X | −96 | −10.706 | −2.010 | −55.525 | 1.00 | 59.61 | C |
| ATOM | 5 | OD1 | ASP | X | −96 | −10.085 | −1.182 | −56.231 | 1.00 | 61.01 | O |
| ATOM | 6 | OD2 | ASP | X | −96 | −10.135 | −2.823 | −54.769 | 1.00 | 59.92 | O |
| ATOM | 7 | C | ASP | X | −96 | −12.493 | −1.868 | −53.068 | 1.00 | 57.94 | C |
| ATOM | 8 | O | ASP | X | −96 | −12.011 | −1.159 | −52.172 | 1.00 | 57.92 | O |
| ATOM | 9 | N | SER | X | −95 | −12.702 | −3.181 | −52.940 | 1.00 | 56.99 | N |
| ATOM | 10 | CA | SER | X | −95 | −12.605 | −3.896 | −51.661 | 1.00 | 56.03 | C |
| ATOM | 11 | CB | SER | X | −95 | −13.609 | −5.055 | −51.639 | 1.00 | 56.36 | C |
| ATOM | 12 | OG | SER | X | −95 | −14.894 | −4.623 | −52.054 | 1.00 | 56.91 | O |
| ATOM | 13 | C | SER | X | −95 | −11.199 | −4.418 | −51.352 | 1.00 | 54.92 | C |
| ATOM | 14 | O | SER | X | −95 | −10.870 | −4.688 | −50.193 | 1.00 | 55.05 | O |
| ATOM | 15 | N | LYS | X | −94 | −10.390 | −4.575 | −52.398 | 1.00 | 53.31 | N |
| ATOM | 16 | CA | LYS | X | −94 | −8.969 | −4.881 | −52.271 | 1.00 | 51.78 | C |
| ATOM | 17 | CB | LYS | X | −94 | −8.393 | −5.212 | −53.651 | 1.00 | 51.89 | C |
| ATOM | 18 | CG | LYS | X | −94 | −6.926 | −5.626 | −53.670 | 1.00 | 52.50 | C |
| ATOM | 19 | CD | LYS | X | −94 | −6.521 | −6.219 | −55.027 | 1.00 | 52.96 | C |
| ATOM | 20 | CE | LYS | X | −94 | −7.252 | −7.529 | −55.322 | 1.00 | 54.36 | C |
| ATOM | 21 | NZ | LYS | X | −94 | −6.753 | −8.187 | −56.560 | 1.00 | 55.99 | N |
| ATOM | 22 | C | LYS | X | −94 | −8.213 | −3.697 | −51.642 | 1.00 | 50.21 | C |
| ATOM | 23 | O | LYS | X | −94 | −7.248 | −3.895 | −50.904 | 1.00 | 49.64 | O |
| ATOM | 24 | N | LEU | X | −93 | −8.660 | −2.475 | −51.939 | 1.00 | 48.36 | N |
| ATOM | 25 | CA | LEU | X | −93 | −8.067 | −1.260 | −51.363 | 1.00 | 46.57 | C |
| ATOM | 26 | CB | LEU | X | −93 | −7.957 | −0.161 | −52.433 | 1.00 | 46.24 | C |
| ATOM | 27 | CG | LEU | X | −93 | −7.180 | −0.482 | −53.722 | 1.00 | 45.25 | C |
| ATOM | 28 | CD1 | LEU | X | −93 | −7.428 | 0.563 | −54.806 | 1.00 | 45.02 | C |
| ATOM | 29 | CD2 | LEU | X | −93 | −5.674 | −0.648 | −53.479 | 1.00 | 44.66 | C |

-continued

| ATOM | 30 | C | LEU | X | −93 | −8.835 | −0.747 | −50.132 | 1.00 | 45.92 | C |
|---|---|---|---|---|---|---|---|---|---|---|---|
| ATOM | 31 | O | LEU | X | −93 | −10.009 | −1.081 | −49.935 | 1.00 | 45.62 | O |
| ATOM | 32 | N | LYS | X | −92 | −8.138 | 0.025 | −49.298 | 1.00 | 44.54 | N |
| ATOM | 33 | CA | LYS | X | −92 | −8.708 | 0.821 | −48.198 | 1.00 | 44.24 | C |
| ATOM | 34 | CB | LYS | X | −92 | −7.632 | 0.884 | −47.105 | 1.00 | 44.19 | C |
| ATOM | 35 | CG | LYS | X | −92 | −7.775 | 1.955 | −46.033 | 1.00 | 46.39 | C |
| ATOM | 36 | CD | LYS | X | −92 | −8.474 | 1.424 | −44.790 | 1.00 | 49.21 | C |
| ATOM | 37 | CE | LYS | X | −92 | −8.758 | 2.563 | −43.808 | 1.00 | 50.74 | C |
| ATOM | 38 | NZ | LYS | X | −92 | −9.683 | 2.160 | −42.712 | 1.00 | 51.81 | N |
| ATOM | 39 | C | LYS | X | −92 | −8.906 | 2.167 | −48.919 | 1.00 | 43.10 | C |
| ATOM | 40 | O | LYS | X | −92 | −7.931 | 2.828 | −49.157 | 1.00 | 43.24 | O |
| ATOM | 41 | N | ASP | X | −91 | −10.109 | 2.673 | −49.195 | 1.00 | 42.41 | N |
| ATOM | 42 | CA | ASP | X | −91 | −11.040 | 3.345 | −48.270 | 1.00 | 40.07 | C |
| ATOM | 43 | CB | ASP | X | −91 | −12.460 | 2.816 | −48.177 | 1.00 | 40.99 | C |
| ATOM | 44 | CG | ASP | X | −91 | −13.454 | 3.814 | −48.781 | 1.00 | 42.19 | C |
| ATOM | 45 | OD1 | ASP | X | −91 | −13.049 | 4.995 | −48.948 | 1.00 | 41.22 | O |
| ATOM | 46 | OD2 | ASP | X | −91 | −14.613 | 3.444 | −49.089 | 1.00 | 43.71 | O |
| ATOM | 47 | C | ASP | X | −91 | −10.581 | 4.290 | −47.147 | 1.00 | 38.40 | C |
| ATOM | 48 | O | ASP | X | −91 | −10.811 | 4.067 | −45.954 | 1.00 | 37.95 | O |
| ATOM | 49 | N | PHE | X | −90 | −9.955 | 5.374 | −47.605 | 1.00 | 35.70 | N |
| ATOM | 50 | CA | PHE | X | −90 | −9.498 | 6.476 | −46.774 | 1.00 | 33.75 | C |
| ATOM | 51 | CB | PHE | X | −90 | −8.280 | 7.154 | −47.423 | 1.00 | 33.30 | C |
| ATOM | 52 | CG | PHE | X | −90 | −7.738 | 8.316 | −46.638 | 1.00 | 32.37 | C |
| ATOM | 53 | CD1 | PHE | X | −90 | −6.863 | 8.106 | −45.577 | 1.00 | 32.51 | C |
| ATOM | 54 | CE1 | PHE | X | −90 | −6.364 | 9.177 | −44.834 | 1.00 | 32.69 | C |
| ATOM | 55 | CZ | PHE | X | −90 | −6.739 | 10.481 | −45.166 | 1.00 | 33.10 | C |
| ATOM | 56 | CE2 | PHE | X | −90 | −7.622 | 10.696 | −46.228 | 1.00 | 31.88 | C |
| ATOM | 57 | CD2 | PHE | X | −90 | −8.102 | 9.626 | −46.960 | 1.00 | 32.39 | C |
| ATOM | 58 | C | PHE | X | −90 | −10.625 | 7.496 | −46.621 | 1.00 | 32.73 | C |
| ATOM | 59 | O | PHE | X | −90 | −10.610 | 8.304 | −45.689 | 1.00 | 33.16 | O |
| ATOM | 60 | N | GLY | X | −89 | −11.579 | 7.443 | −47.544 | 1.00 | 30.58 | N |
| ATOM | 61 | CA | GLY | X | −89 | −12.726 | 8.352 | −47.558 | 1.00 | 29.57 | C |
| ATOM | 62 | C | GLY | X | −89 | −12.469 | 9.556 | −48.443 | 1.00 | 27.95 | C |
| ATOM | 63 | O | GLY | X | −89 | −11.500 | 9.566 | −49.201 | 1.00 | 26.45 | O |
| ATOM | 64 | N | LYS | X | −88 | −13.338 | 10.569 | −48.355 | 1.00 | 26.02 | N |
| ATOM | 65 | CA | LYS | X | −88 | −13.156 | 11.787 | −49.134 | 1.00 | 25.54 | C |
| ATOM | 66 | CB | LYS | X | −88 | −14.491 | 12.464 | −49.483 | 1.00 | 26.40 | C |
| ATOM | 67 | CG | LYS | X | −88 | −15.224 | 11.865 | −50.695 | 1.00 | 30.50 | C |
| ATOM | 68 | CD | LYS | X | −88 | −16.059 | 10.662 | −50.326 | 1.00 | 36.67 | C |
| ATOM | 69 | CE | LYS | X | −88 | −17.298 | 11.062 | −49.536 | 1.00 | 40.18 | C |
| ATOM | 70 | NZ | LYS | X | −88 | −18.208 | 9.891 | −49.300 | 1.00 | 42.06 | N |
| ATOM | 71 | C | LYS | X | −88 | −12.271 | 12.765 | −48.374 | 1.00 | 23.22 | C |
| ATOM | 72 | O | LYS | X | −88 | −12.285 | 12.832 | −47.141 | 1.00 | 23.52 | O |
| ATOM | 73 | N | THR | X | −87 | −11.492 | 13.529 | −49.123 | 1.00 | 21.66 | N |
| ATOM | 74 | CA | THR | X | −87 | −10.657 | 14.540 | −48.534 | 1.00 | 20.71 | C |
| ATOM | 75 | CB | THR | X | −87 | −9.359 | 13.927 | −47.954 | 1.00 | 20.85 | C |
| ATOM | 76 | OG1 | THR | X | −87 | −8.636 | 14.941 | −47.238 | 1.00 | 22.40 | O |
| ATOM | 77 | CG2 | THR | X | −87 | −8.519 | 13.349 | −49.073 | 1.00 | 21.11 | C |
| ATOM | 78 | C | THR | X | −87 | −10.308 | 15.567 | −49.596 | 1.00 | 19.45 | C |
| ATOM | 79 | O | THR | X | −87 | −10.626 | 15.383 | −50.770 | 1.00 | 20.99 | O |
| ATOM | 80 | N | VAL | X | −86 | −9.652 | 16.646 | −49.173 | 1.00 | 18.56 | N |
| ATOM | 81 | CA | VAL | X | −86 | −9.186 | 17.651 | −50.099 | 1.00 | 16.70 | C |
| ATOM | 82 | CB | VAL | X | −86 | −9.642 | 19.059 | −49.694 | 1.00 | 18.11 | C |
| ATOM | 83 | CG1 | VAL | X | −86 | −9.037 | 20.079 | −50.638 | 1.00 | 16.18 | C |
| ATOM | 84 | CG2 | VAL | X | −86 | −11.189 | 19.132 | −49.699 | 1.00 | 18.28 | C |
| ATOM | 85 | C | VAL | X | −86 | −7.652 | 17.619 | −50.079 | 1.00 | 16.92 | C |
| ATOM | 86 | O | VAL | X | −86 | −7.035 | 17.897 | −49.061 | 1.00 | 15.94 | O |
| ATOM | 87 | N | PRO | X | −85 | −7.048 | 17.297 | −51.219 | 1.00 | 15.93 | N |
| ATOM | 88 | CA | PRO | X | −85 | −5.585 | 17.359 | −51.269 | 1.00 | 16.25 | C |
| ATOM | 89 | CB | PRO | X | −85 | −5.228 | 16.680 | −52.592 | 1.00 | 16.80 | C |
| ATOM | 90 | CG | PRO | X | −85 | −6.471 | 16.696 | −53.393 | 1.00 | 17.38 | C |
| ATOM | 91 | CD | PRO | X | −85 | −7.657 | 16.883 | −52.491 | 1.00 | 16.40 | C |
| ATOM | 92 | C | PRO | X | −85 | −5.123 | 18.820 | −51.267 | 1.00 | 16.09 | C |
| ATOM | 93 | O | PRO | X | −85 | −5.766 | 19.666 | −51.887 | 1.00 | 15.24 | O |
| ATOM | 94 | N | VAL | X | −84 | −4.023 | 19.096 | −50.570 | 1.00 | 15.70 | N |
| ATOM | 95 | CA | VAL | X | −84 | −3.529 | 20.468 | −50.401 | 1.00 | 15.87 | C |
| ATOM | 96 | CB | VAL | X | −84 | −3.657 | 20.955 | −48.921 | 1.00 | 15.65 | C |
| ATOM | 97 | CG1 | VAL | X | −84 | −5.136 | 21.022 | −48.543 | 1.00 | 16.92 | C |
| ATOM | 98 | CG2 | VAL | X | −84 | −2.925 | 19.987 | −47.953 | 1.00 | 17.26 | C |
| ATOM | 99 | C | VAL | X | −84 | −2.110 | 20.721 | −50.875 | 1.00 | 16.65 | C |
| ATOM | 100 | O | VAL | X | −84 | −1.644 | 21.880 | −50.871 | 1.00 | 16.16 | O |
| ATOM | 101 | N | GLY | X | −83 | −1.419 | 19.654 | −51.259 | 1.00 | 16.37 | N |
| ATOM | 102 | CA | GLY | X | −83 | −0.065 | 19.812 | −51.788 | 1.00 | 17.79 | C |
| ATOM | 103 | C | GLY | X | −83 | 0.336 | 18.600 | −52.609 | 1.00 | 18.02 | C |
| ATOM | 104 | O | GLY | X | −83 | −0.104 | 17.483 | −52.356 | 1.00 | 17.55 | O |
| ATOM | 105 | N | ILE | X | −82 | 1.164 | 18.837 | −53.617 | 1.00 | 19.69 | N |
| ATOM | 106 | CA | ILE | X | −82 | 1.662 | 17.761 | −54.435 | 1.00 | 22.96 | C |
| ATOM | 107 | CB | ILE | X | −82 | 0.679 | 17.448 | −55.608 | 1.00 | 22.30 | C |
| ATOM | 108 | CG1 | ILE | X | −82 | 1.123 | 16.196 | −56.379 | 1.00 | 24.47 | C |
| ATOM | 109 | CD1 | ILE | X | −82 | −0.021 | 15.546 | −57.175 | 1.00 | 23.85 | C |

-continued

| | | | | | | | | | | |
|---|---|---|---|---|---|---|---|---|---|---|
| ATOM | 110 | CG2 | ILE | X | −82 | 0.449 | 18.668 | −56.517 | 1.00 | 23.02 | C |
| ATOM | 111 | C | ILE | X | −82 | 3.066 | 18.143 | −54.903 | 1.00 | 25.62 | C |
| ATOM | 112 | O | ILE | X | −82 | 3.286 | 19.267 | −55.347 | 1.00 | 25.20 | O |
| ATOM | 113 | N | ASP | X | −81 | 4.022 | 17.237 | −54.729 | 1.00 | 28.63 | N |
| ATOM | 114 | CA | AASP | X | −81 | 5.385 | 17.425 | −55.242 | 0.50 | 31.28 | C |
| ATOM | 115 | CA | BASP | X | −81 | 5.342 | 17.420 | −55.348 | 0.50 | 31.17 | C |
| ATOM | 116 | CB | AASP | X | −81 | 6.278 | 18.042 | −54.157 | 0.50 | 31.61 | C |
| ATOM | 117 | CB | BASP | X | −81 | 6.286 | 18.248 | −54.467 | 0.50 | 31.48 | C |
| ATOM | 118 | CG | AASP | X | −81 | 5.967 | 19.519 | −53.897 | 0.50 | 32.96 | C |
| ATOM | 119 | CG | BASP | X | −81 | 6.661 | 17.544 | −53.181 | 0.50 | 32.34 | C |
| ATOM | 120 | OD1 | AASP | X | −81 | 5.447 | 19.828 | −52.806 | 0.50 | 33.87 | O |
| ATOM | 121 | OD1 | BASP | X | −81 | 5.796 | 17.442 | −52.295 | 0.50 | 33.24 | O |
| ATOM | 122 | OD2 | AASP | X | −81 | 6.252 | 20.372 | −54.771 | 0.50 | 34.49 | O |
| ATOM | 123 | OD2 | BASP | X | −81 | 7.828 | 17.108 | −53.047 | 0.50 | 34.10 | O |
| ATOM | 124 | C | ASP | X | −81 | 5.972 | 16.087 | −55.716 | 1.00 | 32.61 | C |
| ATOM | 125 | O | ASP | X | −81 | 5.482 | 15.030 | −55.328 | 1.00 | 32.88 | O |
| ATOM | 126 | N | GLU | X | −80 | 7.022 | 16.130 | −56.537 | 1.00 | 34.59 | N |
| ATOM | 127 | CA | GLU | X | −80 | 7.758 | 14.904 | −56.872 | 1.00 | 37.06 | C |
| ATOM | 128 | CB | GLU | X | −80 | 8.023 | 14.780 | −58.381 | 1.00 | 37.51 | C |
| ATOM | 129 | CG | GLU | X | −80 | 8.704 | 13.460 | −58.783 | 1.00 | 38.37 | C |
| ATOM | 130 | CD | GLU | X | −80 | 8.401 | 13.003 | −60.212 | 1.00 | 41.19 | C |
| ATOM | 131 | OE1 | GLU | X | −80 | 7.710 | 13.725 | −60.969 | 1.00 | 42.82 | O |
| ATOM | 132 | OE2 | GLU | X | −80 | 8.851 | 11.893 | −60.580 | 1.00 | 42.05 | O |
| ATOM | 133 | C | GLU | X | −80 | 9.055 | 14.865 | −56.064 | 1.00 | 38.79 | C |
| ATOM | 134 | O | GLU | X | −80 | 9.813 | 15.840 | −56.065 | 1.00 | 39.64 | O |
| ATOM | 135 | N | GLU | X | −79 | 9.269 | 13.763 | −55.340 | 1.00 | 40.20 | N |
| ATOM | 136 | CA | GLU | X | −79 | 10.506 | 13.515 | −54.587 | 1.00 | 41.35 | C |
| ATOM | 137 | CB | GLU | X | −79 | 10.356 | 13.889 | −53.092 | 1.00 | 41.25 | C |
| ATOM | 138 | CG | GLU | X | −79 | 11.664 | 13.719 | −52.249 | 1.00 | 41.65 | C |
| ATOM | 139 | CD | GLU | X | −79 | 11.522 | 14.059 | −50.746 | 1.00 | 43.56 | C |
| ATOM | 140 | OE1 | GLU | X | −79 | 12.369 | 14.828 | −50.222 | 1.00 | 46.51 | O |
| ATOM | 141 | OE2 | GLU | X | −79 | 10.587 | 13.551 | −50.082 | 1.00 | 45.92 | O |
| ATOM | 142 | C | GLU | X | −79 | 10.928 | 12.048 | −54.736 | 1.00 | 41.17 | C |
| ATOM | 143 | O | GLU | X | −79 | 10.190 | 11.143 | −54.362 | 1.00 | 41.12 | O |
| ATOM | 144 | N | ASN | X | −78 | 12.110 | 11.829 | −55.310 | 1.00 | 42.01 | N |
| ATOM | 145 | CA | ASN | X | −78 | 12.811 | 10.527 | −55.254 | 1.00 | 42.48 | C |
| ATOM | 146 | CB | ASN | X | −78 | 13.357 | 10.279 | −53.826 | 1.00 | 43.17 | C |
| ATOM | 147 | CG | ASN | X | −78 | 14.275 | 11.387 | −53.324 | 1.00 | 45.72 | C |
| ATOM | 148 | OD1 | ASN | X | −78 | 14.337 | 11.644 | −52.115 | 1.00 | 49.35 | O |
| ATOM | 149 | ND2 | ASN | X | −78 | 14.999 | 12.037 | −54.237 | 1.00 | 48.66 | N |
| ATOM | 150 | C | ASN | X | −78 | 12.138 | 9.197 | −55.700 | 1.00 | 41.70 | C |
| ATOM | 151 | O | ASN | X | −78 | 11.981 | 8.305 | −54.858 | 1.00 | 42.84 | O |
| ATOM | 152 | N | GLY | X | −77 | 11.669 | 9.016 | −56.934 | 1.00 | 41.02 | N |
| ATOM | 153 | CA | GLY | X | −77 | 10.886 | 9.941 | −57.731 | 1.00 | 38.78 | C |
| ATOM | 154 | C | GLY | X | −77 | 9.491 | 9.370 | −57.452 | 1.00 | 37.18 | C |
| ATOM | 155 | O | GLY | X | −77 | 8.960 | 8.505 | −58.179 | 1.00 | 36.84 | O |
| ATOM | 156 | N | MET | X | −76 | 8.951 | 9.798 | −56.320 | 1.00 | 35.40 | N |
| ATOM | 157 | CA | MET | X | −76 | 7.616 | 9.457 | −55.879 | 1.00 | 33.50 | C |
| ATOM | 158 | CB | MET | X | −76 | 7.642 | 9.035 | −54.408 | 1.00 | 34.57 | C |
| ATOM | 159 | CG | MET | X | −76 | 7.610 | 7.551 | −54.108 | 1.00 | 37.24 | C |
| ATOM | 160 | SD | MET | X | −76 | 6.102 | 6.698 | −54.616 | 1.00 | 43.74 | S |
| ATOM | 161 | CE | MET | X | −76 | 6.883 | 5.673 | −55.819 | 1.00 | 37.02 | C |
| ATOM | 162 | C | MET | X | −76 | 6.853 | 10.762 | −55.945 | 1.00 | 31.30 | C |
| ATOM | 163 | O | MET | X | −76 | 7.444 | 11.830 | −55.838 | 1.00 | 31.09 | O |
| ATOM | 164 | N | ILE | X | −75 | 5.539 | 10.688 | −56.091 | 1.00 | 28.78 | N |
| ATOM | 165 | CA | ILE | X | −75 | 4.734 | 11.882 | −55.936 | 1.00 | 25.95 | C |
| ATOM | 166 | CB | ILE | X | −75 | 3.520 | 11.876 | −56.889 | 1.00 | 26.45 | C |
| ATOM | 167 | CG1 | ILE | X | −75 | 3.937 | 11.735 | −58.382 | 1.00 | 27.99 | C |
| ATOM | 168 | CD1 | ILE | X | −75 | 4.703 | 12.920 | −58.964 | 1.00 | 29.05 | C |
| ATOM | 169 | CG2 | ILE | X | −75 | 2.614 | 13.069 | −56.601 | 1.00 | 26.21 | C |
| ATOM | 170 | C | ILE | X | −75 | 4.270 | 11.883 | −54.477 | 1.00 | 24.53 | C |
| ATOM | 171 | O | ILE | X | −75 | 3.720 | 10.900 | −54.018 | 1.00 | 23.53 | O |
| ATOM | 172 | N | LYS | X | −74 | 4.518 | 12.973 | −53.758 | 1.00 | 22.03 | N |
| ATOM | 173 | CA | LYS | X | −74 | 4.167 | 13.071 | −52.354 | 1.00 | 20.85 | C |
| ATOM | 174 | CB | LYS | X | −74 | 5.294 | 13.773 | −51.624 | 1.00 | 21.48 | C |
| ATOM | 175 | CG | LYS | X | −74 | 5.554 | 13.320 | −50.257 | 1.00 | 27.11 | C |
| ATOM | 176 | CD | LYS | X | −74 | 7.052 | 13.482 | −49.977 | 1.00 | 30.33 | C |
| ATOM | 177 | CE | LYS | X | −74 | 7.246 | 14.303 | −48.744 | 1.00 | 30.20 | C |
| ATOM | 178 | NZ | LYS | X | −74 | 8.661 | 14.600 | −48.474 | 1.00 | 29.98 | N |
| ATOM | 179 | C | LYS | X | −74 | 2.956 | 13.977 | −52.278 | 1.00 | 19.14 | C |
| ATOM | 180 | O | LYS | X | −74 | 3.019 | 15.101 | −52.749 | 1.00 | 19.50 | O |
| ATOM | 181 | N | VAL | X | −73 | 1.889 | 13.511 | −51.657 | 1.00 | 17.73 | N |
| ATOM | 182 | CA | VAL | X | −73 | 0.636 | 14.272 | −51.621 | 1.00 | 16.63 | C |
| ATOM | 183 | CB | VAL | X | −73 | −0.522 | 13.483 | −52.272 | 1.00 | 16.74 | C |
| ATOM | 184 | CG1 | VAL | X | −73 | −1.726 | 14.399 | −52.407 | 1.00 | 17.22 | C |
| ATOM | 185 | CG2 | VAL | X | −73 | −0.108 | 12.938 | −53.654 | 1.00 | 18.22 | C |
| ATOM | 186 | C | VAL | X | −73 | 0.282 | 14.578 | −50.168 | 1.00 | 16.09 | C |
| ATOM | 187 | O | VAL | X | −73 | 0.424 | 13.727 | −49.291 | 1.00 | 16.47 | O |
| ATOM | 188 | N | SER | X | −72 | −0.149 | 15.803 | −49.909 | 1.00 | 15.44 | N |
| ATOM | 189 | CA | SER | X | −72 | −0.631 | 16.124 | −48.573 | 1.00 | 15.75 | C |

-continued

| ATOM | 190 | CB | SER | X | −72 | 0.198 | 17.268 | −47.991 | 1.00 | 16.08 | C |
|---|---|---|---|---|---|---|---|---|---|---|---|
| ATOM | 191 | OG | SER | X | −72 | 0.300 | 18.303 | −48.957 | 1.00 | 19.58 | O |
| ATOM | 192 | C | SER | X | −72 | −2.123 | 16.434 | −48.652 | 1.00 | 15.97 | C |
| ATOM | 193 | O | SER | X | −72 | −2.638 | 16.836 | −49.726 | 1.00 | 15.46 | O |
| ATOM | 194 | N | PHE | X | −71 | −2.832 | 16.206 | −47.550 | 1.00 | 15.99 | N |
| ATOM | 195 | CA | PHE | X | −71 | −4.297 | 16.349 | −47.532 | 1.00 | 17.41 | C |
| ATOM | 196 | CB | PHE | X | −71 | −5.011 | 15.019 | −47.255 | 1.00 | 18.45 | C |
| ATOM | 197 | CG | PHE | X | −71 | −4.796 | 13.939 | −48.287 | 1.00 | 21.09 | C |
| ATOM | 198 | CD1 | PHE | X | −71 | −4.887 | 14.186 | −49.651 | 1.00 | 24.79 | C |
| ATOM | 199 | CE1 | PHE | X | −71 | −4.679 | 13.149 | −50.594 | 1.00 | 23.98 | C |
| ATOM | 200 | CZ | PHE | X | −71 | −4.443 | 11.865 | −50.149 | 1.00 | 23.54 | C |
| ATOM | 201 | CE2 | PHE | X | −71 | −4.431 | 11.588 | −48.794 | 1.00 | 26.62 | C |
| ATOM | 202 | CD2 | PHE | X | −71 | −4.603 | 12.623 | −47.863 | 1.00 | 25.33 | C |
| ATOM | 203 | C | PHE | X | −71 | −4.676 | 17.290 | −46.400 | 1.00 | 17.10 | C |
| ATOM | 204 | O | PHE | X | −71 | −3.927 | 17.458 | −45.431 | 1.00 | 16.79 | O |
| ATOM | 205 | N | MET | X | −70 | −5.865 | 17.871 | −46.479 | 1.00 | 16.68 | N |
| ATOM | 206 | CA | MET | X | −70 | −6.334 | 18.685 | −45.372 | 1.00 | 18.05 | C |
| ATOM | 207 | CB | MET | X | −70 | −7.719 | 19.256 | −45.694 | 1.00 | 17.48 | C |
| ATOM | 208 | CG | MET | X | −70 | −8.795 | 18.179 | −45.783 | 1.00 | 19.50 | C |
| ATOM | 209 | SD | MET | X | −70 | −10.449 | 18.903 | −46.041 | 1.00 | 22.83 | S |
| ATOM | 210 | CE | MET | X | −70 | −10.800 | 19.642 | −44.469 | 1.00 | 22.89 | C |
| ATOM | 211 | C | MET | X | −70 | −6.389 | 17.911 | −44.041 | 1.00 | 16.49 | C |
| ATOM | 212 | O | MET | X | −70 | −6.645 | 16.697 | −44.024 | 1.00 | 16.56 | O |
| ATOM | 213 | N | LEU | X | −69 | −6.138 | 18.646 | −42.952 | 1.00 | 15.65 | N |
| ATOM | 214 | CA | ALEU | X | −69 | −6.253 | 18.191 | −41.563 | 0.50 | 15.37 | C |
| ATOM | 215 | CA | BLEU | X | −69 | −6.279 | 18.166 | −41.557 | 0.50 | 16.17 | C |
| ATOM | 216 | CB | ALEU | X | −69 | −7.673 | 17.714 | −41.226 | 0.50 | 15.02 | C |
| ATOM | 217 | CB | BLEU | X | −69 | −7.680 | 17.584 | −41.264 | 0.50 | 16.28 | C |
| ATOM | 218 | CG | ALEU | X | −69 | −7.916 | 17.543 | −39.732 | 0.50 | 13.76 | C |
| ATOM | 219 | CG | BLEU | X | −69 | −8.764 | 18.357 | −40.506 | 0.50 | 18.96 | C |
| ATOM | 220 | CD1 | ALEU | X | −69 | −7.829 | 18.889 | −39.001 | 0.50 | 15.17 | C |
| ATOM | 221 | CD1 | BLEU | X | −69 | −9.957 | 17.422 | −40.296 | 0.50 | 18.74 | C |
| ATOM | 222 | CD2 | ALEU | X | −69 | −9.265 | 16.894 | −39.513 | 0.50 | 13.62 | C |
| ATOM | 223 | CD2 | BLEU | X | −69 | −8.281 | 18.910 | −39.168 | 0.50 | 20.64 | C |
| ATOM | 224 | C | LEU | X | −69 | −5.200 | 17.180 | −41.109 | 1.00 | 14.90 | C |
| ATOM | 225 | O | LEU | X | −69 | −4.464 | 17.443 | −40.172 | 1.00 | 15.81 | O |
| ATOM | 226 | N | THR | X | −68 | −5.118 | 16.030 | −41.777 | 1.00 | 15.19 | N |
| ATOM | 227 | CA | THR | X | −68 | −4.073 | 15.090 | −41.456 | 1.00 | 14.88 | C |
| ATOM | 228 | CB | THR | X | −68 | −4.237 | 13.723 | −42.149 | 1.00 | 14.69 | C |
| ATOM | 229 | OG1 | THR | X | −68 | −3.076 | 12.931 | −41.860 | 1.00 | 14.68 | O |
| ATOM | 230 | CG2 | THR | X | −68 | −4.386 | 13.874 | −43.658 | 1.00 | 15.54 | C |
| ATOM | 231 | C | THR | X | −68 | −2.708 | 15.691 | −41.806 | 1.00 | 14.87 | C |
| ATOM | 232 | O | THR | X | −68 | −2.565 | 16.364 | −42.836 | 1.00 | 15.62 | O |
| ATOM | 233 | N | ALA | X | −67 | −1.741 | 15.511 | −40.924 | 1.00 | 14.47 | N |
| ATOM | 234 | CA | ALA | X | −67 | −0.365 | 15.980 | −41.203 | 1.00 | 15.64 | C |
| ATOM | 235 | CB | ALA | X | −67 | 0.351 | 16.325 | −39.891 | 1.00 | 15.70 | C |
| ATOM | 236 | C | ALA | X | −67 | 0.450 | 14.945 | −41.985 | 1.00 | 16.15 | C |
| ATOM | 237 | O | ALA | X | −67 | 1.624 | 15.164 | −42.260 | 1.00 | 18.22 | O |
| ATOM | 238 | N | GLN | X | −66 | −0.140 | 13.805 | −42.319 | 1.00 | 17.36 | N |
| ATOM | 239 | CA | GLN | X | −66 | 0.649 | 12.753 | −42.976 | 1.00 | 17.46 | C |
| ATOM | 240 | CB | GLN | X | −66 | −0.012 | 11.408 | −42.734 | 1.00 | 17.47 | C |
| ATOM | 241 | CG | GLN | X | −66 | −0.144 | 11.117 | −41.246 | 1.00 | 21.02 | C |
| ATOM | 242 | CD | GLN | X | −66 | −1.044 | 9.917 | −41.006 | 1.00 | 27.56 | C |
| ATOM | 243 | OE1 | GLN | X | −66 | −0.555 | 8.867 | −40.660 | 1.00 | 29.26 | O |
| ATOM | 244 | NE2 | GLN | X | −66 | −2.345 | 10.063 | −41.257 | 1.00 | 28.99 | N |
| ATOM | 245 | C | GLN | X | −66 | 0.776 | 12.966 | −44.473 | 1.00 | 17.80 | C |
| ATOM | 246 | O | GLN | X | −66 | −0.151 | 13.459 | −45.124 | 1.00 | 17.91 | O |
| ATOM | 247 | N | PHE | X | −65 | 1.924 | 12.558 | −45.019 | 1.00 | 17.41 | N |
| ATOM | 248 | CA | PHE | X | −65 | 2.089 | 12.443 | −46.456 | 1.00 | 16.64 | C |
| ATOM | 249 | CB | PHE | X | −65 | 3.555 | 12.570 | −46.830 | 1.00 | 17.40 | C |
| ATOM | 250 | CG | PHE | X | −65 | 4.078 | 13.973 | −46.782 | 1.00 | 15.89 | C |
| ATOM | 251 | CD1 | PHE | X | −65 | 5.039 | 14.340 | −45.835 | 1.00 | 18.22 | C |
| ATOM | 252 | CE1 | PHE | X | −65 | 5.549 | 15.636 | −45.809 | 1.00 | 18.44 | C |
| ATOM | 253 | CZ | PHE | X | −65 | 5.107 | 16.576 | −46.719 | 1.00 | 15.26 | C |
| ATOM | 254 | CE2 | PHE | X | −65 | 4.132 | 16.216 | −47.681 | 1.00 | 16.07 | C |
| ATOM | 255 | CD2 | PHE | X | −65 | 3.636 | 14.915 | −47.705 | 1.00 | 15.83 | C |
| ATOM | 256 | C | PHE | X | −65 | 1.642 | 11.094 | −46.960 | 1.00 | 17.64 | C |
| ATOM | 257 | O | PHE | X | −65 | 1.815 | 10.065 | −46.279 | 1.00 | 17.39 | O |
| ATOM | 258 | N | TYR | X | −64 | 1.089 | 11.128 | −48.166 | 1.00 | 18.05 | N |
| ATOM | 259 | CA | TYR | X | −64 | 0.736 | 9.938 | −48.913 | 1.00 | 19.14 | C |
| ATOM | 260 | CB | TYR | X | −64 | −0.767 | 9.935 | −49.146 | 1.00 | 20.45 | C |
| ATOM | 261 | CG | TYR | X | −64 | −1.484 | 9.770 | −47.842 | 1.00 | 22.81 | C |
| ATOM | 262 | CD1 | TYR | X | −64 | −1.727 | 10.876 | −47.014 | 1.00 | 24.05 | C |
| ATOM | 263 | CE1 | TYR | X | −64 | −2.354 | 10.717 | −45.806 | 1.00 | 28.09 | C |
| ATOM | 264 | CZ | TYR | X | −64 | −2.723 | 9.438 | −45.395 | 1.00 | 27.91 | C |
| ATOM | 265 | OH | TYR | X | −64 | −3.334 | 9.262 | −44.184 | 1.00 | 30.01 | O |
| ATOM | 266 | CE2 | TYR | X | −64 | −2.468 | 8.324 | −46.178 | 1.00 | 27.89 | C |
| ATOM | 267 | CD2 | TYR | X | −64 | −1.842 | 8.504 | −47.397 | 1.00 | 27.47 | C |
| ATOM | 268 | C | TYR | X | −64 | 1.507 | 9.965 | −50.213 | 1.00 | 20.03 | C |
| ATOM | 269 | O | TYR | X | −64 | 1.934 | 11.010 | −50.666 | 1.00 | 21.37 | O |

-continued

| | | | | | | | | | |
|---|---|---|---|---|---|---|---|---|---|
| ATOM | 270 | N | GLU | X | −63 | 1.692 | 8.822 | −50.839 | 1.00 | 19.82 | N |
| ATOM | 271 | CA | AGLU | X | −63 | 2.561 | 8.759 | −52.007 | 0.50 | 20.64 | C |
| ATOM | 272 | CA | BGLU | X | −63 | 2.535 | 8.802 | −52.021 | 0.50 | 20.86 | C |
| ATOM | 273 | CB | AGLU | X | −63 | 3.860 | 8.018 | −51.662 | 0.50 | 20.85 | C |
| ATOM | 274 | CB | BGLU | X | −63 | 3.911 | 8.203 | −51.699 | 0.50 | 21.09 | C |
| ATOM | 275 | CG | AGLU | X | −63 | 3.671 | 6.551 | −51.287 | 0.50 | 22.71 | C |
| ATOM | 276 | CG | BGLU | X | −63 | 4.688 | 8.955 | −50.606 | 0.50 | 23.31 | C |
| ATOM | 277 | CD | AGLU | X | −63 | 4.973 | 5.742 | −51.286 | 0.50 | 23.36 | C |
| ATOM | 278 | CD | BGLU | X | −63 | 6.171 | 8.633 | −50.591 | 0.50 | 24.18 | C |
| ATOM | 279 | OE1 | AGLU | X | −63 | 6.002 | 6.250 | −50.791 | 0.50 | 26.77 | O |
| ATOM | 280 | OE1 | BGLU | X | −63 | 6.546 | 7.488 | −50.934 | 0.50 | 28.76 | O |
| ATOM | 281 | OE2 | AGLU | X | −63 | 4.959 | 4.590 | −51.781 | 0.50 | 28.06 | O |
| ATOM | 282 | OE2 | BGLU | X | −63 | 6.960 | 9.532 | −50.236 | 0.50 | 27.71 | O |
| ATOM | 283 | C | GLU | X | −63 | 1.871 | 8.063 | −53.161 | 1.00 | 19.96 | C |
| ATOM | 284 | O | GLU | X | −63 | 1.042 | 7.196 | −52.951 | 1.00 | 20.20 | O |
| ATOM | 285 | N | ILE | X | −62 | 2.242 | 8.416 | −54.377 | 1.00 | 19.55 | N |
| ATOM | 286 | CA | ILE | X | −62 | 1.776 | 7.652 | −55.523 | 1.00 | 20.92 | C |
| ATOM | 287 | CB | ILE | X | −62 | 0.457 | 8.213 | −56.094 | 1.00 | 20.02 | C |
| ATOM | 288 | CG1 | ILE | X | −62 | −0.067 | 7.350 | −57.258 | 1.00 | 21.74 | C |
| ATOM | 289 | CD1 | ILE | X | −62 | −1.457 | 7.767 | −57.733 | 1.00 | 21.58 | C |
| ATOM | 290 | CG2 | ILE | X | −62 | 0.600 | 9.686 | −56.477 | 1.00 | 20.83 | C |
| ATOM | 291 | C | ILE | X | −62 | 2.888 | 7.615 | −56.569 | 1.00 | 21.22 | C |
| ATOM | 292 | O | ILE | X | −62 | 3.557 | 8.635 | −56.783 | 1.00 | 21.14 | O |
| ATOM | 293 | N | LYS | X | −61 | 3.103 | 6.451 | −57.194 | 1.00 | 22.12 | N |
| ATOM | 294 | CA | ALYS | X | −61 | 4.162 | 6.304 | −58.196 | 0.50 | 22.94 | C |
| ATOM | 295 | CA | BLYS | X | −61 | 4.173 | 6.326 | −58.190 | 0.50 | 23.00 | C |
| ATOM | 296 | CB | ALYS | X | −61 | 4.515 | 4.829 | −58.411 | 0.50 | 23.26 | C |
| ATOM | 297 | CB | BLYS | X | −61 | 4.636 | 4.872 | −58.375 | 0.50 | 23.70 | C |
| ATOM | 298 | CG | ALYS | X | −61 | 5.791 | 4.638 | −59.224 | 0.50 | 25.78 | C |
| ATOM | 299 | CG | BLYS | X | −61 | 5.987 | 4.763 | −59.112 | 0.50 | 25.65 | C |
| ATOM | 300 | CD | ALYS | X | −61 | 6.207 | 3.179 | −59.285 | 0.50 | 27.71 | C |
| ATOM | 301 | CD | BLYS | X | −61 | 6.772 | 3.503 | −58.726 | 0.50 | 27.54 | C |
| ATOM | 302 | CE | ALYS | X | −61 | 7.371 | 2.994 | −60.243 | 0.50 | 29.74 | C |
| ATOM | 303 | CE | BLYS | X | −61 | 8.187 | 3.510 | −59.320 | 0.50 | 27.29 | C |
| ATOM | 304 | NZ | ALYS | X | −61 | 7.601 | 1.553 | −60.502 | 0.50 | 31.73 | N |
| ATOM | 305 | NZ | BLYS | X | −61 | 9.086 | 4.558 | −58.731 | 0.50 | 30.24 | N |
| ATOM | 306 | C | LYS | X | −61 | 3.769 | 6.931 | −59.527 | 1.00 | 22.57 | C |
| ATOM | 307 | O | LYS | X | −61 | 2.662 | 6.692 | −60.002 | 1.00 | 21.95 | O |
| ATOM | 308 | N | PRO | X | −60 | 4.666 | 7.757 | −60.122 | 1.00 | 23.55 | N |
| ATOM | 309 | CA | PRO | X | −60 | 4.346 | 8.371 | −61.414 | 1.00 | 24.40 | C |
| ATOM | 310 | CB | PRO | X | −60 | 5.317 | 9.561 | −61.489 | 1.00 | 24.63 | C |
| ATOM | 311 | CG | PRO | X | −60 | 6.504 | 9.104 | −60.735 | 1.00 | 24.40 | C |
| ATOM | 312 | CD | PRO | X | −60 | 5.978 | 8.221 | −59.619 | 1.00 | 24.11 | C |
| ATOM | 313 | C | PRO | X | −60 | 4.553 | 7.400 | −62.570 | 1.00 | 25.23 | C |
| ATOM | 314 | O | PRO | X | −60 | 5.517 | 7.515 | −63.332 | 1.00 | 26.68 | O |
| ATOM | 315 | N | THR | X | −59 | 3.658 | 6.432 | −62.663 | 1.00 | 24.88 | N |
| ATOM | 316 | CA | THR | X | −59 | 3.648 | 5.477 | −63.752 | 1.00 | 25.65 | C |
| ATOM | 317 | CB | THR | X | −59 | 3.270 | 4.105 | −63.226 | 1.00 | 25.60 | C |
| ATOM | 318 | OG1 | THR | X | −59 | 1.990 | 4.191 | −62.579 | 1.00 | 26.32 | O |
| ATOM | 319 | CG2 | THR | X | −59 | 4.303 | 3.641 | −62.222 | 1.00 | 27.41 | C |
| ATOM | 320 | C | THR | X | −59 | 2.591 | 5.888 | −64.769 | 1.00 | 25.63 | C |
| ATOM | 321 | O | THR | X | −59 | 1.715 | 6.708 | −64.455 | 1.00 | 24.72 | O |
| ATOM | 322 | N | LYS | X | −58 | 2.663 | 5.317 | −65.975 | 1.00 | 25.64 | N |
| ATOM | 323 | CA | LYS | X | −58 | 1.647 | 5.568 | −66.990 | 1.00 | 26.49 | C |
| ATOM | 324 | CB | LYS | X | −58 | 1.946 | 4.783 | −68.281 | 1.00 | 26.59 | C |
| ATOM | 325 | CG | LYS | X | −58 | 3.121 | 5.351 | −69.064 | 1.00 | 26.28 | C |
| ATOM | 326 | CD | LYS | X | −58 | 3.440 | 4.517 | −70.298 | 1.00 | 28.51 | C |
| ATOM | 327 | CE | LYS | X | −58 | 4.482 | 5.213 | −71.157 | 1.00 | 31.01 | C |
| ATOM | 328 | NZ | LYS | X | −58 | 4.866 | 4.395 | −72.354 | 1.00 | 36.58 | N |
| ATOM | 329 | C | LYS | X | −58 | 0.277 | 5.198 | −66.447 | 1.00 | 26.21 | C |
| ATOM | 330 | O | LYS | X | −58 | −0.718 | 5.894 | −66.705 | 1.00 | 27.19 | O |
| ATOM | 331 | N | GLU | X | −57 | 0.228 | 4.136 | −65.657 | 1.00 | 25.99 | N |
| ATOM | 332 | CA | AGLU | X | −57 | −1.004 | 3.638 | −65.052 | 0.50 | 26.70 | C |
| ATOM | 333 | CA | BGLU | X | −57 | −1.059 | 3.710 | −65.138 | 0.50 | 26.43 | C |
| ATOM | 334 | CB | AGLU | X | −57 | −0.709 | 2.332 | −64.290 | 0.50 | 26.64 | C |
| ATOM | 335 | CB | BGLU | X | −57 | −1.035 | 2.294 | −64.568 | 0.50 | 27.10 | C |
| ATOM | 336 | CG | AGLU | X | −57 | −0.643 | 2.470 | −62.773 | 0.50 | 27.96 | C |
| ATOM | 337 | CG | BGLU | X | −57 | −2.463 | 1.795 | −64.363 | 0.50 | 27.84 | C |
| ATOM | 338 | CD | AGLU | X | −57 | 0.222 | 1.427 | −62.081 | 0.50 | 28.21 | C |
| ATOM | 339 | CD | BGLU | X | −57 | −2.585 | 0.499 | −63.596 | 0.50 | 31.52 | C |
| ATOM | 340 | OE1 | AGLU | X | −57 | 1.252 | 1.813 | −61.465 | 0.50 | 27.36 | O |
| ATOM | 341 | OE1 | BGLU | X | −57 | −1.789 | 0.269 | −62.655 | 0.50 | 32.65 | O |
| ATOM | 342 | OE2 | AGLU | X | −57 | −0.143 | 0.230 | −62.129 | 0.50 | 29.67 | O |
| ATOM | 343 | OE2 | BGLU | X | −57 | −3.515 | −0.272 | −63.927 | 0.50 | 31.05 | O |
| ATOM | 344 | C | GLU | X | −57 | −1.632 | 4.659 | −64.095 | 1.00 | 26.10 | C |
| ATOM | 345 | O | GLU | X | −57 | −2.850 | 4.705 | −63.921 | 1.00 | 27.07 | O |
| ATOM | 346 | N | ASN | X | −56 | −0.771 | 5.429 | −63.429 | 1.00 | 24.42 | N |
| ATOM | 347 | CA | ASN | X | −56 | −1.244 | 6.377 | −62.424 | 1.00 | 22.73 | C |
| ATOM | 348 | CB | ASN | X | −56 | −0.302 | 6.391 | −61.216 | 1.00 | 23.46 | C |
| ATOM | 349 | CG | ASN | X | −56 | −0.504 | 5.184 | −60.316 | 1.00 | 23.89 | C |

-continued

| | | | | | | | | | | |
|---|---|---|---|---|---|---|---|---|---|---|
| ATOM | 350 | OD1 | ASN | X | −56 | −1.583 | 4.582 | −60.302 | 1.00 | 25.12 | O |
| ATOM | 351 | ND2 | ASN | X | −56 | 0.528 | 4.822 | −59.569 | 1.00 | 25.40 | N |
| ATOM | 352 | C | ASN | X | −56 | −1.431 | 7.789 | −62.943 | 1.00 | 21.59 | C |
| ATOM | 353 | O | ASN | X | −56 | −1.782 | 8.672 | −62.170 | 1.00 | 20.38 | O |
| ATOM | 354 | N | GLU | X | −55 | −1.204 | 7.997 | −64.242 | 1.00 | 20.38 | N |
| ATOM | 355 | CA | GLU | X | −55 | −1.136 | 9.355 | −64.774 | 1.00 | 20.13 | C |
| ATOM | 356 | CB | GLU | X | −55 | −0.697 | 9.360 | −66.244 | 1.00 | 20.34 | C |
| ATOM | 357 | CG | GLU | X | −55 | −0.417 | 10.772 | −66.708 | 1.00 | 22.05 | C |
| ATOM | 358 | CD | GLU | X | −55 | 0.287 | 10.855 | −68.031 | 1.00 | 25.87 | C |
| ATOM | 359 | OE1 | GLU | X | −55 | 0.481 | 9.808 | −68.705 | 1.00 | 25.16 | O |
| ATOM | 360 | OE2 | GLU | X | −55 | 0.626 | 11.990 | −68.383 | 1.00 | 25.68 | O |
| ATOM | 361 | C | GLU | X | −55 | −2.432 | 10.150 | −64.556 | 1.00 | 18.84 | C |
| ATOM | 362 | O | GLU | X | −55 | −2.398 | 11.360 | −64.256 | 1.00 | 18.70 | O |
| ATOM | 363 | N | GLN | X | −54 | −3.571 | 9.470 | −64.688 | 1.00 | 19.13 | N |
| ATOM | 364 | CA | GLN | X | −54 | −4.855 | 10.146 | −64.481 | 1.00 | 18.24 | C |
| ATOM | 365 | CB | GLN | X | −54 | −6.024 | 9.402 | −65.164 | 1.00 | 18.87 | C |
| ATOM | 366 | CG | GLN | X | −54 | −5.872 | 9.332 | −66.677 | 1.00 | 19.52 | C |
| ATOM | 367 | CD | GLN | X | −54 | −5.299 | 10.588 | −67.275 | 1.00 | 17.74 | C |
| ATOM | 368 | OE1 | GLN | X | −54 | −5.805 | 11.697 | −67.036 | 1.00 | 19.06 | O |
| ATOM | 369 | NE2 | GLN | X | −54 | −4.225 | 10.441 | −68.056 | 1.00 | 17.11 | N |
| ATOM | 370 | C | GLN | X | −54 | −5.163 | 10.427 | −63.015 | 1.00 | 18.20 | C |
| ATOM | 371 | O | GLN | X | −54 | −5.627 | 11.515 | −62.690 | 1.00 | 17.73 | O |
| ATOM | 372 | N | TYR | X | −53 | −4.889 | 9.472 | −62.133 | 1.00 | 17.30 | N |
| ATOM | 373 | CA | TYR | X | −53 | −5.027 | 9.707 | −60.682 | 1.00 | 17.69 | C |
| ATOM | 374 | CB | TYR | X | −53 | −4.575 | 8.481 | −59.878 | 1.00 | 18.67 | C |
| ATOM | 375 | CG | TYR | X | −53 | −5.348 | 7.220 | −60.204 | 1.00 | 20.07 | C |
| ATOM | 376 | CD1 | TYR | X | −53 | −6.713 | 7.273 | −60.470 | 1.00 | 22.45 | C |
| ATOM | 377 | CE1 | TYR | X | −53 | −7.435 | 6.104 | −60.778 | 1.00 | 24.69 | C |
| ATOM | 378 | CZ | TYR | X | −53 | −6.785 | 4.889 | −60.776 | 1.00 | 24.21 | C |
| ATOM | 379 | OH | TYR | X | −53 | −7.498 | 3.751 | −61.080 | 1.00 | 25.23 | O |
| ATOM | 380 | CE2 | TYR | X | −53 | −5.430 | 4.800 | −60.502 | 1.00 | 24.67 | C |
| ATOM | 381 | CD2 | TYR | X | −53 | −4.709 | 5.974 | −60.219 | 1.00 | 23.86 | C |
| ATOM | 382 | C | TYR | X | −53 | −4.200 | 10.911 | −60.266 | 1.00 | 16.86 | C |
| ATOM | 383 | O | TYR | X | −53 | −4.641 | 11.760 | −59.485 | 1.00 | 16.11 | O |
| ATOM | 384 | N | ILE | X | −52 | −2.989 | 10.971 | −60.788 | 1.00 | 16.99 | N |
| ATOM | 385 | CA | ILE | X | −52 | −2.086 | 12.086 | −60.452 | 1.00 | 17.22 | C |
| ATOM | 386 | CB | ILE | X | −52 | −0.640 | 11.837 | −60.931 | 1.00 | 17.20 | C |
| ATOM | 387 | CG1 | ILE | X | −52 | −0.041 | 10.661 | −60.138 | 1.00 | 17.03 | C |
| ATOM | 388 | CD1 | ILE | X | −52 | 1.254 | 10.041 | −60.789 | 1.00 | 17.73 | C |
| ATOM | 389 | CG2 | ILE | X | −52 | 0.192 | 13.114 | −60.784 | 1.00 | 18.10 | C |
| ATOM | 390 | C | ILE | X | −52 | −2.642 | 13.398 | −60.968 | 1.00 | 17.01 | C |
| ATOM | 391 | O | ILE | X | −52 | −2.624 | 14.398 | −60.252 | 1.00 | 16.12 | O |
| ATOM | 392 | N | GLY | X | −51 | −3.162 | 13.408 | −62.197 | 1.00 | 17.09 | N |
| ATOM | 393 | CA | GLY | X | −51 | −3.806 | 14.628 | −62.716 | 1.00 | 16.32 | C |
| ATOM | 394 | C | GLY | X | −51 | −5.024 | 15.061 | −61.904 | 1.00 | 17.20 | C |
| ATOM | 395 | O | GLY | X | −51 | −5.186 | 16.238 | −61.612 | 1.00 | 16.35 | O |
| ATOM | 396 | N | MET | X | −50 | −5.869 | 14.108 | −61.525 | 1.00 | 18.21 | N |
| ATOM | 397 | CA | MET | X | −50 | −6.997 | 14.396 | −60.650 | 1.00 | 19.19 | C |
| ATOM | 398 | CB | MET | X | −50 | −7.752 | 13.132 | −60.279 | 1.00 | 19.88 | C |
| ATOM | 399 | CG | MET | X | −50 | −8.290 | 12.386 | −61.459 | 1.00 | 21.48 | C |
| ATOM | 400 | SD | MET | X | −50 | −9.026 | 10.845 | −60.923 | 1.00 | 24.52 | S |
| ATOM | 401 | CE | MET | X | −50 | −10.434 | 11.508 | −60.085 | 1.00 | 24.71 | C |
| ATOM | 402 | C | MET | X | −50 | −6.525 | 15.065 | −59.364 | 1.00 | 18.47 | C |
| ATOM | 403 | O | MET | X | −50 | −7.137 | 16.039 | −58.908 | 1.00 | 18.44 | O |
| ATOM | 404 | N | LEU | X | −49 | −5.450 | 14.526 | −58.787 | 1.00 | 16.47 | N |
| ATOM | 405 | CA | LEU | X | −49 | −4.875 | 15.103 | −57.564 | 1.00 | 16.45 | C |
| ATOM | 406 | CB | LEU | X | −49 | −3.772 | 14.194 | −57.016 | 1.00 | 16.04 | C |
| ATOM | 407 | CG | LEU | X | −49 | −4.348 | 12.888 | −56.429 | 1.00 | 16.84 | C |
| ATOM | 408 | CD1 | LEU | X | −49 | −3.235 | 11.893 | −56.231 | 1.00 | 19.06 | C |
| ATOM | 409 | CD2 | LEU | X | −49 | −5.102 | 13.113 | −55.121 | 1.00 | 19.18 | C |
| ATOM | 410 | C | LEU | X | −49 | −4.339 | 16.506 | −57.782 | 1.00 | 16.06 | C |
| ATOM | 411 | O | LEU | X | −49 | −4.580 | 17.397 | −56.954 | 1.00 | 16.91 | O |
| ATOM | 412 | N | ARG | X | −48 | −3.623 | 16.703 | −58.886 | 1.00 | 16.06 | N |
| ATOM | 413 | CA | AARG | X | −48 | −3.044 | 18.015 | −59.205 | 0.50 | 16.52 | C |
| ATOM | 414 | CA | BARG | X | −48 | −3.036 | 18.012 | −59.188 | 0.50 | 16.76 | C |
| ATOM | 415 | CB | AARG | X | −48 | −2.212 | 17.944 | −60.478 | 0.50 | 16.93 | C |
| ATOM | 416 | CB | BARG | X | −48 | −2.158 | 17.944 | −60.435 | 0.50 | 16.86 | C |
| ATOM | 417 | CG | AARG | X | −48 | −0.946 | 17.176 | −60.293 | 0.50 | 17.97 | C |
| ATOM | 418 | CG | BARG | X | −48 | −1.267 | 19.159 | −60.617 | 0.50 | 17.39 | C |
| ATOM | 419 | CD | AARG | X | −48 | −0.033 | 17.312 | −61.485 | 0.50 | 20.60 | C |
| ATOM | 420 | CD | BARG | X | −48 | −0.302 | 18.995 | −61.789 | 0.50 | 18.44 | C |
| ATOM | 421 | NE | AARG | X | −48 | 1.269 | 16.700 | −61.217 | 0.50 | 22.91 | N |
| ATOM | 422 | NE | BARG | X | −48 | 0.661 | 17.920 | −61.583 | 0.50 | 22.65 | N |
| ATOM | 423 | CZ | AARG | X | −48 | 2.273 | 17.293 | −60.577 | 0.50 | 23.51 | C |
| ATOM | 424 | CZ | BARG | X | −48 | 0.576 | 16.708 | −62.134 | 0.50 | 24.82 | C |
| ATOM | 425 | NH1 | AARG | X | −48 | 2.155 | 18.535 | −60.123 | 0.50 | 22.87 | N |
| ATOM | 426 | NH1 | BARG | X | −48 | −0.433 | 16.394 | −62.946 | 0.50 | 24.09 | N |
| ATOM | 427 | NH2 | AARG | X | −48 | 3.407 | 16.635 | −60.396 | 0.50 | 25.51 | N |
| ATOM | 428 | NH2 | BARG | X | −48 | 1.515 | 15.807 | −61.875 | 0.50 | 27.44 | N |
| ATOM | 429 | C | ARG | X | −48 | −4.129 | 19.073 | −59.346 | 1.00 | 16.95 | C |

-continued

| | | | | | | | | | | |
|---|---|---|---|---|---|---|---|---|---|---|
| ATOM | 430 | O | ARG | X | −48 | −4.010 | 20.183 | −58.822 | 1.00 | 15.28 | O |
| ATOM | 431 | N | GLN | X | −47 | −5.197 | 18.718 | −60.054 | 1.00 | 17.19 | N |
| ATOM | 432 | CA | GLN | X | −47 | −6.302 | 19.654 | −60.249 | 1.00 | 17.94 | C |
| ATOM | 433 | CB | GLN | X | −47 | −7.267 | 19.103 | −61.327 | 1.00 | 19.32 | C |
| ATOM | 434 | CG | GLN | X | −47 | −6.642 | 19.124 | −62.717 | 1.00 | 20.46 | C |
| ATOM | 435 | CD | GLN | X | −47 | −6.328 | 20.535 | −63.168 | 1.00 | 23.39 | C |
| ATOM | 436 | OE1 | GLN | X | −47 | −5.193 | 20.864 | −63.416 | 1.00 | 27.74 | O |
| ATOM | 437 | NE2 | GLN | X | −47 | −7.339 | 21.379 | −63.221 | 1.00 | 24.81 | N |
| ATOM | 438 | C | GLN | X | −47 | −7.049 | 19.939 | −58.954 | 1.00 | 18.21 | C |
| ATOM | 439 | O | GLN | X | −47 | −7.466 | 21.094 | −58.694 | 1.00 | 18.81 | O |
| ATOM | 440 | N | ALA | X | −46 | −7.209 | 18.909 | −58.122 | 1.00 | 16.79 | N |
| ATOM | 441 | CA | ALA | X | −46 | −7.868 | 19.068 | −56.832 | 1.00 | 16.86 | C |
| ATOM | 442 | CB | ALA | X | −46 | −8.197 | 17.699 | −56.209 | 1.00 | 17.32 | C |
| ATOM | 443 | C | ALA | X | −46 | −7.024 | 19.933 | −55.890 | 1.00 | 17.30 | C |
| ATOM | 444 | O | ALA | X | −46 | −7.561 | 20.723 | −55.132 | 1.00 | 17.90 | O |
| ATOM | 445 | N | VAL | X | −45 | −5.702 | 19.783 | −55.929 | 1.00 | 16.89 | N |
| ATOM | 446 | CA | VAL | X | −45 | −4.848 | 20.676 | −55.124 | 1.00 | 17.01 | C |
| ATOM | 447 | CB | VAL | X | −45 | −3.375 | 20.284 | −55.215 | 1.00 | 16.62 | C |
| ATOM | 448 | CG1 | VAL | X | −45 | −2.477 | 21.391 | −54.600 | 1.00 | 17.96 | C |
| ATOM | 449 | CG2 | VAL | X | −45 | −3.148 | 18.963 | −54.514 | 1.00 | 16.03 | C |
| ATOM | 450 | C | VAL | X | −45 | −5.033 | 22.125 | −55.604 | 1.00 | 18.02 | C |
| ATOM | 451 | O | VAL | X | −45 | −5.245 | 23.052 | −54.808 | 1.00 | 18.21 | O |
| ATOM | 452 | N | LYS | X | −44 | −4.976 | 22.314 | −56.915 | 1.00 | 19.32 | N |
| ATOM | 453 | CA | LYS | X | −44 | −5.101 | 23.641 | −57.486 | 1.00 | 21.42 | C |
| ATOM | 454 | CB | LYS | X | −44 | −5.077 | 23.562 | −59.022 | 1.00 | 21.25 | C |
| ATOM | 455 | CG | LYS | X | −44 | −5.089 | 24.914 | −59.695 | 1.00 | 24.93 | C |
| ATOM | 456 | CD | LYS | X | −44 | −4.974 | 24.781 | −61.206 | 1.00 | 30.79 | C |
| ATOM | 457 | CE | LYS | X | −44 | −6.344 | 24.632 | −61.832 | 1.00 | 35.86 | C |
| ATOM | 458 | NZ | LYS | X | −44 | −6.245 | 24.755 | −63.335 | 1.00 | 37.41 | N |
| ATOM | 459 | C | LYS | X | −44 | −6.367 | 24.312 | −57.009 | 1.00 | 22.62 | C |
| ATOM | 460 | O | LYS | X | −44 | −6.330 | 25.450 | −56.521 | 1.00 | 23.81 | O |
| ATOM | 461 | N | ASN | X | −43 | −7.482 | 23.592 | −57.100 | 1.00 | 23.02 | N |
| ATOM | 462 | CA | ASN | X | −43 | −8.787 | 24.161 | −56.855 | 1.00 | 23.99 | C |
| ATOM | 463 | CB | ASN | X | −43 | −9.763 | 23.617 | −57.890 | 1.00 | 25.16 | C |
| ATOM | 464 | CG | ASN | X | −43 | −9.384 | 24.037 | −59.309 | 1.00 | 27.67 | C |
| ATOM | 465 | OD1 | ASN | X | −43 | −8.967 | 25.181 | −59.537 | 1.00 | 30.47 | O |
| ATOM | 466 | ND2 | ASN | X | −43 | −9.487 | 23.107 | −60.255 | 1.00 | 31.42 | N |
| ATOM | 467 | C | ASN | X | −43 | −9.326 | 23.972 | −55.434 | 1.00 | 23.43 | C |
| ATOM | 468 | O | ASN | X | −43 | −10.450 | 24.400 | −55.128 | 1.00 | 23.02 | O |
| ATOM | 469 | N | GLU | X | −42 | −8.521 | 23.344 | −54.566 | 1.00 | 21.76 | N |
| ATOM | 470 | CA | GLU | X | −42 | −8.953 | 22.972 | −53.203 | 1.00 | 21.65 | C |
| ATOM | 471 | CB | GLU | X | −42 | −8.978 | 24.189 | −52.269 | 1.00 | 21.42 | C |
| ATOM | 472 | CG | GLU | X | −42 | −9.175 | 23.843 | −50.802 | 1.00 | 21.51 | C |
| ATOM | 473 | CD | GLU | X | −42 | −9.022 | 25.043 | −49.908 | 1.00 | 22.61 | C |
| ATOM | 474 | OE1 | GLU | X | −42 | −10.000 | 25.809 | −49.764 | 1.00 | 22.09 | O |
| ATOM | 475 | OE2 | GLU | X | −42 | −7.909 | 25.225 | −49.345 | 1.00 | 21.14 | O |
| ATOM | 476 | C | GLU | X | −42 | −10.302 | 22.250 | −53.253 | 1.00 | 21.20 | C |
| ATOM | 477 | O | GLU | X | −42 | −11.300 | 22.646 | −52.617 | 1.00 | 21.64 | O |
| ATOM | 478 | N | SER | X | −41 | −10.324 | 21.169 | −54.022 | 1.00 | 20.53 | N |
| ATOM | 479 | CA | ASER | X | −41 | −11.558 | 20.447 | −54.243 | 0.50 | 20.54 | C |
| ATOM | 480 | CA | BSER | X | −41 | −11.550 | 20.435 | −54.283 | 0.50 | 21.07 | C |
| ATOM | 481 | CB | ASER | X | −41 | −11.983 | 20.544 | −55.712 | 0.50 | 20.69 | C |
| ATOM | 482 | CB | BSER | X | −41 | −11.857 | 20.447 | −55.781 | 0.50 | 21.28 | C |
| ATOM | 483 | OG | ASER | X | −41 | −11.012 | 19.998 | −56.582 | 0.50 | 20.18 | O |
| ATOM | 484 | OG | BSER | X | −41 | −13.187 | 20.021 | −56.029 | 0.50 | 23.98 | O |
| ATOM | 485 | C | SER | X | −41 | −11.398 | 19.009 | −53.776 | 1.00 | 20.83 | C |
| ATOM | 486 | O | SER | X | −41 | −10.272 | 18.495 | −53.729 | 1.00 | 20.59 | O |
| ATOM | 487 | N | PRO | X | −40 | −12.510 | 18.374 | −53.366 | 1.00 | 20.70 | N |
| ATOM | 488 | CA | PRO | X | −40 | −12.372 | 17.026 | −52.818 | 1.00 | 20.46 | C |
| ATOM | 489 | CB | PRO | X | −40 | −13.644 | 16.849 | −51.972 | 1.00 | 21.20 | C |
| ATOM | 490 | CG | PRO | X | −40 | −14.654 | 17.742 | −52.635 | 1.00 | 20.47 | C |
| ATOM | 491 | CD | PRO | X | −40 | −13.904 | 18.873 | −53.262 | 1.00 | 21.50 | C |
| ATOM | 492 | C | PRO | X | −40 | −12.241 | 15.907 | −53.853 | 1.00 | 20.46 | C |
| ATOM | 493 | O | PRO | X | −40 | −12.620 | 16.075 | −55.020 | 1.00 | 21.17 | O |
| ATOM | 494 | N | VAL | X | −39 | −11.647 | 14.801 | −53.408 | 1.00 | 20.40 | N |
| ATOM | 495 | CA | VAL | X | −39 | −11.566 | 13.552 | −54.158 | 1.00 | 21.51 | C |
| ATOM | 496 | CB | VAL | X | −39 | −10.195 | 13.331 | −54.838 | 1.00 | 21.18 | C |
| ATOM | 497 | CG1 | VAL | X | −39 | −9.954 | 14.353 | −55.920 | 1.00 | 22.84 | C |
| ATOM | 498 | CG2 | VAL | X | −39 | −9.085 | 13.382 | −53.786 | 1.00 | 21.84 | C |
| ATOM | 499 | C | VAL | X | −39 | −11.791 | 12.428 | −53.167 | 1.00 | 21.39 | C |
| ATOM | 500 | O | VAL | X | −39 | −11.793 | 12.644 | −51.961 | 1.00 | 21.40 | O |
| ATOM | 501 | N | HIS | X | −38 | −11.993 | 11.229 | −53.697 | 1.00 | 21.93 | N |
| ATOM | 502 | CA | HIS | X | −38 | −12.109 | 10.041 | −52.891 | 1.00 | 23.32 | C |
| ATOM | 503 | CB | HIS | X | −38 | −13.269 | 9.196 | −53.393 | 1.00 | 23.99 | C |
| ATOM | 504 | CG | HIS | X | −38 | −13.657 | 8.103 | −52.449 | 1.00 | 26.91 | C |
| ATOM | 505 | ND1 | HIS | X | −38 | −14.883 | 7.481 | −52.502 | 1.00 | 31.61 | N |
| ATOM | 506 | CE1 | HIS | X | −38 | −14.954 | 6.568 | −51.549 | 1.00 | 31.82 | C |
| ATOM | 507 | NE2 | HIS | X | −38 | −13.830 | 6.598 | −50.857 | 1.00 | 32.26 | N |
| ATOM | 508 | CD2 | HIS | X | −38 | −12.997 | 7.544 | −51.404 | 1.00 | 30.43 | C |
| ATOM | 509 | C | HIS | X | −38 | −10.830 | 9.225 | −53.032 | 1.00 | 22.50 | C |

-continued

| | | | | | | | | | | |
|---|---|---|---|---|---|---|---|---|---|---|
| ATOM | 510 | O | HIS | X | −38 | −10.457 | 8.858 | −54.148 | 1.00 | 23.16 | O |
| ATOM | 511 | N | ILE | X | −37 | −10.189 | 8.941 | −51.903 | 1.00 | 22.43 | N |
| ATOM | 512 | CA | ILE | X | −37 | −8.887 | 8.270 | −51.889 | 1.00 | 22.65 | C |
| ATOM | 513 | CB | ILE | X | −37 | −7.924 | 8.977 | −50.914 | 1.00 | 22.32 | C |
| ATOM | 514 | CG1 | ILE | X | −37 | −7.634 | 10.407 | −51.390 | 1.00 | 19.84 | C |
| ATOM | 515 | CD1 | ILE | X | −37 | −6.964 | 10.516 | −52.779 | 1.00 | 21.74 | C |
| ATOM | 516 | CG2 | ILE | X | −37 | −6.626 | 8.170 | −50.693 | 1.00 | 20.69 | C |
| ATOM | 517 | C | ILE | X | −37 | −8.997 | 6.796 | −51.493 | 1.00 | 23.88 | C |
| ATOM | 518 | O | ILE | X | −37 | −9.589 | 6.479 | −50.474 | 1.00 | 24.45 | O |
| ATOM | 519 | N | PHE | X | −36 | −8.374 | 5.919 | −52.289 | 1.00 | 24.63 | N |
| ATOM | 520 | CA | PHE | X | −36 | −8.209 | 4.507 | −51.914 | 1.00 | 25.58 | C |
| ATOM | 521 | CB | PHE | X | −36 | −8.860 | 3.595 | −52.949 | 1.00 | 26.96 | C |
| ATOM | 522 | CG | PHE | X | −36 | −10.329 | 3.797 | −53.074 | 1.00 | 29.92 | C |
| ATOM | 523 | CD1 | PHE | X | −36 | −11.214 | 3.005 | −52.339 | 1.00 | 32.18 | C |
| ATOM | 524 | CE1 | PHE | X | −36 | −12.588 | 3.200 | −52.451 | 1.00 | 33.14 | C |
| ATOM | 525 | CZ | PHE | X | −36 | −13.075 | 4.200 | −53.287 | 1.00 | 32.73 | C |
| ATOM | 526 | CE2 | PHE | X | −36 | −12.197 | 5.001 | −54.016 | 1.00 | 32.82 | C |
| ATOM | 527 | CD2 | PHE | X | −36 | −10.834 | 4.796 | −53.909 | 1.00 | 30.13 | C |
| ATOM | 528 | C | PHE | X | −36 | −6.732 | 4.205 | −51.792 | 1.00 | 25.15 | C |
| ATOM | 529 | O | PHE | X | −36 | −5.944 | 4.595 | −52.655 | 1.00 | 24.99 | O |
| ATOM | 530 | N | LEU | X | −35 | −6.361 | 3.557 | −50.696 | 1.00 | 24.09 | N |
| ATOM | 531 | CA | LEU | X | −35 | −4.965 | 3.317 | −50.369 | 1.00 | 23.60 | C |
| ATOM | 532 | CB | LEU | X | −35 | −4.719 | 3.686 | −48.908 | 1.00 | 23.86 | C |
| ATOM | 533 | CG | LEU | X | −35 | −4.862 | 5.158 | −48.516 | 1.00 | 21.91 | C |
| ATOM | 534 | CD1 | LEU | X | −35 | −4.503 | 5.262 | −47.057 | 1.00 | 23.63 | C |
| ATOM | 535 | CD2 | LEU | X | −35 | −3.928 | 6.024 | −49.377 | 1.00 | 22.02 | C |
| ATOM | 536 | C | LEU | X | −35 | −4.613 | 1.852 | −50.564 | 1.00 | 24.33 | C |
| ATOM | 537 | O | LEU | X | −35 | −5.470 | 0.984 | −50.367 | 1.00 | 24.95 | O |
| ATOM | 538 | N | LYS | X | −34 | −3.377 | 1.571 | −50.974 | 1.00 | 25.23 | N |
| ATOM | 539 | CA | LYS | X | −34 | −2.893 | 0.184 | −50.889 | 1.00 | 26.37 | C |
| ATOM | 540 | CB | LYS | X | −34 | −1.514 | 0.047 | −51.523 | 1.00 | 25.87 | C |
| ATOM | 541 | CG | LYS | X | −34 | −1.571 | 0.303 | −53.017 | 1.00 | 28.54 | C |
| ATOM | 542 | CD | LYS | X | −34 | −0.235 | 0.106 | −53.703 | 1.00 | 32.40 | C |
| ATOM | 543 | CE | LYS | X | −34 | −0.354 | 0.467 | −55.185 | 1.00 | 35.20 | C |
| ATOM | 544 | NZ | LYS | X | −34 | 0.819 | −0.025 | −55.990 | 1.00 | 38.42 | N |
| ATOM | 545 | C | LYS | X | −34 | −2.870 | −0.190 | −49.415 | 1.00 | 26.92 | C |
| ATOM | 546 | O | LYS | X | −34 | −2.417 | 0.587 | −48.585 | 1.00 | 26.68 | O |
| ATOM | 547 | N | PRO | X | −33 | −3.397 | −1.380 | −49.073 | 1.00 | 28.47 | N |
| ATOM | 548 | CA | PRO | X | −33 | −3.527 | −1.742 | −47.664 | 1.00 | 28.87 | C |
| ATOM | 549 | CB | PRO | X | −33 | −4.056 | −3.186 | −47.726 | 1.00 | 29.50 | C |
| ATOM | 550 | CG | PRO | X | −33 | −4.759 | −3.262 | −49.009 | 1.00 | 29.50 | C |
| ATOM | 551 | CD | PRO | X | −33 | −3.933 | −2.428 | −49.960 | 1.00 | 28.90 | C |
| ATOM | 552 | C | PRO | X | −33 | −2.211 | −1.671 | −46.891 | 1.00 | 29.27 | C |
| ATOM | 553 | O | PRO | X | −33 | −1.136 | −1.950 | −47.450 | 1.00 | 28.50 | O |
| ATOM | 554 | N | ASN | X | −32 | −2.310 | −1.261 | −45.623 | 1.00 | 29.55 | N |
| ATOM | 555 | CA | ASN | X | −32 | −1.158 | −1.198 | −44.722 | 1.00 | 29.90 | C |
| ATOM | 556 | CB | ASN | X | −32 | −0.616 | −2.618 | −44.480 | 1.00 | 30.74 | C |
| ATOM | 557 | CG | ASN | X | −32 | −1.729 | −3.597 | −44.165 | 1.00 | 31.10 | C |
| ATOM | 558 | OD1 | ASN | X | −32 | −2.462 | −3.413 | −43.195 | 1.00 | 33.03 | O |
| ATOM | 559 | ND2 | ASN | X | −32 | −1.905 | −4.602 | −45.017 | 1.00 | 30.36 | N |
| ATOM | 560 | C | ASN | X | −32 | −0.078 | −0.267 | −45.244 | 1.00 | 29.56 | C |
| ATOM | 561 | O | ASN | X | −32 | 1.123 | −0.545 | −45.117 | 1.00 | 30.93 | O |
| ATOM | 562 | N | SER | X | −31 | −0.509 | 0.841 | −45.846 | 1.00 | 27.42 | N |
| ATOM | 563 | CA | SER | X | −31 | 0.436 | 1.787 | −46.430 | 1.00 | 26.42 | C |
| ATOM | 564 | CB | SER | X | −31 | 0.837 | 1.347 | −47.836 | 1.00 | 26.12 | C |
| ATOM | 565 | OG | SER | X | −31 | −0.143 | 1.761 | −48.770 | 1.00 | 24.67 | O |
| ATOM | 566 | C | SER | X | −31 | −0.152 | 3.180 | −46.533 | 1.00 | 25.38 | C |
| ATOM | 567 | O | SER | X | −31 | −1.376 | 3.359 | −46.439 | 1.00 | 24.06 | O |
| ATOM | 568 | N | ASN | X | −30 | 0.748 | 4.130 | −46.800 | 1.00 | 24.55 | N |
| ATOM | 569 | CA | ASN | X | −30 | 0.420 | 5.499 | −47.196 | 1.00 | 24.76 | C |
| ATOM | 570 | CB | ASN | X | −30 | 1.391 | 6.504 | −46.528 | 1.00 | 24.41 | C |
| ATOM | 571 | CG | ASN | X | −30 | 2.781 | 6.575 | −47.207 | 1.00 | 27.19 | C |
| ATOM | 572 | OD1 | ASN | X | −30 | 3.292 | 5.592 | −47.748 | 1.00 | 28.11 | O |
| ATOM | 573 | ND2 | ASN | X | −30 | 3.388 | 7.776 | −47.187 | 1.00 | 26.95 | N |
| ATOM | 574 | C | ASN | X | −30 | 0.423 | 5.678 | −48.720 | 1.00 | 23.54 | C |
| ATOM | 575 | O | ASN | X | −30 | 0.482 | 6.809 | −49.224 | 1.00 | 23.46 | O |
| ATOM | 576 | N | GLU | X | −29 | 0.382 | 4.568 | −49.452 | 1.00 | 22.78 | N |
| ATOM | 577 | CA | GLU | X | −29 | 0.424 | 4.637 | −50.914 | 1.00 | 21.87 | C |
| ATOM | 578 | CB | GLU | X | −29 | 1.210 | 3.460 | −51.489 | 1.00 | 22.21 | C |
| ATOM | 579 | CG | GLU | X | −29 | 1.502 | 3.625 | −52.953 | 1.00 | 23.54 | C |
| ATOM | 580 | CD | GLU | X | −29 | 2.298 | 2.478 | −53.545 | 1.00 | 28.81 | C |
| ATOM | 581 | OE1 | GLU | X | −29 | 2.831 | 1.658 | −52.776 | 1.00 | 27.98 | O |
| ATOM | 582 | OE2 | GLU | X | −29 | 2.372 | 2.399 | −54.783 | 1.00 | 29.57 | O |
| ATOM | 583 | C | GLU | X | −29 | −0.968 | 4.694 | −51.518 | 1.00 | 21.32 | C |
| ATOM | 584 | O | GLU | X | −29 | −1.838 | 3.867 | −51.215 | 1.00 | 22.17 | O |
| ATOM | 585 | N | ILE | X | −28 | −1.191 | 5.685 | −52.371 | 1.00 | 20.00 | N |
| ATOM | 586 | CA | ILE | X | −28 | −2.464 | 5.823 | −53.043 | 1.00 | 19.65 | C |
| ATOM | 587 | CB | ILE | X | −28 | −2.635 | 7.255 | −53.570 | 1.00 | 18.67 | C |
| ATOM | 588 | CG1 | ILE | X | −28 | −2.505 | 8.239 | −52.405 | 1.00 | 19.41 | C |
| ATOM | 589 | CD1 | ILE | X | −28 | −2.428 | 9.697 | −52.854 | 1.00 | 19.23 | C |

-continued

| | | | | | | | | | | |
|---|---|---|---|---|---|---|---|---|---|---|
| ATOM | 590 | CG2 | ILE | X | −28 | −3.981 | 7.436 | −54.323 | 1.00 | 19.75 | C |
| ATOM | 591 | C | ILE | X | −28 | −2.568 | 4.813 | −54.190 | 1.00 | 20.33 | C |
| ATOM | 592 | O | ILE | X | −28 | −1.719 | 4.790 | −55.089 | 1.00 | 19.86 | O |
| ATOM | 593 | N | GLY | X | −27 | −3.633 | 4.007 | −54.162 | 1.00 | 21.28 | N |
| ATOM | 594 | CA | GLY | X | −27 | −3.910 | 3.027 | −55.233 | 1.00 | 22.13 | C |
| ATOM | 595 | C | GLY | X | −27 | −4.899 | 3.470 | −56.297 | 1.00 | 22.80 | C |
| ATOM | 596 | O | GLY | X | −27 | −4.798 | 3.076 | −57.470 | 1.00 | 23.36 | O |
| ATOM | 597 | N | LYS | X | −26 | −5.849 | 4.316 | −55.889 | 1.00 | 23.19 | N |
| ATOM | 598 | CA | ALYS | X | −26 | −6.920 | 4.792 | −56.748 | 0.50 | 23.09 | C |
| ATOM | 599 | CA | BLYS | X | −26 | −6.836 | 4.849 | −56.812 | 0.50 | 23.08 | C |
| ATOM | 600 | CB | ALYS | X | −26 | −8.095 | 3.809 | −56.663 | 0.50 | 23.61 | C |
| ATOM | 601 | CB | BLYS | X | −26 | −7.970 | 3.832 | −57.078 | 0.50 | 23.57 | C |
| ATOM | 602 | CG | ALYS | X | −26 | −9.275 | 4.143 | −57.530 | 0.50 | 24.88 | C |
| ATOM | 603 | CG | BLYS | X | −26 | −8.863 | 4.158 | −58.276 | 0.50 | 24.00 | C |
| ATOM | 604 | CD | ALYS | X | −26 | −10.226 | 2.965 | −57.608 | 0.50 | 24.94 | C |
| ATOM | 605 | CD | BLYS | X | −26 | −9.766 | 2.980 | −58.702 | 0.50 | 23.72 | C |
| ATOM | 606 | CE | ALYS | X | −26 | −11.050 | 3.014 | −58.878 | 0.50 | 27.81 | C |
| ATOM | 607 | CE | BLYS | X | −26 | −10.678 | 3.338 | −59.897 | 0.50 | 25.09 | C |
| ATOM | 608 | NZ | ALYS | X | −26 | −11.836 | 1.757 | −59.053 | 0.50 | 28.24 | N |
| ATOM | 609 | NZ | BLYS | X | −26 | −9.985 | 3.588 | −61.226 | 0.50 | 26.03 | N |
| ATOM | 610 | C | LYS | X | −26 | −7.380 | 6.166 | −56.267 | 1.00 | 22.48 | C |
| ATOM | 611 | O | LYS | X | −26 | −7.378 | 6.407 | −55.068 | 1.00 | 22.05 | O |
| ATOM | 612 | N | VAL | X | −25 | −7.788 | 7.030 | −57.191 | 1.00 | 22.89 | N |
| ATOM | 613 | CA | VAL | X | −25 | −8.447 | 8.306 | −56.851 | 1.00 | 23.29 | C |
| ATOM | 614 | CB | VAL | X | −25 | −7.566 | 9.518 | −57.170 | 1.00 | 23.33 | C |
| ATOM | 615 | CG1 | VAL | X | −25 | −8.299 | 10.842 | −56.871 | 1.00 | 22.55 | C |
| ATOM | 616 | CG2 | VAL | X | −25 | −6.263 | 9.438 | −56.369 | 1.00 | 22.25 | C |
| ATOM | 617 | C | VAL | X | −25 | −9.736 | 8.364 | −57.662 | 1.00 | 25.02 | C |
| ATOM | 618 | O | VAL | X | −25 | −9.727 | 8.128 | −58.873 | 1.00 | 24.45 | O |
| ATOM | 619 | N | GLU | X | −24 | −10.847 | 8.637 | −56.980 | 1.00 | 27.00 | N |
| ATOM | 620 | CA | GLU | X | −24 | −12.134 | 8.807 | −57.660 | 1.00 | 29.52 | C |
| ATOM | 621 | CB | GLU | X | −24 | −13.154 | 7.763 | −57.157 | 1.00 | 29.38 | C |
| ATOM | 622 | CG | GLU | X | −24 | −12.802 | 6.319 | −57.531 | 1.00 | 32.35 | C |
| ATOM | 623 | CD | GLU | X | −24 | −13.680 | 5.276 | −56.843 | 1.00 | 33.32 | C |
| ATOM | 624 | OE1 | GLU | X | −24 | −14.653 | 5.652 | −56.147 | 1.00 | 37.37 | O |
| ATOM | 625 | OE2 | GLU | X | −24 | −13.377 | 4.060 | −56.980 | 1.00 | 39.76 | O |
| ATOM | 626 | C | GLU | X | −24 | −12.663 | 10.228 | −57.451 | 1.00 | 30.15 | C |
| ATOM | 627 | O | GLU | X | −24 | −12.294 | 10.905 | −56.493 | 1.00 | 30.01 | O |
| ATOM | 628 | N | SER | X | −23 | −13.538 | 10.660 | −58.356 | 1.00 | 31.54 | N |
| ATOM | 629 | CA | ASER | X | −23 | −14.164 | 11.983 | −58.281 | 0.40 | 32.14 | C |
| ATOM | 630 | CA | BSER | X | −23 | −14.165 | 11.981 | −58.278 | 0.60 | 32.20 | C |
| ATOM | 631 | CB | ASER | X | −23 | −14.998 | 12.250 | −59.535 | 0.40 | 32.08 | C |
| ATOM | 632 | CB | BSER | X | −23 | −15.012 | 12.210 | −59.521 | 0.60 | 32.15 | C |
| ATOM | 633 | OG | ASER | X | −23 | −14.429 | 11.642 | −60.681 | 0.40 | 32.31 | O |
| ATOM | 634 | OG | BSER | X | −23 | −16.064 | 11.262 | −59.557 | 0.60 | 32.75 | O |
| ATOM | 635 | C | SER | X | −23 | −15.055 | 12.101 | −57.049 | 1.00 | 32.53 | C |
| ATOM | 636 | O | SER | X | −23 | −15.593 | 11.102 | −56.556 | 1.00 | 33.17 | O |
| ATOM | 637 | N | ALA | X | −22 | −15.216 | 13.323 | −56.554 | 1.00 | 33.23 | N |
| ATOM | 638 | CA | ALA | X | −22 | −16.139 | 13.579 | −55.449 | 1.00 | 34.12 | C |
| ATOM | 639 | CB | ALA | X | −22 | −15.633 | 14.719 | −54.587 | 1.00 | 34.37 | C |
| ATOM | 640 | C | ALA | X | −22 | −17.509 | 13.920 | −56.031 | 1.00 | 34.27 | C |
| ATOM | 641 | O | ALA | X | −22 | −17.602 | 14.403 | −57.159 | 1.00 | 34.28 | O |
| ATOM | 642 | N | SER | X | −21 | −18.563 | 13.676 | −55.259 | 1.00 | 34.97 | N |
| ATOM | 643 | CA | SER | X | −21 | −19.910 | 14.008 | −55.705 | 1.00 | 35.01 | C |
| ATOM | 644 | CB | SER | X | −21 | −20.930 | 13.215 | −54.899 | 1.00 | 35.01 | C |
| ATOM | 645 | OG | SER | X | −21 | −20.990 | 13.666 | −53.559 | 1.00 | 36.32 | O |
| ATOM | 646 | C | SER | X | −21 | −20.190 | 15.519 | −55.585 | 1.00 | 35.15 | C |
| ATOM | 647 | O | SER | X | −21 | −19.438 | 16.251 | −54.917 | 1.00 | 35.31 | O |
| ATOM | 648 | N | PRO | X | −20 | −21.278 | 16.001 | −56.223 | 1.00 | 34.78 | N |
| ATOM | 649 | CA | PRO | X | −20 | −21.633 | 17.404 | −55.995 | 1.00 | 34.14 | C |
| ATOM | 650 | CB | PRO | X | −20 | −22.894 | 17.605 | −56.860 | 1.00 | 34.43 | C |
| ATOM | 651 | CG | PRO | X | −20 | −22.834 | 16.501 | −57.884 | 1.00 | 34.61 | C |
| ATOM | 652 | CD | PRO | X | −20 | −22.215 | 15.338 | −57.157 | 1.00 | 34.86 | C |
| ATOM | 653 | C | PRO | X | −20 | −21.939 | 17.635 | −54.517 | 1.00 | 33.77 | C |
| ATOM | 654 | O | PRO | X | −20 | −21.626 | 18.712 | −53.985 | 1.00 | 33.95 | O |
| ATOM | 655 | N | GLU | X | −19 | −22.510 | 16.629 | −53.860 | 1.00 | 33.20 | N |
| ATOM | 656 | CA | GLU | X | −19 | −22.800 | 16.698 | −52.427 | 1.00 | 33.92 | C |
| ATOM | 657 | CB | GLU | X | −19 | −23.556 | 15.456 | −51.939 | 1.00 | 34.52 | C |
| ATOM | 658 | CG | GLU | X | −19 | −25.002 | 15.348 | −52.456 | 1.00 | 38.68 | C |
| ATOM | 659 | CD | GLU | X | −19 | −25.116 | 14.699 | −53.839 | 1.00 | 44.12 | C |
| ATOM | 660 | OE1 | GLU | X | −19 | −26.270 | 14.477 | −54.286 | 1.00 | 46.40 | O |
| ATOM | 661 | OE2 | GLU | X | −19 | −24.069 | 14.409 | −54.482 | 1.00 | 45.98 | O |
| ATOM | 662 | C | GLU | X | −19 | −21.503 | 16.861 | −51.629 | 1.00 | 32.90 | C |
| ATOM | 663 | O | GLU | X | −19 | −21.440 | 17.653 | −50.686 | 1.00 | 32.90 | O |
| ATOM | 664 | N | ASP | X | −18 | −20.484 | 16.093 | −52.017 | 1.00 | 31.62 | N |
| ATOM | 665 | CA | ASP | X | −18 | −19.150 | 16.219 | −51.433 | 1.00 | 30.57 | C |
| ATOM | 666 | CB | ASP | X | −18 | −18.180 | 15.221 | −52.073 | 1.00 | 30.51 | C |
| ATOM | 667 | CG | ASP | X | −18 | −18.556 | 13.774 | −51.810 | 1.00 | 31.78 | C |
| ATOM | 668 | OD1 | ASP | X | −18 | −19.223 | 13.478 | −50.792 | 1.00 | 34.74 | O |
| ATOM | 669 | OD2 | ASP | X | −18 | −18.162 | 12.925 | −52.631 | 1.00 | 34.52 | O |

-continued

| | | | | | | | | | | |
|---|---|---|---|---|---|---|---|---|---|---|
| ATOM | 670 | C | ASP | X | −18 | −18.584 | 17.625 | −51.613 | 1.00 | 29.39 | C |
| ATOM | 671 | O | ASP | X | −18 | −18.085 | 18.225 | −50.654 | 1.00 | 29.00 | O |
| ATOM | 672 | N | VAL | X | −17 | −18.657 | 18.131 | −52.840 | 1.00 | 28.40 | N |
| ATOM | 673 | CA | VAL | X | −17 | −18.122 | 19.451 | −53.167 | 1.00 | 29.17 | C |
| ATOM | 674 | CB | VAL | X | −17 | −18.283 | 19.781 | −54.673 | 1.00 | 29.41 | C |
| ATOM | 675 | CG1 | VAL | X | −17 | −17.915 | 21.251 | −54.969 | 1.00 | 30.08 | C |
| ATOM | 676 | CG2 | VAL | X | −17 | −17.436 | 18.824 | −55.523 | 1.00 | 30.03 | C |
| ATOM | 677 | C | VAL | X | −17 | −18.772 | 20.521 | −52.287 | 1.00 | 28.87 | C |
| ATOM | 678 | O | VAL | X | −17 | −18.081 | 21.362 | −51.708 | 1.00 | 27.04 | O |
| ATOM | 679 | N | ARG | X | −16 | −20.098 | 20.457 | −52.177 | 1.00 | 29.24 | N |
| ATOM | 680 | CA | ARG | X | −16 | −20.849 | 21.376 | −51.325 | 1.00 | 29.97 | C |
| ATOM | 681 | CB | ARG | X | −16 | −22.355 | 21.081 | −51.438 | 1.00 | 30.14 | C |
| ATOM | 682 | CG | ARG | X | −16 | −23.266 | 22.273 | −51.142 | 1.00 | 31.83 | C |
| ATOM | 683 | CD | ARG | X | −16 | −24.754 | 21.831 | −51.056 | 1.00 | 33.54 | C |
| ATOM | 684 | NE | ARG | X | −16 | −25.175 | 21.132 | −52.263 | 1.00 | 40.54 | N |
| ATOM | 685 | CZ | ARG | X | −16 | −25.567 | 19.858 | −52.317 | 1.00 | 42.39 | C |
| ATOM | 686 | NH1 | ARG | X | −16 | −25.638 | 19.104 | −51.215 | 1.00 | 41.60 | N |
| ATOM | 687 | NH2 | ARG | X | −16 | −25.900 | 19.339 | −53.493 | 1.00 | 44.12 | N |
| ATOM | 688 | C | ARG | X | −16 | −20.394 | 21.244 | −49.879 | 1.00 | 28.81 | C |
| ATOM | 689 | O | ARG | X | −16 | −20.098 | 22.247 | −49.206 | 1.00 | 28.27 | O |
| ATOM | 690 | N | TYR | X | −15 | −20.338 | 20.002 | −49.403 | 1.00 | 27.65 | N |
| ATOM | 691 | CA | TYR | X | −15 | −19.957 | 19.729 | −48.036 | 1.00 | 27.55 | C |
| ATOM | 692 | CB | TYR | X | −15 | −19.991 | 18.226 | −47.751 | 1.00 | 28.41 | C |
| ATOM | 693 | CG | TYR | X | −15 | −19.475 | 17.941 | −46.372 | 1.00 | 29.45 | C |
| ATOM | 694 | CD1 | TYR | X | −15 | −20.218 | 18.241 | −45.242 | 1.00 | 30.48 | C |
| ATOM | 695 | CE1 | TYR | X | −15 | −19.740 | 17.978 | −43.974 | 1.00 | 31.43 | C |
| ATOM | 696 | CZ | TYR | X | −15 | −18.500 | 17.393 | −43.823 | 1.00 | 31.13 | C |
| ATOM | 697 | OH | TYR | X | −15 | −18.036 | 17.131 | −42.557 | 1.00 | 31.35 | O |
| ATOM | 698 | CE2 | TYR | X | −15 | −17.738 | 17.062 | −44.929 | 1.00 | 30.57 | C |
| ATOM | 699 | CD2 | TYR | X | −15 | −18.223 | 17.327 | −46.191 | 1.00 | 29.51 | C |
| ATOM | 700 | C | TYR | X | −15 | −18.575 | 20.297 | −47.659 | 1.00 | 26.62 | C |
| ATOM | 701 | O | TYR | X | −15 | −18.436 | 20.959 | −46.625 | 1.00 | 25.69 | O |
| ATOM | 702 | N | PHE | X | −14 | −17.566 | 19.999 | −48.480 | 1.00 | 26.24 | N |
| ATOM | 703 | CA | PHE | X | −14 | −16.198 | 20.478 | −48.224 | 1.00 | 25.75 | C |
| ATOM | 704 | CB | PHE | X | −14 | −15.165 | 19.755 | −49.107 | 1.00 | 25.52 | C |
| ATOM | 705 | CG | PHE | X | −14 | −14.838 | 18.384 | −48.593 | 1.00 | 23.76 | C |
| ATOM | 706 | CD1 | PHE | X | −14 | −15.522 | 17.263 | −49.062 | 1.00 | 24.67 | C |
| ATOM | 707 | CE1 | PHE | X | −14 | −15.239 | 15.992 | −48.551 | 1.00 | 24.22 | C |
| ATOM | 708 | CZ | PHE | X | −14 | −14.287 | 15.841 | −47.558 | 1.00 | 23.78 | C |
| ATOM | 709 | CE2 | PHE | X | −14 | −13.609 | 16.950 | −47.074 | 1.00 | 23.90 | C |
| ATOM | 710 | CD2 | PHE | X | −14 | −13.892 | 18.216 | −47.589 | 1.00 | 22.64 | C |
| ATOM | 711 | C | PHE | X | −14 | −16.097 | 21.989 | −48.315 | 1.00 | 26.54 | C |
| ATOM | 712 | O | PHE | X | −14 | −15.343 | 22.591 | −47.558 | 1.00 | 26.45 | O |
| ATOM | 713 | N | LYS | X | −13 | −16.879 | 22.604 | −49.206 | 1.00 | 26.78 | N |
| ATOM | 714 | CA | ALYS | X | −13 | −16.897 | 24.062 | −49.293 | 0.40 | 27.55 | C |
| ATOM | 715 | CA | BLYS | X | −13 | −16.919 | 24.068 | −49.314 | 0.60 | 28.06 | C |
| ATOM | 716 | CB | ALYS | X | −13 | −17.647 | 24.547 | −50.534 | 0.40 | 27.72 | C |
| ATOM | 717 | CB | BLYS | X | −13 | −17.737 | 24.512 | −50.535 | 0.60 | 28.15 | C |
| ATOM | 718 | CG | ALYS | X | −13 | −16.722 | 24.904 | −51.677 | 0.40 | 28.55 | C |
| ATOM | 719 | CG | BLYS | X | −13 | −16.972 | 24.420 | −51.847 | 0.60 | 29.25 | C |
| ATOM | 720 | CD | ALYS | X | −13 | −15.864 | 26.115 | −51.327 | 0.40 | 28.59 | C |
| ATOM | 721 | CD | BLYS | X | −13 | −17.815 | 24.808 | −53.071 | 0.60 | 29.74 | C |
| ATOM | 722 | CE | ALYS | X | −13 | −14.541 | 26.073 | −52.059 | 0.40 | 28.93 | C |
| ATOM | 723 | CE | BLYS | X | −13 | −16.898 | 25.248 | −54.219 | 0.60 | 31.54 | C |
| ATOM | 724 | NZ | ALYS | X | −13 | −13.706 | 27.252 | −51.714 | 0.40 | 29.70 | N |
| ATOM | 725 | NZ | BLYS | X | −13 | −17.390 | 24.884 | −55.583 | 0.60 | 33.31 | N |
| ATOM | 726 | C | LYS | X | −13 | −17.454 | 24.702 | −48.030 | 1.00 | 27.61 | C |
| ATOM | 727 | O | LYS | X | −13 | −17.037 | 25.813 | −47.661 | 1.00 | 28.15 | O |
| ATOM | 728 | N | THR | X | −12 | −18.361 | 23.994 | −47.351 | 1.00 | 27.34 | N |
| ATOM | 729 | CA | ATHR | X | −12 | −18.932 | 24.497 | −46.114 | 0.50 | 27.52 | C |
| ATOM | 730 | CA | BTHR | X | −12 | −18.955 | 24.449 | −46.072 | 0.50 | 27.51 | C |
| ATOM | 731 | CB | ATHR | X | −12 | −20.302 | 23.845 | −45.851 | 0.50 | 27.56 | C |
| ATOM | 732 | CB | BTHR | X | −12 | −20.244 | 23.652 | −45.614 | 0.50 | 27.55 | C |
| ATOM | 733 | OG1 | ATHR | X | −12 | −21.123 | 24.053 | −47.007 | 0.50 | 28.11 | O |
| ATOM | 734 | OG1 | BTHR | X | −12 | −19.898 | 22.347 | −45.119 | 0.50 | 28.29 | O |
| ATOM | 735 | CG2 | ATHR | X | −12 | −20.986 | 24.466 | −44.648 | 0.50 | 28.22 | C |
| ATOM | 736 | CG2 | BTHR | X | −12 | −21.265 | 23.524 | −46.713 | 0.50 | 28.14 | C |
| ATOM | 737 | C | THR | X | −12 | −17.978 | 24.424 | −44.905 | 1.00 | 27.20 | C |
| ATOM | 738 | O | THR | X | −12 | −17.888 | 25.383 | −44.144 | 1.00 | 28.27 | O |
| ATOM | 739 | N | ILE | X | −11 | −17.260 | 23.309 | −44.747 | 1.00 | 25.50 | N |
| ATOM | 740 | CA | ILE | X | −11 | −16.380 | 23.126 | −43.589 | 1.00 | 24.26 | C |
| ATOM | 741 | CB | ILE | X | −11 | −16.251 | 21.633 | −43.153 | 1.00 | 24.43 | C |
| ATOM | 742 | CG1 | ILE | X | −11 | −15.639 | 20.776 | −44.265 | 1.00 | 24.73 | C |
| ATOM | 743 | CD1 | ILE | X | −11 | −15.165 | 19.449 | −43.787 | 1.00 | 25.38 | C |
| ATOM | 744 | CG2 | ILE | X | −11 | −17.646 | 21.071 | −42.743 | 1.00 | 25.49 | C |
| ATOM | 745 | C | ILE | X | −11 | −14.993 | 23.755 | −43.773 | 1.00 | 23.19 | C |
| ATOM | 746 | O | ILE | X | −11 | −14.386 | 24.225 | −42.809 | 1.00 | 23.34 | O |
| ATOM | 747 | N | LEU | X | −10 | −14.522 | 23.757 | −45.014 | 1.00 | 21.94 | N |
| ATOM | 748 | CA | LEU | X | −10 | −13.222 | 24.339 | −45.345 | 1.00 | 21.35 | C |
| ATOM | 749 | CB | LEU | X | −10 | −12.395 | 23.360 | −46.204 | 1.00 | 21.00 | C |

-continued

| | | | | | | | | | | |
|---|---|---|---|---|---|---|---|---|---|---|
| ATOM | 750 | CG | LEU | X | −10 | −10.933 | 23.774 | −46.464 | 1.00 | 20.13 | C |
| ATOM | 751 | CD1 | LEU | X | −10 | −10.155 | 23.985 | −45.168 | 1.00 | 19.81 | C |
| ATOM | 752 | CD2 | LEU | X | −10 | −10.221 | 22.769 | −47.379 | 1.00 | 20.94 | C |
| ATOM | 753 | C | LEU | X | −10 | −13.508 | 25.662 | −46.039 | 1.00 | 21.76 | C |
| ATOM | 754 | O | LEU | X | −10 | −13.678 | 25.735 | −47.264 | 1.00 | 22.31 | O |
| ATOM | 755 | N | THR | X | −9 | −13.560 | 26.714 | −45.237 | 1.00 | 22.34 | N |
| ATOM | 756 | CA | THR | X | −9 | −14.266 | 27.925 | −45.633 | 1.00 | 23.81 | C |
| ATOM | 757 | CB | THR | X | −9 | −15.492 | 28.139 | −44.694 | 1.00 | 23.97 | C |
| ATOM | 758 | OG1 | THR | X | −9 | −16.223 | 29.281 | −45.151 | 1.00 | 26.76 | O |
| ATOM | 759 | CG2 | THR | X | −9 | −15.042 | 28.349 | −43.229 | 1.00 | 23.92 | C |
| ATOM | 760 | C | THR | X | −9 | −13.420 | 29.183 | −45.669 | 1.00 | 24.93 | C |
| ATOM | 761 | O | THR | X | −9 | −12.362 | 29.259 | −45.043 | 1.00 | 23.52 | O |
| ATOM | 762 | N | LYS | X | −8 | −13.892 | 30.169 | −46.433 | 1.00 | 26.04 | N |
| ATOM | 763 | CA | LYS | X | −8 | −13.291 | 31.505 | −46.413 | 1.00 | 28.19 | C |
| ATOM | 764 | CB | LYS | X | −8 | −13.174 | 32.086 | −47.830 | 1.00 | 28.65 | C |
| ATOM | 765 | CG | LYS | X | −8 | −11.992 | 31.504 | −48.647 | 1.00 | 31.17 | C |
| ATOM | 766 | CD | LYS | X | −8 | −10.653 | 31.818 | −47.961 | 1.00 | 31.96 | C |
| ATOM | 767 | CE | LYS | X | −8 | −9.467 | 31.650 | −48.888 | 1.00 | 34.08 | C |
| ATOM | 768 | NZ | LYS | X | −8 | −9.219 | 30.234 | −49.250 | 1.00 | 31.97 | N |
| ATOM | 769 | C | LYS | X | −8 | −14.062 | 32.442 | −45.474 | 1.00 | 29.13 | C |
| ATOM | 770 | O | LYS | X | −8 | −13.661 | 33.579 | −45.233 | 1.00 | 29.06 | O |
| ATOM | 771 | N | GLU | X | −7 | −15.142 | 31.925 | −44.913 | 1.00 | 31.23 | N |
| ATOM | 772 | CA | GLU | X | −7 | −15.906 | 32.638 | −43.899 | 1.00 | 34.13 | C |
| ATOM | 773 | CB | GLU | X | −7 | −17.258 | 31.962 | −43.677 | 1.00 | 34.39 | C |
| ATOM | 774 | CG | GLU | X | −7 | −18.189 | 32.040 | −44.889 | 1.00 | 38.05 | C |
| ATOM | 775 | CD | GLU | X | −7 | −18.542 | 33.472 | −45.276 | 1.00 | 42.11 | C |
| ATOM | 776 | OE1 | GLU | X | −7 | −18.683 | 34.337 | −44.381 | 1.00 | 43.86 | O |
| ATOM | 777 | OE2 | GLU | X | −7 | −18.674 | 33.731 | −46.487 | 1.00 | 45.58 | O |
| ATOM | 778 | C | GLU | X | −7 | −15.110 | 32.634 | −42.616 | 1.00 | 35.09 | C |
| ATOM | 779 | O | GLU | X | −7 | −14.649 | 31.574 | −42.159 | 1.00 | 36.08 | O |
| ATOM | 780 | N | VAL | X | −6 | −14.912 | 33.820 | −42.058 | 1.00 | 35.59 | N |
| ATOM | 781 | CA | VAL | X | −6 | −14.168 | 33.957 | −40.815 | 1.00 | 36.56 | C |
| ATOM | 782 | CB | VAL | X | −6 | −13.119 | 35.090 | −40.895 | 1.00 | 36.66 | C |
| ATOM | 783 | CG1 | VAL | X | −6 | −12.423 | 35.304 | −39.554 | 1.00 | 35.42 | C |
| ATOM | 784 | CG2 | VAL | X | −6 | −12.092 | 34.774 | −41.982 | 1.00 | 36.09 | C |
| ATOM | 785 | C | VAL | X | −6 | −15.162 | 34.145 | −39.677 | 1.00 | 37.94 | C |
| ATOM | 786 | O | VAL | X | −6 | −16.053 | 34.991 | −39.750 | 1.00 | 37.84 | O |
| ATOM | 787 | N | LYS | X | −5 | −15.003 | 33.325 | −38.647 | 1.00 | 39.40 | N |
| ATOM | 788 | CA | LYS | X | −5 | −15.920 | 33.267 | −37.527 | 1.00 | 41.86 | C |
| ATOM | 789 | CB | LYS | X | −5 | −16.576 | 31.882 | −37.485 | 1.00 | 41.87 | C |
| ATOM | 790 | CG | LYS | X | −5 | −17.225 | 31.442 | −38.813 | 1.00 | 43.39 | C |
| ATOM | 791 | CD | LYS | X | −5 | −17.538 | 29.941 | −38.828 | 1.00 | 43.03 | C |
| ATOM | 792 | CE | LYS | X | −5 | −18.529 | 29.580 | −39.929 | 1.00 | 45.46 | C |
| ATOM | 793 | NZ | LYS | X | −5 | −17.919 | 29.530 | −41.287 | 1.00 | 46.23 | N |
| ATOM | 794 | C | LYS | X | −5 | −15.147 | 33.529 | −36.240 | 1.00 | 42.30 | C |
| ATOM | 795 | O | LYS | X | −5 | −14.447 | 32.651 | −35.751 | 1.00 | 42.92 | O |
| ATOM | 796 | N | GLY | X | −4 | −15.260 | 34.739 | −35.699 | 1.00 | 42.91 | N |
| ATOM | 797 | CA | GLY | X | −4 | −14.598 | 35.087 | −34.435 | 1.00 | 43.18 | C |
| ATOM | 798 | C | GLY | X | −4 | −15.123 | 34.319 | −33.229 | 1.00 | 43.29 | C |
| ATOM | 799 | O | GLY | X | −4 | −16.264 | 33.848 | −33.232 | 1.00 | 43.65 | O |
| ATOM | 800 | N | GLN | X | −3 | −14.280 | 34.186 | −32.203 | 1.00 | 43.35 | N |
| ATOM | 801 | CA | GLN | X | −3 | −14.644 | 33.538 | −30.943 | 1.00 | 43.24 | C |
| ATOM | 802 | CB | GLN | X | −3 | −13.392 | 33.399 | −30.062 | 1.00 | 42.96 | C |
| ATOM | 803 | CG | GLN | X | −3 | −13.628 | 32.926 | −28.626 | 1.00 | 41.63 | C |
| ATOM | 804 | CD | GLN | X | −3 | −14.359 | 31.594 | −28.544 | 1.00 | 40.69 | C |
| ATOM | 805 | OE1 | GLN | X | −3 | −13.935 | 30.590 | −29.132 | 1.00 | 38.10 | O |
| ATOM | 806 | NE2 | GLN | X | −3 | −15.459 | 31.575 | −27.794 | 1.00 | 39.40 | N |
| ATOM | 807 | C | GLN | X | −3 | −15.747 | 34.350 | −30.235 | 1.00 | 43.98 | C |
| ATOM | 808 | O | GLN | X | −3 | −15.648 | 35.576 | −30.140 | 1.00 | 43.40 | O |
| ATOM | 809 | N | THR | X | −2 | −16.793 | 33.666 | −29.761 | 1.00 | 44.81 | N |
| ATOM | 810 | CA | THR | X | −2 | −17.967 | 34.355 | −29.184 | 1.00 | 46.04 | C |
| ATOM | 811 | CB | THR | X | −2 | −19.297 | 33.572 | −29.368 | 1.00 | 45.81 | C |
| ATOM | 812 | OG1 | THR | X | −2 | −19.059 | 32.167 | −29.239 | 1.00 | 47.12 | O |
| ATOM | 813 | CG2 | THR | X | −2 | −19.897 | 33.851 | −30.732 | 1.00 | 46.50 | C |
| ATOM | 814 | C | THR | X | −2 | −17.810 | 34.813 | −27.729 | 1.00 | 46.36 | C |
| ATOM | 815 | O | THR | X | −2 | −18.226 | 35.918 | −27.389 | 1.00 | 46.56 | O |
| ATOM | 816 | N | ASN | X | −1 | −17.220 | 33.989 | −26.868 | 1.00 | 46.95 | N |
| ATOM | 817 | CA | ASN | X | −1 | −16.928 | 34.478 | −25.521 | 1.00 | 47.47 | C |
| ATOM | 818 | CB | ASN | X | −1 | −17.140 | 33.419 | −24.422 | 1.00 | 47.99 | C |
| ATOM | 819 | CG | ASN | X | −1 | −16.583 | 32.061 | −24.781 | 1.00 | 49.70 | C |
| ATOM | 820 | OD1 | ASN | X | −1 | −17.340 | 31.109 | −25.002 | 1.00 | 50.88 | O |
| ATOM | 821 | ND2 | ASN | X | −1 | −15.257 | 31.952 | −24.818 | 1.00 | 51.70 | N |
| ATOM | 822 | C | ASN | X | −1 | −15.573 | 35.166 | −25.421 | 1.00 | 47.00 | C |
| ATOM | 823 | O | ASN | X | −1 | −14.769 | 35.109 | −26.347 | 1.00 | 47.32 | O |
| ATOM | 824 | N | LYS | X | 0 | −15.349 | 35.859 | −24.311 | 1.00 | 46.35 | N |
| ATOM | 825 | CA | LYS | X | 0 | −14.104 | 36.606 | −24.104 | 1.00 | 45.29 | C |
| ATOM | 826 | CB | LYS | X | 0 | −14.291 | 38.080 | −24.497 | 1.00 | 45.96 | C |
| ATOM | 827 | CG | LYS | X | 0 | −15.653 | 38.715 | −24.133 | 1.00 | 47.16 | C |
| ATOM | 828 | CD | LYS | X | 0 | −16.554 | 38.846 | −25.369 | 1.00 | 49.84 | C |
| ATOM | 829 | CE | LYS | X | 0 | −17.499 | 40.054 | −25.274 | 1.00 | 50.41 | C |

-continued

| | | | | | | | | | | |
|---|---|---|---|---|---|---|---|---|---|---|
| ATOM | 830 | NZ | LYS | X | 0 | −18.753 | 39.753 | −24.532 | 1.00 | 52.05 | N |
| ATOM | 831 | C | LYS | X | 0 | −13.747 | 36.477 | −22.633 | 1.00 | 43.30 | C |
| ATOM | 832 | O | LYS | X | 0 | −14.640 | 36.721 | −21.820 | 1.00 | 44.85 | O |
| ATOM | 833 | N | LEU | X | 1 | −12.529 | 36.100 | −22.192 | 1.00 | 41.07 | N |
| ATOM | 834 | CA | ALEU | X | 1 | −11.323 | 35.755 | −22.986 | 0.60 | 38.71 | C |
| ATOM | 835 | CA | BLEU | X | 1 | −11.321 | 35.750 | −22.985 | 0.40 | 38.49 | C |
| ATOM | 836 | CB | ALEU | X | 1 | −11.607 | 34.862 | −24.207 | 0.60 | 38.92 | C |
| ATOM | 837 | CB | BLEU | X | 1 | −11.601 | 34.869 | −24.217 | 0.40 | 38.65 | C |
| ATOM | 838 | CG | ALEU | X | 1 | −11.343 | 33.361 | −24.040 | 0.60 | 39.19 | C |
| ATOM | 839 | CG | BLEU | X | 1 | −12.161 | 33.452 | −24.034 | 0.40 | 38.02 | C |
| ATOM | 840 | CD1 | ALEU | X | 1 | −12.036 | 32.740 | −22.819 | 0.60 | 38.90 | C |
| ATOM | 841 | CD1 | BLEU | X | 1 | −11.884 | 32.661 | −25.302 | 0.40 | 38.45 | C |
| ATOM | 842 | CD2 | ALEU | X | 1 | −11.709 | 32.619 | −25.320 | 0.60 | 38.86 | C |
| ATOM | 843 | CD2 | BLEU | X | 1 | −11.588 | 32.717 | −22.817 | 0.40 | 37.64 | C |
| ATOM | 844 | C | LEU | X | 1 | −10.335 | 36.891 | −23.293 | 1.00 | 36.93 | C |
| ATOM | 845 | O | LEU | X | 1 | −10.516 | 37.679 | −24.232 | 1.00 | 36.78 | O |
| ATOM | 846 | N | ALA | X | 2 | −9.286 | 36.931 | −22.478 | 1.00 | 33.62 | N |
| ATOM | 847 | CA | ALA | X | 2 | −8.151 | 37.821 | −22.618 | 1.00 | 30.84 | C |
| ATOM | 848 | CB | ALA | X | 2 | −7.461 | 37.995 | −21.295 | 1.00 | 30.15 | C |
| ATOM | 849 | C | ALA | X | 2 | −7.180 | 37.192 | −23.608 | 1.00 | 29.03 | C |
| ATOM | 850 | O | ALA | X | 2 | −6.813 | 36.022 | −23.472 | 1.00 | 27.05 | O |
| ATOM | 851 | N | SER | X | 3 | −6.749 | 37.983 | −24.579 | 1.00 | 27.79 | N |
| ATOM | 852 | CA | ASER | X | 3 | −5.817 | 37.502 | −25.594 | 0.64 | 27.29 | C |
| ATOM | 853 | CA | BSER | X | 3 | −5.817 | 37.508 | −25.600 | 0.36 | 26.91 | C |
| ATOM | 854 | CB | ASER | X | 3 | −5.970 | 38.315 | −26.883 | 0.64 | 27.29 | C |
| ATOM | 855 | CB | BSER | X | 3 | −5.945 | 38.353 | −26.871 | 0.36 | 26.85 | C |
| ATOM | 856 | OG | ASER | X | 3 | −7.137 | 37.914 | −27.581 | 0.64 | 29.43 | O |
| ATOM | 857 | OG | BSER | X | 3 | −5.466 | 39.666 | −26.655 | 0.36 | 26.02 | O |
| ATOM | 858 | C | SER | X | 3 | −4.369 | 37.504 | −25.114 | 1.00 | 26.68 | C |
| ATOM | 859 | O | SER | X | 3 | −3.498 | 36.872 | −25.722 | 1.00 | 26.53 | O |
| ATOM | 860 | N | VAL | X | 4 | −4.103 | 38.213 | −24.019 | 1.00 | 25.77 | N |
| ATOM | 861 | CA | VAL | X | 4 | −2.741 | 38.374 | −23.535 | 1.00 | 25.24 | C |
| ATOM | 862 | CB | VAL | X | 4 | −2.212 | 39.843 | −23.730 | 1.00 | 24.77 | C |
| ATOM | 863 | CG1 | VAL | X | 4 | −0.776 | 39.953 | −23.268 | 1.00 | 25.57 | C |
| ATOM | 864 | CG2 | VAL | X | 4 | −2.357 | 40.274 | −25.189 | 1.00 | 24.23 | C |
| ATOM | 865 | C | VAL | X | 4 | −2.622 | 37.965 | −22.074 | 1.00 | 25.68 | C |
| ATOM | 866 | O | VAL | X | 4 | −3.325 | 38.495 | −21.204 | 1.00 | 26.15 | O |
| ATOM | 867 | N | ILE | X | 5 | −1.740 | 37.007 | −21.817 | 1.00 | 24.64 | N |
| ATOM | 868 | CA | ILE | X | 5 | −1.548 | 36.428 | −20.491 | 1.00 | 24.70 | C |
| ATOM | 869 | CB | ILE | X | 5 | −0.815 | 35.060 | −20.599 | 1.00 | 24.30 | C |
| ATOM | 870 | CG1 | ILE | X | 5 | −1.807 | 33.962 | −20.986 | 1.00 | 23.45 | C |
| ATOM | 871 | CD1 | ILE | X | 5 | −2.584 | 34.187 | −22.269 | 1.00 | 23.56 | C |
| ATOM | 872 | CG2 | ILE | X | 5 | −0.132 | 34.658 | −19.282 | 1.00 | 23.31 | C |
| ATOM | 873 | C | ILE | X | 5 | −0.751 | 37.446 | −19.686 | 1.00 | 24.92 | C |
| ATOM | 874 | O | ILE | X | 5 | 0.201 | 38.012 | −20.209 | 1.00 | 24.72 | O |
| ATOM | 875 | N | PRO | X | 6 | −1.159 | 37.706 | −18.426 | 1.00 | 26.15 | N |
| ATOM | 876 | CA | PRO | X | 6 | −0.593 | 38.859 | −17.662 | 1.00 | 26.72 | C |
| ATOM | 877 | CB | PRO | X | 6 | −1.457 | 38.888 | −16.395 | 1.00 | 26.68 | C |
| ATOM | 878 | CG | PRO | X | 6 | −1.901 | 37.434 | −16.213 | 1.00 | 26.57 | C |
| ATOM | 879 | CD | PRO | X | 6 | −2.184 | 36.986 | −17.647 | 1.00 | 25.77 | C |
| ATOM | 880 | C | PRO | X | 6 | 0.891 | 38.789 | −17.303 | 1.00 | 27.44 | C |
| ATOM | 881 | O | PRO | X | 6 | 1.540 | 39.835 | −17.127 | 1.00 | 27.93 | O |
| ATOM | 882 | N | ASP | X | 7 | 1.445 | 37.583 | −17.181 | 1.00 | 27.39 | N |
| ATOM | 883 | CA | ASP | X | 7 | 2.842 | 37.428 | −16.780 | 1.00 | 28.49 | C |
| ATOM | 884 | CB | ASP | X | 7 | 3.031 | 37.808 | −15.302 | 1.00 | 28.45 | C |
| ATOM | 885 | CG | ASP | X | 7 | 2.055 | 37.105 | −14.377 | 1.00 | 32.54 | C |
| ATOM | 886 | OD1 | ASP | X | 7 | 1.506 | 37.776 | −13.473 | 1.00 | 34.04 | O |
| ATOM | 887 | OD2 | ASP | X | 7 | 1.823 | 35.879 | −14.533 | 1.00 | 34.39 | O |
| ATOM | 888 | C | ASP | X | 7 | 3.377 | 36.012 | −17.035 | 1.00 | 28.34 | C |
| ATOM | 889 | O | ASP | X | 7 | 2.605 | 35.089 | −17.324 | 1.00 | 27.78 | O |
| ATOM | 890 | N | VAL | X | 8 | 4.694 | 35.866 | −16.934 | 1.00 | 28.61 | N |
| ATOM | 891 | CA | AVAL | X | 8 | 5.398 | 34.597 | −17.176 | 0.50 | 28.87 | C |
| ATOM | 892 | CA | BVAL | X | 8 | 5.317 | 34.585 | −17.243 | 0.50 | 28.37 | C |
| ATOM | 893 | CB | AVAL | X | 8 | 6.935 | 34.775 | −17.055 | 0.50 | 29.00 | C |
| ATOM | 894 | CB | BVAL | X | 8 | 6.848 | 34.715 | −17.493 | 0.50 | 28.47 | C |
| ATOM | 895 | CG1 | AVAL | X | 8 | 7.653 | 33.417 | −16.991 | 0.50 | 29.77 | C |
| ATOM | 896 | CG1 | BVAL | X | 8 | 7.601 | 34.994 | −16.200 | 0.50 | 27.67 | C |
| ATOM | 897 | CG2 | AVAL | X | 8 | 7.454 | 35.569 | −18.216 | 0.50 | 29.64 | C |
| ATOM | 898 | CG2 | BVAL | X | 8 | 7.395 | 33.462 | −18.209 | 0.50 | 27.65 | C |
| ATOM | 899 | C | VAL | X | 8 | 4.953 | 33.513 | −16.203 | 1.00 | 28.78 | C |
| ATOM | 900 | O | VAL | X | 8 | 4.871 | 32.329 | −16.548 | 1.00 | 28.47 | O |
| ATOM | 901 | N | ALA | X | 9 | 4.690 | 33.923 | −14.964 | 1.00 | 29.04 | N |
| ATOM | 902 | CA | ALA | X | 9 | 4.217 | 32.995 | −13.931 | 1.00 | 28.98 | C |
| ATOM | 903 | CB | ALA | X | 9 | 4.061 | 33.704 | −12.585 | 1.00 | 29.25 | C |
| ATOM | 904 | C | ALA | X | 9 | 2.907 | 32.329 | −14.345 | 1.00 | 28.57 | C |
| ATOM | 905 | O | ALA | X | 9 | 2.726 | 31.111 | −14.153 | 1.00 | 28.70 | O |
| ATOM | 906 | N | THR | X | 10 | 1.999 | 33.118 | −14.912 | 1.00 | 27.69 | N |
| ATOM | 907 | CA | THR | X | 10 | 0.721 | 32.602 | −15.382 | 1.00 | 26.95 | C |
| ATOM | 908 | CB | THR | X | 10 | −0.290 | 33.738 | −15.647 | 1.00 | 27.20 | C |
| ATOM | 909 | OG1 | THR | X | 10 | −0.465 | 34.489 | −14.428 | 1.00 | 29.02 | O |

-continued

| | | | | | | | | | | |
|---|---|---|---|---|---|---|---|---|---|---|
| ATOM | 910 | CG2 | THR | X | 10 | −1.653 | 33.180 | −16.093 | 1.00 | 27.03 | C |
| ATOM | 911 | C | THR | X | 10 | 0.930 | 31.748 | −16.639 | 1.00 | 26.63 | C |
| ATOM | 912 | O | THR | X | 10 | 0.312 | 30.689 | −16.779 | 1.00 | 26.55 | O |
| ATOM | 913 | N | LEU | X | 11 | 1.811 | 32.195 | −17.529 | 1.00 | 25.77 | N |
| ATOM | 914 | CA | LEU | X | 11 | 2.204 | 31.381 | −18.697 | 1.00 | 25.47 | C |
| ATOM | 915 | CB | LEU | X | 11 | 3.315 | 32.058 | −19.496 | 1.00 | 24.96 | C |
| ATOM | 916 | CG | LEU | X | 11 | 3.776 | 31.317 | −20.761 | 1.00 | 25.08 | C |
| ATOM | 917 | CD1 | LEU | X | 11 | 2.665 | 31.300 | −21.802 | 1.00 | 24.06 | C |
| ATOM | 918 | CD2 | LEU | X | 11 | 5.038 | 31.949 | −21.314 | 1.00 | 25.43 | C |
| ATOM | 919 | C | LEU | X | 11 | 2.704 | 29.999 | −18.257 | 1.00 | 25.90 | C |
| ATOM | 920 | O | LEU | X | 11 | 2.300 | 28.972 | −18.825 | 1.00 | 25.39 | O |
| ATOM | 921 | N | ASN | X | 12 | 3.591 | 29.986 | −17.265 | 1.00 | 26.09 | N |
| ATOM | 922 | CA | ASN | X | 12 | 4.121 | 28.720 | −16.727 | 1.00 | 26.60 | C |
| ATOM | 923 | CB | ASN | X | 12 | 5.282 | 28.984 | −15.763 | 1.00 | 27.47 | C |
| ATOM | 924 | CG | ASN | X | 12 | 6.518 | 29.514 | −16.471 | 1.00 | 28.94 | C |
| ATOM | 925 | OD1 | ASN | X | 12 | 6.729 | 29.273 | −17.664 | 1.00 | 31.89 | O |
| ATOM | 926 | ND2 | ASN | X | 12 | 7.343 | 30.247 | −15.738 | 1.00 | 32.04 | N |
| ATOM | 927 | C | ASN | X | 12 | 3.028 | 27.867 | −16.090 | 1.00 | 26.22 | C |
| ATOM | 928 | O | ASN | X | 12 | 3.027 | 26.630 | −16.238 | 1.00 | 25.47 | O |
| ATOM | 929 | N | SER | X | 13 | 2.090 | 28.514 | −15.401 | 1.00 | 25.94 | N |
| ATOM | 930 | CA | SER | X | 13 | 0.943 | 27.809 | −14.838 | 1.00 | 25.81 | C |
| ATOM | 931 | CB | SER | X | 13 | 0.035 | 28.723 | −14.019 | 1.00 | 26.10 | C |
| ATOM | 932 | OG | SER | X | 13 | −1.130 | 27.990 | −13.655 | 1.00 | 27.52 | O |
| ATOM | 933 | C | SER | X | 13 | 0.137 | 27.115 | −15.934 | 1.00 | 25.21 | C |
| ATOM | 934 | O | SER | X | 13 | −0.177 | 25.915 | −15.834 | 1.00 | 24.54 | O |
| ATOM | 935 | N | LEU | X | 14 | −0.176 | 27.866 | −16.988 | 1.00 | 23.93 | N |
| ATOM | 936 | CA | LEU | X | 14 | −0.889 | 27.310 | −18.126 | 1.00 | 23.56 | C |
| ATOM | 937 | CB | LEU | X | 14 | −1.211 | 28.399 | −19.146 | 1.00 | 23.21 | C |
| ATOM | 938 | CG | LEU | X | 14 | −2.123 | 29.493 | −18.599 | 1.00 | 23.11 | C |
| ATOM | 939 | CD1 | LEU | X | 14 | −2.098 | 30.655 | −19.583 | 1.00 | 20.97 | C |
| ATOM | 940 | CD2 | LEU | X | 14 | −3.526 | 28.948 | −18.465 | 1.00 | 21.94 | C |
| ATOM | 941 | C | LEU | X | 14 | −0.098 | 26.186 | −18.785 | 1.00 | 22.27 | C |
| ATOM | 942 | O | LEU | X | 14 | −0.685 | 25.170 | −19.143 | 1.00 | 22.27 | O |
| ATOM | 943 | N | PHE | X | 15 | 1.221 | 26.345 | −18.920 | 1.00 | 22.15 | N |
| ATOM | 944 | CA | PHE | X | 15 | 2.039 | 25.260 | −19.481 | 1.00 | 21.36 | C |
| ATOM | 945 | CB | PHE | X | 15 | 3.530 | 25.615 | −19.568 | 1.00 | 21.74 | C |
| ATOM | 946 | CG | PHE | X | 15 | 4.369 | 24.469 | −20.069 | 1.00 | 20.30 | C |
| ATOM | 947 | CD1 | PHE | X | 15 | 4.997 | 23.593 | −19.179 | 1.00 | 21.28 | C |
| ATOM | 948 | CE1 | PHE | X | 15 | 5.724 | 22.506 | −19.639 | 1.00 | 22.95 | C |
| ATOM | 949 | CZ | PHE | X | 15 | 5.826 | 22.281 | −20.997 | 1.00 | 22.72 | C |
| ATOM | 950 | CE2 | PHE | X | 15 | 5.193 | 23.139 | −21.889 | 1.00 | 20.46 | C |
| ATOM | 951 | CD2 | PHE | X | 15 | 4.465 | 24.213 | −21.427 | 1.00 | 20.73 | C |
| ATOM | 952 | C | PHE | X | 15 | 1.891 | 23.973 | −18.636 | 1.00 | 22.52 | C |
| ATOM | 953 | O | PHE | X | 15 | 1.746 | 22.861 | −19.173 | 1.00 | 21.49 | O |
| ATOM | 954 | N | ASN | X | 16 | 1.997 | 24.134 | −17.317 | 1.00 | 22.04 | N |
| ATOM | 955 | CA | ASN | X | 16 | 1.843 | 23.002 | −16.415 | 1.00 | 23.13 | C |
| ATOM | 956 | CB | ASN | X | 16 | 2.227 | 23.401 | −14.991 | 1.00 | 23.49 | C |
| ATOM | 957 | CG | ASN | X | 16 | 3.715 | 23.626 | −14.842 | 1.00 | 27.25 | C |
| ATOM | 958 | OD1 | ASN | X | 16 | 4.517 | 22.998 | −15.520 | 1.00 | 32.04 | O |
| ATOM | 959 | ND2 | ASN | X | 16 | 4.090 | 24.537 | −13.943 | 1.00 | 34.01 | N |
| ATOM | 960 | C | ASN | X | 16 | 0.465 | 22.372 | −16.474 | 1.00 | 22.05 | C |
| ATOM | 961 | O | ASN | X | 16 | 0.341 | 21.129 | −16.480 | 1.00 | 22.46 | O |
| ATOM | 962 | N | GLN | X | 17 | −0.575 | 23.184 | −16.571 | 1.00 | 21.36 | N |
| ATOM | 963 | CA | GLN | X | 17 | −1.920 | 22.641 | −16.714 | 1.00 | 20.99 | C |
| ATOM | 964 | CB | GLN | X | 17 | −2.961 | 23.726 | −16.722 | 1.00 | 21.67 | C |
| ATOM | 965 | CG | GLN | X | 17 | −3.123 | 24.444 | −15.358 | 1.00 | 21.97 | C |
| ATOM | 966 | CD | GLN | X | 17 | −4.197 | 25.483 | −15.437 | 1.00 | 23.99 | C |
| ATOM | 967 | OE1 | GLN | X | 17 | −5.326 | 25.197 | −15.837 | 1.00 | 25.85 | O |
| ATOM | 968 | NE2 | GLN | X | 17 | −3.851 | 26.724 | −15.075 | 1.00 | 26.51 | N |
| ATOM | 969 | C | GLN | X | 17 | −2.072 | 21.827 | −17.990 | 1.00 | 21.12 | C |
| ATOM | 970 | O | GLN | X | 17 | −2.688 | 20.762 | −17.992 | 1.00 | 20.05 | O |
| ATOM | 971 | N | ILE | X | 18 | −1.536 | 22.366 | −19.082 | 1.00 | 19.71 | N |
| ATOM | 972 | CA | ILE | X | 18 | −1.502 | 21.626 | −20.341 | 1.00 | 19.71 | C |
| ATOM | 973 | CB | ILE | X | 18 | −0.971 | 22.526 | −21.462 | 1.00 | 19.58 | C |
| ATOM | 974 | CG1 | ILE | X | 18 | −2.041 | 23.556 | −21.793 | 1.00 | 19.28 | C |
| ATOM | 975 | CD1 | ILE | X | 18 | −1.500 | 24.711 | −22.683 | 1.00 | 20.14 | C |
| ATOM | 976 | CG2 | ILE | X | 18 | −0.472 | 21.691 | −22.689 | 1.00 | 20.43 | C |
| ATOM | 977 | C | ILE | X | 18 | −0.703 | 20.322 | −20.249 | 1.00 | 19.12 | C |
| ATOM | 978 | O | ILE | X | 18 | −1.189 | 19.267 | −20.671 | 1.00 | 19.87 | O |
| ATOM | 979 | N | LYS | X | 19 | 0.512 | 20.377 | −19.732 | 1.00 | 19.60 | N |
| ATOM | 980 | CA | LYS | X | 19 | 1.323 | 19.162 | −19.628 | 1.00 | 20.87 | C |
| ATOM | 981 | CB | LYS | X | 19 | 2.752 | 19.477 | −19.198 | 1.00 | 21.81 | C |
| ATOM | 982 | CG | LYS | X | 19 | 3.685 | 18.337 | −19.426 | 1.00 | 23.53 | C |
| ATOM | 983 | CD | LYS | X | 19 | 5.088 | 18.716 | −19.043 | 1.00 | 25.39 | C |
| ATOM | 984 | CE | LYS | X | 19 | 6.016 | 17.533 | −19.170 | 1.00 | 28.23 | C |
| ATOM | 985 | NZ | LYS | X | 19 | 7.329 | 17.910 | −18.585 | 1.00 | 28.51 | N |
| ATOM | 986 | C | LYS | X | 19 | 0.691 | 18.121 | −18.694 | 1.00 | 21.00 | C |
| ATOM | 987 | O | LYS | X | 19 | 0.832 | 16.896 | −18.914 | 1.00 | 21.11 | O |
| ATOM | 988 | N | ASN | X | 20 | −0.014 | 18.600 | −17.665 | 1.00 | 20.96 | N |
| ATOM | 989 | CA | ASN | X | 20 | −0.773 | 17.702 | −16.769 | 1.00 | 21.16 | C |

-continued

| | | | | | | | | | | |
|---|---|---|---|---|---|---|---|---|---|---|
| ATOM | 990 | CB | ASN | X | 20 | −1.353 | 18.483 | −15.592 | 1.00 | 21.86 | C |
| ATOM | 991 | CG | ASN | X | 20 | −0.337 | 18.784 | −14.519 | 1.00 | 21.91 | C |
| ATOM | 992 | OD1 | ASN | X | 20 | 0.828 | 18.382 | −14.579 | 1.00 | 24.93 | O |
| ATOM | 993 | ND2 | ASN | X | 20 | −0.780 | 19.527 | −13.522 | 1.00 | 27.61 | N |
| ATOM | 994 | C | ASN | X | 20 | −1.921 | 16.964 | −17.433 | 1.00 | 21.65 | C |
| ATOM | 995 | O | ASN | X | 20 | −2.502 | 16.035 | −16.836 | 1.00 | 22.58 | O |
| ATOM | 996 | N | GLN | X | 21 | −2.269 | 17.372 | −18.654 | 1.00 | 20.72 | N |
| ATOM | 997 | CA | GLN | X | 21 | −3.316 | 16.701 | −19.412 | 1.00 | 20.30 | C |
| ATOM | 998 | CB | GLN | X | 21 | −4.265 | 17.707 | −20.077 | 1.00 | 21.25 | C |
| ATOM | 999 | CG | GLN | X | 21 | −5.138 | 18.486 | −19.079 | 1.00 | 20.15 | C |
| ATOM | 1000 | CD | GLN | X | 21 | −5.926 | 17.558 | −18.145 | 1.00 | 22.69 | C |
| ATOM | 1001 | OE1 | GLN | X | 21 | −6.531 | 16.559 | −18.580 | 1.00 | 21.96 | O |
| ATOM | 1002 | NE2 | GLN | X | 21 | −5.913 | 17.882 | −16.854 | 1.00 | 21.66 | N |
| ATOM | 1003 | C | GLN | X | 21 | −2.780 | 15.667 | −20.430 | 1.00 | 20.06 | C |
| ATOM | 1004 | O | GLN | X | 21 | −3.558 | 15.092 | −21.172 | 1.00 | 19.93 | O |
| ATOM | 1005 | N | SER | X | 22 | −1.472 | 15.431 | −20.402 | 1.00 | 19.79 | N |
| ATOM | 1006 | CA | SER | X | 22 | −0.790 | 14.481 | −21.293 | 1.00 | 19.60 | C |
| ATOM | 1007 | CB | SER | X | 22 | 0.721 | 14.484 | −21.076 | 1.00 | 19.80 | C |
| ATOM | 1008 | OG | SER | X | 22 | 1.324 | 15.770 | −21.206 | 1.00 | 22.66 | O |
| ATOM | 1009 | C | SER | X | 22 | −1.273 | 13.062 | −21.022 | 1.00 | 19.56 | C |
| ATOM | 1010 | O | SER | X | 22 | −1.354 | 12.647 | −19.861 | 1.00 | 18.61 | O |
| ATOM | 1011 | N | CYS | X | 23 | −1.599 | 12.332 | −22.088 | 1.00 | 19.12 | N |
| ATOM | 1012 | CA | CYS | X | 23 | −1.787 | 10.877 | −21.971 | 1.00 | 19.27 | C |
| ATOM | 1013 | CB | CYS | X | 23 | −2.091 | 10.268 | −23.352 | 1.00 | 18.65 | C |
| ATOM | 1014 | SG | CYS | X | 23 | −3.640 | 10.819 | −24.006 | 1.00 | 19.19 | S |
| ATOM | 1015 | C | CYS | X | 23 | −0.538 | 10.245 | −21.371 | 1.00 | 19.80 | C |
| ATOM | 1016 | O | CYS | X | 23 | 0.571 | 10.565 | −21.761 | 1.00 | 20.04 | O |
| ATOM | 1017 | N | AGLY | X | 24 | −0.727 | 9.337 | −20.409 | 0.57 | 20.12 | N |
| ATOM | 1018 | N | BGLY | X | 24 | −0.737 | 9.337 | −20.412 | 0.43 | 20.16 | N |
| ATOM | 1019 | CA | AGLY | X | 24 | 0.403 | 8.709 | −19.754 | 0.57 | 21.01 | C |
| ATOM | 1020 | CA | BGLY | X | 24 | 0.378 | 8.693 | −19.743 | 0.43 | 20.96 | C |
| ATOM | 1021 | C | AGLY | X | 24 | 0.778 | 9.383 | −18.444 | 0.57 | 21.44 | C |
| ATOM | 1022 | C | BGLY | X | 24 | 0.663 | 9.282 | −18.372 | 0.43 | 21.35 | C |
| ATOM | 1023 | O | AGLY | X | 24 | 1.788 | 9.018 | −17.824 | 0.57 | 21.52 | O |
| ATOM | 1024 | O | BGLY | X | 24 | 1.495 | 8.758 | −17.632 | 0.43 | 21.39 | O |
| ATOM | 1025 | N | THR | X | 25 | −0.012 | 10.379 | −18.040 | 1.00 | 21.98 | N |
| ATOM | 1026 | CA | THR | X | 25 | 0.167 | 11.035 | −16.718 | 1.00 | 23.05 | C |
| ATOM | 1027 | CB | THR | X | 25 | 0.464 | 12.564 | −16.821 | 1.00 | 23.35 | C |
| ATOM | 1028 | OG1 | THR | X | 25 | −0.703 | 13.236 | −17.300 | 1.00 | 25.53 | O |
| ATOM | 1029 | CG2 | THR | X | 25 | 1.642 | 12.823 | −17.696 | 1.00 | 24.50 | C |
| ATOM | 1030 | C | THR | X | 25 | −1.053 | 10.884 | −15.852 | 1.00 | 23.42 | C |
| ATOM | 1031 | O | THR | X | 25 | −2.174 | 11.058 | −16.326 | 1.00 | 24.08 | O |
| ATOM | 1032 | N | SER | X | 26 | −0.840 | 10.601 | −14.557 | 1.00 | 24.57 | N |
| ATOM | 1033 | CA | ASER | X | 26 | −1.955 | 10.365 | −13.649 | 0.50 | 24.72 | C |
| ATOM | 1034 | CA | BSER | X | 26 | −1.954 | 10.366 | −13.645 | 0.50 | 24.88 | C |
| ATOM | 1035 | CB | ASER | X | 26 | −1.455 | 9.786 | −12.322 | 0.50 | 25.08 | C |
| ATOM | 1036 | CB | BSER | X | 26 | −1.449 | 9.814 | −12.312 | 0.50 | 25.27 | C |
| ATOM | 1037 | OG | ASER | X | 26 | −0.784 | 8.557 | −12.541 | 0.50 | 23.63 | O |
| ATOM | 1038 | OG | BSER | X | 26 | −0.272 | 10.488 | −11.916 | 0.50 | 24.80 | O |
| ATOM | 1039 | C | SER | X | 26 | −2.817 | 11.600 | −13.419 | 1.00 | 24.62 | C |
| ATOM | 1040 | O | SER | X | 26 | −3.986 | 11.480 | −13.073 | 1.00 | 25.42 | O |
| ATOM | 1041 | N | THR | X | 27 | −2.247 | 12.790 | −13.633 | 1.00 | 25.05 | N |
| ATOM | 1042 | CA | THR | X | 27 | −3.022 | 14.044 | −13.534 | 1.00 | 25.25 | C |
| ATOM | 1043 | CB | THR | X | 27 | −2.091 | 15.274 | −13.532 | 1.00 | 25.96 | C |
| ATOM | 1044 | OG1 | THR | X | 27 | −1.121 | 15.139 | −14.582 | 1.00 | 24.52 | O |
| ATOM | 1045 | CG2 | THR | X | 27 | −1.351 | 15.378 | −12.198 | 1.00 | 26.69 | C |
| ATOM | 1046 | C | THR | X | 27 | −4.083 | 14.269 | −14.624 | 1.00 | 25.53 | C |
| ATOM | 1047 | O | THR | X | 27 | −5.042 | 15.036 | −14.428 | 1.00 | 25.57 | O |
| ATOM | 1048 | N | ALA | X | 28 | −3.903 | 13.627 | −15.785 | 1.00 | 24.68 | N |
| ATOM | 1049 | CA | ALA | X | 28 | −4.765 | 13.873 | −16.927 | 1.00 | 24.38 | C |
| ATOM | 1050 | CB | ALA | X | 28 | −4.138 | 13.267 | −18.193 | 1.00 | 24.08 | C |
| ATOM | 1051 | C | ALA | X | 28 | −6.196 | 13.373 | −16.758 | 1.00 | 24.75 | C |
| ATOM | 1052 | O | ALA | X | 28 | −6.426 | 12.323 | −16.152 | 1.00 | 25.70 | O |
| ATOM | 1053 | N | SER | X | 29 | −7.145 | 14.117 | −17.308 | 1.00 | 25.13 | N |
| ATOM | 1054 | CA | SER | X | 29 | −8.533 | 13.691 | −17.393 | 1.00 | 26.05 | C |
| ATOM | 1055 | CB | SER | X | 29 | −9.485 | 14.819 | −16.987 | 1.00 | 27.22 | C |
| ATOM | 1056 | OG | SER | X | 29 | −9.339 | 15.114 | −15.607 | 1.00 | 28.29 | O |
| ATOM | 1057 | C | SER | X | 29 | −8.809 | 13.264 | −18.824 | 1.00 | 26.65 | C |
| ATOM | 1058 | O | SER | X | 29 | −8.086 | 13.674 | −19.735 | 1.00 | 28.08 | O |
| ATOM | 1059 | N | SER | X | 30 | −9.851 | 12.460 | −19.029 | 1.00 | 26.69 | N |
| ATOM | 1060 | CA | SER | X | 30 | −10.225 | 11.987 | −20.363 | 1.00 | 26.66 | C |
| ATOM | 1061 | CB | SER | X | 30 | −11.053 | 10.686 | −20.287 | 1.00 | 26.84 | C |
| ATOM | 1062 | OG | SER | X | 30 | −10.292 | 9.634 | −19.719 | 1.00 | 28.21 | O |
| ATOM | 1063 | C | SER | X | 30 | −11.043 | 13.043 | −21.094 | 1.00 | 26.20 | C |
| ATOM | 1064 | O | SER | X | 30 | −11.869 | 13.723 | −20.473 | 1.00 | 26.72 | O |
| ATOM | 1065 | N | PRO | X | 31 | −10.824 | 13.195 | −22.419 | 1.00 | 25.65 | N |
| ATOM | 1066 | CA | PRO | X | 31 | −9.719 | 12.578 | −23.163 | 1.00 | 24.40 | C |
| ATOM | 1067 | CB | PRO | X | 31 | −10.099 | 12.773 | −24.626 | 1.00 | 24.69 | C |
| ATOM | 1068 | CG | PRO | X | 31 | −11.413 | 13.494 | −24.653 | 1.00 | 25.56 | C |
| ATOM | 1069 | CD | PRO | X | 31 | −11.699 | 14.006 | −23.286 | 1.00 | 25.14 | C |

-continued

| | | | | | | | | | |
|---|---|---|---|---|---|---|---|---|---|
| ATOM | 1070 | C | PRO | X | 31 | −8.423 | 13.313 | −22.882 | 1.00 | 23.27 | C |
| ATOM | 1071 | O | PRO | X | 31 | −8.388 | 14.567 | −22.866 | 1.00 | 23.82 | O |
| ATOM | 1072 | N | CYS | X | 32 | −7.373 | 12.553 | −22.646 | 1.00 | 21.09 | N |
| ATOM | 1073 | CA | CYS | X | 32 | −6.051 | 13.141 | −22.408 | 1.00 | 19.98 | C |
| ATOM | 1074 | CB | CYS | X | 32 | −5.112 | 12.170 | −21.706 | 1.00 | 19.73 | C |
| ATOM | 1075 | SG | CYS | X | 32 | −5.035 | 10.520 | −22.505 | 1.00 | 21.80 | S |
| ATOM | 1076 | C | CYS | X | 32 | −5.469 | 13.621 | −23.731 | 1.00 | 19.51 | C |
| ATOM | 1077 | O | CYS | X | 32 | −5.906 | 13.187 | −24.821 | 1.00 | 18.36 | O |
| ATOM | 1078 | N | ILE | X | 33 | −4.511 | 14.540 | −23.650 | 1.00 | 18.04 | N |
| ATOM | 1079 | CA | ILE | X | 33 | −3.890 | 15.031 | −24.879 | 1.00 | 17.56 | C |
| ATOM | 1080 | CB | ILE | X | 33 | −3.359 | 16.465 | −24.737 | 1.00 | 17.47 | C |
| ATOM | 1081 | CG1 | ILE | X | 33 | −4.487 | 17.378 | −24.238 | 1.00 | 19.13 | C |
| ATOM | 1082 | CD1 | ILE | X | 33 | −4.011 | 18.787 | −23.899 | 1.00 | 19.04 | C |
| ATOM | 1083 | CG2 | ILE | X | 33 | −2.818 | 16.934 | −26.124 | 1.00 | 16.89 | C |
| ATOM | 1084 | C | ILE | X | 33 | −2.764 | 14.086 | −25.286 | 1.00 | 16.62 | C |
| ATOM | 1085 | O | ILE | X | 33 | −1.840 | 13.820 | −24.530 | 1.00 | 17.40 | O |
| ATOM | 1086 | N | THR | X | 34 | −2.838 | 13.615 | −26.526 | 1.00 | 16.78 | N |
| ATOM | 1087 | CA | THR | X | 34 | −1.959 | 12.547 | −27.030 | 1.00 | 16.38 | C |
| ATOM | 1088 | CB | THR | X | 34 | −2.680 | 11.839 | −28.190 | 1.00 | 16.07 | C |
| ATOM | 1089 | OG1 | THR | X | 34 | −3.163 | 12.843 | −29.100 | 1.00 | 17.72 | O |
| ATOM | 1090 | CG2 | THR | X | 34 | −3.893 | 11.041 | −27.654 | 1.00 | 17.24 | C |
| ATOM | 1091 | C | THR | X | 34 | −0.550 | 13.009 | −27.473 | 1.00 | 15.98 | C |
| ATOM | 1092 | O | THR | X | 34 | −0.064 | 12.665 | −28.567 | 1.00 | 15.99 | O |
| ATOM | 1093 | N | PHE | X | 35 | 0.111 | 13.792 | −26.633 | 1.00 | 16.58 | N |
| ATOM | 1094 | CA | PHE | X | 35 | 1.434 | 14.307 | −26.965 | 1.00 | 16.83 | C |
| ATOM | 1095 | CB | PHE | X | 35 | 1.981 | 15.153 | −25.806 | 1.00 | 17.01 | C |
| ATOM | 1096 | CG | PHE | X | 35 | 1.204 | 16.406 | −25.543 | 1.00 | 17.51 | C |
| ATOM | 1097 | CD1 | PHE | X | 35 | 1.017 | 17.373 | −26.550 | 1.00 | 18.73 | C |
| ATOM | 1098 | CE1 | PHE | X | 35 | 0.296 | 18.554 | −26.269 | 1.00 | 17.48 | C |
| ATOM | 1099 | CZ | PHE | X | 35 | −0.204 | 18.787 | −24.996 | 1.00 | 18.05 | C |
| ATOM | 1100 | CE2 | PHE | X | 35 | −0.001 | 17.841 | −23.981 | 1.00 | 19.00 | C |
| ATOM | 1101 | CD2 | PHE | X | 35 | 0.681 | 16.654 | −24.263 | 1.00 | 17.85 | C |
| ATOM | 1102 | C | PHE | X | 35 | 2.450 | 13.219 | −27.262 | 1.00 | 17.33 | C |
| ATOM | 1103 | O | PHE | X | 35 | 3.357 | 13.417 | −28.085 | 1.00 | 17.40 | O |
| ATOM | 1104 | N | ARG | X | 36 | 2.300 | 12.067 | −26.591 | 1.00 | 16.08 | N |
| ATOM | 1105 | CA | ARG | X | 36 | 3.244 | 10.967 | −26.761 | 1.00 | 16.67 | C |
| ATOM | 1106 | CB | ARG | X | 36 | 3.094 | 9.935 | −25.637 | 1.00 | 16.76 | C |
| ATOM | 1107 | CG | ARG | X | 36 | 1.700 | 9.381 | −25.552 | 1.00 | 17.04 | C |
| ATOM | 1108 | CD | ARG | X | 36 | 1.571 | 8.364 | −24.388 | 1.00 | 16.39 | C |
| ATOM | 1109 | NE | ARG | X | 36 | 0.227 | 7.803 | −24.366 | 1.00 | 18.54 | N |
| ATOM | 1110 | CZ | ARG | X | 36 | −0.223 | 6.962 | −23.438 | 1.00 | 18.62 | C |
| ATOM | 1111 | NH1 | ARG | X | 36 | 0.588 | 6.580 | −22.462 | 1.00 | 21.25 | N |
| ATOM | 1112 | NH2 | ARG | X | 36 | −1.484 | 6.528 | −23.485 | 1.00 | 20.35 | N |
| ATOM | 1113 | C | ARG | X | 36 | 3.097 | 10.253 | −28.101 | 1.00 | 16.71 | C |
| ATOM | 1114 | O | ARG | X | 36 | 3.912 | 9.393 | −28.411 | 1.00 | 17.01 | O |
| ATOM | 1115 | N | TYR | X | 37 | 2.070 | 10.604 | −28.871 | 1.00 | 16.22 | N |
| ATOM | 1116 | CA | TYR | X | 37 | 1.879 | 10.031 | −30.188 | 1.00 | 16.33 | C |
| ATOM | 1117 | CB | TYR | X | 37 | 0.490 | 9.405 | −30.284 | 1.00 | 15.75 | C |
| ATOM | 1118 | CG | TYR | X | 37 | 0.193 | 8.736 | −31.613 | 1.00 | 16.26 | C |
| ATOM | 1119 | CD1 | TYR | X | 37 | 0.976 | 7.668 | −32.080 | 1.00 | 16.01 | C |
| ATOM | 1120 | CE1 | TYR | X | 37 | 0.692 | 7.034 | −33.306 | 1.00 | 16.04 | C |
| ATOM | 1121 | CZ | TYR | X | 37 | −0.424 | 7.451 | −34.033 | 1.00 | 15.66 | C |
| ATOM | 1122 | OH | TYR | X | 37 | −0.730 | 6.852 | −35.209 | 1.00 | 16.80 | O |
| ATOM | 1123 | CE2 | TYR | X | 37 | −1.224 | 8.508 | −33.593 | 1.00 | 15.15 | C |
| ATOM | 1124 | CD2 | TYR | X | 37 | −0.909 | 9.139 | −32.370 | 1.00 | 12.97 | C |
| ATOM | 1125 | C | TYR | X | 37 | 2.017 | 11.130 | −31.245 | 1.00 | 16.17 | C |
| ATOM | 1126 | O | TYR | X | 37 | 1.014 | 11.722 | −31.630 | 1.00 | 16.50 | O |
| ATOM | 1127 | N | PRO | X | 38 | 3.256 | 11.380 | −31.705 | 1.00 | 16.40 | N |
| ATOM | 1128 | CA | PRO | X | 38 | 3.567 | 12.448 | −32.689 | 1.00 | 16.88 | C |
| ATOM | 1129 | CB | PRO | X | 38 | 5.086 | 12.569 | −32.645 | 1.00 | 17.61 | C |
| ATOM | 1130 | CG | PRO | X | 38 | 5.506 | 11.234 | −32.261 | 1.00 | 17.20 | C |
| ATOM | 1131 | CD | PRO | X | 38 | 4.486 | 10.717 | −31.269 | 1.00 | 16.50 | C |
| ATOM | 1132 | C | PRO | X | 38 | 2.961 | 12.255 | −34.090 | 1.00 | 17.13 | C |
| ATOM | 1133 | O | PRO | X | 38 | 3.112 | 13.158 | −34.918 | 1.00 | 15.80 | O |
| ATOM | 1134 | N | VAL | X | 39 | 2.464 | 11.067 | −34.467 | 1.00 | 16.12 | N |
| ATOM | 1135 | CA | VAL | X | 39 | 2.558 | 10.585 | −35.833 | 1.00 | 16.25 | C |
| ATOM | 1136 | CB | VAL | X | 39 | 2.039 | 9.138 | −35.958 | 1.00 | 15.59 | C |
| ATOM | 1137 | CG1 | VAL | X | 39 | 1.579 | 8.827 | −37.386 | 1.00 | 17.51 | C |
| ATOM | 1138 | CG2 | VAL | X | 39 | 3.126 | 8.170 | −35.514 | 1.00 | 16.91 | C |
| ATOM | 1139 | C | VAL | X | 39 | 1.483 | 11.505 | −36.509 | 1.00 | 15.97 | C |
| ATOM | 1140 | O | VAL | X | 39 | 1.650 | 12.028 | −37.660 | 1.00 | 15.54 | O |
| ATOM | 1141 | N | ASP | X | 40 | 0.345 | 11.693 | −35.820 | 1.00 | 15.71 | N |
| ATOM | 1142 | CA | ASP | X | 40 | −0.744 | 12.586 | −36.364 | 1.00 | 16.21 | C |
| ATOM | 1143 | CB | ASP | X | 40 | −1.694 | 11.898 | −37.334 | 1.00 | 15.73 | C |
| ATOM | 1144 | CG | ASP | X | 40 | −2.187 | 12.823 | −38.448 | 1.00 | 17.57 | C |
| ATOM | 1145 | OD1 | ASP | X | 40 | −2.725 | 12.282 | −39.410 | 1.00 | 16.85 | O |
| ATOM | 1146 | OD2 | ASP | X | 40 | −2.051 | 14.075 | −38.369 | 1.00 | 17.34 | O |
| ATOM | 1147 | C | ASP | X | 40 | −1.415 | 13.316 | −35.185 | 1.00 | 16.13 | C |
| ATOM | 1148 | O | ASP | X | 40 | −1.305 | 12.870 | −34.054 | 1.00 | 16.63 | O |
| ATOM | 1149 | N | GLY | X | 41 | −2.197 | 14.356 | −35.413 | 1.00 | 17.00 | N |

-continued

| | | | | | | | | | | |
|---|---|---|---|---|---|---|---|---|---|---|
| ATOM | 1150 | CA | GLY | X | 41 | −3.461 | 14.629 | −34.760 | 1.00 | 16.01 | C |
| ATOM | 1151 | C | GLY | X | 41 | −3.003 | 15.934 | −34.023 | 1.00 | 15.82 | C |
| ATOM | 1152 | O | GLY | X | 41 | −3.607 | 16.389 | −33.023 | 1.00 | 14.91 | O |
| ATOM | 1153 | N | CYS | X | 42 | −1.961 | 16.609 | −34.547 | 1.00 | 15.17 | N |
| ATOM | 1154 | CA | CYS | X | 42 | −1.494 | 17.902 | −33.984 | 1.00 | 15.71 | C |
| ATOM | 1155 | CB | CYS | X | 42 | −0.446 | 18.568 | −34.897 | 1.00 | 16.18 | C |
| ATOM | 1156 | SG | CYS | X | 42 | −1.003 | 18.837 | −36.611 | 1.00 | 17.05 | S |
| ATOM | 1157 | C | CYS | X | 42 | −2.622 | 18.912 | −33.816 | 1.00 | 15.11 | C |
| ATOM | 1158 | O | CYS | X | 42 | −2.647 | 19.678 | −32.837 | 1.00 | 14.81 | O |
| ATOM | 1159 | N | TYR | X | 43 | −3.542 | 18.887 | −34.778 | 1.00 | 15.28 | N |
| ATOM | 1160 | CA | TYR | X | 43 | −4.665 | 19.825 | −34.829 | 1.00 | 15.81 | C |
| ATOM | 1161 | CB | TYR | X | 43 | −5.399 | 19.647 | −36.157 | 1.00 | 16.97 | C |
| ATOM | 1162 | CG | TYR | X | 43 | −5.825 | 18.222 | −36.460 | 1.00 | 18.18 | C |
| ATOM | 1163 | CD1 | TYR | X | 43 | −4.989 | 17.342 | −37.157 | 1.00 | 17.62 | C |
| ATOM | 1164 | CE1 | TYR | X | 43 | −5.391 | 16.010 | −37.432 | 1.00 | 18.43 | C |
| ATOM | 1165 | CZ | TYR | X | 43 | −6.641 | 15.579 | −37.014 | 1.00 | 18.42 | C |
| ATOM | 1166 | OH | TYR | X | 43 | −7.040 | 14.292 | −37.309 | 1.00 | 20.03 | O |
| ATOM | 1167 | CE2 | TYR | X | 43 | −7.486 | 16.447 | −36.328 | 1.00 | 19.22 | C |
| ATOM | 1168 | CD2 | TYR | X | 43 | −7.070 | 17.754 | −36.056 | 1.00 | 17.99 | C |
| ATOM | 1169 | C | TYR | X | 43 | −5.599 | 19.641 | −33.601 | 1.00 | 16.72 | C |
| ATOM | 1170 | O | TYR | X | 43 | −6.027 | 20.622 | −32.971 | 1.00 | 16.12 | O |
| ATOM | 1171 | N | ALA | X | 44 | −5.857 | 18.380 | −33.248 | 1.00 | 15.99 | N |
| ATOM | 1172 | CA | ALA | X | 44 | −6.635 | 18.056 | −32.038 | 1.00 | 16.06 | C |
| ATOM | 1173 | CB | ALA | X | 44 | −7.039 | 16.564 | −32.058 | 1.00 | 15.43 | C |
| ATOM | 1174 | C | ALA | X | 44 | −5.885 | 18.415 | −30.772 | 1.00 | 15.97 | C |
| ATOM | 1175 | O | ALA | X | 44 | −6.470 | 18.973 | −29.846 | 1.00 | 17.19 | O |
| ATOM | 1176 | N | ARG | X | 45 | −4.581 | 18.126 | −30.707 | 1.00 | 15.26 | N |
| ATOM | 1177 | CA | ARG | X | 45 | −3.802 | 18.477 | −29.525 | 1.00 | 15.64 | C |
| ATOM | 1178 | CB | ARG | X | 45 | −2.365 | 17.988 | −29.619 | 1.00 | 15.01 | C |
| ATOM | 1179 | CG | ARG | X | 45 | −2.260 | 16.437 | −29.805 | 1.00 | 15.05 | C |
| ATOM | 1180 | CD | ARG | X | 45 | −0.899 | 15.913 | −29.421 | 1.00 | 14.72 | C |
| ATOM | 1181 | NE | ARG | X | 45 | 0.179 | 16.500 | −30.209 | 1.00 | 13.99 | N |
| ATOM | 1182 | CZ | ARG | X | 45 | 0.540 | 16.100 | −31.428 | 1.00 | 15.52 | C |
| ATOM | 1183 | NH1 | ARG | X | 45 | −0.091 | 15.093 | −32.043 | 1.00 | 14.02 | N |
| ATOM | 1184 | NH2 | ARG | X | 45 | 1.562 | 16.732 | −32.028 | 1.00 | 14.30 | N |
| ATOM | 1185 | C | ARG | X | 45 | −3.801 | 19.986 | −29.304 | 1.00 | 15.28 | C |
| ATOM | 1186 | O | ARG | X | 45 | −3.951 | 20.450 | −28.174 | 1.00 | 15.43 | O |
| ATOM | 1187 | N | ALA | X | 46 | −3.623 | 20.743 | −30.385 | 1.00 | 15.00 | N |
| ATOM | 1188 | CA | ALA | X | 46 | −3.577 | 22.200 | −30.266 | 1.00 | 15.47 | C |
| ATOM | 1189 | CB | ALA | X | 46 | −3.162 | 22.849 | −31.614 | 1.00 | 14.97 | C |
| ATOM | 1190 | C | ALA | X | 46 | −4.914 | 22.773 | −29.806 | 1.00 | 15.68 | C |
| ATOM | 1191 | O | ALA | X | 46 | −4.941 | 23.721 | −29.001 | 1.00 | 15.76 | O |
| ATOM | 1192 | N | HIS | X | 47 | −6.007 | 22.219 | −30.332 | 1.00 | 16.33 | N |
| ATOM | 1193 | CA | HIS | X | 47 | −7.336 | 22.727 | −29.986 | 1.00 | 17.07 | C |
| ATOM | 1194 | CB | HIS | X | 47 | −8.430 | 22.198 | −30.907 | 1.00 | 17.39 | C |
| ATOM | 1195 | CG | HIS | X | 47 | −9.401 | 23.248 | −31.359 | 1.00 | 18.44 | C |
| ATOM | 1196 | ND1 | HIS | X | 47 | −9.000 | 24.485 | −31.833 | 1.00 | 18.43 | N |
| ATOM | 1197 | CE1 | HIS | X | 47 | −10.064 | 25.182 | −32.180 | 1.00 | 21.80 | C |
| ATOM | 1198 | NE2 | HIS | X | 47 | −11.139 | 24.447 | −31.961 | 1.00 | 21.01 | N |
| ATOM | 1199 | CD2 | HIS | X | 47 | −10.752 | 23.234 | −31.440 | 1.00 | 20.49 | C |
| ATOM | 1200 | C | HIS | X | 47 | −7.635 | 22.387 | −28.528 | 1.00 | 17.72 | C |
| ATOM | 1201 | O | HIS | X | 47 | −8.278 | 23.174 | −27.832 | 1.00 | 17.51 | O |
| ATOM | 1202 | N | LYS | X | 48 | −7.206 | 21.210 | −28.079 | 1.00 | 16.37 | N |
| ATOM | 1203 | CA | LYS | X | 48 | −7.403 | 20.874 | −26.658 | 1.00 | 16.28 | C |
| ATOM | 1204 | CB | LYS | X | 48 | −7.123 | 19.377 | −26.434 | 1.00 | 16.38 | C |
| ATOM | 1205 | CG | LYS | X | 48 | −7.701 | 18.800 | −25.101 | 1.00 | 16.38 | C |
| ATOM | 1206 | CD | LYS | X | 48 | −9.246 | 18.740 | −25.186 | 1.00 | 16.81 | C |
| ATOM | 1207 | CE | LYS | X | 48 | −9.834 | 18.020 | −23.963 | 1.00 | 18.81 | C |
| ATOM | 1208 | NZ | LYS | X | 48 | −11.318 | 18.043 | −24.070 | 1.00 | 19.45 | N |
| ATOM | 1209 | C | LYS | X | 48 | −6.533 | 21.743 | −25.733 | 1.00 | 16.64 | C |
| ATOM | 1210 | O | LYS | X | 48 | −6.984 | 22.135 | −24.636 | 1.00 | 16.69 | O |
| ATOM | 1211 | N | MET | X | 49 | −5.302 | 22.055 | −26.143 | 1.00 | 16.28 | N |
| ATOM | 1212 | CA | MET | X | 49 | −4.453 | 23.000 | −25.376 | 1.00 | 16.31 | C |
| ATOM | 1213 | CB | MET | X | 49 | −3.067 | 23.202 | −26.012 | 1.00 | 16.23 | C |
| ATOM | 1214 | CG | MET | X | 49 | −2.187 | 21.948 | −25.964 | 1.00 | 17.24 | C |
| ATOM | 1215 | SD | MET | X | 49 | −0.490 | 22.322 | −26.360 | 1.00 | 17.04 | S |
| ATOM | 1216 | CE | MET | X | 49 | −0.511 | 22.380 | −28.167 | 1.00 | 18.03 | C |
| ATOM | 1217 | C | MET | X | 49 | −5.167 | 24.356 | −25.263 | 1.00 | 17.02 | C |
| ATOM | 1218 | O | MET | X | 49 | −5.179 | 24.985 | −24.193 | 1.00 | 16.91 | O |
| ATOM | 1219 | N | ARG | X | 50 | −5.773 | 24.787 | −26.361 | 1.00 | 17.47 | N |
| ATOM | 1220 | CA | ARG | X | 50 | −6.467 | 26.084 | −26.372 | 1.00 | 18.24 | C |
| ATOM | 1221 | CB | ARG | X | 50 | −7.037 | 26.381 | −27.741 | 1.00 | 18.03 | C |
| ATOM | 1222 | CG | ARG | X | 50 | −7.862 | 27.659 | −27.717 | 1.00 | 18.49 | C |
| ATOM | 1223 | CD | ARG | X | 50 | −8.243 | 28.043 | −29.116 | 1.00 | 19.00 | C |
| ATOM | 1224 | NE | ARG | X | 50 | −9.116 | 29.206 | −29.137 | 1.00 | 17.75 | N |
| ATOM | 1225 | CZ | ARG | X | 50 | −10.423 | 29.167 | −29.365 | 1.00 | 20.14 | C |
| ATOM | 1226 | NH1 | ARG | X | 50 | −11.023 | 28.018 | −29.586 | 1.00 | 18.68 | N |
| ATOM | 1227 | NH2 | ARG | X | 50 | −11.133 | 30.298 | −29.359 | 1.00 | 20.46 | N |
| ATOM | 1228 | C | ARG | X | 50 | −7.626 | 26.042 | −25.386 | 1.00 | 19.18 | C |
| ATOM | 1229 | O | ARG | X | 50 | −7.865 | 27.010 | −24.648 | 1.00 | 19.70 | O |

-continued

| | | | | | | | | | | |
|---|---|---|---|---|---|---|---|---|---|---|
| ATOM | 1230 | N | GLN | X | 51 | −8.339 | 24.917 | −25.356 | 1.00 | 19.39 | N |
| ATOM | 1231 | CA | GLN | X | 51 | −9.462 | 24.787 | −24.408 | 1.00 | 20.51 | C |
| ATOM | 1232 | CB | GLN | X | 51 | −10.187 | 23.453 | −24.591 | 1.00 | 19.64 | C |
| ATOM | 1233 | CG | GLN | X | 51 | −11.428 | 23.324 | −23.685 | 1.00 | 22.57 | C |
| ATOM | 1234 | CD | GLN | X | 51 | −12.055 | 21.965 | −23.760 | 1.00 | 23.54 | C |
| ATOM | 1235 | OE1 | GLN | X | 51 | −11.374 | 20.950 | −23.625 | 1.00 | 22.95 | O |
| ATOM | 1236 | NE2 | GLN | X | 51 | −13.372 | 21.931 | −23.943 | 1.00 | 25.85 | N |
| ATOM | 1237 | C | GLN | X | 51 | −9.027 | 24.968 | −22.953 | 1.00 | 20.23 | C |
| ATOM | 1238 | O | GLN | X | 51 | −9.753 | 25.606 | −22.160 | 1.00 | 22.75 | O |
| ATOM | 1239 | N | ILE | X | 52 | −7.869 | 24.426 | −22.589 | 1.00 | 20.40 | N |
| ATOM | 1240 | CA | ILE | X | 52 | −7.304 | 24.626 | −21.251 | 1.00 | 20.81 | C |
| ATOM | 1241 | CB | ILE | X | 52 | −6.018 | 23.826 | −21.025 | 1.00 | 21.50 | C |
| ATOM | 1242 | CG1 | ILE | X | 52 | −6.318 | 22.318 | −21.191 | 1.00 | 22.03 | C |
| ATOM | 1243 | CD1 | ILE | X | 52 | −5.106 | 21.459 | −21.110 | 1.00 | 25.90 | C |
| ATOM | 1244 | CG2 | ILE | X | 52 | −5.384 | 24.196 | −19.657 | 1.00 | 20.43 | C |
| ATOM | 1245 | C | ILE | X | 52 | −7.070 | 26.124 | −21.000 | 1.00 | 21.51 | C |
| ATOM | 1246 | O | ILE | X | 52 | −7.460 | 26.641 | −19.959 | 1.00 | 21.54 | O |
| ATOM | 1247 | N | LEU | X | 53 | −6.459 | 26.830 | −21.954 | 1.00 | 20.38 | N |
| ATOM | 1248 | CA | LEU | X | 53 | −6.325 | 28.285 | −21.798 | 1.00 | 20.55 | C |
| ATOM | 1249 | CB | LEU | X | 53 | −5.629 | 28.918 | −23.015 | 1.00 | 20.08 | C |
| ATOM | 1250 | CG | LEU | X | 53 | −4.155 | 29.235 | −22.805 | 1.00 | 20.87 | C |
| ATOM | 1251 | CD1 | LEU | X | 53 | −3.333 | 27.955 | −22.569 | 1.00 | 22.18 | C |
| ATOM | 1252 | CD2 | LEU | X | 53 | −3.639 | 30.044 | −24.010 | 1.00 | 22.18 | C |
| ATOM | 1253 | C | LEU | X | 53 | −7.692 | 28.940 | −21.614 | 1.00 | 21.51 | C |
| ATOM | 1254 | O | LEU | X | 53 | −7.858 | 29.810 | −20.741 | 1.00 | 21.61 | O |
| ATOM | 1255 | N | MET | X | 54 | −8.667 | 28.519 | −22.408 | 1.00 | 22.23 | N |
| ATOM | 1256 | CA | MET | X | 54 | −10.009 | 29.112 | −22.328 | 1.00 | 23.62 | C |
| ATOM | 1257 | CB | MET | X | 54 | −10.897 | 28.626 | −23.454 | 1.00 | 23.52 | C |
| ATOM | 1258 | CG | MET | X | 54 | −10.454 | 29.170 | −24.816 | 1.00 | 24.11 | C |
| ATOM | 1259 | SD | MET | X | 54 | −11.521 | 28.652 | −26.133 | 1.00 | 26.86 | S |
| ATOM | 1260 | CE | MET | X | 54 | −13.127 | 29.338 | −25.734 | 1.00 | 31.24 | C |
| ATOM | 1261 | C | MET | X | 54 | −10.691 | 28.854 | −20.990 | 1.00 | 24.52 | C |
| ATOM | 1262 | O | MET | X | 54 | −11.439 | 29.719 | −20.507 | 1.00 | 24.59 | O |
| ATOM | 1263 | N | ASN | X | 55 | −10.391 | 27.697 | −20.398 | 1.00 | 24.35 | N |
| ATOM | 1264 | CA | ASN | X | 55 | −10.884 | 27.344 | −19.056 | 1.00 | 25.79 | C |
| ATOM | 1265 | CB | ASN | X | 55 | −10.500 | 25.904 | −18.688 | 1.00 | 25.85 | C |
| ATOM | 1266 | CG | ASN | X | 55 | −11.265 | 24.835 | −19.490 | 1.00 | 26.61 | C |
| ATOM | 1267 | OD1 | ASN | X | 55 | −10.878 | 23.662 | −19.477 | 1.00 | 29.01 | O |
| ATOM | 1268 | ND2 | ASN | X | 55 | −12.343 | 25.216 | −20.147 | 1.00 | 28.24 | N |
| ATOM | 1269 | C | ASN | X | 55 | −10.341 | 28.297 | −18.001 | 1.00 | 26.00 | C |
| ATOM | 1270 | O | ASN | X | 55 | −10.936 | 28.433 | −16.920 | 1.00 | 26.90 | O |
| ATOM | 1271 | N | ASN | X | 56 | −9.212 | 28.935 | −18.311 | 1.00 | 25.36 | N |
| ATOM | 1272 | CA | ASN | X | 56 | −8.540 | 29.897 | −17.442 | 1.00 | 25.43 | C |
| ATOM | 1273 | CB | ASN | X | 56 | −7.024 | 29.707 | −17.492 | 1.00 | 25.45 | C |
| ATOM | 1274 | CG | ASN | X | 56 | −6.550 | 28.507 | −16.712 | 1.00 | 27.26 | C |
| ATOM | 1275 | OD1 | ASN | X | 56 | −5.968 | 28.643 | −15.626 | 1.00 | 27.92 | O |
| ATOM | 1276 | ND2 | ASN | X | 56 | −6.760 | 27.310 | −17.276 | 1.00 | 27.03 | N |
| ATOM | 1277 | C | ASN | X | 56 | −8.848 | 31.348 | −17.816 | 1.00 | 25.35 | C |
| ATOM | 1278 | O | ASN | X | 56 | −8.306 | 32.275 | −17.199 | 1.00 | 26.98 | O |
| ATOM | 1279 | N | GLY | X | 57 | −9.682 | 31.547 | −18.825 | 1.00 | 24.61 | N |
| ATOM | 1280 | CA | GLY | X | 57 | −10.090 | 32.891 | −19.233 | 1.00 | 24.45 | C |
| ATOM | 1281 | C | GLY | X | 57 | −9.190 | 33.523 | −20.286 | 1.00 | 24.47 | C |
| ATOM | 1282 | O | GLY | X | 57 | −9.179 | 34.758 | −20.457 | 1.00 | 24.19 | O |
| ATOM | 1283 | N | TYR | X | 58 | −8.454 | 32.682 | −21.020 | 1.00 | 23.62 | N |
| ATOM | 1284 | CA | TYR | X | 58 | −7.529 | 33.175 | −22.054 | 1.00 | 23.10 | C |
| ATOM | 1285 | CB | TYR | X | 58 | −6.071 | 32.866 | −21.690 | 1.00 | 23.30 | C |
| ATOM | 1286 | CG | TYR | X | 58 | −5.658 | 33.482 | −20.395 | 1.00 | 23.77 | C |
| ATOM | 1287 | CD1 | TYR | X | 58 | −5.419 | 32.701 | −19.265 | 1.00 | 22.90 | C |
| ATOM | 1288 | CE1 | TYR | X | 58 | −5.046 | 33.290 | −18.046 | 1.00 | 25.04 | C |
| ATOM | 1289 | CZ | TYR | X | 58 | −4.945 | 34.665 | −17.970 | 1.00 | 25.01 | C |
| ATOM | 1290 | OH | TYR | X | 58 | −4.593 | 35.276 | −16.783 | 1.00 | 25.65 | O |
| ATOM | 1291 | CE2 | TYR | X | 58 | −5.184 | 35.456 | −19.088 | 1.00 | 24.84 | C |
| ATOM | 1292 | CD2 | TYR | X | 58 | −5.539 | 34.867 | −20.282 | 1.00 | 25.03 | C |
| ATOM | 1293 | C | TYR | X | 58 | −7.811 | 32.605 | −23.425 | 1.00 | 22.63 | C |
| ATOM | 1294 | O | TYR | X | 58 | −8.315 | 31.487 | −23.554 | 1.00 | 22.45 | O |
| ATOM | 1295 | N | ASP | X | 59 | −7.488 | 33.387 | −24.452 | 1.00 | 21.75 | N |
| ATOM | 1296 | CA | ASP | X | 59 | −7.402 | 32.843 | −25.804 | 1.00 | 21.03 | C |
| ATOM | 1297 | CB | ASP | X | 59 | −8.348 | 33.573 | −26.774 | 1.00 | 22.15 | C |
| ATOM | 1298 | CG | ASP | X | 59 | −8.896 | 32.657 | −27.884 | 1.00 | 22.92 | C |
| ATOM | 1299 | OD1 | ASP | X | 59 | −8.253 | 31.629 | −28.231 | 1.00 | 20.18 | O |
| ATOM | 1300 | OD2 | ASP | X | 59 | −9.978 | 32.969 | −28.439 | 1.00 | 22.36 | O |
| ATOM | 1301 | C | ASP | X | 59 | −5.939 | 32.892 | −26.260 | 1.00 | 20.88 | C |
| ATOM | 1302 | O | ASP | X | 59 | −5.059 | 33.281 | −25.505 | 1.00 | 19.95 | O |
| ATOM | 1303 | N | CYS | X | 60 | −5.695 | 32.421 | −27.477 | 1.00 | 20.02 | N |
| ATOM | 1304 | CA | CYS | X | 60 | −4.356 | 32.382 | −28.019 | 1.00 | 18.73 | C |
| ATOM | 1305 | CB | CYS | X | 60 | −3.596 | 31.128 | −27.531 | 1.00 | 19.29 | C |
| ATOM | 1306 | SG | CYS | X | 60 | −4.413 | 29.580 | −27.984 | 1.00 | 20.53 | S |
| ATOM | 1307 | C | CYS | X | 60 | −4.486 | 32.348 | −29.530 | 1.00 | 17.87 | C |
| ATOM | 1308 | O | CYS | X | 60 | −5.593 | 32.372 | −30.080 | 1.00 | 17.72 | O |
| ATOM | 1309 | N | GLU | X | 61 | −3.346 | 32.341 | −30.191 | 1.00 | 16.00 | N |

-continued

| | | | | | | | | | | |
|---|---|---|---|---|---|---|---|---|---|---|
| ATOM | 1310 | CA | GLU | X | 61 | −3.280 | 32.114 | −31.620 | 1.00 | 15.16 | C |
| ATOM | 1311 | CB | GLU | X | 61 | −2.239 | 33.045 | −32.243 | 1.00 | 15.68 | C |
| ATOM | 1312 | CG | GLU | X | 61 | −2.728 | 34.504 | −32.373 | 1.00 | 17.69 | C |
| ATOM | 1313 | CD | GLU | X | 61 | −1.606 | 35.405 | −32.803 | 1.00 | 19.92 | C |
| ATOM | 1314 | OE1 | GLU | X | 61 | −0.694 | 35.628 | −31.985 | 1.00 | 22.67 | O |
| ATOM | 1315 | OE2 | GLU | X | 61 | −1.635 | 35.882 | −33.971 | 1.00 | 22.78 | O |
| ATOM | 1316 | C | GLU | X | 61 | −2.887 | 30.656 | −31.899 | 1.00 | 14.78 | C |
| ATOM | 1317 | O | GLU | X | 61 | −2.483 | 29.939 | −30.980 | 1.00 | 15.30 | O |
| ATOM | 1318 | N | LYS | X | 62 | −3.039 | 30.240 | −33.154 | 1.00 | 15.34 | N |
| ATOM | 1319 | CA | LYS | X | 62 | −2.380 | 29.008 | −33.650 | 1.00 | 15.66 | C |
| ATOM | 1320 | CB | LYS | X | 62 | −3.336 | 28.180 | −34.492 | 1.00 | 15.90 | C |
| ATOM | 1321 | CG | LYS | X | 62 | −4.595 | 27.669 | −33.750 | 1.00 | 16.08 | C |
| ATOM | 1322 | CD | LYS | X | 62 | −4.244 | 26.606 | −32.713 | 1.00 | 18.47 | C |
| ATOM | 1323 | CE | LYS | X | 62 | −5.529 | 26.136 | −31.974 | 1.00 | 15.81 | C |
| ATOM | 1324 | NZ | LYS | X | 62 | −6.623 | 25.629 | −32.882 | 1.00 | 15.28 | N |
| ATOM | 1325 | C | LYS | X | 62 | −1.257 | 29.485 | −34.562 | 1.00 | 15.57 | C |
| ATOM | 1326 | O | LYS | X | 62 | −1.395 | 30.518 | −35.242 | 1.00 | 15.57 | O |
| ATOM | 1327 | N | GLN | X | 63 | −0.155 | 28.741 | −34.573 | 1.00 | 14.46 | N |
| ATOM | 1328 | CA | GLN | X | 63 | 0.809 | 28.884 | −35.671 | 1.00 | 14.09 | C |
| ATOM | 1329 | CB | GLN | X | 63 | 2.220 | 29.222 | −35.162 | 1.00 | 14.01 | C |
| ATOM | 1330 | CG | GLN | X | 63 | 3.178 | 29.406 | −36.366 | 1.00 | 14.62 | C |
| ATOM | 1331 | CD | GLN | X | 63 | 4.496 | 29.999 | −35.981 | 1.00 | 16.22 | C |
| ATOM | 1332 | OE1 | GLN | X | 63 | 5.536 | 29.345 | −36.067 | 1.00 | 17.74 | O |
| ATOM | 1333 | NE2 | GLN | X | 63 | 4.466 | 31.241 | −35.516 | 1.00 | 15.91 | N |
| ATOM | 1334 | C | GLN | X | 63 | 0.805 | 27.574 | −36.444 | 1.00 | 14.10 | C |
| ATOM | 1335 | O | GLN | X | 63 | 0.977 | 26.507 | −35.822 | 1.00 | 13.78 | O |
| ATOM | 1336 | N | PHE | X | 64 | 0.549 | 27.652 | −37.746 | 1.00 | 13.74 | N |
| ATOM | 1337 | CA | PHE | X | 64 | 0.638 | 26.492 | −38.670 | 1.00 | 13.64 | C |
| ATOM | 1338 | CB | PHE | X | 64 | −0.525 | 26.491 | −39.653 | 1.00 | 13.69 | C |
| ATOM | 1339 | CG | PHE | X | 64 | −1.856 | 26.225 | −39.011 | 1.00 | 14.24 | C |
| ATOM | 1340 | CD1 | PHE | X | 64 | −2.371 | 24.919 | −38.950 | 1.00 | 14.22 | C |
| ATOM | 1341 | CE1 | PHE | X | 64 | −3.630 | 24.652 | −38.337 | 1.00 | 12.26 | C |
| ATOM | 1342 | CZ | PHE | X | 64 | −4.372 | 25.719 | −37.811 | 1.00 | 12.18 | C |
| ATOM | 1343 | CE2 | PHE | X | 64 | −3.849 | 27.026 | −37.865 | 1.00 | 14.82 | C |
| ATOM | 1344 | CD2 | PHE | X | 64 | −2.601 | 27.274 | −38.468 | 1.00 | 14.15 | C |
| ATOM | 1345 | C | PHE | X | 64 | 1.933 | 26.635 | −39.439 | 1.00 | 14.39 | C |
| ATOM | 1346 | O | PHE | X | 64 | 2.171 | 27.680 | −40.058 | 1.00 | 14.50 | O |
| ATOM | 1347 | N | VAL | X | 65 | 2.769 | 25.588 | −39.415 | 1.00 | 13.41 | N |
| ATOM | 1348 | CA | VAL | X | 65 | 4.007 | 25.596 | −40.198 | 1.00 | 13.54 | C |
| ATOM | 1349 | CB | VAL | X | 65 | 5.278 | 25.408 | −39.319 | 1.00 | 13.61 | C |
| ATOM | 1350 | CG1 | VAL | X | 65 | 5.224 | 24.116 | −38.427 | 1.00 | 13.43 | C |
| ATOM | 1351 | CG2 | VAL | X | 65 | 6.539 | 25.477 | −40.194 | 1.00 | 13.72 | C |
| ATOM | 1352 | C | VAL | X | 65 | 3.864 | 24.487 | −41.241 | 1.00 | 13.42 | C |
| ATOM | 1353 | O | VAL | X | 65 | 3.333 | 23.427 | −40.932 | 1.00 | 12.31 | O |
| ATOM | 1354 | N | TYR | X | 66 | 4.301 | 24.741 | −42.467 | 1.00 | 12.66 | N |
| ATOM | 1355 | CA | TYR | X | 66 | 4.072 | 23.798 | −43.557 | 1.00 | 13.47 | C |
| ATOM | 1356 | CB | TYR | X | 66 | 3.137 | 24.366 | −44.622 | 1.00 | 13.30 | C |
| ATOM | 1357 | CG | TYR | X | 66 | 1.796 | 24.855 | −44.103 | 1.00 | 12.81 | C |
| ATOM | 1358 | CD1 | TYR | X | 66 | 0.644 | 24.069 | −44.241 | 1.00 | 13.99 | C |
| ATOM | 1359 | CE1 | TYR | X | 66 | −0.607 | 24.514 | −43.762 | 1.00 | 13.90 | C |
| ATOM | 1360 | CZ | TYR | X | 66 | −0.671 | 25.770 | −43.167 | 1.00 | 14.22 | C |
| ATOM | 1361 | OH | TYR | X | 66 | −1.854 | 26.296 | −42.676 | 1.00 | 13.31 | O |
| ATOM | 1362 | CE2 | TYR | X | 66 | 0.452 | 26.555 | −42.994 | 1.00 | 11.76 | C |
| ATOM | 1363 | CD2 | TYR | X | 66 | 1.703 | 26.106 | −43.491 | 1.00 | 12.83 | C |
| ATOM | 1364 | C | TYR | X | 66 | 5.377 | 23.534 | −44.275 | 1.00 | 13.71 | C |
| ATOM | 1365 | O | TYR | X | 66 | 6.204 | 24.426 | −44.414 | 1.00 | 14.47 | O |
| ATOM | 1366 | N | GLY | X | 67 | 5.527 | 22.319 | −44.774 | 1.00 | 14.84 | N |
| ATOM | 1367 | CA | GLY | X | 67 | 6.699 | 22.024 | −45.591 | 1.00 | 15.18 | C |
| ATOM | 1368 | C | GLY | X | 67 | 7.000 | 20.541 | −45.634 | 1.00 | 14.59 | C |
| ATOM | 1369 | O | GLY | X | 67 | 6.123 | 19.696 | −45.444 | 1.00 | 15.46 | O |
| ATOM | 1370 | N | ASN | X | 68 | 8.262 | 20.237 | −45.918 | 1.00 | 15.41 | N |
| ATOM | 1371 | CA | ASN | X | 68 | 8.738 | 18.867 | −45.856 | 1.00 | 15.00 | C |
| ATOM | 1372 | CB | ASN | X | 68 | 9.881 | 18.710 | −46.857 | 1.00 | 15.24 | C |
| ATOM | 1373 | CG | ASN | X | 68 | 10.441 | 17.297 | −46.874 | 1.00 | 17.42 | C |
| ATOM | 1374 | OD1 | ASN | X | 68 | 9.731 | 16.333 | −46.593 | 1.00 | 17.91 | O |
| ATOM | 1375 | ND2 | ASN | X | 68 | 11.739 | 17.173 | −47.207 | 1.00 | 21.74 | N |
| ATOM | 1376 | C | ASN | X | 68 | 9.232 | 18.708 | −44.414 | 1.00 | 14.73 | C |
| ATOM | 1377 | O | ASN | X | 68 | 10.408 | 18.903 | −44.138 | 1.00 | 14.38 | O |
| ATOM | 1378 | N | LEU | X | 69 | 8.331 | 18.403 | −43.481 | 1.00 | 13.30 | N |
| ATOM | 1379 | CA | LEU | X | 69 | 8.705 | 18.479 | −42.071 | 1.00 | 13.43 | C |
| ATOM | 1380 | CB | LEU | X | 69 | 7.576 | 19.056 | −41.216 | 1.00 | 14.19 | C |
| ATOM | 1381 | CG | LEU | X | 69 | 6.922 | 20.327 | −41.777 | 1.00 | 12.92 | C |
| ATOM | 1382 | CD1 | LEU | X | 69 | 5.875 | 20.776 | −40.744 | 1.00 | 15.38 | C |
| ATOM | 1383 | CD2 | LEU | X | 69 | 7.950 | 21.438 | −41.948 | 1.00 | 14.58 | C |
| ATOM | 1384 | C | LEU | X | 69 | 9.095 | 17.105 | −41.511 | 1.00 | 13.87 | C |
| ATOM | 1385 | O | LEU | X | 69 | 8.525 | 16.070 | −41.907 | 1.00 | 14.97 | O |
| ATOM | 1386 | N | LYS | X | 70 | 10.058 | 17.108 | −40.593 | 1.00 | 15.12 | N |
| ATOM | 1387 | CA | LYS | X | 70 | 10.454 | 15.880 | −39.860 | 1.00 | 15.83 | C |
| ATOM | 1388 | CB | LYS | X | 70 | 11.626 | 15.158 | −40.542 | 1.00 | 17.13 | C |
| ATOM | 1389 | CG | LYS | X | 70 | 11.237 | 14.585 | −41.901 | 1.00 | 18.62 | C |

-continued

| | | | | | | | | | | |
|---|---|---|---|---|---|---|---|---|---|---|
| ATOM | 1390 | CD | LYS | X | 70 | 12.300 | 13.667 | −42.446 | 1.00 | 21.04 | C |
| ATOM | 1391 | CE | LYS | X | 70 | 11.814 | 13.028 | −43.725 | 1.00 | 18.64 | C |
| ATOM | 1392 | NZ | LYS | X | 70 | 11.670 | 13.975 | −44.877 | 1.00 | 18.60 | N |
| ATOM | 1393 | C | LYS | X | 70 | 10.800 | 16.265 | −38.440 | 1.00 | 15.62 | C |
| ATOM | 1394 | O | LYS | X | 70 | 11.433 | 17.307 | −38.208 | 1.00 | 15.95 | O |
| ATOM | 1395 | N | ALA | X | 71 | 10.335 | 15.461 | −37.494 | 1.00 | 16.81 | N |
| ATOM | 1396 | CA | ALA | X | 71 | 10.606 | 15.706 | −36.075 | 1.00 | 17.29 | C |
| ATOM | 1397 | CB | ALA | X | 71 | 9.416 | 16.337 | −35.412 | 1.00 | 16.66 | C |
| ATOM | 1398 | C | ALA | X | 71 | 10.961 | 14.405 | −35.377 | 1.00 | 18.43 | C |
| ATOM | 1399 | O | ALA | X | 71 | 10.543 | 13.333 | −35.797 | 1.00 | 18.33 | O |
| ATOM | 1400 | N | SER | X | 72 | 11.732 | 14.531 | −34.309 | 1.00 | 19.57 | N |
| ATOM | 1401 | CA | SER | X | 72 | 12.181 | 13.353 | −33.541 | 1.00 | 21.76 | C |
| ATOM | 1402 | CB | SER | X | 72 | 13.701 | 13.274 | −33.568 | 1.00 | 22.22 | C |
| ATOM | 1403 | OG | SER | X | 72 | 14.143 | 12.255 | −32.664 | 1.00 | 24.53 | O |
| ATOM | 1404 | C | SER | X | 72 | 11.705 | 13.457 | −32.113 | 1.00 | 22.89 | C |
| ATOM | 1405 | O | SER | X | 72 | 11.773 | 14.542 | −31.527 | 1.00 | 22.89 | O |
| ATOM | 1406 | N | THR | X | 73 | 11.228 | 12.338 | −31.552 | 1.00 | 23.55 | N |
| ATOM | 1407 | CA | THR | X | 73 | 10.892 | 12.258 | −30.125 | 1.00 | 24.97 | C |
| ATOM | 1408 | CB | THR | X | 73 | 9.965 | 11.066 | −29.817 | 1.00 | 25.17 | C |
| ATOM | 1409 | OG1 | THR | X | 73 | 10.667 | 9.845 | −30.092 | 1.00 | 25.85 | O |
| ATOM | 1410 | CG2 | THR | X | 73 | 8.648 | 11.138 | −30.624 | 1.00 | 25.89 | C |
| ATOM | 1411 | C | THR | X | 73 | 12.119 | 12.053 | −29.243 | 1.00 | 26.11 | C |
| ATOM | 1412 | O | THR | X | 73 | 11.993 | 11.977 | −28.009 | 1.00 | 26.35 | O |
| ATOM | 1413 | N | GLY | X | 74 | 13.288 | 11.931 | −29.868 | 1.00 | 26.21 | N |
| ATOM | 1414 | CA | GLY | X | 74 | 14.502 | 11.448 | −29.180 | 1.00 | 27.69 | C |
| ATOM | 1415 | C | GLY | X | 74 | 14.780 | 9.975 | −29.484 | 1.00 | 27.75 | C |
| ATOM | 1416 | O | GLY | X | 74 | 15.922 | 9.528 | −29.425 | 1.00 | 29.34 | O |
| ATOM | 1417 | N | THR | X | 75 | 13.743 | 9.211 | −29.825 | 1.00 | 27.09 | N |
| ATOM | 1418 | CA | THR | X | 75 | 13.914 | 7.797 | −30.119 | 1.00 | 27.33 | C |
| ATOM | 1419 | CB | THR | X | 75 | 13.317 | 6.897 | −28.997 | 1.00 | 27.78 | C |
| ATOM | 1420 | OG1 | THR | X | 75 | 11.926 | 7.195 | −28.820 | 1.00 | 29.69 | O |
| ATOM | 1421 | CG2 | THR | X | 75 | 14.056 | 7.123 | −27.667 | 1.00 | 27.68 | C |
| ATOM | 1422 | C | THR | X | 75 | 13.362 | 7.349 | −31.475 | 1.00 | 26.68 | C |
| ATOM | 1423 | O | THR | X | 75 | 13.688 | 6.262 | −31.953 | 1.00 | 26.86 | O |
| ATOM | 1424 | N | CYS | X | 76 | 12.504 | 8.165 | −32.085 | 1.00 | 24.38 | N |
| ATOM | 1425 | CA | CYS | X | 76 | 11.963 | 7.822 | −33.393 | 1.00 | 22.91 | C |
| ATOM | 1426 | CB | CYS | X | 76 | 10.798 | 6.825 | −33.273 | 1.00 | 22.50 | C |
| ATOM | 1427 | SG | CYS | X | 76 | 9.399 | 7.359 | −32.320 | 1.00 | 23.58 | S |
| ATOM | 1428 | C | CYS | X | 76 | 11.550 | 9.113 | −34.115 | 1.00 | 21.67 | C |
| ATOM | 1429 | O | CYS | X | 76 | 11.329 | 10.142 | −33.464 | 1.00 | 21.35 | O |
| ATOM | 1430 | N | CYS | X | 77 | 11.493 | 9.037 | −35.440 | 1.00 | 21.32 | N |
| ATOM | 1431 | CA | CYS | X | 77 | 11.156 | 10.191 | −36.282 | 1.00 | 21.34 | C |
| ATOM | 1432 | CB | CYS | X | 77 | 12.140 | 10.328 | −37.435 | 1.00 | 22.02 | C |
| ATOM | 1433 | SG | CYS | X | 77 | 13.798 | 10.804 | −36.934 | 1.00 | 28.71 | S |
| ATOM | 1434 | C | CYS | X | 77 | 9.758 | 10.045 | −36.852 | 1.00 | 20.32 | C |
| ATOM | 1435 | O | CYS | X | 77 | 9.281 | 8.929 | −37.106 | 1.00 | 20.24 | O |
| ATOM | 1436 | N | VAL | X | 78 | 9.103 | 11.196 | −37.058 | 1.00 | 18.30 | N |
| ATOM | 1437 | CA | VAL | X | 78 | 7.894 | 11.248 | −37.850 | 1.00 | 18.16 | C |
| ATOM | 1438 | CB | VAL | X | 78 | 6.653 | 11.600 | −36.981 | 1.00 | 17.82 | C |
| ATOM | 1439 | CG1 | VAL | X | 78 | 6.419 | 10.521 | −35.918 | 1.00 | 18.61 | C |
| ATOM | 1440 | CG2 | VAL | X | 78 | 6.851 | 12.937 | −36.255 | 1.00 | 18.16 | C |
| ATOM | 1441 | C | VAL | X | 78 | 8.075 | 12.278 | −38.984 | 1.00 | 16.32 | C |
| ATOM | 1442 | O | VAL | X | 78 | 8.883 | 13.201 | −38.875 | 1.00 | 16.36 | O |
| ATOM | 1443 | N | ALA | X | 79 | 7.313 | 12.095 | −40.064 | 1.00 | 16.33 | N |
| ATOM | 1444 | CA | ALA | X | 79 | 7.283 | 13.049 | −41.183 | 1.00 | 14.60 | C |
| ATOM | 1445 | CB | ALA | X | 79 | 7.557 | 12.363 | −42.512 | 1.00 | 15.52 | C |
| ATOM | 1446 | C | ALA | X | 79 | 5.915 | 13.698 | −41.233 | 1.00 | 13.80 | C |
| ATOM | 1447 | O | ALA | X | 79 | 4.883 | 13.031 | −41.093 | 1.00 | 13.90 | O |
| ATOM | 1448 | N | TRP | X | 80 | 5.922 | 15.002 | −41.459 | 1.00 | 13.65 | N |
| ATOM | 1449 | CA | TRP | X | 80 | 4.662 | 15.738 | −41.531 | 1.00 | 12.96 | C |
| ATOM | 1450 | CB | TRP | X | 80 | 4.523 | 16.629 | −40.300 | 1.00 | 13.88 | C |
| ATOM | 1451 | CG | TRP | X | 80 | 4.408 | 15.978 | −38.956 | 1.00 | 13.65 | C |
| ATOM | 1452 | CD1 | TRP | X | 80 | 3.708 | 14.815 | −38.617 | 1.00 | 13.60 | C |
| ATOM | 1453 | NE1 | TRP | X | 80 | 3.803 | 14.613 | −37.228 | 1.00 | 14.32 | N |
| ATOM | 1454 | CE2 | TRP | X | 80 | 4.558 | 15.634 | −36.683 | 1.00 | 14.83 | C |
| ATOM | 1455 | CD2 | TRP | X | 80 | 4.935 | 16.513 | −37.749 | 1.00 | 14.21 | C |
| ATOM | 1456 | CE3 | TRP | X | 80 | 5.715 | 17.656 | −37.456 | 1.00 | 13.05 | C |
| ATOM | 1457 | CZ3 | TRP | X | 80 | 6.081 | 17.906 | −36.120 | 1.00 | 14.20 | C |
| ATOM | 1458 | CH2 | TRP | X | 80 | 5.693 | 17.010 | −35.081 | 1.00 | 14.15 | C |
| ATOM | 1459 | CZ2 | TRP | X | 80 | 4.916 | 15.890 | −35.339 | 1.00 | 14.46 | C |
| ATOM | 1460 | C | TRP | X | 80 | 4.662 | 16.707 | −42.704 | 1.00 | 13.58 | C |
| ATOM | 1461 | O | TRP | X | 80 | 5.702 | 17.284 | −43.053 | 1.00 | 12.55 | O |
| ATOM | 1462 | N | SER | X | 81 | 3.478 | 16.967 | −43.237 | 1.00 | 12.82 | N |
| ATOM | 1463 | CA | SER | X | 81 | 3.295 | 18.037 | −44.217 | 1.00 | 13.11 | C |
| ATOM | 1464 | CB | SER | X | 81 | 2.140 | 17.698 | −45.159 | 1.00 | 12.74 | C |
| ATOM | 1465 | OG | SER | X | 81 | 0.920 | 17.728 | −44.447 | 1.00 | 14.52 | O |
| ATOM | 1466 | C | SER | X | 81 | 3.029 | 19.412 | −43.572 | 1.00 | 12.65 | C |
| ATOM | 1467 | O | SER | X | 81 | 3.228 | 20.441 | −44.220 | 1.00 | 13.54 | O |
| ATOM | 1468 | N | TYR | X | 82 | 2.572 | 19.414 | −42.324 | 1.00 | 12.93 | N |
| ATOM | 1469 | CA | TYR | X | 82 | 2.406 | 20.639 | −41.564 | 1.00 | 12.19 | C |

-continued

| ATOM | 1470 | CB | TYR | X | 82 | 1.098 | 21.348 | −41.968 | 1.00 | 13.15 | C |
| --- | --- | --- | --- | --- | --- | --- | --- | --- | --- | --- | --- |
| ATOM | 1471 | CG | TYR | X | 82 | −0.132 | 20.896 | −41.200 | 1.00 | 12.72 | C |
| ATOM | 1472 | CD1 | TYR | X | 82 | −0.848 | 19.753 | −41.603 | 1.00 | 13.66 | C |
| ATOM | 1473 | CE1 | TYR | X | 82 | −1.988 | 19.341 | −40.907 | 1.00 | 14.29 | C |
| ATOM | 1474 | CZ | TYR | X | 82 | −2.421 | 20.085 | −39.814 | 1.00 | 14.19 | C |
| ATOM | 1475 | OH | TYR | X | 82 | −3.562 | 19.684 | −39.151 | 1.00 | 13.95 | O |
| ATOM | 1476 | CE2 | TYR | X | 82 | −1.762 | 21.244 | −39.418 | 1.00 | 15.64 | C |
| ATOM | 1477 | CD2 | TYR | X | 82 | −0.617 | 21.646 | −40.102 | 1.00 | 14.13 | C |
| ATOM | 1478 | C | TYR | X | 82 | 2.372 | 20.263 | −40.107 | 1.00 | 12.48 | C |
| ATOM | 1479 | O | TYR | X | 82 | 2.185 | 19.078 | −39.755 | 1.00 | 12.38 | O |
| ATOM | 1480 | N | HIS | X | 83 | 2.579 | 21.250 | −39.254 | 1.00 | 11.71 | N |
| ATOM | 1481 | CA | HIS | X | 83 | 2.372 | 21.045 | −37.840 | 1.00 | 12.16 | C |
| ATOM | 1482 | CB | HIS | X | 83 | 3.725 | 20.798 | −37.174 | 1.00 | 12.15 | C |
| ATOM | 1483 | CG | HIS | X | 83 | 3.635 | 20.369 | −35.738 | 1.00 | 13.16 | C |
| ATOM | 1484 | ND1 | HIS | X | 83 | 2.790 | 19.368 | −35.316 | 1.00 | 14.77 | N |
| ATOM | 1485 | CE1 | HIS | X | 83 | 2.919 | 19.217 | −34.003 | 1.00 | 15.52 | C |
| ATOM | 1486 | NE2 | HIS | X | 83 | 3.851 | 20.056 | −33.575 | 1.00 | 13.88 | N |
| ATOM | 1487 | CD2 | HIS | X | 83 | 4.303 | 20.798 | −34.637 | 1.00 | 14.23 | C |
| ATOM | 1488 | C | HIS | X | 83 | 1.658 | 22.291 | −37.295 | 1.00 | 13.58 | C |
| ATOM | 1489 | O | HIS | X | 83 | 1.730 | 23.360 | −37.897 | 1.00 | 14.11 | O |
| ATOM | 1490 | N | VAL | X | 84 | 1.000 | 22.159 | −36.152 | 1.00 | 13.09 | N |
| ATOM | 1491 | CA | VAL | X | 84 | 0.354 | 23.314 | −35.513 | 1.00 | 12.85 | C |
| ATOM | 1492 | CB | VAL | X | 84 | −1.153 | 23.438 | −35.911 | 1.00 | 12.93 | C |
| ATOM | 1493 | CG1 | VAL | X | 84 | −1.954 | 22.212 | −35.491 | 1.00 | 14.19 | C |
| ATOM | 1494 | CG2 | VAL | X | 84 | −1.796 | 24.759 | −35.345 | 1.00 | 12.79 | C |
| ATOM | 1495 | C | VAL | X | 84 | 0.540 | 23.187 | −34.008 | 1.00 | 12.68 | C |
| ATOM | 1496 | O | VAL | X | 84 | 0.611 | 22.069 | −33.466 | 1.00 | 12.80 | O |
| ATOM | 1497 | N | ALA | X | 85 | 0.618 | 24.331 | −33.336 | 1.00 | 12.86 | N |
| ATOM | 1498 | CA | ALA | X | 85 | 0.570 | 24.377 | −31.866 | 1.00 | 12.81 | C |
| ATOM | 1499 | CB | ALA | X | 85 | 1.964 | 24.236 | −31.272 | 1.00 | 13.52 | C |
| ATOM | 1500 | C | ALA | X | 85 | −0.008 | 25.746 | −31.490 | 1.00 | 13.36 | C |
| ATOM | 1501 | O | ALA | X | 85 | −0.267 | 26.594 | −32.358 | 1.00 | 13.70 | O |
| ATOM | 1502 | N | ILE | X | 86 | −0.250 | 25.922 | −30.200 | 1.00 | 13.92 | N |
| ATOM | 1503 | CA | ILE | X | 86 | −0.788 | 27.209 | −29.731 | 1.00 | 14.48 | C |
| ATOM | 1504 | CB | ILE | X | 86 | −1.627 | 27.061 | −28.438 | 1.00 | 14.19 | C |
| ATOM | 1505 | CG1 | ILE | X | 86 | −0.813 | 26.505 | −27.264 | 1.00 | 15.53 | C |
| ATOM | 1506 | CD1 | ILE | X | 86 | −1.597 | 26.707 | −25.898 | 1.00 | 15.36 | C |
| ATOM | 1507 | CG2 | ILE | X | 86 | −2.886 | 26.217 | −28.722 | 1.00 | 15.95 | C |
| ATOM | 1508 | C | ILE | X | 86 | 0.338 | 28.201 | −29.576 | 1.00 | 14.70 | C |
| ATOM | 1509 | O | ILE | X | 86 | 1.436 | 27.863 | −29.095 | 1.00 | 14.57 | O |
| ATOM | 1510 | N | LEU | X | 87 | 0.057 | 29.437 | −30.003 | 1.00 | 14.77 | N |
| ATOM | 1511 | CA | LEU | X | 87 | 1.012 | 30.536 | −29.916 | 1.00 | 15.02 | C |
| ATOM | 1512 | CB | LEU | X | 87 | 1.183 | 31.219 | −31.270 | 1.00 | 14.40 | C |
| ATOM | 1513 | CG | LEU | X | 87 | 2.174 | 32.391 | −31.340 | 1.00 | 14.91 | C |
| ATOM | 1514 | CD1 | LEU | X | 87 | 3.597 | 31.903 | −31.098 | 1.00 | 15.97 | C |
| ATOM | 1515 | CD2 | LEU | X | 87 | 2.094 | 33.013 | −32.772 | 1.00 | 15.74 | C |
| ATOM | 1516 | C | LEU | X | 87 | 0.431 | 31.525 | −28.911 | 1.00 | 15.52 | C |
| ATOM | 1517 | O | LEU | X | 87 | −0.578 | 32.177 | −29.188 | 1.00 | 16.07 | O |
| ATOM | 1518 | N | VAL | X | 88 | 1.052 | 31.591 | −27.745 | 1.00 | 16.09 | N |
| ATOM | 1519 | CA | AVAL | X | 88 | 0.487 | 32.299 | −26.592 | 0.56 | 16.43 | C |
| ATOM | 1520 | CA | BVAL | X | 88 | 0.463 | 32.326 | −26.631 | 0.44 | 16.97 | C |
| ATOM | 1521 | CB | AVAL | X | 88 | 0.633 | 31.463 | −25.282 | 0.56 | 16.47 | C |
| ATOM | 1522 | CB | BVAL | X | 88 | 0.440 | 31.487 | −25.329 | 0.44 | 17.18 | C |
| ATOM | 1523 | CG1 | AVAL | X | 88 | −0.115 | 32.112 | −24.138 | 0.56 | 13.61 | C |
| ATOM | 1524 | CG1 | BVAL | X | 88 | −0.449 | 30.231 | −25.503 | 0.44 | 16.50 | C |
| ATOM | 1525 | CG2 | AVAL | X | 88 | 0.116 | 30.009 | −25.471 | 0.56 | 16.77 | C |
| ATOM | 1526 | CG2 | BVAL | X | 88 | 1.843 | 31.090 | −24.923 | 0.44 | 18.06 | C |
| ATOM | 1527 | C | VAL | X | 88 | 1.175 | 33.650 | −26.403 | 1.00 | 17.24 | C |
| ATOM | 1528 | O | VAL | X | 88 | 2.403 | 33.713 | −26.371 | 1.00 | 17.59 | O |
| ATOM | 1529 | N | SER | X | 89 | 0.381 | 34.712 | −26.245 | 1.00 | 18.38 | N |
| ATOM | 1530 | CA | SER | X | 89 | 0.925 | 36.046 | −26.001 | 1.00 | 19.53 | C |
| ATOM | 1531 | CB | SER | X | 89 | 0.079 | 37.118 | −26.701 | 1.00 | 18.99 | C |
| ATOM | 1532 | OG | SER | X | 89 | 0.131 | 37.005 | −28.117 | 1.00 | 20.62 | O |
| ATOM | 1533 | C | SER | X | 89 | 0.904 | 36.283 | −24.502 | 1.00 | 20.81 | C |
| ATOM | 1534 | O | SER | X | 89 | −0.102 | 35.972 | −23.846 | 1.00 | 20.70 | O |
| ATOM | 1535 | N | TYR | X | 90 | 2.003 | 36.806 | −23.956 | 1.00 | 21.04 | N |
| ATOM | 1536 | CA | TYR | X | 90 | 2.072 | 37.126 | −22.525 | 1.00 | 22.97 | C |
| ATOM | 1537 | CB | TYR | X | 90 | 2.691 | 35.978 | −21.694 | 1.00 | 23.08 | C |
| ATOM | 1538 | CG | TYR | X | 90 | 4.153 | 35.787 | −21.984 | 1.00 | 23.59 | C |
| ATOM | 1539 | CD1 | TYR | X | 90 | 4.558 | 35.183 | −23.175 | 1.00 | 22.56 | C |
| ATOM | 1540 | CE1 | TYR | X | 90 | 5.899 | 35.041 | −23.486 | 1.00 | 24.44 | C |
| ATOM | 1541 | CZ | TYR | X | 90 | 6.850 | 35.462 | −22.603 | 1.00 | 24.72 | C |
| ATOM | 1542 | OH | TYR | X | 90 | 8.161 | 35.304 | −22.947 | 1.00 | 29.30 | O |
| ATOM | 1543 | CE2 | TYR | X | 90 | 6.499 | 36.091 | −21.404 | 1.00 | 22.80 | C |
| ATOM | 1544 | CD2 | TYR | X | 90 | 5.141 | 36.236 | −21.098 | 1.00 | 22.84 | C |
| ATOM | 1545 | C | TYR | X | 90 | 2.898 | 38.404 | −22.324 | 1.00 | 24.10 | C |
| ATOM | 1546 | O | TYR | X | 90 | 3.756 | 38.750 | −23.156 | 1.00 | 23.12 | O |
| ATOM | 1547 | N | LYS | X | 91 | 2.651 | 39.091 | −21.215 | 1.00 | 25.22 | N |
| ATOM | 1548 | CA | ALYS | X | 91 | 3.466 | 40.257 | −20.887 | 0.50 | 26.14 | C |
| ATOM | 1549 | CA | BLYS | X | 91 | 3.454 | 40.264 | −20.856 | 0.50 | 25.87 | C |

-continued

| | | | | | | | | | |
|---|---|---|---|---|---|---|---|---|---|
| ATOM | 1550 CB | ALYS | X | 91 | 2.634 | 41.313 | −20.146 | 0.50 | 26.08 C |
| ATOM | 1551 CB | BLYS | X | 91 | 2.633 | 41.246 | −20.004 | 0.50 | 25.56 C |
| ATOM | 1552 CG | ALYS | X | 91 | 1.666 | 42.036 | −21.069 | 0.50 | 28.25 C |
| ATOM | 1553 CG | BLYS | X | 91 | 1.484 | 41.917 | −20.740 | 0.50 | 26.48 C |
| ATOM | 1554 CD | ALYS | X | 91 | 0.543 | 42.710 | −20.304 | 0.50 | 29.95 C |
| ATOM | 1555 CD | BLYS | X | 91 | 1.957 | 42.590 | −22.024 | 0.50 | 25.18 C |
| ATOM | 1556 CE | ALYS | X | 91 | −0.524 | 43.227 | −21.252 | 0.50 | 30.86 C |
| ATOM | 1557 CE | BLYS | X | 91 | 1.052 | 43.743 | −22.436 | 0.50 | 24.16 C |
| ATOM | 1558 NZ | ALYS | X | 91 | −1.751 | 43.665 | −20.518 | 0.50 | 33.46 N |
| ATOM | 1559 NZ | BLYS | X | 91 | 1.731 | 44.556 | −23.519 | 0.50 | 21.99 N |
| ATOM | 1560 C | LYS | X | 91 | 4.712 | 39.857 | −20.111 | 1.00 | 26.02 C |
| ATOM | 1561 O | LYS | X | 91 | 4.633 | 39.165 | −19.087 | 1.00 | 26.39 O |
| ATOM | 1562 N | ASN | X | 92 | 5.871 | 40.268 | −20.624 | 1.00 | 27.24 N |
| ATOM | 1563 CA | ASN | X | 92 | 7.126 | 39.987 | −19.944 | 1.00 | 28.90 C |
| ATOM | 1564 CB | ASN | X | 92 | 8.342 | 40.088 | −20.892 | 1.00 | 29.08 C |
| ATOM | 1565 CG | ASN | X | 92 | 8.638 | 41.522 | −21.352 | 1.00 | 30.60 C |
| ATOM | 1566 OD1 | ASN | X | 92 | 8.103 | 42.495 | −20.808 | 1.00 | 29.88 O |
| ATOM | 1567 ND2 | ASN | X | 92 | 9.496 | 41.649 | −22.359 | 1.00 | 31.85 N |
| ATOM | 1568 C | ASN | X | 92 | 7.258 | 40.874 | −18.690 | 1.00 | 29.88 C |
| ATOM | 1569 O | ASN | X | 92 | 6.318 | 41.598 | −18.325 | 1.00 | 30.66 O |
| ATOM | 1570 N | ALA | X | 93 | 8.413 | 40.805 | −18.049 | 1.00 | 31.13 N |
| ATOM | 1571 CA | ALA | X | 93 | 8.682 | 41.556 | −16.826 | 1.00 | 32.02 C |
| ATOM | 1572 CB | ALA | X | 93 | 10.088 | 41.263 | −16.355 | 1.00 | 32.22 C |
| ATOM | 1573 C | ALA | X | 93 | 8.467 | 43.083 | −16.977 | 1.00 | 32.07 C |
| ATOM | 1574 O | ALA | X | 93 | 8.123 | 43.753 | −16.001 | 1.00 | 32.93 O |
| ATOM | 1575 N | SER | X | 94 | 8.661 | 43.604 | −18.194 | 1.00 | 32.17 N |
| ATOM | 1576 CA | ASER | X | 94 | 8.565 | 45.047 | −18.433 | 0.40 | 31.93 C |
| ATOM | 1577 CA | BSER | X | 94 | 8.577 | 45.042 | −18.471 | 0.60 | 32.16 C |
| ATOM | 1578 CB | ASER | X | 94 | 9.746 | 45.532 | −19.271 | 0.40 | 31.92 C |
| ATOM | 1579 CB | BSER | X | 94 | 9.707 | 45.454 | −19.405 | 0.60 | 32.10 C |
| ATOM | 1580 OG | ASER | X | 94 | 9.706 | 44.990 | −20.576 | 0.40 | 32.17 O |
| ATOM | 1581 OG | BSER | X | 94 | 10.958 | 45.066 | −18.874 | 0.60 | 33.56 O |
| ATOM | 1582 C | SER | X | 94 | 7.242 | 45.458 | −19.076 | 1.00 | 31.79 C |
| ATOM | 1583 O | SER | X | 94 | 7.051 | 46.623 | −19.449 | 1.00 | 31.41 O |
| ATOM | 1584 N | GLY | X | 95 | 6.321 | 44.505 | −19.203 | 1.00 | 30.82 N |
| ATOM | 1585 CA | GLY | X | 95 | 5.010 | 44.802 | −19.761 | 1.00 | 29.73 C |
| ATOM | 1586 C | GLY | X | 95 | 4.929 | 44.712 | −21.275 | 1.00 | 29.17 C |
| ATOM | 1587 O | GLY | X | 95 | 3.912 | 45.072 | −21.851 | 1.00 | 29.28 O |
| ATOM | 1588 N | VAL | X | 96 | 5.995 | 44.228 | −21.912 | 1.00 | 28.31 N |
| ATOM | 1589 CA | VAL | X | 96 | 6.070 | 44.106 | −23.366 | 1.00 | 27.56 C |
| ATOM | 1590 CB | VAL | X | 96 | 7.536 | 44.194 | −23.879 | 1.00 | 27.72 C |
| ATOM | 1591 CG1 | VAL | X | 96 | 7.598 | 43.923 | −25.378 | 1.00 | 28.74 C |
| ATOM | 1592 CG2 | VAL | X | 96 | 8.127 | 45.580 | −23.587 | 1.00 | 28.45 C |
| ATOM | 1593 C | VAL | X | 96 | 5.487 | 42.751 | −23.762 | 1.00 | 26.72 C |
| ATOM | 1594 O | VAL | X | 96 | 5.818 | 41.755 | −23.139 | 1.00 | 26.72 O |
| ATOM | 1595 N | THR | X | 97 | 4.639 | 42.728 | −24.783 | 1.00 | 26.53 N |
| ATOM | 1596 CA | THR | X | 97 | 3.998 | 41.462 | −25.197 | 1.00 | 25.71 C |
| ATOM | 1597 CB | THR | X | 97 | 2.745 | 41.697 | −26.021 | 1.00 | 26.49 C |
| ATOM | 1598 OG1 | THR | X | 97 | 1.800 | 42.423 | −25.226 | 1.00 | 27.60 O |
| ATOM | 1599 CG2 | THR | X | 97 | 2.090 | 40.359 | −26.464 | 1.00 | 26.39 C |
| ATOM | 1600 C | THR | X | 97 | 5.008 | 40.637 | −25.968 | 1.00 | 25.26 C |
| ATOM | 1601 O | THR | X | 97 | 5.637 | 41.116 | −26.928 | 1.00 | 25.18 O |
| ATOM | 1602 N | GLU | X | 98 | 5.191 | 39.407 | −25.498 | 1.00 | 23.72 N |
| ATOM | 1603 CA | GLU | X | 98 | 6.022 | 38.433 | −26.169 | 1.00 | 23.13 C |
| ATOM | 1604 CB | GLU | X | 98 | 7.185 | 38.019 | −25.275 | 1.00 | 24.20 C |
| ATOM | 1605 CG | GLU | X | 98 | 8.242 | 39.097 | −25.126 | 1.00 | 27.20 C |
| ATOM | 1606 CD | GLU | X | 98 | 9.551 | 38.561 | −24.614 | 1.00 | 33.43 C |
| ATOM | 1607 OE1 | GLU | X | 98 | 10.052 | 37.543 | −25.161 | 1.00 | 35.54 O |
| ATOM | 1608 OE2 | GLU | X | 98 | 10.099 | 39.172 | −23.673 | 1.00 | 37.03 O |
| ATOM | 1609 C | GLU | X | 98 | 5.144 | 37.233 | −26.453 | 1.00 | 21.71 C |
| ATOM | 1610 O | GLU | X | 98 | 4.069 | 37.115 | −25.875 | 1.00 | 21.01 O |
| ATOM | 1611 N | LYS | X | 99 | 5.584 | 36.378 | −27.373 | 1.00 | 20.40 N |
| ATOM | 1612 CA | LYS | X | 99 | 4.808 | 35.177 | −27.720 | 1.00 | 19.47 C |
| ATOM | 1613 CB | LYS | X | 99 | 4.243 | 35.253 | −29.140 | 1.00 | 20.14 C |
| ATOM | 1614 CG | LYS | X | 99 | 3.272 | 36.438 | −29.392 | 1.00 | 20.67 C |
| ATOM | 1615 CD | LYS | X | 99 | 2.750 | 36.392 | −30.799 | 1.00 | 22.36 C |
| ATOM | 1616 CE | LYS | X | 99 | 1.933 | 37.674 | −31.125 | 1.00 | 25.13 C |
| ATOM | 1617 NZ | LYS | X | 99 | 1.181 | 37.554 | −32.424 | 1.00 | 25.92 N |
| ATOM | 1618 C | LYS | X | 99 | 5.673 | 33.943 | −27.595 | 1.00 | 18.33 C |
| ATOM | 1619 O | LYS | X | 99 | 6.877 | 33.976 | −27.856 | 1.00 | 18.78 O |
| ATOM | 1620 N | ARG | X | 100 | 5.044 | 32.849 | −27.176 | 1.00 | 17.90 N |
| ATOM | 1621 CA | ARG | X | 100 | 5.731 | 31.554 | −27.133 | 1.00 | 16.39 C |
| ATOM | 1622 CB | ARG | X | 100 | 6.159 | 31.215 | −25.704 | 1.00 | 16.69 C |
| ATOM | 1623 CG | ARG | X | 100 | 7.232 | 32.140 | −25.117 | 1.00 | 17.03 C |
| ATOM | 1624 CD | ARG | X | 100 | 8.597 | 31.921 | −25.752 | 1.00 | 19.97 C |
| ATOM | 1625 NE | ARG | X | 100 | 9.633 | 32.721 | −25.068 | 1.00 | 22.92 N |
| ATOM | 1626 CZ | ARG | X | 100 | 9.879 | 34.012 | −25.322 | 1.00 | 24.72 C |
| ATOM | 1627 NH1 | ARG | X | 100 | 9.158 | 34.682 | −26.219 | 1.00 | 25.46 N |
| ATOM | 1628 NH2 | ARG | X | 100 | 10.841 | 34.644 | −24.642 | 1.00 | 26.80 N |
| ATOM | 1629 C | ARG | X | 100 | 4.798 | 30.477 | −27.632 | 1.00 | 15.76 C |

-continued

| | | | | | | | | | |
|---|---|---|---|---|---|---|---|---|---|
| ATOM | 1630 | O | ARG | X | 100 | 3.576 | 30.551 | −27.438 | 1.00 | 15.99 | O |
| ATOM | 1631 | N | ILE | X | 101 | 5.386 | 29.452 | −28.255 | 1.00 | 14.97 | N |
| ATOM | 1632 | CA | ILE | X | 101 | 4.649 | 28.242 | −28.548 | 1.00 | 14.82 | C |
| ATOM | 1633 | CB | ILE | X | 101 | 5.369 | 27.437 | −29.675 | 1.00 | 14.40 | C |
| ATOM | 1634 | CG1 | ILE | X | 101 | 5.269 | 28.193 | −31.021 | 1.00 | 14.29 | C |
| ATOM | 1635 | CD1 | ILE | X | 101 | 3.896 | 28.158 | −31.669 | 1.00 | 13.31 | C |
| ATOM | 1636 | CG2 | ILE | X | 101 | 4.799 | 25.986 | −29.778 | 1.00 | 14.41 | C |
| ATOM | 1637 | C | ILE | X | 101 | 4.583 | 27.362 | −27.298 | 1.00 | 15.01 | C |
| ATOM | 1638 | O | ILE | X | 101 | 5.563 | 27.235 | −26.557 | 1.00 | 16.78 | O |
| ATOM | 1639 | N | ILE | X | 102 | 3.432 | 26.743 | −27.086 | 1.00 | 15.22 | N |
| ATOM | 1640 | CA | ILE | X | 102 | 3.368 | 25.618 | −26.155 | 1.00 | 15.53 | C |
| ATOM | 1641 | CB | ILE | X | 102 | 2.289 | 25.824 | −25.082 | 1.00 | 15.85 | C |
| ATOM | 1642 | CG1 | ILE | X | 102 | 2.775 | 26.896 | −24.102 | 1.00 | 15.35 | C |
| ATOM | 1643 | CD1 | ILE | X | 102 | 1.676 | 27.371 | −23.088 | 1.00 | 16.52 | C |
| ATOM | 1644 | CG2 | ILE | X | 102 | 2.079 | 24.497 | −24.270 | 1.00 | 16.17 | C |
| ATOM | 1645 | C | ILE | X | 102 | 3.109 | 24.354 | −26.970 | 1.00 | 14.71 | C |
| ATOM | 1646 | O | ILE | X | 102 | 2.112 | 24.254 | −27.676 | 1.00 | 14.75 | O |
| ATOM | 1647 | N | ASP | X | 103 | 4.042 | 23.401 | −26.885 | 1.00 | 15.19 | N |
| ATOM | 1648 | CA | ASP | X | 103 | 3.873 | 22.130 | −27.605 | 1.00 | 15.75 | C |
| ATOM | 1649 | CB | ASP | X | 103 | 4.339 | 22.258 | −29.073 | 1.00 | 15.62 | C |
| ATOM | 1650 | CG | ASP | X | 103 | 4.084 | 21.012 | −29.862 | 1.00 | 17.16 | C |
| ATOM | 1651 | OD1 | ASP | X | 103 | 3.508 | 20.047 | −29.287 | 1.00 | 14.98 | O |
| ATOM | 1652 | OD2 | ASP | X | 103 | 4.459 | 20.986 | −31.036 | 1.00 | 15.79 | O |
| ATOM | 1653 | C | ASP | X | 103 | 4.648 | 21.004 | −26.921 | 1.00 | 15.61 | C |
| ATOM | 1654 | O | ASP | X | 103 | 5.777 | 20.707 | −27.317 | 1.00 | 15.70 | O |
| ATOM | 1655 | N | PRO | X | 104 | 4.037 | 20.380 | −25.892 | 1.00 | 16.56 | N |
| ATOM | 1656 | CA | PRO | X | 104 | 4.657 | 19.228 | −25.215 | 1.00 | 16.96 | C |
| ATOM | 1657 | CB | PRO | X | 104 | 3.663 | 18.912 | −24.078 | 1.00 | 18.10 | C |
| ATOM | 1658 | CG | PRO | X | 104 | 2.981 | 20.267 | −23.800 | 1.00 | 17.71 | C |
| ATOM | 1659 | CD | PRO | X | 104 | 2.790 | 20.787 | −25.226 | 1.00 | 16.52 | C |
| ATOM | 1660 | C | PRO | X | 104 | 4.934 | 17.997 | −26.093 | 1.00 | 18.27 | C |
| ATOM | 1661 | O | PRO | X | 104 | 5.658 | 17.100 | −25.633 | 1.00 | 18.00 | O |
| ATOM | 1662 | N | SER | X | 105 | 4.437 | 17.968 | −27.337 | 1.00 | 17.32 | N |
| ATOM | 1663 | CA | ASER | X | 105 | 4.796 | 16.861 | −28.244 | 0.78 | 16.75 | C |
| ATOM | 1664 | CA | BSER | X | 105 | 4.785 | 16.885 | −28.265 | 0.22 | 17.67 | C |
| ATOM | 1665 | CB | ASER | X | 105 | 3.815 | 16.685 | −29.401 | 0.78 | 16.65 | C |
| ATOM | 1666 | CB | BSER | X | 105 | 3.847 | 16.871 | −29.467 | 0.22 | 17.61 | C |
| ATOM | 1667 | OG | ASER | X | 105 | 3.947 | 17.665 | −30.405 | 0.78 | 13.87 | O |
| ATOM | 1668 | OG | BSER | X | 105 | 2.515 | 16.631 | −29.054 | 0.22 | 18.40 | O |
| ATOM | 1669 | C | SER | X | 105 | 6.234 | 17.007 | −28.734 | 1.00 | 17.76 | C |
| ATOM | 1670 | O | SER | X | 105 | 6.832 | 16.032 | −29.183 | 1.00 | 18.72 | O |
| ATOM | 1671 | N | LEU | X | 106 | 6.780 | 18.224 | −28.631 | 1.00 | 16.83 | N |
| ATOM | 1672 | CA | LEU | X | 106 | 8.127 | 18.537 | −29.080 | 1.00 | 18.10 | C |
| ATOM | 1673 | CB | LEU | X | 106 | 8.089 | 19.473 | −30.296 | 1.00 | 17.88 | C |
| ATOM | 1674 | CG | LEU | X | 106 | 7.557 | 18.886 | −31.610 | 1.00 | 17.69 | C |
| ATOM | 1675 | CD1 | LEU | X | 106 | 7.637 | 19.984 | −32.683 | 1.00 | 16.63 | C |
| ATOM | 1676 | CD2 | LEU | X | 106 | 8.332 | 17.628 | −32.022 | 1.00 | 17.37 | C |
| ATOM | 1677 | C | LEU | X | 106 | 9.023 | 19.135 | −27.999 | 1.00 | 19.04 | C |
| ATOM | 1678 | O | LEU | X | 106 | 10.253 | 18.934 | −28.034 | 1.00 | 19.97 | O |
| ATOM | 1679 | N | PHE | X | 107 | 8.430 | 19.844 | −27.039 | 1.00 | 19.10 | N |
| ATOM | 1680 | CA | PHE | X | 107 | 9.210 | 20.493 | −25.972 | 1.00 | 20.07 | C |
| ATOM | 1681 | CB | PHE | X | 107 | 9.329 | 22.000 | −26.211 | 1.00 | 20.09 | C |
| ATOM | 1682 | CG | PHE | X | 107 | 10.088 | 22.340 | −27.457 | 1.00 | 19.71 | C |
| ATOM | 1683 | CD1 | PHE | X | 107 | 11.464 | 22.530 | −27.417 | 1.00 | 19.10 | C |
| ATOM | 1684 | CE1 | PHE | X | 107 | 12.180 | 22.840 | −28.577 | 1.00 | 20.27 | C |
| ATOM | 1685 | CZ | PHE | X | 107 | 11.500 | 22.923 | −29.798 | 1.00 | 18.73 | C |
| ATOM | 1686 | CE2 | PHE | X | 107 | 10.137 | 22.715 | −29.842 | 1.00 | 19.08 | C |
| ATOM | 1687 | CD2 | PHE | X | 107 | 9.436 | 22.419 | −28.688 | 1.00 | 19.91 | C |
| ATOM | 1688 | C | PHE | X | 107 | 8.544 | 20.227 | −24.646 | 1.00 | 20.78 | C |
| ATOM | 1689 | O | PHE | X | 107 | 7.481 | 20.768 | −24.357 | 1.00 | 20.16 | O |
| ATOM | 1690 | N | SER | X | 108 | 9.158 | 19.350 | −23.864 | 1.00 | 21.20 | N |
| ATOM | 1691 | CA | ASER | X | 108 | 8.567 | 18.928 | −22.600 | 0.72 | 22.20 | C |
| ATOM | 1692 | CA | BSER | X | 108 | 8.571 | 18.930 | −22.604 | 0.28 | 22.30 | C |
| ATOM | 1693 | CB | ASER | X | 108 | 9.080 | 17.530 | −22.204 | 0.72 | 22.16 | C |
| ATOM | 1694 | CB | BSER | X | 108 | 9.070 | 17.527 | −22.239 | 0.28 | 22.23 | C |
| ATOM | 1695 | OG | ASER | X | 108 | 10.482 | 17.576 | −21.998 | 0.72 | 22.71 | O |
| ATOM | 1696 | OG | BSER | X | 108 | 8.795 | 17.232 | −20.889 | 0.28 | 22.80 | O |
| ATOM | 1697 | C | SER | X | 108 | 8.852 | 19.920 | −21.472 | 1.00 | 22.87 | C |
| ATOM | 1698 | O | SER | X | 108 | 8.155 | 19.922 | −20.455 | 1.00 | 23.86 | O |
| ATOM | 1699 | N | SER | X | 109 | 9.862 | 20.761 | −21.660 | 1.00 | 23.39 | N |
| ATOM | 1700 | CA | ASER | X | 109 | 10.389 | 21.656 | −20.618 | 0.50 | 24.24 | C |
| ATOM | 1701 | CA | BSER | X | 109 | 10.311 | 21.587 | −20.540 | 0.50 | 24.27 | C |
| ATOM | 1702 | CB | ASER | X | 109 | 11.777 | 22.147 | −21.034 | 0.50 | 24.89 | C |
| ATOM | 1703 | CB | BSER | X | 109 | 11.814 | 21.846 | −20.609 | 0.50 | 24.84 | C |
| ATOM | 1704 | OG | ASER | X | 109 | 11.752 | 22.752 | −22.325 | 0.50 | 27.11 | O |
| ATOM | 1705 | OG | BSER | X | 109 | 12.533 | 20.627 | −20.455 | 0.50 | 26.94 | O |
| ATOM | 1706 | C | SER | X | 109 | 9.497 | 22.864 | −20.299 | 1.00 | 24.26 | C |
| ATOM | 1707 | O | SER | X | 109 | 9.416 | 23.328 | −19.155 | 1.00 | 24.39 | O |
| ATOM | 1708 | N | GLY | X | 110 | 8.853 | 23.416 | −21.328 | 1.00 | 22.94 | N |
| ATOM | 1709 | CA | GLY | X | 110 | 8.116 | 24.660 | −21.135 | 1.00 | 21.33 | C |

-continued

| | | | | | | | | | | |
|---|---|---|---|---|---|---|---|---|---|---|
| ATOM | 1710 | C | GLY | X | 110 | 7.844 | 25.319 | −22.469 | 1.00 | 20.72 | C |
| ATOM | 1711 | O | GLY | X | 110 | 8.184 | 24.742 | −23.524 | 1.00 | 19.63 | O |
| ATOM | 1712 | N | PRO | X | 111 | 7.254 | 26.532 | −22.438 | 1.00 | 20.71 | N |
| ATOM | 1713 | CA | PRO | X | 111 | 7.013 | 27.258 | −23.697 | 1.00 | 19.89 | C |
| ATOM | 1714 | CB | PRO | X | 111 | 6.269 | 28.543 | −23.246 | 1.00 | 19.98 | C |
| ATOM | 1715 | CG | PRO | X | 111 | 5.769 | 28.226 | −21.808 | 1.00 | 20.31 | C |
| ATOM | 1716 | CD | PRO | X | 111 | 6.877 | 27.337 | −21.260 | 1.00 | 20.71 | C |
| ATOM | 1717 | C | PRO | X | 111 | 8.342 | 27.603 | −24.373 | 1.00 | 19.55 | C |
| ATOM | 1718 | O | PRO | X | 111 | 9.385 | 27.745 | −23.705 | 1.00 | 20.50 | O |
| ATOM | 1719 | N | VAL | X | 112 | 8.324 | 27.700 | −25.699 | 1.00 | 18.44 | N |
| ATOM | 1720 | CA | VAL | X | 112 | 9.537 | 27.983 | −26.472 | 1.00 | 17.97 | C |
| ATOM | 1721 | CB | VAL | X | 112 | 10.117 | 26.722 | −27.170 | 1.00 | 18.18 | C |
| ATOM | 1722 | CG1 | VAL | X | 112 | 10.703 | 25.731 | −26.110 | 1.00 | 17.68 | C |
| ATOM | 1723 | CG2 | VAL | X | 112 | 9.077 | 26.048 | −28.068 | 1.00 | 18.25 | C |
| ATOM | 1724 | C | VAL | X | 112 | 9.213 | 29.022 | −27.532 | 1.00 | 17.42 | C |
| ATOM | 1725 | O | VAL | X | 112 | 8.047 | 29.288 | −27.809 | 1.00 | 16.70 | O |
| ATOM | 1726 | N | THR | X | 113 | 10.238 | 29.606 | −28.133 | 1.00 | 17.16 | N |
| ATOM | 1727 | CA | THR | X | 113 | 9.958 | 30.565 | −29.210 | 1.00 | 17.34 | C |
| ATOM | 1728 | CB | THR | X | 113 | 11.197 | 31.349 | −29.652 | 1.00 | 17.41 | C |
| ATOM | 1729 | OG1 | THR | X | 113 | 12.183 | 30.447 | −30.161 | 1.00 | 18.71 | O |
| ATOM | 1730 | CG2 | THR | X | 113 | 11.765 | 32.146 | −28.481 | 1.00 | 18.73 | C |
| ATOM | 1731 | C | THR | X | 113 | 9.433 | 29.818 | −30.423 | 1.00 | 17.16 | C |
| ATOM | 1732 | O | THR | X | 113 | 9.704 | 28.618 | −30.581 | 1.00 | 15.26 | O |
| ATOM | 1733 | N | ASP | X | 114 | 8.666 | 30.518 | −31.261 | 1.00 | 16.38 | N |
| ATOM | 1734 | CA | ASP | X | 114 | 8.164 | 29.858 | −32.459 | 1.00 | 16.52 | C |
| ATOM | 1735 | CB | ASP | X | 114 | 7.042 | 30.642 | −33.169 | 1.00 | 16.69 | C |
| ATOM | 1736 | CG | ASP | X | 114 | 7.448 | 32.058 | −33.574 | 1.00 | 18.71 | C |
| ATOM | 1737 | OD1 | ASP | X | 114 | 6.619 | 32.687 | −34.264 | 1.00 | 17.53 | O |
| ATOM | 1738 | OD2 | ASP | X | 114 | 8.577 | 32.525 | −33.270 | 1.00 | 18.40 | O |
| ATOM | 1739 | C | ASP | X | 114 | 9.316 | 29.500 | −33.385 | 1.00 | 16.11 | C |
| ATOM | 1740 | O | ASP | X | 114 | 9.277 | 28.482 | −34.049 | 1.00 | 16.68 | O |
| ATOM | 1741 | N | THR | X | 115 | 10.366 | 30.330 | −33.368 | 1.00 | 16.24 | N |
| ATOM | 1742 | CA | THR | X | 115 | 11.583 | 30.041 | −34.115 | 1.00 | 17.11 | C |
| ATOM | 1743 | CB | THR | X | 115 | 12.588 | 31.154 | −33.857 | 1.00 | 18.33 | C |
| ATOM | 1744 | OG1 | THR | X | 115 | 11.972 | 32.404 | −34.228 | 1.00 | 20.33 | O |
| ATOM | 1745 | CG2 | THR | X | 115 | 13.851 | 30.918 | −34.684 | 1.00 | 20.09 | C |
| ATOM | 1746 | C | THR | X | 115 | 12.168 | 28.668 | −33.759 | 1.00 | 17.40 | C |
| ATOM | 1747 | O | THR | X | 115 | 12.438 | 27.824 | −34.644 | 1.00 | 16.95 | O |
| ATOM | 1748 | N | ALA | X | 116 | 12.349 | 28.446 | −32.461 | 1.00 | 16.55 | N |
| ATOM | 1749 | CA | ALA | X | 116 | 12.838 | 27.161 | −31.957 | 1.00 | 16.20 | C |
| ATOM | 1750 | CB | ALA | X | 116 | 13.067 | 27.237 | −30.447 | 1.00 | 16.34 | C |
| ATOM | 1751 | C | ALA | X | 116 | 11.905 | 26.005 | −32.295 | 1.00 | 16.00 | C |
| ATOM | 1752 | O | ALA | X | 116 | 12.353 | 24.897 | −32.621 | 1.00 | 16.05 | O |
| ATOM | 1753 | N | TRP | X | 117 | 10.603 | 26.248 | −32.206 | 1.00 | 14.69 | N |
| ATOM | 1754 | CA | TRP | X | 117 | 9.615 | 25.220 | −32.487 | 1.00 | 14.37 | C |
| ATOM | 1755 | CB | TRP | X | 117 | 8.266 | 25.780 | −32.086 | 1.00 | 13.61 | C |
| ATOM | 1756 | CG | TRP | X | 117 | 7.100 | 24.916 | −32.393 | 1.00 | 14.74 | C |
| ATOM | 1757 | CD1 | TRP | X | 117 | 6.731 | 23.761 | −31.756 | 1.00 | 13.28 | C |
| ATOM | 1758 | NE1 | TRP | X | 117 | 5.559 | 23.278 | −32.299 | 1.00 | 13.18 | N |
| ATOM | 1759 | CE2 | TRP | X | 117 | 5.166 | 24.117 | −33.312 | 1.00 | 13.42 | C |
| ATOM | 1760 | CD2 | TRP | X | 117 | 6.117 | 25.163 | −33.391 | 1.00 | 14.22 | C |
| ATOM | 1761 | CE3 | TRP | X | 117 | 5.932 | 26.189 | −34.347 | 1.00 | 12.97 | C |
| ATOM | 1762 | CZ3 | TRP | X | 117 | 4.849 | 26.114 | −35.193 | 1.00 | 12.92 | C |
| ATOM | 1763 | CH2 | TRP | X | 117 | 3.901 | 25.053 | −35.094 | 1.00 | 13.74 | C |
| ATOM | 1764 | CZ2 | TRP | X | 117 | 4.053 | 24.046 | −34.168 | 1.00 | 13.98 | C |
| ATOM | 1765 | C | TRP | X | 117 | 9.635 | 24.844 | −33.982 | 1.00 | 14.26 | C |
| ATOM | 1766 | O | TRP | X | 117 | 9.678 | 23.656 | −34.340 | 1.00 | 15.00 | O |
| ATOM | 1767 | N | ARG | X | 118 | 9.638 | 25.843 | −34.863 | 1.00 | 14.87 | N |
| ATOM | 1768 | CA | ARG | X | 118 | 9.740 | 25.534 | −36.307 | 1.00 | 14.99 | C |
| ATOM | 1769 | CB | ARG | X | 118 | 9.590 | 26.780 | −37.182 | 1.00 | 15.24 | C |
| ATOM | 1770 | CG | ARG | X | 118 | 8.188 | 27.416 | −37.038 | 1.00 | 13.83 | C |
| ATOM | 1771 | CD | ARG | X | 118 | 7.888 | 28.452 | −38.183 | 1.00 | 14.53 | C |
| ATOM | 1772 | NE | ARG | X | 118 | 8.912 | 29.496 | −38.266 | 1.00 | 13.44 | N |
| ATOM | 1773 | CZ | ARG | X | 118 | 8.884 | 30.635 | −37.561 | 1.00 | 15.32 | C |
| ATOM | 1774 | NH1 | ARG | X | 118 | 7.898 | 30.877 | −36.685 | 1.00 | 15.11 | N |
| ATOM | 1775 | NH2 | ARG | X | 118 | 9.847 | 31.538 | −37.730 | 1.00 | 15.64 | N |
| ATOM | 1776 | C | ARG | X | 118 | 11.022 | 24.752 | −36.619 | 1.00 | 16.11 | C |
| ATOM | 1777 | O | ARG | X | 118 | 11.019 | 23.829 | −37.431 | 1.00 | 15.49 | O |
| ATOM | 1778 | N | ASN | X | 119 | 12.113 | 25.106 | −35.948 | 1.00 | 16.64 | N |
| ATOM | 1779 | CA | ASN | X | 119 | 13.365 | 24.377 | −36.149 | 1.00 | 17.61 | C |
| ATOM | 1780 | CB | ASN | X | 119 | 14.500 | 25.032 | −35.344 | 1.00 | 18.62 | C |
| ATOM | 1781 | CG | ASN | X | 119 | 15.818 | 24.288 | −35.505 | 1.00 | 22.10 | C |
| ATOM | 1782 | OD1 | ASN | X | 119 | 16.273 | 23.623 | −34.581 | 1.00 | 26.99 | O |
| ATOM | 1783 | ND2 | ASN | X | 119 | 16.391 | 24.346 | −36.704 | 1.00 | 24.26 | N |
| ATOM | 1784 | C | ASN | X | 119 | 13.231 | 22.895 | −35.770 | 1.00 | 17.71 | C |
| ATOM | 1785 | O | ASN | X | 119 | 13.807 | 22.026 | −36.436 | 1.00 | 17.97 | O |
| ATOM | 1786 | N | ALA | X | 120 | 12.447 | 22.602 | −34.727 | 1.00 | 16.46 | N |
| ATOM | 1787 | CA | ALA | X | 120 | 12.219 | 21.215 | −34.294 | 1.00 | 16.76 | C |
| ATOM | 1788 | CB | ALA | X | 120 | 11.587 | 21.174 | −32.900 | 1.00 | 16.90 | C |
| ATOM | 1789 | C | ALA | X | 120 | 11.403 | 20.408 | −35.301 | 1.00 | 16.95 | C |

-continued

| | | | | | | | | | | |
|---|---|---|---|---|---|---|---|---|---|---|
| ATOM | 1790 | O | ALA | X | 120 | 11.399 | 19.145 | −35.265 | 1.00 | 17.32 | O |
| ATOM | 1791 | N | CYS | X | 121 | 10.738 | 21.126 | −36.219 | 1.00 | 15.83 | N |
| ATOM | 1792 | CA | CYS | X | 121 | 9.949 | 20.504 | −37.276 | 1.00 | 16.37 | C |
| ATOM | 1793 | CB | CYS | X | 121 | 8.730 | 21.356 | −37.640 | 1.00 | 15.45 | C |
| ATOM | 1794 | SG | CYS | X | 121 | 7.545 | 21.568 | −36.286 | 1.00 | 16.83 | S |
| ATOM | 1795 | C | CYS | X | 121 | 10.759 | 20.266 | −38.518 | 1.00 | 16.37 | C |
| ATOM | 1796 | O | CYS | X | 121 | 10.223 | 19.761 | −39.516 | 1.00 | 16.94 | O |
| ATOM | 1797 | N | VAL | X | 122 | 12.033 | 20.644 | −38.486 | 1.00 | 16.17 | N |
| ATOM | 1798 | CA | VAL | X | 122 | 12.912 | 20.370 | −39.622 | 1.00 | 17.26 | C |
| ATOM | 1799 | CB | VAL | X | 122 | 13.158 | 21.596 | −40.536 | 1.00 | 17.96 | C |
| ATOM | 1800 | CG1 | VAL | X | 122 | 11.895 | 21.860 | −41.412 | 1.00 | 19.88 | C |
| ATOM | 1801 | CG2 | VAL | X | 122 | 13.518 | 22.801 | −39.738 | 1.00 | 18.67 | C |
| ATOM | 1802 | C | VAL | X | 122 | 14.181 | 19.690 | −39.122 | 1.00 | 18.34 | C |
| ATOM | 1803 | O | VAL | X | 122 | 15.304 | 20.146 | −39.339 | 1.00 | 19.16 | O |
| ATOM | 1804 | N | ASN | X | 123 | 13.942 | 18.592 | −38.420 | 1.00 | 18.44 | N |
| ATOM | 1805 | CA | ASN | X | 123 | 15.022 | 17.832 | −37.821 | 1.00 | 20.32 | C |
| ATOM | 1806 | CB | ASN | X | 123 | 14.491 | 17.047 | −36.626 | 1.00 | 20.45 | C |
| ATOM | 1807 | CG | ASN | X | 123 | 15.624 | 16.462 | −35.790 | 1.00 | 22.04 | C |
| ATOM | 1808 | OD1 | ASN | X | 123 | 16.696 | 16.182 | −36.316 | 1.00 | 23.74 | O |
| ATOM | 1809 | ND2 | ASN | X | 123 | 15.388 | 16.287 | −34.507 | 1.00 | 22.83 | N |
| ATOM | 1810 | C | ASN | X | 123 | 15.707 | 16.949 | −38.862 | 1.00 | 21.10 | C |
| ATOM | 1811 | O | ASN | X | 123 | 15.215 | 15.893 | −39.232 | 1.00 | 20.24 | O |
| ATOM | 1812 | N | THR | X | 124 | 16.850 | 17.417 | −39.351 | 1.00 | 22.78 | N |
| ATOM | 1813 | CA | THR | X | 124 | 17.513 | 16.746 | −40.480 | 1.00 | 24.52 | C |
| ATOM | 1814 | CB | THR | X | 124 | 18.468 | 17.687 | −41.230 | 1.00 | 25.13 | C |
| ATOM | 1815 | OG1 | THR | X | 124 | 19.328 | 18.303 | −40.283 | 1.00 | 27.49 | O |
| ATOM | 1816 | CG2 | THR | X | 124 | 17.698 | 18.774 | −41.973 | 1.00 | 25.34 | C |
| ATOM | 1817 | C | THR | X | 124 | 18.256 | 15.469 | −40.057 | 1.00 | 25.36 | C |
| ATOM | 1818 | O | THR | X | 124 | 18.771 | 14.747 | −40.913 | 1.00 | 25.90 | O |
| ATOM | 1819 | N | SER | X | 125 | 18.292 | 15.183 | −38.757 | 1.00 | 25.82 | N |
| ATOM | 1820 | CA | ASER | X | 125 | 18.759 | 13.865 | −38.299 | 0.60 | 25.78 | C |
| ATOM | 1821 | CA | BSER | X | 125 | 18.738 | 13.868 | −38.267 | 0.40 | 25.92 | C |
| ATOM | 1822 | CB | ASER | X | 125 | 18.991 | 13.849 | −36.787 | 0.60 | 26.20 | C |
| ATOM | 1823 | CB | BSER | X | 125 | 18.846 | 13.870 | −36.744 | 0.40 | 26.24 | C |
| ATOM | 1824 | OG | ASER | X | 125 | 17.774 | 13.827 | −36.070 | 0.60 | 26.57 | O |
| ATOM | 1825 | OG | BSER | X | 125 | 19.724 | 14.889 | −36.301 | 0.40 | 27.87 | O |
| ATOM | 1826 | C | SER | X | 125 | 17.767 | 12.776 | −38.710 | 1.00 | 25.78 | C |
| ATOM | 1827 | O | SER | X | 125 | 18.100 | 11.576 | −38.718 | 1.00 | 25.75 | O |
| ATOM | 1828 | N | CYS | X | 126 | 16.554 | 13.195 | −39.079 | 1.00 | 24.55 | N |
| ATOM | 1829 | CA | CYS | X | 126 | 15.496 | 12.289 | −39.512 | 1.00 | 24.16 | C |
| ATOM | 1830 | CB | CYS | X | 126 | 14.137 | 12.858 | −39.086 | 1.00 | 24.30 | C |
| ATOM | 1831 | SG | CYS | X | 126 | 13.896 | 12.814 | −37.327 | 1.00 | 25.51 | S |
| ATOM | 1832 | C | CYS | X | 126 | 15.467 | 12.046 | −41.011 | 1.00 | 23.59 | C |
| ATOM | 1833 | O | CYS | X | 126 | 14.806 | 11.113 | −41.483 | 1.00 | 24.69 | O |
| ATOM | 1834 | N | GLY | X | 127 | 16.156 | 12.899 | −41.755 | 1.00 | 22.38 | N |
| ATOM | 1835 | CA | GLY | X | 127 | 16.111 | 12.894 | −43.218 | 1.00 | 22.60 | C |
| ATOM | 1836 | C | GLY | X | 127 | 16.040 | 14.319 | −43.745 | 1.00 | 22.21 | C |
| ATOM | 1837 | O | GLY | X | 127 | 16.312 | 15.271 | −42.999 | 1.00 | 22.76 | O |
| ATOM | 1838 | N | SER | X | 128 | 15.657 | 14.467 | −45.016 | 1.00 | 22.23 | N |
| ATOM | 1839 | CA | SER | X | 128 | 15.547 | 15.784 | −45.636 | 1.00 | 21.66 | C |
| ATOM | 1840 | CB | SER | X | 128 | 15.304 | 15.677 | −47.147 | 1.00 | 22.57 | C |
| ATOM | 1841 | OG | SER | X | 128 | 14.016 | 15.111 | −47.432 | 1.00 | 26.97 | O |
| ATOM | 1842 | C | SER | X | 128 | 14.376 | 16.533 | −44.972 | 1.00 | 19.71 | C |
| ATOM | 1843 | O | SER | X | 128 | 13.350 | 15.925 | −44.633 | 1.00 | 19.72 | O |
| ATOM | 1844 | N | ALA | X | 129 | 14.554 | 17.828 | −44.752 | 1.00 | 18.57 | N |
| ATOM | 1845 | CA | ALA | X | 129 | 13.464 | 18.640 | −44.186 | 1.00 | 17.54 | C |
| ATOM | 1846 | CB | ALA | X | 129 | 13.389 | 18.440 | −42.660 | 1.00 | 17.54 | C |
| ATOM | 1847 | C | ALA | X | 129 | 13.634 | 20.118 | −44.498 | 1.00 | 16.86 | C |
| ATOM | 1848 | O | ALA | X | 129 | 14.752 | 20.638 | −44.522 | 1.00 | 16.96 | O |
| ATOM | 1849 | N | SER | X | 130 | 12.516 | 20.810 | −44.716 | 1.00 | 16.49 | N |
| ATOM | 1850 | CA | SER | X | 130 | 12.554 | 22.250 | −44.864 | 1.00 | 16.38 | C |
| ATOM | 1851 | CB | SER | X | 130 | 13.095 | 22.691 | −46.234 | 1.00 | 17.02 | C |
| ATOM | 1852 | OG | SER | X | 130 | 12.262 | 22.292 | −47.297 | 1.00 | 17.88 | O |
| ATOM | 1853 | C | SER | X | 130 | 11.151 | 22.802 | −44.642 | 1.00 | 15.94 | C |
| ATOM | 1854 | O | SER | X | 130 | 10.155 | 22.097 | −44.852 | 1.00 | 15.75 | O |
| ATOM | 1855 | N | VAL | X | 131 | 11.113 | 24.051 | −44.212 | 1.00 | 15.83 | N |
| ATOM | 1856 | CA | VAL | X | 131 | 9.849 | 24.788 | −44.067 | 1.00 | 14.86 | C |
| ATOM | 1857 | CB | VAL | X | 131 | 9.930 | 25.768 | −42.895 | 1.00 | 15.08 | C |
| ATOM | 1858 | CG1 | VAL | X | 131 | 8.717 | 26.733 | −42.906 | 1.00 | 13.48 | C |
| ATOM | 1859 | CG2 | VAL | X | 131 | 10.056 | 25.018 | −41.566 | 1.00 | 14.75 | C |
| ATOM | 1860 | C | VAL | X | 131 | 9.570 | 25.548 | −45.362 | 1.00 | 15.59 | C |
| ATOM | 1861 | O | VAL | X | 131 | 10.471 | 26.196 | −45.933 | 1.00 | 15.28 | O |
| ATOM | 1862 | N | SER | X | 132 | 8.317 | 25.528 | −45.815 | 1.00 | 14.40 | N |
| ATOM | 1863 | CA | ASER | X | 132 | 7.931 | 26.330 | −46.985 | 0.69 | 15.08 | C |
| ATOM | 1864 | CA | BSER | X | 132 | 7.942 | 26.340 | −46.973 | 0.30 | 14.35 | C |
| ATOM | 1865 | CB | ASER | X | 132 | 7.146 | 25.481 | −47.974 | 0.69 | 16.47 | C |
| ATOM | 1866 | CB | BSER | X | 132 | 7.259 | 25.487 | −48.037 | 0.30 | 14.98 | C |
| ATOM | 1867 | OG | ASER | X | 132 | 5.952 | 25.052 | −47.366 | 0.69 | 19.82 | O |
| ATOM | 1868 | OG | BSER | X | 132 | 8.215 | 24.645 | −48.650 | 0.30 | 13.46 | O |
| ATOM | 1869 | C | SER | X | 132 | 7.084 | 27.553 | −46.616 | 1.00 | 14.91 | C |

-continued

| | | | | | | | | | | |
|---|---|---|---|---|---|---|---|---|---|---|
| ATOM | 1870 | O | SER | X | 132 | 7.018 | 28.504 | −47.384 | 1.00 | 14.35 | O |
| ATOM | 1871 | N | SER | X | 133 | 6.431 | 27.515 | −45.457 | 1.00 | 13.67 | N |
| ATOM | 1872 | CA | ASER | X | 133 | 5.584 | 28.645 | −45.041 | 0.60 | 12.89 | C |
| ATOM | 1873 | CA | BSER | X | 133 | 5.550 | 28.622 | −45.051 | 0.40 | 13.31 | C |
| ATOM | 1874 | CB | ASER | X | 133 | 4.332 | 28.707 | −45.926 | 0.60 | 12.76 | C |
| ATOM | 1875 | CB | BSER | X | 133 | 4.275 | 28.612 | −45.910 | 0.40 | 13.21 | C |
| ATOM | 1876 | OG | ASER | X | 133 | 3.517 | 27.562 | −45.754 | 0.60 | 12.74 | O |
| ATOM | 1877 | OG | BSER | X | 133 | 3.292 | 29.514 | −45.419 | 0.40 | 14.47 | O |
| ATOM | 1878 | C | SER | X | 133 | 5.173 | 28.478 | −43.589 | 1.00 | 13.01 | C |
| ATOM | 1879 | O | SER | X | 133 | 5.244 | 27.383 | −43.024 | 1.00 | 12.91 | O |
| ATOM | 1880 | N | TYR | X | 134 | 4.766 | 29.574 | −42.972 | 1.00 | 13.09 | N |
| ATOM | 1881 | CA | TYR | X | 134 | 4.008 | 29.453 | −41.741 | 1.00 | 13.26 | C |
| ATOM | 1882 | CB | TYR | X | 134 | 4.861 | 29.519 | −40.460 | 1.00 | 14.34 | C |
| ATOM | 1883 | CG | TYR | X | 134 | 5.312 | 30.889 | −39.986 | 1.00 | 13.28 | C |
| ATOM | 1884 | CD1 | TYR | X | 134 | 6.644 | 31.303 | −40.150 | 1.00 | 14.94 | C |
| ATOM | 1885 | CE1 | TYR | X | 134 | 7.086 | 32.552 | −39.667 | 1.00 | 13.50 | C |
| ATOM | 1886 | CZ | TYR | X | 134 | 6.167 | 33.375 | −39.018 | 1.00 | 16.59 | C |
| ATOM | 1887 | OH | TYR | X | 134 | 6.537 | 34.598 | −38.537 | 1.00 | 15.34 | O |
| ATOM | 1888 | CE2 | TYR | X | 134 | 4.847 | 32.967 | −38.834 | 1.00 | 14.57 | C |
| ATOM | 1889 | CD2 | TYR | X | 134 | 4.430 | 31.739 | −39.304 | 1.00 | 14.73 | C |
| ATOM | 1890 | C | TYR | X | 134 | 2.957 | 30.558 | −41.757 | 1.00 | 13.33 | C |
| ATOM | 1891 | O | TYR | X | 134 | 3.125 | 31.578 | −42.433 | 1.00 | 13.51 | O |
| ATOM | 1892 | N | ALA | X | 135 | 1.900 | 30.351 | −40.984 | 1.00 | 13.62 | N |
| ATOM | 1893 | CA | ALA | X | 135 | 0.882 | 31.385 | −40.830 | 1.00 | 13.55 | C |
| ATOM | 1894 | CB | ALA | X | 135 | −0.276 | 31.120 | −41.792 | 1.00 | 13.85 | C |
| ATOM | 1895 | C | ALA | X | 135 | 0.382 | 31.376 | −39.394 | 1.00 | 14.39 | C |
| ATOM | 1896 | O | ALA | X | 135 | 0.156 | 30.296 | −38.832 | 1.00 | 16.19 | O |
| ATOM | 1897 | N | ASN | X | 136 | 0.160 | 32.573 | −38.827 | 1.00 | 14.16 | N |
| ATOM | 1898 | CA | ASN | X | 136 | −0.475 | 32.693 | −37.503 | 1.00 | 14.61 | C |
| ATOM | 1899 | CB | ASN | X | 136 | 0.137 | 33.838 | −36.703 | 1.00 | 14.18 | C |
| ATOM | 1900 | CG | ASN | X | 136 | 1.583 | 33.574 | −36.324 | 1.00 | 17.06 | C |
| ATOM | 1901 | OD1 | ASN | X | 136 | 1.995 | 32.417 | −36.163 | 1.00 | 16.37 | O |
| ATOM | 1902 | ND2 | ASN | X | 136 | 2.347 | 34.636 | −36.154 | 1.00 | 18.99 | N |
| ATOM | 1903 | C | ASN | X | 136 | −1.950 | 32.945 | −37.714 | 1.00 | 15.00 | C |
| ATOM | 1904 | O | ASN | X | 136 | −2.316 | 33.754 | −38.589 | 1.00 | 15.92 | O |
| ATOM | 1905 | N | THR | X | 137 | −2.800 | 32.257 | −36.943 | 1.00 | 15.01 | N |
| ATOM | 1906 | CA | THR | X | 137 | −4.250 | 32.456 | −37.054 | 1.00 | 15.19 | C |
| ATOM | 1907 | CB | THR | X | 137 | −4.988 | 31.211 | −37.641 | 1.00 | 15.55 | C |
| ATOM | 1908 | OG1 | THR | X | 137 | −5.015 | 30.159 | −36.670 | 1.00 | 15.90 | O |
| ATOM | 1909 | CG2 | THR | X | 137 | −4.348 | 30.707 | −38.958 | 1.00 | 15.48 | C |
| ATOM | 1910 | C | THR | X | 137 | −4.863 | 32.710 | −35.688 | 1.00 | 14.32 | C |
| ATOM | 1911 | O | THR | X | 137 | −4.230 | 32.477 | −34.658 | 1.00 | 12.95 | O |
| ATOM | 1912 | N | ALA | X | 138 | −6.114 | 33.182 | −35.678 | 1.00 | 15.37 | N |
| ATOM | 1913 | CA | ALA | X | 138 | −6.902 | 33.150 | −34.444 | 1.00 | 15.56 | C |
| ATOM | 1914 | CB | ALA | X | 138 | −8.340 | 33.586 | −34.714 | 1.00 | 15.74 | C |
| ATOM | 1915 | C | ALA | X | 138 | −6.900 | 31.747 | −33.838 | 1.00 | 15.79 | C |
| ATOM | 1916 | O | ALA | X | 138 | −6.902 | 30.753 | −34.568 | 1.00 | 16.65 | O |
| ATOM | 1917 | N | GLY | X | 139 | −6.978 | 31.679 | −32.508 | 1.00 | 17.01 | N |
| ATOM | 1918 | CA | GLY | X | 139 | −6.970 | 30.383 | −31.802 | 1.00 | 16.90 | C |
| ATOM | 1919 | C | GLY | X | 139 | −8.082 | 29.453 | −32.227 | 1.00 | 17.48 | C |
| ATOM | 1920 | O | GLY | X | 139 | −7.917 | 28.231 | −32.245 | 1.00 | 17.64 | O |
| ATOM | 1921 | N | ASN | X | 140 | −9.230 | 30.010 | −32.583 | 1.00 | 18.37 | N |
| ATOM | 1922 | CA | ASN | X | 140 | −10.381 | 29.157 | −32.883 | 1.00 | 18.44 | C |
| ATOM | 1923 | CB | ASN | X | 140 | −11.709 | 29.928 | −32.739 | 1.00 | 19.93 | C |
| ATOM | 1924 | CG | ASN | X | 140 | −11.923 | 30.951 | −33.830 | 1.00 | 22.46 | C |
| ATOM | 1925 | OD1 | ASN | X | 140 | −10.992 | 31.355 | −34.542 | 1.00 | 22.88 | O |
| ATOM | 1926 | ND2 | ASN | X | 140 | −13.181 | 31.403 | −33.963 | 1.00 | 25.46 | N |
| ATOM | 1927 | C | ASN | X | 140 | −10.296 | 28.421 | −34.228 | 1.00 | 17.81 | C |
| ATOM | 1928 | O | ASN | X | 140 | −11.109 | 27.554 | −34.525 | 1.00 | 18.36 | O |
| ATOM | 1929 | N | VAL | X | 141 | −9.274 | 28.747 | −35.036 | 1.00 | 16.61 | N |
| ATOM | 1930 | CA | VAL | X | 141 | −9.058 | 28.010 | −36.279 | 1.00 | 16.54 | C |
| ATOM | 1931 | CB | VAL | X | 141 | −8.064 | 28.764 | −37.166 | 1.00 | 15.12 | C |
| ATOM | 1932 | CG1 | VAL | X | 141 | −7.734 | 27.939 | −38.425 | 1.00 | 17.52 | C |
| ATOM | 1933 | CG2 | VAL | X | 141 | −8.679 | 30.085 | −37.587 | 1.00 | 17.37 | C |
| ATOM | 1934 | C | VAL | X | 141 | −8.510 | 26.608 | −35.926 | 1.00 | 15.86 | C |
| ATOM | 1935 | O | VAL | X | 141 | −7.456 | 26.496 | −35.314 | 1.00 | 15.69 | O |
| ATOM | 1936 | N | TYR | X | 142 | −9.236 | 25.569 | −36.312 | 1.00 | 15.85 | N |
| ATOM | 1937 | CA | TYR | X | 142 | −8.822 | 24.181 | −36.043 | 1.00 | 15.79 | C |
| ATOM | 1938 | CB | TYR | X | 142 | −10.027 | 23.261 | −36.201 | 1.00 | 16.60 | C |
| ATOM | 1939 | CG | TYR | X | 142 | −9.914 | 21.838 | −35.705 | 1.00 | 16.02 | C |
| ATOM | 1940 | CD1 | TYR | X | 142 | −10.460 | 20.791 | −36.461 | 1.00 | 17.45 | C |
| ATOM | 1941 | CE1 | TYR | X | 142 | −10.416 | 19.467 | −35.996 | 1.00 | 16.49 | C |
| ATOM | 1942 | CZ | TYR | X | 142 | −9.833 | 19.197 | −34.766 | 1.00 | 16.65 | C |
| ATOM | 1943 | OH | TYR | X | 142 | −9.812 | 17.903 | −34.343 | 1.00 | 17.69 | O |
| ATOM | 1944 | CE2 | TYR | X | 142 | −9.249 | 20.196 | −33.993 | 1.00 | 16.05 | C |
| ATOM | 1945 | CD2 | TYR | X | 142 | −9.320 | 21.538 | −34.459 | 1.00 | 16.90 | C |
| ATOM | 1946 | C | TYR | X | 142 | −7.755 | 23.753 | −37.042 | 1.00 | 15.78 | C |
| ATOM | 1947 | O | TYR | X | 142 | −6.784 | 23.124 | −36.677 | 1.00 | 16.03 | O |
| ATOM | 1948 | N | TYR | X | 143 | −7.954 | 24.119 | −38.294 | 1.00 | 15.42 | N |
| ATOM | 1949 | CA | TYR | X | 143 | −7.022 | 23.767 | −39.363 | 1.00 | 15.59 | C |

-continued

| | | | | | | | | | | |
|---|---|---|---|---|---|---|---|---|---|---|
| ATOM | 1950 | CB | TYR | X | 143 | −7.397 | 22.443 | −40.029 | 1.00 | 15.86 | C |
| ATOM | 1951 | CG | TYR | X | 143 | −6.593 | 22.201 | −41.296 | 1.00 | 15.84 | C |
| ATOM | 1952 | CD1 | TYR | X | 143 | −5.248 | 21.803 | −41.232 | 1.00 | 15.77 | C |
| ATOM | 1953 | CE1 | TYR | X | 143 | −4.503 | 21.636 | −42.390 | 1.00 | 15.78 | C |
| ATOM | 1954 | CZ | TYR | X | 143 | −5.099 | 21.860 | −43.624 | 1.00 | 15.90 | C |
| ATOM | 1955 | OH | TYR | X | 143 | −4.423 | 21.711 | −44.795 | 1.00 | 16.80 | O |
| ATOM | 1956 | CE2 | TYR | X | 143 | −6.421 | 22.279 | −43.705 | 1.00 | 17.29 | C |
| ATOM | 1957 | CD2 | TYR | X | 143 | −7.149 | 22.438 | −42.540 | 1.00 | 17.06 | C |
| ATOM | 1958 | C | TYR | X | 143 | −7.055 | 24.895 | −40.374 | 1.00 | 16.03 | C |
| ATOM | 1959 | O | TYR | X | 143 | −8.146 | 25.411 | −40.683 | 1.00 | 16.16 | O |
| ATOM | 1960 | N | ARG | X | 144 | −5.882 | 25.298 | −40.860 | 1.00 | 15.43 | N |
| ATOM | 1961 | CA | ARG | X | 144 | −5.807 | 26.282 | −41.950 | 1.00 | 15.05 | C |
| ATOM | 1962 | CB | ARG | X | 144 | −4.936 | 27.471 | −41.517 | 1.00 | 16.14 | C |
| ATOM | 1963 | CG | ARG | X | 144 | −4.549 | 28.377 | −42.710 | 1.00 | 13.65 | C |
| ATOM | 1964 | CD | ARG | X | 144 | −3.529 | 29.442 | −42.289 | 1.00 | 15.10 | C |
| ATOM | 1965 | NE | ARG | X | 144 | −3.119 | 30.267 | −43.428 | 1.00 | 17.44 | N |
| ATOM | 1966 | CZ | ARG | X | 144 | −2.186 | 29.936 | −44.327 | 1.00 | 17.17 | C |
| ATOM | 1967 | NH1 | ARG | X | 144 | −1.525 | 28.782 | −44.264 | 1.00 | 15.13 | N |
| ATOM | 1968 | NH2 | ARG | X | 144 | −1.879 | 30.790 | −45.296 | 1.00 | 18.05 | N |
| ATOM | 1969 | C | ARG | X | 144 | −5.169 | 25.599 | −43.144 | 1.00 | 15.29 | C |
| ATOM | 1970 | O | ARG | X | 144 | −4.109 | 24.996 | −43.005 | 1.00 | 13.71 | O |
| ATOM | 1971 | N | SER | X | 145 | −5.789 | 25.683 | −44.317 | 1.00 | 14.22 | N |
| ATOM | 1972 | CA | SER | X | 145 | −5.204 | 25.079 | −45.523 | 1.00 | 15.67 | C |
| ATOM | 1973 | CB | SER | X | 145 | −6.262 | 24.841 | −46.592 | 1.00 | 16.28 | C |
| ATOM | 1974 | OG | SER | X | 145 | −6.533 | 26.098 | −47.223 | 1.00 | 17.57 | O |
| ATOM | 1975 | C | SER | X | 145 | −4.103 | 25.985 | −46.078 | 1.00 | 15.76 | C |
| ATOM | 1976 | O | SER | X | 145 | −3.992 | 27.175 | −45.702 | 1.00 | 15.58 | O |
| ATOM | 1977 | N | PRO | X | 146 | −3.242 | 25.423 | −46.954 | 1.00 | 15.86 | N |
| ATOM | 1978 | CA | PRO | X | 146 | −2.267 | 26.269 | −47.640 | 1.00 | 16.10 | C |
| ATOM | 1979 | CB | PRO | X | 146 | −1.487 | 25.268 | −48.500 | 1.00 | 16.54 | C |
| ATOM | 1980 | CG | PRO | X | 146 | −1.602 | 23.960 | −47.732 | 1.00 | 16.47 | C |
| ATOM | 1981 | CD | PRO | X | 146 | −3.035 | 23.985 | −47.253 | 1.00 | 15.56 | C |
| ATOM | 1982 | C | PRO | X | 146 | −2.893 | 27.380 | −48.490 | 1.00 | 16.80 | C |
| ATOM | 1983 | O | PRO | X | 146 | −2.189 | 28.314 | −48.855 | 1.00 | 18.30 | O |
| ATOM | 1984 | N | SER | X | 147 | −4.199 | 27.298 | −48.755 | 1.00 | 15.96 | N |
| ATOM | 1985 | CA | ASER | X | 147 | −4.896 | 28.361 | −49.496 | 0.60 | 17.42 | C |
| ATOM | 1986 | CA | BSER | X | 147 | −4.882 | 28.374 | −49.496 | 0.40 | 17.61 | C |
| ATOM | 1987 | CB | ASER | X | 147 | −5.847 | 27.754 | −50.517 | 0.60 | 17.42 | C |
| ATOM | 1988 | CB | BSER | X | 147 | −5.819 | 27.814 | −50.563 | 0.40 | 17.68 | C |
| ATOM | 1989 | OG | ASER | X | 147 | −5.138 | 26.950 | −51.456 | 0.60 | 18.16 | O |
| ATOM | 1990 | OG | BSER | X | 147 | −7.100 | 27.521 | −50.039 | 0.40 | 20.55 | O |
| ATOM | 1991 | C | SER | X | 147 | −5.607 | 29.351 | −48.573 | 1.00 | 17.58 | C |
| ATOM | 1992 | O | SER | X | 147 | −6.425 | 30.193 | −49.037 | 1.00 | 17.46 | O |
| ATOM | 1993 | N | ASN | X | 148 | −5.278 | 29.270 | −47.285 | 1.00 | 16.48 | N |
| ATOM | 1994 | CA | ASN | X | 148 | −5.805 | 30.165 | −46.250 | 1.00 | 16.74 | C |
| ATOM | 1995 | CB | ASN | X | 148 | −5.526 | 31.637 | −46.586 | 1.00 | 15.89 | C |
| ATOM | 1996 | CG | ASN | X | 148 | −5.541 | 32.523 | −45.350 | 1.00 | 15.00 | C |
| ATOM | 1997 | OD1 | ASN | X | 148 | −5.094 | 32.129 | −44.275 | 1.00 | 16.09 | O |
| ATOM | 1998 | ND2 | ASN | X | 148 | −6.120 | 33.729 | −45.496 | 1.00 | 17.34 | N |
| ATOM | 1999 | C | ASN | X | 148 | −7.315 | 29.970 | −46.004 | 1.00 | 17.08 | C |
| ATOM | 2000 | O | ASN | X | 148 | −7.999 | 30.901 | −45.525 | 1.00 | 18.12 | O |
| ATOM | 2001 | N | SER | X | 149 | −7.829 | 28.789 | −46.335 | 1.00 | 16.34 | N |
| ATOM | 2002 | CA | SER | X | 149 | −9.175 | 28.386 | −45.894 | 1.00 | 17.52 | C |
| ATOM | 2003 | CB | SER | X | 149 | −9.788 | 27.316 | −46.793 | 1.00 | 17.61 | C |
| ATOM | 2004 | OG | SER | X | 149 | −9.923 | 27.805 | −48.107 | 1.00 | 18.82 | O |
| ATOM | 2005 | C | SER | X | 149 | −9.086 | 27.876 | −44.468 | 1.00 | 18.30 | C |
| ATOM | 2006 | O | SER | X | 149 | −8.044 | 27.331 | −44.049 | 1.00 | 16.60 | O |
| ATOM | 2007 | N | TYR | X | 150 | −10.176 | 28.065 | −43.722 | 1.00 | 17.02 | N |
| ATOM | 2008 | CA | TYR | X | 150 | −10.223 | 27.714 | −42.309 | 1.00 | 18.28 | C |
| ATOM | 2009 | CB | TYR | X | 150 | −10.653 | 28.918 | −41.435 | 1.00 | 18.32 | C |
| ATOM | 2010 | CG | TYR | X | 150 | −9.643 | 30.049 | −41.274 | 1.00 | 19.57 | C |
| ATOM | 2011 | CD1 | TYR | X | 150 | −8.311 | 29.901 | −41.638 | 1.00 | 19.33 | C |
| ATOM | 2012 | CE1 | TYR | X | 150 | −7.388 | 30.963 | −41.461 | 1.00 | 18.26 | C |
| ATOM | 2013 | CZ | TYR | X | 150 | −7.830 | 32.166 | −40.905 | 1.00 | 19.55 | C |
| ATOM | 2014 | OH | TYR | X | 150 | −6.962 | 33.228 | −40.715 | 1.00 | 21.46 | O |
| ATOM | 2015 | CE2 | TYR | X | 150 | −9.154 | 32.305 | −40.537 | 1.00 | 20.35 | C |
| ATOM | 2016 | CD2 | TYR | X | 150 | −10.035 | 31.264 | −40.719 | 1.00 | 19.90 | C |
| ATOM | 2017 | C | TYR | X | 150 | −11.213 | 26.582 | −42.105 | 1.00 | 18.34 | C |
| ATOM | 2018 | O | TYR | X | 150 | −12.236 | 26.498 | −42.795 | 1.00 | 18.75 | O |
| ATOM | 2019 | N | LEU | X | 151 | −10.878 | 25.700 | −41.178 | 1.00 | 18.74 | N |
| ATOM | 2020 | CA | LEU | X | 151 | −11.790 | 24.682 | −40.694 | 1.00 | 19.70 | C |
| ATOM | 2021 | CB | LEU | X | 151 | −11.213 | 23.288 | −41.016 | 1.00 | 19.51 | C |
| ATOM | 2022 | CG | LEU | X | 151 | −11.869 | 22.083 | −40.360 | 1.00 | 21.37 | C |
| ATOM | 2023 | CD1 | LEU | X | 151 | −13.283 | 21.883 | −40.850 | 1.00 | 22.97 | C |
| ATOM | 2024 | CD2 | LEU | X | 151 | −11.040 | 20.838 | −40.663 | 1.00 | 22.05 | C |
| ATOM | 2025 | C | LEU | X | 151 | −11.935 | 24.894 | −39.202 | 1.00 | 19.30 | C |
| ATOM | 2026 | O | LEU | X | 151 | −10.953 | 25.156 | −38.502 | 1.00 | 18.08 | O |
| ATOM | 2027 | N | TYR | X | 152 | −13.178 | 24.845 | −38.715 | 1.00 | 19.57 | N |
| ATOM | 2028 | CA | TYR | X | 152 | −13.447 | 25.082 | −37.307 | 1.00 | 20.01 | C |
| ATOM | 2029 | CB | TYR | X | 152 | −14.537 | 26.156 | −37.168 | 1.00 | 19.97 | C |

-continued

| | | | | | | | | | | |
|---|---|---|---|---|---|---|---|---|---|---|
| ATOM | 2030 | CG | TYR | X | 152 | −14.081 | 27.520 | −37.618 | 1.00 | 21.44 | C |
| ATOM | 2031 | CD1 | TYR | X | 152 | −13.280 | 28.298 | −36.798 | 1.00 | 20.62 | C |
| ATOM | 2032 | CE1 | TYR | X | 152 | −12.833 | 29.568 | −37.196 | 1.00 | 21.57 | C |
| ATOM | 2033 | CZ | TYR | X | 152 | −13.217 | 30.056 | −38.443 | 1.00 | 21.99 | C |
| ATOM | 2034 | OH | TYR | X | 152 | −12.792 | 31.308 | −38.816 | 1.00 | 23.87 | O |
| ATOM | 2035 | CE2 | TYR | X | 152 | −14.014 | 29.305 | −39.288 | 1.00 | 21.47 | C |
| ATOM | 2036 | CD2 | TYR | X | 152 | −14.449 | 28.025 | −38.866 | 1.00 | 22.96 | C |
| ATOM | 2037 | C | TYR | X | 152 | −13.902 | 23.799 | −36.603 | 1.00 | 20.64 | C |
| ATOM | 2038 | O | TYR | X | 152 | −14.309 | 22.844 | −37.258 | 1.00 | 21.25 | O |
| ATOM | 2039 | N | ASP | X | 153 | −13.818 | 23.801 | −35.274 | 1.00 | 20.88 | N |
| ATOM | 2040 | CA | ASP | X | 153 | −14.287 | 22.686 | −34.443 | 1.00 | 22.62 | C |
| ATOM | 2041 | CB | ASP | X | 153 | −13.125 | 21.722 | −34.162 | 1.00 | 21.41 | C |
| ATOM | 2042 | CG | ASP | X | 153 | −13.575 | 20.444 | −33.478 | 1.00 | 21.91 | C |
| ATOM | 2043 | OD1 | ASP | X | 153 | −14.706 | 19.966 | −33.757 | 1.00 | 19.60 | O |
| ATOM | 2044 | OD2 | ASP | X | 153 | −12.782 | 19.926 | −32.686 | 1.00 | 20.19 | O |
| ATOM | 2045 | C | ASP | X | 153 | −14.776 | 23.300 | −33.145 | 1.00 | 23.76 | C |
| ATOM | 2046 | O | ASP | X | 153 | −14.201 | 23.093 | −32.082 | 1.00 | 23.25 | O |
| ATOM | 2047 | N | ASN | X | 154 | −15.826 | 24.109 | −33.237 | 1.00 | 26.72 | N |
| ATOM | 2048 | CA | ASN | X | 154 | −16.176 | 24.989 | −32.114 | 1.00 | 28.77 | C |
| ATOM | 2049 | CB | ASN | X | 154 | −17.172 | 26.065 | −32.547 | 1.00 | 29.10 | C |
| ATOM | 2050 | CG | ASN | X | 154 | −16.538 | 27.100 | −33.455 | 1.00 | 32.64 | C |
| ATOM | 2051 | OD1 | ASN | X | 154 | −17.185 | 27.618 | −34.372 | 1.00 | 37.50 | O |
| ATOM | 2052 | ND2 | ASN | X | 154 | −15.260 | 27.407 | −33.206 | 1.00 | 32.00 | N |
| ATOM | 2053 | C | ASN | X | 154 | −16.612 | 24.328 | −30.811 | 1.00 | 29.03 | C |
| ATOM | 2054 | O | ASN | X | 154 | −16.447 | 24.920 | −29.737 | 1.00 | 30.38 | O |
| ATOM | 2055 | N | ASN | X | 155 | −17.132 | 23.105 | −30.907 | 1.00 | 28.57 | N |
| ATOM | 2056 | CA | ASN | X | 155 | −17.553 | 22.355 | −29.726 | 1.00 | 28.05 | C |
| ATOM | 2057 | CB | ASN | X | 155 | −18.983 | 21.860 | −29.919 | 1.00 | 29.02 | C |
| ATOM | 2058 | CG | ASN | X | 155 | −19.963 | 23.000 | −30.038 | 1.00 | 33.19 | C |
| ATOM | 2059 | OD1 | ASN | X | 155 | −20.656 | 23.137 | −31.054 | 1.00 | 39.38 | O |
| ATOM | 2060 | ND2 | ASN | X | 155 | −19.995 | 23.860 | −29.018 | 1.00 | 34.63 | N |
| ATOM | 2061 | C | ASN | X | 155 | −16.611 | 21.209 | −29.394 | 1.00 | 26.14 | C |
| ATOM | 2962 | O | ASN | X | 155 | −16.951 | 20.316 | −28.623 | 1.00 | 25.00 | O |
| ATOM | 2063 | N | LEU | X | 156 | −15.410 | 21.255 | −29.987 | 1.00 | 24.52 | N |
| ATOM | 2064 | CA | ALEU | X | 156 | −14.391 | 20.220 | −29.788 | 0.44 | 23.67 | C |
| ATOM | 2065 | CA | BLEU | X | 156 | −14.391 | 20.215 | −29.813 | 0.56 | 23.51 | C |
| ATOM | 2066 | CB | ALEU | X | 156 | −13.766 | 20.306 | −28.381 | 0.44 | 23.96 | C |
| ATOM | 2067 | CB | BLEU | X | 156 | −13.689 | 20.308 | −28.448 | 0.56 | 23.70 | C |
| ATOM | 2068 | CG | ALEU | X | 156 | −12.932 | 21.531 | −27.935 | 0.44 | 24.54 | C |
| ATOM | 2069 | CG | BLEU | X | 156 | −12.414 | 21.170 | −28.406 | 0.56 | 23.76 | C |
| ATOM | 2070 | CD1 | ALEU | X | 156 | −11.429 | 21.324 | −28.110 | 0.44 | 24.38 | C |
| ATOM | 2071 | CD1 | BLEU | X | 156 | −12.701 | 22.649 | −28.550 | 0.56 | 24.50 | C |
| ATOM | 2072 | CD2 | ALEU | X | 156 | −13.365 | 22.849 | −28.579 | 0.44 | 26.49 | C |
| ATOM | 2073 | CD2 | BLEU | X | 156 | −11.639 | 20.928 | −27.120 | 0.56 | 23.72 | C |
| ATOM | 2074 | C | LEU | X | 156 | −14.909 | 18.796 | −30.078 | 1.00 | 23.21 | C |
| ATOM | 2075 | O | LEU | X | 156 | −14.384 | 17.821 | −29.539 | 1.00 | 22.81 | O |
| ATOM | 2076 | N | ILE | X | 157 | −15.910 | 18.688 | −30.938 | 1.00 | 22.98 | N |
| ATOM | 2077 | CA | AILE | X | 157 | −16.461 | 17.382 | −31.343 | 0.50 | 23.40 | C |
| ATOM | 2078 | CA | BILE | X | 157 | −16.441 | 17.370 | −31.288 | 0.50 | 23.39 | C |
| ATOM | 2079 | CB | AILE | X | 157 | −17.677 | 17.557 | −32.306 | 0.50 | 23.20 | C |
| ATOM | 2080 | CB | BILE | X | 157 | −17.757 | 17.465 | −32.110 | 0.50 | 23.32 | C |
| ATOM | 2081 | CG1 | AILE | X | 157 | −18.940 | 17.876 | −31.505 | 0.50 | 24.91 | C |
| ATOM | 2082 | CG1 | BILE | X | 157 | −18.830 | 18.227 | −31.308 | 0.50 | 24.65 | C |
| ATOM | 2083 | CD1 | AILE | X | 157 | −19.965 | 18.627 | −32.293 | 0.50 | 25.95 | C |
| ATOM | 2084 | CD1 | BILE | X | 157 | −19.145 | 17.625 | −29.934 | 0.50 | 24.89 | C |
| ATOM | 2085 | CG2 | AILE | X | 157 | −17.931 | 16.310 | −33.155 | 0.50 | 24.28 | C |
| ATOM | 2086 | CG2 | BILE | X | 157 | −18.275 | 16.077 | −32.493 | 0.50 | 24.37 | C |
| ATOM | 2087 | C | ILE | X | 157 | −15.362 | 16.570 | −32.016 | 1.00 | 23.14 | C |
| ATOM | 2088 | O | ILE | X | 157 | −15.098 | 15.412 | −31.663 | 1.00 | 23.53 | O |
| ATOM | 2089 | N | ASN | X | 158 | −14.706 | 17.199 | −32.990 | 1.00 | 22.71 | N |
| ATOM | 2090 | CA | ASN | X | 158 | −13.664 | 16.489 | −33.711 | 1.00 | 21.39 | C |
| ATOM | 2091 | CB | ASN | X | 158 | −13.278 | 17.235 | −34.983 | 1.00 | 21.86 | C |
| ATOM | 2092 | CG | ASN | X | 158 | −12.522 | 16.346 | −35.945 | 1.00 | 23.52 | C |
| ATOM | 2093 | OD1 | ASN | X | 158 | −11.288 | 16.340 | −35.967 | 1.00 | 20.15 | O |
| ATOM | 2094 | ND2 | ASN | X | 158 | −13.255 | 15.540 | −36.696 | 1.00 | 21.44 | N |
| ATOM | 2095 | C | ASN | X | 158 | −12.456 | 16.240 | −32.808 | 1.00 | 20.49 | C |
| ATOM | 2096 | O | ASN | X | 158 | −11.926 | 15.125 | −32.773 | 1.00 | 19.44 | O |
| ATOM | 2097 | N | THR | X | 159 | −12.043 | 17.287 | −32.081 | 1.00 | 19.09 | N |
| ATOM | 2098 | CA | THR | X | 159 | −10.910 | 17.219 | −31.160 | 1.00 | 18.36 | C |
| ATOM | 2099 | CB | THR | X | 159 | −10.742 | 18.536 | −30.366 | 1.00 | 18.50 | C |
| ATOM | 2100 | OG1 | THR | X | 159 | −10.405 | 19.597 | −31.276 | 1.00 | 17.89 | O |
| ATOM | 2101 | CG2 | THR | X | 159 | −9.666 | 18.434 | −29.315 | 1.00 | 17.39 | C |
| ATOM | 2102 | C | THR | X | 159 | −11.004 | 16.034 | −30.210 | 1.00 | 18.76 | C |
| ATOM | 2103 | O | THR | X | 159 | −10.104 | 15.212 | −30.110 | 1.00 | 18.14 | O |
| ATOM | 2104 | N | ASN | X | 160 | −12.112 | 15.962 | −29.488 | 1.00 | 18.94 | N |
| ATOM | 2105 | CA | ASN | X | 160 | −12.243 | 14.923 | −28.496 | 1.00 | 19.48 | C |
| ATOM | 2106 | CB | ASN | X | 160 | −13.461 | 15.222 | −27.626 | 1.00 | 19.71 | C |
| ATOM | 2107 | CG | ASN | X | 160 | −13.233 | 16.417 | −26.728 | 1.00 | 20.20 | C |
| ATOM | 2108 | OD1 | ASN | X | 160 | −12.100 | 16.733 | −26.359 | 1.00 | 20.53 | O |
| ATOM | 2109 | ND2 | ASN | X | 160 | −14.321 | 17.089 | −26.351 | 1.00 | 23.98 | N |

-continued

| | | | | | | | | | | |
|---|---|---|---|---|---|---|---|---|---|---|
| ATOM | 2110 | C | ASN | X | 160 | −12.319 | 13.531 | −29.100 | 1.00 | 19.55 | C |
| ATOM | 2111 | O | ASN | X | 160 | −11.776 | 12.587 | −28.528 | 1.00 | 19.96 | O |
| ATOM | 2112 | N | CYS | X | 161 | −12.967 | 13.430 | −30.250 | 1.00 | 21.19 | N |
| ATOM | 2113 | CA | CYS | X | 161 | −13.067 | 12.160 | −30.983 | 1.00 | 21.32 | C |
| ATOM | 2114 | CB | CYS | X | 161 | −13.973 | 12.334 | −32.194 | 1.00 | 22.84 | C |
| ATOM | 2115 | SG | CYS | X | 161 | −14.218 | 10.805 | −33.137 | 1.00 | 25.46 | S |
| ATOM | 2116 | C | CYS | X | 161 | −11.667 | 11.677 | −31.403 | 1.00 | 21.19 | C |
| ATOM | 2117 | O | CYS | X | 161 | −11.286 | 10.510 | −31.180 | 1.00 | 20.33 | O |
| ATOM | 2118 | N | VAL | X | 162 | −10.888 | 12.591 | −31.974 | 1.00 | 20.25 | N |
| ATOM | 2119 | CA | VAL | X | 162 | −9.511 | 12.251 | −32.387 | 1.00 | 18.91 | C |
| ATOM | 2120 | CB | VAL | X | 162 | −8.893 | 13.397 | −33.219 | 1.00 | 19.50 | C |
| ATOM | 2121 | CG1 | VAL | X | 162 | −7.403 | 13.098 | −33.465 | 1.00 | 18.88 | C |
| ATOM | 2122 | CG2 | VAL | X | 162 | −9.696 | 13.569 | −34.521 | 1.00 | 18.97 | C |
| ATOM | 2123 | C | VAL | X | 162 | −8.613 | 11.861 | −31.196 | 1.00 | 18.68 | C |
| ATOM | 2124 | O | VAL | X | 162 | −7.907 | 10.852 | −31.230 | 1.00 | 17.48 | O |
| ATOM | 2125 | N | LEU | X | 163 | −8.642 | 12.666 | −30.133 | 1.00 | 17.69 | N |
| ATOM | 2126 | CA | LEU | X | 163 | −7.896 | 12.365 | −28.939 | 1.00 | 17.62 | C |
| ATOM | 2127 | CB | LEU | X | 163 | −8.105 | 13.466 | −27.908 | 1.00 | 17.65 | C |
| ATOM | 2128 | CG | LEU | X | 163 | −7.480 | 14.815 | −28.270 | 1.00 | 16.26 | C |
| ATOM | 2129 | CD1 | LEU | X | 163 | −7.822 | 15.763 | −27.133 | 1.00 | 18.05 | C |
| ATOM | 2130 | CD2 | LEU | X | 163 | −5.954 | 14.728 | −28.476 | 1.00 | 16.46 | C |
| ATOM | 2131 | C | LEU | X | 163 | −8.295 | 11.008 | −28.349 | 1.00 | 18.16 | C |
| ATOM | 2132 | O | LEU | X | 163 | −7.441 | 10.254 | −27.899 | 1.00 | 18.23 | O |
| ATOM | 2133 | N | THR | X | 164 | −9.589 | 10.726 | −28.345 | 1.00 | 18.60 | N |
| ATOM | 2134 | CA | THR | X | 164 | −10.071 | 9.416 | −27.878 | 1.00 | 19.69 | C |
| ATOM | 2135 | CB | THR | X | 164 | −11.609 | 9.387 | −27.797 | 1.00 | 19.96 | C |
| ATOM | 2136 | OG1 | THR | X | 164 | −12.015 | 10.365 | −26.829 | 1.00 | 20.69 | O |
| ATOM | 2137 | CG2 | THR | X | 164 | −12.096 | 7.987 | −27.323 | 1.00 | 21.08 | C |
| ATOM | 2138 | C | THR | X | 164 | −9.534 | 8.278 | −28.762 | 1.00 | 20.14 | C |
| ATOM | 2139 | O | THR | X | 164 | −9.083 | 7.249 | −28.248 | 1.00 | 20.87 | O |
| ATOM | 2140 | N | LYS | X | 165 | −9.576 | 8.465 | −30.078 | 1.00 | 19.68 | N |
| ATOM | 2141 | CA | LYS | X | 165 | −9.077 | 7.448 | −30.988 | 1.00 | 20.04 | C |
| ATOM | 2142 | CB | LYS | X | 165 | −9.298 | 7.831 | −32.452 | 1.00 | 21.31 | C |
| ATOM | 2143 | CG | LYS | X | 165 | −8.966 | 6.713 | −33.441 | 1.00 | 22.30 | C |
| ATOM | 2144 | CD | LYS | X | 165 | −10.051 | 5.619 | −33.396 | 1.00 | 27.58 | C |
| ATOM | 2145 | CE | LYS | X | 165 | −9.879 | 4.539 | −34.465 | 1.00 | 28.08 | C |
| ATOM | 2146 | NZ | LYS | X | 165 | −10.852 | 3.414 | −34.217 | 1.00 | 31.64 | N |
| ATOM | 2147 | C | LYS | X | 165 | −7.602 | 7.173 | −30.766 | 1.00 | 18.97 | C |
| ATOM | 2148 | O | LYS | X | 165 | −7.177 | 6.025 | −30.828 | 1.00 | 18.97 | O |
| ATOM | 2149 | N | PHE | X | 166 | −6.821 | 8.224 | −30.506 | 1.00 | 18.60 | N |
| ATOM | 2150 | CA | PHE | X | 166 | −5.364 | 8.071 | −30.323 | 1.00 | 18.26 | C |
| ATOM | 2151 | CB | PHE | X | 166 | −4.592 | 9.284 | −30.899 | 1.00 | 17.53 | C |
| ATOM | 2152 | CG | PHE | X | 166 | −4.765 | 9.502 | −32.401 | 1.00 | 18.08 | C |
| ATOM | 2153 | CD1 | PHE | X | 166 | −5.367 | 8.557 | −33.238 | 1.00 | 19.26 | C |
| ATOM | 2154 | CE1 | PHE | X | 166 | −5.535 | 8.802 | −34.625 | 1.00 | 18.50 | C |
| ATOM | 2155 | CZ | PHE | X | 166 | −5.063 | 10.005 | −35.176 | 1.00 | 19.23 | C |
| ATOM | 2156 | CE2 | PHE | X | 166 | −4.455 | 10.942 | −34.352 | 1.00 | 17.96 | C |
| ATOM | 2157 | CD2 | PHE | X | 166 | −4.306 | 10.688 | −32.967 | 1.00 | 16.89 | C |
| ATOM | 2158 | C | PHE | X | 166 | −4.911 | 7.858 | −28.888 | 1.00 | 18.51 | C |
| ATOM | 2159 | O | PHE | X | 166 | −3.708 | 7.770 | −28.605 | 1.00 | 17.52 | O |
| ATOM | 2160 | N | SER | X | 167 | −5.874 | 7.741 | −27.979 | 1.00 | 18.77 | N |
| ATOM | 2161 | CA | ASER | X | 167 | −5.588 | 7.777 | −26.545 | 0.59 | 19.40 | C |
| ATOM | 2162 | CA | BSER | X | 167 | −5.574 | 7.780 | −26.549 | 0.41 | 19.06 | C |
| ATOM | 2163 | CB | ASER | X | 167 | −6.887 | 7.561 | −25.767 | 0.59 | 19.15 | C |
| ATOM | 2164 | CB | BSER | X | 167 | −6.846 | 7.625 | −25.712 | 0.41 | 18.91 | C |
| ATOM | 2165 | OG | ASER | X | 167 | −7.429 | 6.286 | −26.055 | 0.59 | 21.34 | O |
| ATOM | 2166 | OG | BSER | X | 167 | −6.543 | 7.826 | −24.340 | 0.41 | 19.44 | O |
| ATOM | 2167 | C | SER | X | 167 | −4.517 | 6.781 | −26.106 | 1.00 | 18.81 | C |
| ATOM | 2168 | O | SER | X | 167 | −3.657 | 7.109 | −25.267 | 1.00 | 20.00 | O |
| ATOM | 2169 | N | ALEU | X | 168 | −4.577 | 5.575 | −26.679 | 0.22 | 18.93 | N |
| ATOM | 2170 | N | BLEU | X | 168 | −4.542 | 5.562 | −26.665 | 0.78 | 18.52 | N |
| ATOM | 2171 | CA | ALEU | X | 168 | −3.702 | 4.464 | −26.306 | 0.22 | 18.95 | C |
| ATOM | 2172 | CA | BLEU | X | 168 | −3.614 | 4.532 | −26.208 | 0.78 | 19.16 | C |
| ATOM | 2173 | CB | ALEU | X | 168 | −4.518 | 3.178 | −26.140 | 0.22 | 18.98 | C |
| ATOM | 2174 | CB | BLEU | X | 168 | −4.320 | 3.171 | −26.129 | 0.78 | 18.82 | C |
| ATOM | 2175 | CG | ALEU | X | 168 | −5.458 | 2.983 | −24.955 | 0.22 | 19.31 | C |
| ATOM | 2176 | CG | BLEU | X | 168 | −5.532 | 3.178 | −25.208 | 0.78 | 17.93 | C |
| ATOM | 2177 | CD1 | ALEU | X | 168 | −6.547 | 4.035 | −24.907 | 0.22 | 19.74 | C |
| ATOM | 2178 | CD1 | BLEU | X | 168 | −6.297 | 1.855 | −25.364 | 0.78 | 18.63 | C |
| ATOM | 2179 | CD2 | ALEU | X | 168 | −6.059 | 1.591 | −25.066 | 0.22 | 18.96 | C |
| ATOM | 2180 | CD2 | BLEU | X | 168 | −5.039 | 3.388 | −23.761 | 0.78 | 16.96 | C |
| ATOM | 2181 | C | ALEU | X | 168 | −2.597 | 4.223 | −27.329 | 0.22 | 18.85 | C |
| ATOM | 2182 | C | BLEU | X | 168 | −2.350 | 4.420 | −27.050 | 0.78 | 19.66 | C |
| ATOM | 2183 | O | ALEU | X | 168 | −2.069 | 3.112 | −27.442 | 0.22 | 18.25 | O |
| ATOM | 2184 | O | BLEU | X | 168 | −1.478 | 3.584 | −26.770 | 0.78 | 20.21 | O |
| ATOM | 2185 | N | LEU | X | 169 | −2.254 | 5.264 | −28.077 | 1.00 | 19.02 | N |
| ATOM | 2186 | CA | LEU | X | 169 | −1.137 | 5.187 | −29.010 | 1.00 | 18.66 | C |
| ATOM | 2187 | CB | LEU | X | 169 | −1.583 | 5.688 | −30.383 | 1.00 | 18.31 | C |
| ATOM | 2188 | CG | LEU | X | 169 | −2.888 | 5.104 | −30.922 | 1.00 | 18.81 | C |
| ATOM | 2189 | CD1 | LEU | X | 169 | −3.167 | 5.757 | −32.264 | 1.00 | 19.69 | C |

-continued

| | | | | | | | | | | |
|---|---|---|---|---|---|---|---|---|---|---|
| ATOM | 2190 | CD2 | LEU | X | 169 | −2.812 | 3.553 | −31.039 | 1.00 | 19.38 | C |
| ATOM | 2191 | C | LEU | X | 169 | 0.030 | 6.010 | −28.487 | 1.00 | 19.62 | C |
| ATOM | 2192 | O | LEU | X | 169 | −0.147 | 7.030 | −27.814 | 1.00 | 19.04 | O |
| ATOM | 2193 | N | SER | X | 170 | 1.231 | 5.542 | −28.772 | 1.00 | 19.60 | N |
| ATOM | 2194 | CA | ASER | X | 170 | 2.434 | 6.185 | −28.286 | 0.55 | 20.45 | C |
| ATOM | 2195 | CA | BSER | X | 170 | 2.432 | 6.222 | −28.317 | 0.45 | 21.04 | C |
| ATOM | 2196 | CB | ASER | X | 170 | 2.739 | 5.694 | −26.863 | 0.55 | 20.57 | C |
| ATOM | 2197 | CB | BSER | X | 170 | 2.761 | 5.875 | −26.850 | 0.45 | 21.21 | C |
| ATOM | 2198 | OG | ASER | X | 170 | 3.858 | 6.362 | −26.311 | 0.55 | 18.68 | O |
| ATOM | 2199 | OG | BSER | X | 170 | 3.736 | 4.848 | −26.741 | 0.45 | 23.00 | O |
| ATOM | 2200 | C | SER | X | 170 | 3.577 | 5.861 | −29.242 | 1.00 | 21.18 | C |
| ATOM | 2201 | O | SER | X | 170 | 3.599 | 4.763 | −29.825 | 1.00 | 22.50 | O |
| ATOM | 2202 | N | GLY | X | 171 | 4.509 | 6.797 | −29.399 | 1.00 | 21.00 | N |
| ATOM | 2203 | CA | GLY | X | 171 | 5.652 | 6.625 | −30.280 | 1.00 | 20.85 | C |
| ATOM | 2204 | C | GLY | X | 171 | 5.330 | 6.910 | −31.736 | 1.00 | 21.42 | C |
| ATOM | 2205 | O | GLY | X | 171 | 4.363 | 7.620 | −32.047 | 1.00 | 20.35 | O |
| ATOM | 2206 | N | CYS | X | 172 | 6.139 | 6.346 | −32.634 | 1.00 | 20.42 | N |
| ATOM | 2207 | CA | CYS | X | 172 | 6.058 | 6.718 | −34.064 | 1.00 | 21.24 | C |
| ATOM | 2208 | CB | CYS | X | 172 | 7.449 | 7.059 | −34.610 | 1.00 | 21.75 | C |
| ATOM | 2209 | SG | CYS | X | 172 | 8.285 | 8.377 | −33.709 | 1.00 | 22.99 | S |
| ATOM | 2210 | C | CYS | X | 172 | 5.339 | 5.679 | −34.921 | 1.00 | 21.50 | C |
| ATOM | 2211 | O | CYS | X | 172 | 5.400 | 5.740 | −36.161 | 1.00 | 21.28 | O |
| ATOM | 2212 | N | SER | X | 173 | 4.652 | 4.750 | −34.239 | 1.00 | 20.36 | N |
| ATOM | 2213 | CA | SER | X | 173 | 3.741 | 3.746 | −34.836 | 1.00 | 21.39 | C |
| ATOM | 2214 | CB | SER | X | 173 | 4.409 | 2.365 | −34.863 | 1.00 | 22.59 | C |
| ATOM | 2215 | OG | SER | X | 173 | 5.482 | 2.350 | −35.804 | 1.00 | 24.84 | O |
| ATOM | 2216 | C | SER | X | 173 | 2.420 | 3.669 | −34.046 | 1.00 | 21.15 | C |
| ATOM | 2217 | O | SER | X | 173 | 2.431 | 3.883 | −32.834 | 1.00 | 21.22 | O |
| ATOM | 2218 | N | PRO | X | 174 | 1.283 | 3.361 | −34.710 | 1.00 | 21.36 | N |
| ATOM | 2219 | CA | PRO | X | 174 | 1.114 | 3.025 | −36.128 | 1.00 | 21.43 | C |
| ATOM | 2220 | CB | PRO | X | 174 | −0.334 | 2.523 | −36.197 | 1.00 | 21.45 | C |
| ATOM | 2221 | CG | PRO | X | 174 | −1.037 | 3.224 | −35.085 | 1.00 | 21.17 | C |
| ATOM | 2222 | CD | PRO | X | 174 | −0.015 | 3.341 | −33.993 | 1.00 | 21.49 | C |
| ATOM | 2223 | C | PRO | X | 174 | 1.296 | 4.237 | −37.056 | 1.00 | 21.96 | C |
| ATOM | 2224 | O | PRO | X | 174 | 1.002 | 5.360 | −36.678 | 1.00 | 21.11 | O |
| ATOM | 2225 | N | SER | X | 175 | 1.796 | 3.991 | −38.264 | 1.00 | 22.22 | N |
| ATOM | 2226 | CA | SER | X | 175 | 1.881 | 5.031 | −39.286 | 1.00 | 23.61 | C |
| ATOM | 2227 | CB | SER | X | 175 | 3.270 | 5.673 | −39.301 | 1.00 | 23.68 | C |
| ATOM | 2228 | OG | SER | X | 175 | 3.411 | 6.515 | −40.439 | 1.00 | 24.56 | O |
| ATOM | 2229 | C | SER | X | 175 | 1.569 | 4.320 | −40.600 | 1.00 | 24.44 | C |
| ATOM | 2230 | O | SER | X | 175 | 2.295 | 3.378 | −40.947 | 1.00 | 25.73 | O |
| ATOM | 2231 | N | PRO | X | 176 | 0.494 | 4.731 | −41.319 | 1.00 | 24.20 | N |
| ATOM | 2232 | CA | APRO | X | 176 | −0.409 | 5.838 | −41.000 | 0.40 | 23.82 | C |
| ATOM | 2233 | CA | BPRO | X | 176 | −0.414 | 5.836 | −41.006 | 0.60 | 23.78 | C |
| ATOM | 2234 | CB | APRO | X | 176 | −1.399 | 5.840 | −42.177 | 0.40 | 24.38 | C |
| ATOM | 2235 | CB | BPRO | X | 176 | −1.400 | 5.833 | −42.192 | 0.60 | 24.54 | C |
| ATOM | 2236 | CG | APRO | X | 176 | −1.331 | 4.460 | −42.725 | 0.40 | 24.21 | C |
| ATOM | 2237 | CG | BPRO | X | 176 | −0.659 | 5.132 | −43.296 | 0.60 | 23.71 | C |
| ATOM | 2238 | CD | APRO | X | 176 | 0.099 | 4.064 | −42.576 | 0.40 | 24.81 | C |
| ATOM | 2239 | CD | BPRO | X | 176 | 0.133 | 4.080 | −42.598 | 0.60 | 25.04 | C |
| ATOM | 2240 | C | PRO | X | 176 | −1.169 | 5.647 | −39.686 | 1.00 | 23.46 | C |
| ATOM | 2241 | O | PRO | X | 176 | −1.344 | 4.499 | −39.211 | 1.00 | 22.37 | O |
| ATOM | 2242 | N | ALA | X | 177 | −1.600 | 6.763 | −39.109 | 1.00 | 23.20 | N |
| ATOM | 2243 | CA | ALA | X | 177 | −2.422 | 6.726 | −37.898 | 1.00 | 23.53 | C |
| ATOM | 2244 | CB | ALA | X | 177 | −2.671 | 8.159 | −37.386 | 1.00 | 23.56 | C |
| ATOM | 2245 | C | ALA | X | 177 | −3.746 | 6.027 | −38.222 | 1.00 | 24.05 | C |
| ATOM | 2246 | O | ALA | X | 177 | −4.117 | 5.912 | −39.397 | 1.00 | 24.44 | O |
| ATOM | 2247 | N | PRO | X | 178 | −4.480 | 5.587 | −37.192 | 1.00 | 24.92 | N |
| ATOM | 2248 | CA | PRO | X | 178 | −5.812 | 5.033 | −37.396 | 1.00 | 25.95 | C |
| ATOM | 2249 | CB | PRO | X | 178 | −6.307 | 4.762 | −35.966 | 1.00 | 26.10 | C |
| ATOM | 2250 | CG | PRO | X | 178 | −5.113 | 4.722 | −35.128 | 1.00 | 26.02 | C |
| ATOM | 2251 | CD | PRO | X | 178 | −4.104 | 5.621 | −35.768 | 1.00 | 24.78 | C |
| ATOM | 2252 | C | PRO | X | 178 | −6.779 | 6.005 | −38.059 | 1.00 | 26.40 | C |
| ATOM | 2253 | O | PRO | X | 178 | −6.640 | 7.221 | −37.929 | 1.00 | 25.53 | O |
| ATOM | 2254 | N | ASP | X | 179 | −7.786 | 5.445 | −38.723 | 1.00 | 27.80 | N |
| ATOM | 2255 | CA | ASP | X | 179 | −8.849 | 6.204 | −39.363 | 1.00 | 29.96 | C |
| ATOM | 2256 | CB | ASP | X | 179 | −9.842 | 5.215 | −39.976 | 1.00 | 30.69 | C |
| ATOM | 2257 | CG | ASP | X | 179 | −10.661 | 5.814 | −41.089 | 1.00 | 35.02 | C |
| ATOM | 2258 | OD1 | ASP | X | 179 | −11.138 | 6.966 | −40.966 | 1.00 | 37.70 | O |
| ATOM | 2259 | OD2 | ASP | X | 179 | −10.823 | 5.112 | −42.109 | 1.00 | 40.98 | O |
| ATOM | 2260 | C | ASP | X | 179 | −9.578 | 7.079 | −38.350 | 1.00 | 29.91 | C |
| ATOM | 2261 | O | ASP | X | 179 | −9.932 | 6.614 | −37.255 | 1.00 | 30.07 | O |
| ATOM | 2262 | N | AVAL | X | 180 | −9.835 | 8.322 | −38.743 | 0.31 | 30.56 | N |
| ATOM | 2263 | N | BVAL | X | 180 | −9.775 | 8.353 | −38.697 | 0.69 | 29.78 | N |
| ATOM | 2264 | CA | AVAL | X | 180 | −10.518 | 9.278 | −37.884 | 0.31 | 31.17 | C |
| ATOM | 2265 | CA | BVAL | X | 180 | −10.549 | 9.299 | −37.861 | 0.69 | 29.85 | C |
| ATOM | 2266 | CB | AVAL | X | 180 | −9.470 | 10.220 | −37.208 | 0.31 | 31.26 | C |
| ATOM | 2267 | CB | BVAL | X | 180 | −9.626 | 10.337 | −37.130 | 0.69 | 29.67 | C |
| ATOM | 2268 | CG1 | AVAL | X | 180 | −9.241 | 11.506 | −38.006 | 0.31 | 31.32 | C |
| ATOM | 2269 | CG1 | BVAL | X | 180 | −8.807 | 9.653 | −36.033 | 0.69 | 28.02 | C |

-continued

| | | | | | | | | | |
|---|---|---|---|---|---|---|---|---|---|
| ATOM | 2270 | CG2 | AVAL | X | 180 | −9.849 | 10.497 | −35.772 | 0.31 | 31.74 | C |
| ATOM | 2271 | CG2 | BVAL | X | 180 | −8.700 | 11.053 | −38.106 | 0.69 | 28.97 | C |
| ATOM | 2272 | C | AVAL | X | 180 | −11.622 | 10.023 | −38.661 | 0.31 | 31.59 | C |
| ATOM | 2273 | C | BVAL | X | 180 | −11.645 | 10.028 | −38.655 | 0.69 | 30.70 | C |
| ATOM | 2274 | O | AVAL | X | 180 | −12.169 | 11.030 | −38.199 | 0.31 | 31.43 | O |
| ATOM | 2275 | O | BVAL | X | 180 | −12.191 | 11.050 | −38.202 | 0.69 | 30.38 | O |
| ATOM | 2276 | N | SER | X | 181 | −11.968 | 9.490 | −39.833 | 1.00 | 32.06 | N |
| ATOM | 2277 | CA | ASER | X | 181 | −12.902 | 10.148 | −40.747 | 0.59 | 33.25 | C |
| ATOM | 2278 | CA | BSER | X | 181 | −12.912 | 10.126 | −40.759 | 0.41 | 32.53 | C |
| ATOM | 2279 | CB | ASER | X | 181 | −12.842 | 9.505 | −42.141 | 0.59 | 33.64 | C |
| ATOM | 2280 | CB | BSER | X | 181 | −12.892 | 9.422 | −42.120 | 0.41 | 32.76 | C |
| ATOM | 2281 | OG | ASER | X | 181 | −11.515 | 9.515 | −42.650 | 0.59 | 34.74 | O |
| ATOM | 2282 | OG | BSER | X | 181 | −13.284 | 8.067 | −41.995 | 0.41 | 30.51 | O |
| ATOM | 2283 | C | SER | X | 181 | −14.335 | 10.146 | −40.205 | 1.00 | 33.43 | C |
| ATOM | 2284 | O | SER | X | 181 | −15.127 | 11.036 | −40.544 | 1.00 | 33.88 | O |
| ATOM | 2285 | N | SER | X | 182 | −14.647 | 9.159 | −39.365 | 1.00 | 33.55 | N |
| ATOM | 2286 | CA | SER | X | 182 | −15.952 | 9.067 | −38.704 | 1.00 | 34.59 | C |
| ATOM | 2287 | CB | SER | X | 182 | −16.159 | 7.679 | −38.089 | 1.00 | 34.83 | C |
| ATOM | 2288 | OG | SER | X | 182 | −15.234 | 7.420 | −37.043 | 1.00 | 36.33 | O |
| ATOM | 2289 | C | SER | X | 182 | −16.153 | 10.148 | −37.626 | 1.00 | 34.15 | C |
| ATOM | 2290 | O | SER | X | 182 | −17.294 | 10.479 | −37.284 | 1.00 | 34.80 | O |
| ATOM | 2291 | N | CYS | X | 183 | −15.059 | 10.688 | −37.087 | 1.00 | 32.95 | N |
| ATOM | 2292 | CA | CYS | X | 183 | −15.164 | 11.830 | −36.186 | 1.00 | 32.19 | C |
| ATOM | 2293 | CB | CYS | X | 183 | −13.795 | 12.279 | −35.679 | 1.00 | 31.30 | C |
| ATOM | 2294 | SG | CYS | X | 183 | −12.941 | 11.065 | −34.710 | 1.00 | 27.42 | S |
| ATOM | 2295 | C | CYS | X | 183 | −15.775 | 12.938 | −37.003 | 1.00 | 33.53 | C |
| ATOM | 2296 | O | CYS | X | 183 | −15.281 | 13.262 | −38.083 | 1.00 | 35.18 | O |
| ATOM | 2297 | N | GLY | X | 184 | −16.868 | 13.497 | −36.529 | 1.00 | 33.87 | N |
| ATOM | 2298 | CA | GLY | X | 184 | −17.519 | 14.537 | −37.303 | 1.00 | 34.38 | C |
| ATOM | 2299 | C | GLY | X | 184 | −17.169 | 15.898 | −36.765 | 1.00 | 34.44 | C |
| ATOM | 2300 | O | GLY | X | 184 | −16.108 | 16.080 | −36.159 | 1.00 | 33.39 | O |
| ATOM | 2301 | N | PHE | X | 185 | −18.072 | 16.849 | −37.006 | 1.00 | 34.98 | N |
| ATOM | 2302 | CA | PHE | X | 185 | −17.977 | 18.203 | −36.484 | 1.00 | 35.47 | C |
| ATOM | 2303 | CB | PHE | X | 185 | −17.555 | 19.179 | −37.590 | 1.00 | 35.27 | C |
| ATOM | 2304 | CG | PHE | X | 185 | −16.175 | 18.914 | −38.132 | 1.00 | 35.42 | C |
| ATOM | 2305 | CD1 | PHE | X | 185 | −15.045 | 19.414 | −37.482 | 1.00 | 34.35 | C |
| ATOM | 2306 | CE1 | PHE | X | 185 | −13.767 | 19.165 | −37.981 | 1.00 | 33.67 | C |
| ATOM | 2307 | CZ | PHE | X | 185 | −13.608 | 18.399 | −39.132 | 1.00 | 34.45 | C |
| ATOM | 2308 | CE2 | PHE | X | 185 | −14.724 | 17.898 | −39.791 | 1.00 | 34.94 | C |
| ATOM | 2309 | CD2 | PHE | X | 185 | −16.000 | 18.152 | −39.289 | 1.00 | 35.39 | C |
| ATOM | 2310 | C | PHE | X | 185 | −19.322 | 18.627 | −35.877 | 1.00 | 36.25 | C |
| ATOM | 2311 | O | PHE | X | 185 | −19.362 | 19.441 | −34.947 | 1.00 | 36.71 | O |
| ATOM | 2312 | O5 | CIT | A | 1 | 10.696 | 29.207 | −40.463 | 1.00 | 20.04 | O |
| ATOM | 2313 | C6 | CIT | A | 1 | 11.803 | 29.450 | −39.914 | 1.00 | 18.94 | C |
| ATOM | 2314 | O6 | CIT | A | 1 | 11.964 | 30.400 | −39.104 | 1.00 | 20.90 | O |
| ATOM | 2315 | C3 | CIT | A | 1 | 12.998 | 28.575 | −40.256 | 1.00 | 21.03 | C |
| ATOM | 2316 | O7 | CIT | A | 1 | 14.164 | 29.085 | −39.537 | 1.00 | 22.20 | O |
| ATOM | 2317 | C4 | CIT | A | 1 | 13.253 | 28.635 | −41.763 | 1.00 | 23.23 | C |
| ATOM | 2318 | C5 | CIT | A | 1 | 13.783 | 30.006 | −42.132 | 1.00 | 23.46 | C |
| ATOM | 2319 | O4 | CIT | A | 1 | 13.032 | 31.001 | −41.963 | 1.00 | 21.48 | O |
| ATOM | 2320 | O3 | CIT | A | 1 | 14.965 | 30.146 | −42.577 | 1.00 | 23.26 | O |
| ATOM | 2321 | C2 | CIT | A | 1 | 12.621 | 27.154 | −39.811 | 1.00 | 23.04 | C |
| ATOM | 2322 | C1 | CIT | A | 1 | 13.889 | 26.338 | −39.724 | 1.00 | 24.90 | C |
| ATOM | 2323 | O1 | CIT | A | 1 | 14.386 | 25.853 | −40.763 | 1.00 | 22.08 | O |
| ATOM | 2324 | O2 | CIT | A | 1 | 14.435 | 26.161 | −38.612 | 1.00 | 24.82 | O |
| ATOM | 2325 | O5 | CIT | A | 2 | 9.061 | 35.292 | −39.078 | 1.00 | 18.25 | O |
| ATOM | 2326 | C6 | CIT | A | 2 | 10.019 | 35.317 | −38.260 | 1.00 | 18.17 | C |
| ATOM | 2327 | O6 | CIT | A | 2 | 10.988 | 34.495 | −38.374 | 1.00 | 18.35 | O |
| ATOM | 2328 | C3 | CIT | A | 2 | 9.971 | 36.351 | −37.127 | 1.00 | 19.59 | C |
| ATOM | 2329 | O7 | CIT | A | 2 | 11.091 | 36.141 | −36.236 | 1.00 | 21.96 | O |
| ATOM | 2330 | C4 | CIT | A | 2 | 10.072 | 37.748 | −37.766 | 1.00 | 21.00 | C |
| ATOM | 2331 | C5 | CIT | A | 2 | 10.340 | 38.793 | −36.711 | 1.00 | 22.63 | C |
| ATOM | 2332 | O4 | CIT | A | 2 | 9.415 | 39.160 | −35.962 | 1.00 | 23.25 | O |
| ATOM | 2333 | O3 | CIT | A | 2 | 11.486 | 39.278 | −36.563 | 1.00 | 25.44 | O |
| ATOM | 2334 | C2 | CIT | A | 2 | 8.681 | 36.183 | −36.325 | 1.00 | 21.80 | C |
| ATOM | 2335 | C1 | CIT | A | 2 | 8.759 | 34.869 | −35.566 | 1.00 | 23.04 | C |
| ATOM | 2336 | O1 | CIT | A | 2 | 8.881 | 34.832 | −34.304 | 1.00 | 23.78 | O |
| ATOM | 2337 | O2 | CIT | A | 2 | 8.762 | 33.809 | −36.218 | 1.00 | 16.31 | O |
| ATOM | 2338 | O | HOH | A | 101 | −1.531 | 12.658 | −31.337 | 1.00 | 15.31 | O |
| ATOM | 2339 | O | HOH | A | 102 | 0.986 | 19.102 | −29.507 | 1.00 | 15.94 | O |
| ATOM | 2340 | O | HOH | A | 103 | 13.767 | 28.290 | −36.967 | 1.00 | 24.90 | O |
| ATOM | 2341 | O | HOH | A | 104 | −0.411 | 20.576 | −31.478 | 1.00 | 17.02 | O |
| ATOM | 2342 | O | HOH | A | 105 | −5.711 | 23.165 | −34.163 | 1.00 | 16.23 | O |
| ATOM | 2343 | O | HOH | A | 106 | −0.983 | 34.945 | −29.324 | 1.00 | 20.34 | O |
| ATOM | 2344 | O | HOH | A | 107 | 5.742 | 13.302 | −29.139 | 1.00 | 23.68 | O |
| ATOM | 2345 | O | HOH | A | 108 | −7.200 | 10.647 | −25.284 | 1.00 | 23.55 | O |
| ATOM | 2346 | O | HOH | A | 109 | 5.558 | 34.594 | −35.866 | 1.00 | 21.15 | O |
| ATOM | 2347 | O | HOH | A | 111 | −7.714 | 16.506 | −20.973 | 1.00 | 31.59 | O |
| ATOM | 2348 | O | HOH | A | 112 | −13.073 | 25.939 | −33.716 | 1.00 | 19.33 | O |
| ATOM | 2349 | O | HOH | A | 113 | 11.947 | 20.837 | −23.956 | 1.00 | 47.65 | O |

-continued

| ATOM | 2350 | O | HOH | A | 114 | −9.746 | 18.498 | −16.237 | 0.50 | 50.48 | O |
|---|---|---|---|---|---|---|---|---|---|---|---|
| ATOM | 2351 | O | HOH | A | 115 | 8.882 | 14.953 | −44.331 | 1.00 | 16.03 | O |
| ATOM | 2352 | O | HOH | A | 116 | 7.857 | 37.418 | −28.860 | 1.00 | 30.75 | O |
| ATOM | 2353 | O | HOH | A | 117 | −17.279 | 22.909 | −25.907 | 0.50 | 46.46 | O |
| ATOM | 2354 | O | HOH | A | 118 | 7.927 | 33.211 | −30.190 | 1.00 | 19.37 | O |
| ATOM | 2355 | O | HOH | A | 119 | 6.318 | 23.247 | −25.127 | 1.00 | 16.71 | O |
| ATOM | 2356 | O | HOH | A | 120 | −9.625 | 32.923 | −31.269 | 1.00 | 22.04 | O |
| ATOM | 2357 | O | HOH | A | 121 | −7.361 | 34.462 | −31.317 | 1.00 | 26.55 | O |
| ATOM | 2358 | O | HOH | A | 122 | −17.233 | 20.930 | −32.879 | 1.00 | 33.89 | O |
| ATOM | 2359 | O | HOH | A | 123 | 12.598 | 17.233 | −33.728 | 1.00 | 22.11 | O |
| ATOM | 2360 | O | HOH | A | 124 | −11.345 | 32.752 | −36.815 | 1.00 | 24.47 | O |
| ATOM | 2361 | O | HOH | A | 125 | 12.329 | 2.183 | −31.041 | 1.00 | 35.38 | O |
| ATOM | 2362 | O | HOH | A | 127 | −15.310 | 12.088 | −28.366 | 1.00 | 34.59 | O |
| ATOM | 2363 | O | HOH | A | 128 | −10.228 | 25.263 | −28.486 | 1.00 | 22.20 | O |
| ATOM | 2364 | O | HOH | A | 129 | −6.187 | 4.452 | −28.658 | 1.00 | 25.37 | O |
| ATOM | 2365 | O | HOH | A | 131 | −10.547 | 16.176 | −19.971 | 1.00 | 48.68 | O |
| ATOM | 2366 | O | HOH | A | 132 | −1.508 | 8.814 | −26.380 | 1.00 | 19.37 | O |
| ATOM | 2367 | O | HOH | A | 133 | 16.851 | 21.983 | −40.540 | 1.00 | 31.58 | U |
| ATOM | 2368 | O | HOH | A | 134 | 3.493 | 11.280 | −39.354 | 1.00 | 20.32 | O |
| ATOM | 2369 | O | AHOH | A | 135 | 3.343 | 10.778 | −20.927 | 0.47 | 22.61 | O |
| ATOM | 2370 | O | BHOH | A | 135 | 3.394 | 7.259 | −21.732 | 0.53 | 18.00 | O |
| ATOM | 2371 | O | HOH | A | 137 | 17.223 | 18.707 | −45.679 | 1.00 | 25.59 | O |
| ATOM | 2372 | O | HOH | A | 138 | −13.352 | 26.124 | −22.237 | 1.00 | 64.02 | O |
| ATOM | 2373 | O | HOH | A | 139 | −9.965 | 8.890 | −24.000 | 1.00 | 43.00 | O |
| ATOM | 2374 | O | HOH | A | 140 | −4.241 | 2.071 | −29.185 | 1.00 | 163.93 | O |
| ATOM | 2375 | O | HOH | A | 141 | −7.203 | 34.181 | −38.194 | 1.00 | 21.10 | O |
| ATOM | 2376 | O | HOH | A | 143 | −3.958 | 6.442 | −20.556 | 1.00 | 37.48 | O |
| ATOM | 2377 | O | HOH | A | 144 | 5.045 | 3.071 | −31.407 | 1.00 | 24.14 | O |
| ATOM | 2379 | O | HOH | A | 146 | −13.058 | 8.412 | −30.835 | 1.00 | 27.24 | O |
| ATOM | 2380 | O | HOH | A | 147 | −4.668 | 20.441 | −16.215 | 1.00 | 22.69 | O |
| ATOM | 2381 | O | HOH | A | 148 | −12.205 | 13.604 | −38.805 | 1.00 | 40.59 | O |
| ATOM | 2382 | O | HOH | A | 149 | 19.366 | 14.873 | −43.745 | 1.00 | 47.66 | O |
| ATOM | 2383 | O | HOH | A | 150 | −12.059 | 31.791 | −15.938 | 1.00 | 62.41 | O |
| ATOM | 2384 | O | HOH | A | 151 | −7.035 | 2.170 | −33.927 | 1.00 | 39.47 | O |
| ATOM | 2385 | O | HOH | A | 152 | 12.798 | 28.887 | −26.995 | 1.00 | 24.30 | O |
| ATOM | 2386 | O | HOH | A | 153 | −5.128 | 36.742 | −34.647 | 100 | 46.78 | O |
| ATOM | 2387 | O | HOH | A | 154 | 14.543 | 23.775 | −31.828 | 1.00 | 22.81 | O |
| ATOM | 2388 | O | HOH | A | 155 | 5.726 | 36.388 | −13.336 | 1.00 | 32.05 | O |
| ATOM | 2389 | O | HOH | A | 156 | −4.354 | 1.999 | −33.727 | 1.00 | 47.18 | O |
| ATOM | 2390 | O | HOH | A | 157 | 11.378 | 17.921 | −24.997 | 1.00 | 41.96 | O |
| ATOM | 2391 | O | HOH | A | 159 | 6.179 | 7.308 | −25.997 | 1.00 | 56.96 | O |
| ATOM | 2392 | O | HOH | A | 160 | −7.492 | 36.775 | −32.926 | 1.00 | 56.28 | O |
| ATOM | 2393 | O | HOH | A | 161 | 12.481 | 6.677 | −36.564 | 1.00 | 33.37 | O |
| ATOM | 2394 | O | HOH | A | 162 | −13.566 | 32.920 | −18.115 | 1.00 | 65.89 | O |
| ATOM | 2395 | O | HOH | A | 163 | −12.249 | 25.590 | −26.582 | 1.00 | 41.23 | O |
| ATOM | 2396 | O | HOH | A | 164 | 0.019 | 15.852 | −36.732 | 1.00 | 25.63 | O |
| ATOM | 2397 | O | HOH | A | 165 | −3.300 | 35.641 | −35.681 | 1.00 | 30.33 | O |
| ATOM | 2398 | O | HOH | A | 166 | 13.102 | 19.773 | −47.900 | 1.00 | 22.91 | O |
| ATOM | 2399 | O | HOH | A | 168 | −3.599 | 1.132 | −37.286 | 1.00 | 62.93 | O |
| ATOM | 2400 | O | HOH | A | 169 | −8.053 | 2.566 | −38.795 | 1.00 | 43.90 | O |
| ATOM | 2401 | O | HOH | A | 170 | 5.707 | 9.583 | −39.810 | 1.00 | 23.64 | O |
| ATOM | 2402 | O | HOH | A | 171 | −18.268 | 12.635 | −31.017 | 1.00 | 42.49 | O |
| ATOM | 2403 | O | AHOH | A | 172 | 0.678 | 37.077 | −35.843 | 0.50 | 20.10 | O |
| ATOM | 2404 | O | BHOH | A | 172 | −1.101 | 38.480 | −37.341 | 0.50 | 29.43 | O |
| ATOM | 2405 | O | HOH | A | 173 | −0.673 | 39.350 | −29.268 | 1.00 | 32.61 | O |
| ATOM | 2406 | O | HOH | A | 174 | 6.826 | 9.248 | −27.831 | 1.00 | 32.89 | O |
| ATOM | 2407 | O | HOH | A | 175 | −7.661 | 3.635 | −32.064 | 1.00 | 34.22 | O |
| ATOM | 2408 | O | HOH | A | 176 | 1.946 | 30.944 | −10.568 | 1.00 | 89.96 | O |
| ATOM | 2409 | O | HOH | A | 177 | −8.979 | 22.974 | −17.734 | 1.00 | 44.82 | O |
| ATOM | 2410 | O | AHOH | A | 178 | −7.890 | 40.543 | −24.795 | 0.58 | 29.01 | O |
| ATOM | 2411 | O | BHOH | A | 178 | −4.514 | 42.847 | −24.251 | 0.41 | 28.65 | O |
| ATOM | 2412 | O | HOH | A | 179 | −11.404 | 39.007 | −20.154 | 1.00 | 48.23 | O |
| ATOM | 2413 | O | HOH | A | 180 | 6.378 | 7.366 | −38.212 | 1.00 | 26.51 | O |
| ATOM | 2414 | O | HOH | A | 181 | 9.199 | 6.077 | −37.300 | 1.00 | 32.88 | O |
| ATOM | 2415 | O | HOH | A | 182 | 13.704 | 25.122 | −43.392 | 1.00 | 19.34 | O |
| ATOM | 2416 | O | HOH | A | 183 | −7.226 | 16.454 | −14.708 | 1.00 | 32.53 | O |
| ATOM | 2417 | O | HOH | A | 184 | −0.690 | −0.977 | −25.341 | 1.00 | 36.24 | O |
| ATOM | 2418 | O | HOH | A | 185 | 6.172 | 38.223 | −17.072 | 1.00 | 33.70 | O |
| ATOM | 2419 | O | HOH | A | 186 | 15.651 | 20.087 | −35.506 | 1.00 | 29.67 | O |
| ATOM | 2420 | O | HOH | A | 187 | −8.510 | 9.490 | −41.062 | 1.00 | 30.12 | O |
| ATOM | 2421 | O | HOH | A | 188 | −7.297 | −2.941 | −29.537 | 1.00 | 335.48 | O |
| ATOM | 2422 | O | HOH | A | 189 | 2.826 | 37.953 | −34.436 | 1.00 | 59.09 | O |
| ATOM | 2423 | O | HOH | A | 190 | 9.175 | 8.111 | −28.635 | 1.00 | 31.10 | O |
| ATOM | 2424 | O | HOH | A | 191 | −15.106 | 29.936 | −32.223 | 1.00 | 37.49 | O |
| ATOM | 2425 | O | HOH | A | 192 | 0.313 | 42.270 | −16.951 | 1.00 | 32.52 | O |
| ATOM | 2426 | O | HOH | A | 194 | −5.863 | 9.237 | −39.570 | 1.00 | 36.13 | O |
| ATOM | 2427 | O | HOH | A | 195 | −12.118 | 9.846 | −24.204 | 1.00 | 40.45 | O |
| ATOM | 2428 | O | HOH | A | 196 | −5.711 | 39.350 | −17.899 | 1.00 | 56.35 | O |
| ATOM | 2429 | O | HOH | A | 197 | 3.943 | 15.237 | −21.725 | 1.00 | 29.41 | O |
| ATOM | 2430 | O | HOH | A | 199 | −8.525 | 4.396 | −27.703 | 1.00 | 58.30 | O |

-continued

| | | | | | | | | | | |
|---|---|---|---|---|---|---|---|---|---|---|
| ATOM | 2431 | O | HOH | A | 200 | 6.819 | 38.772 | −14.652 | 1.00 | 39.28 | O |
| ATOM | 2432 | O | HOH | A | 201 | 10.696 | 10.194 | −41.347 | 1.00 | 44.88 | O |
| ATOM | 2433 | O | AHOH | A | 202 | 5.708 | 39.198 | −30.967 | 0.50 | 32.28 | O |
| ATOM | 2434 | O | BHOH | A | 202 | 5.533 | 39.773 | −29.591 | 0.50 | 27.58 | O |
| ATOM | 2435 | O | HOH | A | 203 | 3.734 | 12.975 | −23.342 | 1.00 | 25.53 | O |
| ATOM | 2436 | O | HOH | A | 204 | −5.651 | 40.638 | −22.956 | 1.00 | 32.09 | O |
| ATOM | 2437 | O | HOH | A | 205 | 0.288 | 2.502 | −23.394 | 1.00 | 55.86 | O |
| ATOM | 2438 | O | HOH | A | 206 | 3.821 | 26.180 | −48.087 | 1.00 | 34.85 | O |
| ATOM | 2439 | O | HOH | A | 207 | 9.498 | 22.504 | −48.018 | 1.00 | 22.79 | O |
| ATOM | 2440 | O | HOH | A | 208 | −12.057 | 3.953 | −37.742 | 1.00 | 53.40 | O |
| ATOM | 2441 | O | HOH | A | 209 | 3.946 | 45.188 | −25.710 | 1.00 | 32.01 | O |
| ATOM | 2442 | O | HOH | A | 211 | 2.805 | 1.864 | −28.466 | 1.00 | 44.47 | O |
| ATOM | 2443 | O | HOH | A | 212 | 18.018 | 19.688 | −37.127 | 1.00 | 41.97 | O |
| ATOM | 2444 | O | AHOH | A | 213 | 7.261 | 26.069 | −17.727 | 0.40 | 19.96 | O |
| ATOM | 2445 | O | BHOH | A | 213 | 9.007 | 26.003 | −17.429 | 0.60 | 48.95 | O |
| ATOM | 2446 | O | HOH | A | 214 | 0.493 | 28.503 | −48.806 | 1.00 | 23.27 | O |
| ATOM | 2447 | O | HOH | A | 216 | 14.746 | 31.221 | −30.503 | 1.00 | 35.24 | O |
| ATOM | 2448 | O | HOH | A | 217 | 14.889 | 30.052 | −28.097 | 1.00 | 42.36 | O |
| ATOM | 2449 | O | HOH | A | 219 | 10.882 | 18.32.0 | −19.268 | 1.00 | 57.12 | O |
| ATOM | 2450 | O | HOH | A | 221 | 4.451 | 23.228 | −48.043 | 1.00 | 22.82 | O |
| ATOM | 2451 | O | HOH | A | 222 | 1.736 | 31.349 | −45.503 | 1.00 | 22.75 | O |
| ATOM | 2452 | O | AHOH | A | 224 | 11.252 | 38.015 | −21.741 | 0.48 | 31.04 | O |
| ATOM | 2453 | O | BHOH | A | 224 | 9.796 | 36.294 | −20.769 | 0.52 | 26.52 | O |
| ATOM | 2454 | O | HOH | A | 225 | 1.377 | 45.964 | −25.844 | 1.00 | 82.59 | O |
| ATOM | 2455 | O | HOH | A | 226 | −2.067 | 43.974 | −24.503 | 1.00 | 48.05 | O |
| ATOM | 2456 | O | HOH | A | 227 | −5.138 | 33.788 | −14.555 | 1.00 | 36.41 | O |
| ATOM | 2457 | O | HOH | A | 228 | 4.103 | 41.201 | −16.768 | 1.00 | 34.76 | O |
| ATOM | 2458 | O | HOH | A | 229 | −0.182 | 43.181 | −26.637 | 1.00 | 30.29 | O |
| ATOM | 2459 | O | AHOH | A | 230 | −5.515 | 12.158 | −38.769 | 0.50 | 19.44 | O |
| ATOM | 2460 | O | BHOH | A | 230 | −6.410 | 13.299 | −39.653 | 0.50 | 26.20 | O |
| ATOM | 2461 | O | AHOH | A | 231 | 4.806 | 4.908 | −44.751 | 0.58 | 38.09 | O |
| ATOM | 2462 | O | BHOH | A | 231 | 3.281 | 6.263 | −43.347 | 0.42 | 25.62 | O |
| ATOM | 2463 | O | AHOH | A | 234 | −18.702 | 9.782 | −34.538 | 0.50 | 38.27 | O |
| ATOM | 2464 | O | BHOH | A | 234 | −18.073 | 12.250 | −33.623 | 0.50 | 34.65 | O |
| ATOM | 2465 | O | HOH | A | 236 | 10.629 | 36.300 | −28.229 | 1.00 | 56.87 | O |
| ATOM | 2466 | O | HOH | A | 237 | 17.117 | 10.914 | −35.051 | 1.00 | 55.58 | O |
| ATOM | 2467 | O | HOH | A | 239 | −2.376 | 36.435 | −37.966 | 1.00 | 46.78 | O |
| ATOM | 2468 | O | HOH | A | 240 | 14.364 | 12.071 | −46.206 | 1.00 | 33.48 | O |
| ATOM | 2469 | O | AHOH | A | 241 | −9.851 | 14.427 | −37.430 | 0.52 | 22.83 | O |
| ATOM | 2470 | O | BHOH | A | 241 | −10.019 | 14.712 | −38.089 | 0.48 | 30.46 | O |
| ATOM | 2471 | O | HOH | A | 243 | 2.591 | 1.199 | −38.458 | 1.00 | 40.51 | O |
| ATOM | 2472 | O | HOH | A | 244 | 5.485 | 9.383 | −43.329 | 1.00 | 54.31 | O |
| ATOM | 2473 | O | HOH | A | 246 | 1.174 | 3.101 | −30.487 | 1.00 | 18.90 | O |
| ATOM | 2474 | O | HOH | A | 247 | −0.474 | 0.977 | −30.993 | 1.00 | 28.41 | O |
| ATOM | 2475 | O | HOH | A | 248 | −2.381 | 0.479 | −32.980 | 1.00 | 32.44 | U |
| ATOM | 2476 | U | HOH | A | 249 | 3.885 | 0.646 | −31.701 | 1.00 | 32.40 | U |
| ATOM | 2477 | O | HOH | A | 250 | −5.445 | 10.229 | −16.552 | 1.00 | 36.12 | O |
| ATOM | 2478 | O | HOH | A | 251 | 9.523 | 12.083 | −26.210 | 1.00 | 50.93 | O |
| ATOM | 2479 | O | HOH | A | 252 | −1.079 | 1.943 | −39.924 | 1.00 | 35.42 | O |
| ATOM | 2480 | O | HOH | A | 254 | 15.726 | 7.799 | −34.296 | 1.00 | 74.31 | O |
| ATOM | 2481 | O | HOH | A | 255 | −4.240 | 7.651 | −41.272 | 1.00 | 27.53 | O |
| ATOM | 2482 | O | HOH | A | 256 | 4.587 | 37.305 | −11.207 | 1.00 | 48.17 | O |
| ATOM | 2483 | O | AHOH | A | 257 | −3.570 | 39.808 | −19.062 | 0.59 | 28.62 | O |
| ATOM | 2484 | O | BHOH | A | 257 | −2.049 | 42.193 | −18.594 | 0.41 | 28.15 | O |
| ATOM | 2485 | O | HOH | A | 258 | −3.532 | 20.318 | −13.757 | 1.00 | 34.60 | O |
| ATOM | 2486 | O | HOH | A | 259 | −7.939 | 21.563 | −13.810 | 1.00 | 46.49 | O |
| ATOM | 2487 | O | AHOH | A | 260 | −20.316 | 27.164 | −31.042 | 0.00 | 31.89 | O |
| ATOM | 2488 | O | BHOH | A | 260 | −18.764 | 28.879 | −31.204 | 0.50 | 42.74 | O |
| ATOM | 2489 | O | HOH | A | 262 | 4.228 | 35.574 | −33.729 | 1.00 | 86.53 | O |
| ATOM | 2490 | O | HOH | A | 263 | 4.136 | 29.616 | −12.278 | 1.00 | 38.35 | O |
| ATOM | 2491 | O | HOH | A | 266 | −2.702 | 19.826 | −44.369 | 1.00 | 20.63 | O |
| ATOM | 2492 | O | HOH | A | 267 | −1.169 | 15.957 | −45.143 | 1.00 | 14.29 | O |
| ATOM | 2496 | O | HOH | A | 274 | 1.898 | 17.390 | −37.219 | 1.00 | 18.28 | O |
| ATOM | 2497 | O | HOH | A | 275 | 11.247 | 12.385 | −47.261 | 1.00 | 48.63 | O |
| ATOM | 2498 | O | HOH | A | 276 | 8.323 | 12.867 | −46.035 | 1.00 | 25.04 | O |
| ATOM | 2499 | O | HOH | A | 277 | 2.316 | 8.741 | −43.976 | 1.00 | 34.93 | O |
| ATOM | 2500 | O | HOH | A | 278 | 3.923 | 11.446 | −43.351 | 1.00 | 18.55 | O |
| ATOM | 2501 | O | HOH | A | 279 | 2.232 | −0.091 | −41.515 | 1.00 | 73.91 | O |
| ATOM | 2502 | O | HOH | A | 280 | 16.280 | 22.524 | −43.449 | 1.00 | 43.46 | O |
| ATOM | 2504 | O | HOH | A | 283 | 18.013 | 31.396 | −40.305 | 1.00 | 36.60 | O |
| ATOM | 2505 | O | HOH | A | 285 | −4.563 | 33.064 | −41.806 | 1.00 | 21.56 | O |
| ATOM | 2506 | O | HOH | A | 286 | −2.478 | 34.562 | −41.132 | 1.00 | 25.47 | O |
| ATOM | 2507 | O | HOH | A | 287 | −2.277 | 33.625 | −45.727 | 1.00 | 18.85 | O |
| ATOM | 2508 | O | HOH | A | 288 | −2.453 | 34.236 | −25.704 | 1.00 | 22.88 | O |
| ATOM | 2509 | O | HOH | A | 289 | −3.604 | 35.922 | −28.352 | 1.00 | 24.87 | O |
| ATOM | 2510 | O | HOH | A | 290 | −16.278 | 22.455 | −39.072 | 1.00 | 35.70 | O |
| ATOM | 2511 | O | HOH | A | 291 | −15.480 | 24.693 | −40.469 | 1.00 | 24.37 | O |
| ATOM | 2512 | O | HOH | A | 292 | −13.270 | 22.205 | −50.763 | 1.00 | 24.79 | O |
| ATOM | 2513 | O | HOH | A | 293 | −15.350 | 21.588 | −52.242 | 1.00 | 24.18 | O |
| ATOM | 2514 | O | HOH | A | 294 | −5.907 | 22.482 | −52.137 | 1.00 | 18.68 | O |

-continued

| | | | | | | | | | | |
|---|---|---|---|---|---|---|---|---|---|---|
| ATOM | 2515 | O | HOH | A | 295 | −0.154 | 20.274 | −45.152 | 1.00 | 20.09 | O |
| ATOM | 2516 | O | HOH | A | 296 | 0.937 | 20.708 | −47.708 | 1.00 | 21.77 | O |
| ATOM | 2517 | O | HOH | A | 297 | −12.753 | 24.685 | −49.625 | 1.00 | 27.86 | O |
| ATOM | 2518 | O | HOH | A | 298 | −19.939 | 16.334 | −38.931 | 1.00 | 57.28 | O |
| ATOM | 2522 | O | HOH | A | 302 | −9.915 | 37.497 | −58.431 | 1.00 | 28.27 | O |
| ATOM | 2523 | O | HOH | A | 303 | 13.243 | 37.173 | −37.484 | 1.00 | 28.11 | O |
| ATOM | 2525 | O | HOH | A | 305 | 15.759 | 19.836 | −47.797 | 1.00 | 27.61 | O |
| ATOM | 2526 | O | HOH | A | 306 | 2.168 | 26.997 | −49.988 | 1.00 | 34.53 | O |
| ATOM | 2527 | O | HOH | A | 307 | 10.615 | 40.806 | −34.205 | 1.00 | 35.86 | O |
| ATOM | 2528 | O | HOH | A | 308 | 16.641 | 24.358 | −46.102 | 1.00 | 36.28 | O |
| ATOM | 2529 | O | HOH | A | 309 | 14.999 | 26.071 | −45.427 | 1.00 | 31.56 | O |
| ATOM | 2530 | O | HOH | A | 310 | 18.947 | 21.020 | −44.796 | 1.00 | 37.16 | O |
| ATOM | 2531 | O | HOH | A | 311 | 18.958 | 16.833 | −46.270 | 1.00 | 49.10 | O |
| ATOM | 2532 | O | HOH | C | 1 | 0.687 | 28.888 | −46.114 | 1.00 | 30.00 | O |
| ATOM | 2533 | O | HOH | C | 2 | 1.310 | 12.262 | −23.809 | 1.00 | 30.00 | O |
| ATOM | 2534 | O | HOH | C | 3 | −5.506 | 24.469 | −50.261 | 1.00 | 30.00 | O |
| ATOM | 2535 | O | HOH | C | 4 | −4.537 | 6.847 | −63.694 | 1.00 | 30.00 | O |
| ATOM | 2536 | O | HOH | C | 5 | −3.465 | 7.950 | −69.119 | 1.00 | 30.00 | O |
| ATOM | 2537 | O | HOH | C | 6 | −0.689 | 7.516 | −68.987 | 1.00 | 30.00 | O |
| ATOM | 2538 | O | HOH | C | 7 | 1.465 | 15.227 | −34.512 | 1.00 | 30.00 | O |
| ATOM | 2539 | O | HOH | C | 8 | −2.922 | 18.033 | −64.005 | 1.00 | 30.00 | O |
| ATOM | 2540 | O | HOH | C | 9 | 3.548 | 20.695 | −46.949 | 1.00 | 30.00 | O |
| ATOM | 2541 | O | HOH | C | 10 | 10.780 | 26.497 | −49.641 | 1.00 | 30.00 | O |
| ATOM | 2542 | O | HOH | C | 11 | 12.634 | 33.426 | −36.465 | 1.00 | 30.00 | O |
| ATOM | 2543 | O | HOH | C | 12 | 5.786 | 16.537 | −22.901 | 1.00 | 30.00 | O |
| ATOM | 2544 | O | HOH | C | 13 | 12.937 | 27.054 | −46.857 | 1.00 | 30.00 | O |
| ATOM | 2545 | O | HOH | C | 14 | 6.502 | 39.336 | −35.949 | 1.00 | 30.00 | O |
| ATOM | 2546 | O | HOH | C | 15 | −5.761 | 36.080 | −43.647 | 1.00 | 30.00 | O |
| ATOM | 2547 | O | HOH | C | 16 | −7.585 | 11.943 | −13.663 | 1.00 | 30.00 | O |
| ATOM | 2548 | O | HOH | C | 17 | −9.688 | 16.619 | −59.660 | 1.00 | 30.00 | O |
| ATOM | 2549 | O | HOH | C | 18 | 4.944 | 3.723 | −66.311 | 1.00 | 30.00 | O |
| ATOM | 2550 | O | HOH | C | 19 | 13.295 | 23.779 | −49.541 | 1.00 | 30.00 | O |
| ATOM | 2551 | O | HOH | C | 20 | 1.485 | 21.758 | −54.204 | 1.00 | 30.00 | O |
| ATOM | 2552 | O | HOH | C | 21 | −3.366 | 8.671 | −19.425 | 1.00 | 30.00 | O |
| ATOM | 2553 | O | HOH | C | 22 | −5.683 | 9.873 | −19.059 | 1.00 | 30.00 | O |
| ATOM | 2554 | O | HOH | C | 23 | 2.140 | 1.764 | −65.514 | 1.00 | 30.00 | O |
| ATOM | 2555 | O | HOH | C | 24 | −14.440 | 19.170 | −24.241 | 1.00 | 30.00 | O |
| ATOM | 2556 | O | HOH | C | 25 | −12.733 | 8.522 | −18.759 | 1.00 | 30.00 | O |
| ATOM | 2557 | O | HOH | C | 26 | −7.769 | 14.288 | −44.900 | 1.00 | 30.00 | O |
| ATOM | 2559 | O | HOH | C | 28 | 11.554 | 36.742 | −33.603 | 1.00 | 30.00 | O |
| ATOM | 2560 | O | HOH | C | 29 | −12.352 | 9.366 | −16.171 | 1.00 | 30.00 | O |
| ATOM | 2561 | O | HOH | C | 30 | −1.757 | 24.193 | −52.094 | 1.00 | 30.00 | O |
| ATOM | 2562 | O | HOH | C | 31 | −16.515 | 14.170 | −29.781 | 1.00 | 30.00 | O |
| ATOM | 2563 | O | HOH | C | 32 | −8.003 | 8.675 | −21.019 | 1.00 | 30.00 | O |
| ATOM | 2564 | O | HOH | C | 33 | −3.444 | 25.239 | −54.158 | 1.00 | 30.00 | O |
| ATOM | 2565 | O | HOH | C | 34 | −7.938 | 30.384 | −51.979 | 1.00 | 30.00 | O |
| ATOM | 2566 | O | HOH | C | 35 | 2.468 | 17.449 | −50.602 | 1.00 | 30.00 | O |
| ATOM | 2567 | O | HOH | C | 36 | −6.188 | 24.781 | −66.689 | 1.00 | 30.00 | O |
| ATOM | 2568 | O | HOH | C | 37 | −6.617 | 22.749 | −16.042 | 1.00 | 30.00 | O |
| ATOM | 2569 | O | HOH | C | 38 | −0.619 | 14.262 | −67.206 | 1.00 | 30.00 | O |
| ATOM | 2570 | O | HOH | C | 39 | −9.580 | 32.602 | −44.185 | 1.00 | 30.00 | O |
| ATOM | 2571 | O | HOH | C | 40 | 1.662 | 4.063 | −56.615 | 1.00 | 30.00 | O |
| ATOM | 2572 | O | HOH | C | 41 | 0.933 | 22.593 | −49.906 | 1.00 | 30.00 | O |
| ATOM | 2573 | O | HOH | C | 42 | −3.043 | 35.748 | −44.230 | 1.00 | 30.00 | O |
| ATOM | 2574 | O | HOH | C | 43 | 6.140 | 34.562 | −32.067 | 1.00 | 30.00 | O |
| ATOM | 2575 | O | HOH | C | 44 | −10.742 | 35.560 | −28.151 | 1.00 | 30.00 | O |
| ATOM | 2576 | O | HOH | C | 45 | −1.839 | 22.026 | −58.550 | 1.00 | 30.00 | O |
| ATOM | 2577 | O | HOH | C | 46 | −11.484 | 34.620 | −32.648 | 1.00 | 30.00 | O |
| ATOM | 2578 | O | HOH | C | 47 | 14.664 | 34.861 | −34.845 | 1.00 | 30.00 | O |
| ATOM | 2579 | O | HOH | C | 48 | −6.236 | 35.576 | −29.116 | 1.00 | 30.00 | O |
| ATOM | 2580 | O | HOH | C | 49 | −13.538 | 15.049 | −57.534 | 1.00 | 30.00 | O |
| ATOM | 2581 | O | HOH | C | 50 | −1.601 | 5.182 | −20.763 | 1.00 | 30.00 | O |
| ATOM | 2582 | O | HOH | C | 51 | −8.513 | 35.035 | −42.937 | 1.00 | 30.00 | O |
| ATOM | 2583 | O | HOH | C | 52 | −0.509 | 13.527 | −64.430 | 1.00 | 30.00 | O |
| ATOM | 2584 | O | HOH | C | 53 | −9.850 | 6.324 | −24.875 | 1.00 | 30.00 | O |
| ATOM | 2585 | O | HOH | C | 54 | −7.787 | 6.272 | −22.362 | 1.00 | 30.00 | O |
| ATOM | 2586 | O | HOH | C | 55 | 2.358 | 9.462 | −64.261 | 1.00 | 30.00 | O |
| ATOM | 2587 | O | HOH | C | 56 | −3.487 | 13.317 | −66.019 | 1.00 | 30.00 | O |
| ATOM | 2588 | O | HOH | C | 57 | −0.253 | −5.415 | −47.284 | 1.00 | 30.00 | O |
| ATOM | 2589 | O | HOH | C | 58 | 13.974 | 31.730 | −38.203 | 1.00 | 30.00 | O |
| ATOM | 2590 | O | HOH | C | 59 | 12.195 | 34.379 | −32.195 | 1.00 | 30.00 | O |
| ATOM | 2591 | O | HOH | C | 60 | −21.708 | 20.859 | −55.420 | 1.00 | 30.00 | O |
| ATOM | 2592 | O | HOH | C | 61 | −15.348 | 10.282 | −46.446 | 1.00 | 30.00 | O |
| ATOM | 2593 | O | HOH | C | 62 | 2.963 | 21.782 | −51.323 | 1.00 | 30.00 | O |
| ATOM | 2594 | O | HOH | C | 63 | −7.307 | 6.476 | −64.455 | 1.00 | 30.00 | O |
| ATOM | 2595 | O | HOH | C | 64 | −11.376 | 14.406 | −59.725 | 1.00 | 30.00 | O |
| ATOM | 2596 | O | HOH | C | 65 | 10.159 | 34.915 | −30.356 | 1.00 | 30.00 | O |
| ATOM | 2597 | O | HOH | C | 66 | 4.101 | 19.428 | −50.886 | 1.00 | 30.00 | O |
| ATOM | 2598 | O | HOH | C | 67 | −11.104 | 34.217 | −45.726 | 1.00 | 30.00 | O |
| ATOM | 2599 | O | HOH | C | 68 | 5.358 | 19.708 | −48.662 | 1.00 | 30.00 | O |

-continued

| | | | | | | | | | | |
|---|---|---|---|---|---|---|---|---|---|---|
| ATOM | 2600 | O | HOH | C | 69 | −3.346 | 2.621 | −44.714 | 1.00 | 30.00 | O |
| ATOM | 2601 | O | HOH | C | 70 | −9.453 | 32.208 | −53.173 | 1.00 | 30.00 | O |
| ATOM | 2602 | O | HOH | C | 71 | 2.337 | 1.898 | −58.916 | 1.00 | 30.00 | O |
| ATOM | 2603 | O | HOH | C | 72 | −7.721 | 34.427 | −47.909 | 1.00 | 30.00 | O |
| ATOM | 2604 | O | HOH | C | 73 | 16.829 | 28.278 | −44.664 | 1.00 | 30.00 | O |
| ATOM | 2605 | O | HOH | C | 74 | −10.540 | 36.403 | −18.888 | 1.00 | 30.00 | O |
| ATOM | 2606 | O | HOH | C | 75 | −1.443 | 23.991 | −60.849 | 1.00 | 30.00 | O |
| ATOM | 2607 | O | HOH | C | 76 | −16.952 | 15.622 | −27.468 | 1.00 | 30.00 | O |
| ATOM | 2608 | O | HOH | C | 77 | 2.068 | 12.105 | −63.903 | 1.00 | 30.00 | O |
| ATOM | 2609 | O | HOH | C | 78 | −13.882 | 28.256 | −29.870 | 1.00 | 30.00 | O |
| ATOM | 2610 | O | HOH | C | 79 | −3.417 | 23.201 | −67.341 | 1.00 | 30.00 | O |
| ATOM | 2611 | O | HOH | C | 80 | 16.950 | 33.091 | −35.082 | 1.00 | 30.00 | O |
| ATOM | 2612 | O | HOH | C | 81 | 16.894 | 28.940 | −40.059 | 1.00 | 30.00 | O |
| ATOM | 2613 | O | HOH | C | 82 | 1.916 | 9.042 | −40.885 | 1.00 | 30.00 | O |
| ATOM | 2614 | O | HOH | C | 83 | −4.136 | 3.936 | −65.735 | 1.00 | 30.00 | O |
| ATOM | 2615 | O | HOH | C | 84 | −11.015 | 7.373 | −61.136 | 1.00 | 30.00 | O |
| ATOM | 2616 | O | HOH | C | 85 | −11.594 | 6.222 | −63.829 | 1.00 | 30.00 | O |
| ATOM | 2617 | O | HOH | C | 86 | 7.808 | 21.076 | −49.513 | 1.00 | 30.00 | O |
| ATOM | 2618 | O | HOH | C | 87 | −9.319 | 7.734 | −43.070 | 1.00 | 30.00 | O |
| ATOM | 2619 | O | HOH | C | 88 | 2.987 | 18.410 | −15.929 | 1.00 | 30.00 | O |
| ATOM | 2620 | O | HOH | C | 89 | −11.950 | 31.127 | −43.560 | 1.00 | 30.00 | O |
| ATOM | 2621 | O | HOH | C | 90 | 6.856 | 36.995 | −32.055 | 1.00 | 30.00 | O |
| ATOM | 2622 | O | HOH | C | 91 | −9.684 | 16.350 | −62.596 | 1.00 | 30.00 | O |
| ATOM | 2623 | O | HOH | C | 92 | 8.635 | 30.172 | −19.315 | 1.00 | 30.00 | O |
| ATOM | 2624 | O | HOH | C | 93 | −3.862 | 23.049 | −64.550 | 1.00 | 30.00 | O |
| ATOM | 2625 | O | HOH | C | 94 | −4.176 | 30.890 | −14.889 | 1.00 | 30.00 | O |
| ATOM | 2626 | O | HOH | C | 95 | −8.758 | 36.678 | −47.359 | 1.00 | 30.00 | O |
| ATOM | 2627 | O | HOH | C | 96 | 7.602 | 14.316 | −22.874 | 1.00 | 30.00 | O |
| ATOM | 2628 | O | HOH | C | 97 | 12.595 | 19.409 | −29.552 | 1.00 | 30.00 | O |
| ATOM | 2629 | O | HOH | C | 98 | −5.309 | 3.984 | −41.114 | 1.00 | 30.00 | O |
| ATOM | 2630 | O | HOH | C | 99 | 2.023 | 24.305 | −48.491 | 1.00 | 30.00 | O |
| ATOM | 2631 | O | HOH | C | 100 | 2.187 | 25.383 | −11.731 | 1.00 | 30.00 | O |
| ATOM | 2632 | O | HOH | C | 101 | 14.435 | 3.757 | −30.955 | 1.00 | 30.00 | O |
| ATOM | 2633 | O | HOH | C | 102 | −5.183 | 1.305 | −61.760 | 1.00 | 30.00 | O |
| ATOM | 2634 | O | HOH | C | 103 | 4.805 | 47.440 | −24.003 | 1.00 | 30.00 | O |
| ATOM | 2635 | O | HOH | C | 104 | −6.102 | −6.016 | −50.429 | 1.00 | 30.00 | O |
| ATOM | 2636 | O | HOH | C | 105 | −12.556 | 17.247 | −21.858 | 1.00 | 30.00 | O |
| ATOM | 2637 | O | HOH | C | 106 | −23.771 | 18.511 | −49.022 | 1.00 | 30.00 | O |
| ATOM | 2638 | O | HOH | C | 107 | 9.177 | 37.792 | −18.187 | 1.00 | 30.00 | O |
| ATOM | 2639 | O | HOH | C | 108 | −6.291 | 26.732 | −54.116 | 1.00 | 30.00 | O |
| ATOM | 2640 | O | HOH | C | 109 | 4.910 | 37.182 | −35.474 | 1.00 | 30.00 | O |
| ATOM | 2641 | O | HOH | C | 110 | −17.207 | 23.977 | −35.876 | 1.00 | 30.00 | O |
| ATOM | 2642 | O | HOH | C | 111 | −17.531 | 26.339 | −40.193 | 1.00 | 30.00 | O |
| ATOM | 2643 | O | HOH | C | 112 | −9.447 | 36.637 | −40.470 | 1.00 | 30.00 | O |
| ATOM | 2644 | O | HOH | C | 113 | −12.700 | 28.002 | −48.985 | 1.00 | 30.00 | O |
| ATOM | 2645 | O | HOH | C | 114 | 7.483 | 17.800 | −49.255 | 1.00 | 30.00 | O |
| ATOM | 2646 | O | HOH | C | 115 | −8.550 | 38.067 | −44.729 | 1.00 | 30.00 | O |
| ATOM | 2647 | O | HOH | C | 116 | −0.169 | 25.445 | −12.192 | 1.00 | 30.00 | O |
| ATOM | 2648 | O | HOH | C | 117 | 10.890 | 30.469 | −23.294 | 1.00 | 30.00 | O |
| ATOM | 2649 | O | HOH | C | 118 | −9.067 | 1.422 | −35.546 | 1.00 | 30.00 | O |
| ATOM | 2650 | O | HOH | C | 119 | 4.325 | 10.200 | −66.076 | 1.00 | 30.00 | O |
| ATOM | 2651 | O | HOH | C | 120 | −20.791 | 23.480 | −54.447 | 1.00 | 30.00 | O |
| ATOM | 2652 | O | HOH | C | 121 | −11.009 | 38.418 | −41.185 | 1.00 | 30.00 | O |
| ATOM | 2653 | O | HOH | C | 122 | 15.201 | 37.271 | −35.594 | 1.00 | 30.00 | O |
| ATOM | 2654 | O | HOH | C | 123 | −17.531 | 18.330 | −26.916 | 1.00 | 30.00 | O |
| ATOM | 2655 | O | HOH | C | 124 | −13.042 | 27.100 | −15.982 | 1.00 | 30.00 | O |
| ATOM | 2656 | O | HOH | C | 125 | −9.710 | 34.966 | −37.850 | 1.00 | 30.00 | O |
| ATOM | 2657 | O | HOH | C | 126 | 1.153 | −0.184 | −66.252 | 1.00 | 30.00 | O |
| ATOM | 2658 | O | HOH | C | 127 | −9.588 | 37.421 | −27.013 | 1.00 | 30.00 | O |
| ATOM | 2659 | O | HOH | C | 128 | 11.319 | 43.712 | −23.078 | 1.00 | 30.00 | O |
| ATOM | 2660 | O | HOH | C | 129 | 4.572 | 5.168 | −23.778 | 1.00 | 30.00 | O |
| ATOM | 2661 | O | HOH | C | 130 | 6.057 | 12.563 | −24.837 | 1.00 | 30.00 | O |
| ATOM | 2662 | O | HOH | C | 131 | 0.711 | 21.540 | −59.090 | 1.00 | 30.00 | O |
| ATOM | 2663 | O | HOH | C | 132 | 11.795 | 32.765 | −22.407 | 1.00 | 30.00 | O |
| ATOM | 2664 | O | HOH | C | 133 | 6.550 | 26.332 | −13.169 | 1.00 | 30.00 | O |
| ATOM | 2665 | O | HOH | C | 134 | 1.810 | 14.686 | −14.355 | 1.00 | 30.00 | O |
| ATOM | 2666 | O | HOH | C | 135 | 17.251 | 15.177 | −32.609 | 1.00 | 30.00 | O |
| ATOM | 2667 | O | HOH | C | 136 | −10.895 | 35.903 | −35.230 | 1.00 | 30.00 | O |
| ATOM | 2668 | O | HOH | C | 137 | −9.059 | 20.944 | −22.630 | 1.00 | 30.00 | O |
| ATOM | 2669 | O | HOH | C | 138 | 12.293 | 29.604 | −45.259 | 1.00 | 30.00 | O |
| ATOM | 2672 | O | HOH | C | 141 | −1.037 | 36.155 | −43.204 | 1.00 | 30.00 | O |
| ATOM | 2673 | O | HOH | C | 142 | 1.082 | 25.832 | −51.921 | 1.00 | 30.00 | O |
| ATOM | 2674 | O | HOH | C | 143 | −2.450 | 2.546 | −20.956 | 1.00 | 30.00 | O |
| ATOM | 2675 | O | HOH | C | 144 | −7.978 | 40.912 | −43.510 | 1.00 | 30.00 | O |
| ATOM | 2676 | O | HOH | C | 145 | −10.301 | 19.191 | −63.552 | 1.00 | 30.00 | O |
| ATOM | 2677 | O | HOH | C | 146 | 7.198 | 12.119 | −27.077 | 1.00 | 30.00 | O |
| ATOM | 2678 | O | HOH | C | 147 | −8.442 | 7.340 | −66.926 | 1.00 | 30.00 | O |
| ATOM | 2679 | O | HOH | C | 148 | −6.597 | 4.720 | −20.108 | 1.00 | 30.00 | O |
| ATOM | 2680 | O | HOH | C | 149 | 16.408 | 30.902 | −37.014 | 1.00 | 30.00 | O |
| ATOM | 2681 | O | HOH | C | 150 | 14.728 | 21.080 | −30.890 | 1.00 | 30.00 | O |

-continued

| ATOM | 2682 | O | HOH | C | 151 | −9.687 | 9.762 | −65.728 | 1.00 | 30.00 | O |
| ATOM | 2683 | O | HOH | C | 152 | −9.887 | 34.194 | −50.763 | 1.00 | 30.00 | O |
| ATOM | 2684 | O | HOH | C | 153 | 15.841 | 19.672 | −32.700 | 1.00 | 30.00 | O |
| ATOM | 2685 | O | HOH | C | 154 | 12.832 | 17.817 | −31.060 | 1.00 | 30.00 | O |
| ATOM | 2686 | O | HOH | C | 155 | 17.460 | 38.108 | −36.805 | 1.00 | 30.00 | O |
| ATOM | 2687 | O | HOH | C | 156 | 2.667 | 3.747 | −22.742 | 1.00 | 30.00 | O |
| ATOM | 2689 | O | HOH | C | 158 | 1.806 | 22.266 | −61.250 | 1.00 | 30.00 | O |
| ATOM | 2690 | O | HOH | C | 159 | 16.440 | 28.462 | −35.842 | 1.00 | 30.00 | O |
| ATOM | 2691 | O | HOH | C | 160 | −8.582 | 37.405 | −35.441 | 1.00 | 30.00 | O |
| ATOM | 2693 | O | HOH | C | 162 | −4.983 | 40.946 | −43.126 | 1.00 | 30.00 | O |
| ATOM | 2695 | O | HOH | C | 164 | −5.177 | 2.339 | −20.105 | 1.00 | 30.00 | O |
| ATOM | 2696 | O | HOH | C | 165 | −9.654 | 4.777 | −67.672 | 1.00 | 30.00 | O |
| ATOM | 2697 | O | HOH | C | 166 | −1.738 | 0.099 | −19.501 | 1.00 | 30.00 | O |
| ATOM | 2699 | O | HOH | C | 168 | −4.068 | 40.094 | −45.561 | 1.00 | 30.00 | O |
| END | | | | | | | | | | | |

The invention claimed is:

1. A method for designing a mutant protein deamidase having modified substrate specificity or improved oxidative stability compared to the protein deamidase to be mutated comprising the following steps:
   (A) identifying one or more amino acids in the amino acid sequence for a protein deamidase which correspond to the amino acids at positions 35, 38 to 43, 45, 46, 49, 79 to 84, 103 to 106, 117, 142, 143, 146, 166, or 185 in the amino acid sequence set forth in SEQ ID NO: 2; and
   (B) constructing a mutant amino acid sequence of the protein deamidase by substituting the one or more amino acids identified in step (A) with another amino acid or other amino acids or by deleting the one or more amino acids identified in step (A)
   thereby designing a mutant protein deamidase having modified substrate specificity or improved oxidative stability
   wherein the protein deamidase to be mutated has 90% or more identity to the amino acid sequence set forth in SEQ ID NO: 2.

2. The method for designing a mutant protein deamidase having modified substrate specificity or improved oxidative stability compared to the protein deamidase to be mutated according to claim 1, wherein step (A) identifies one or more amino acids in the amino acid sequence for a protein deamidase which correspond to the amino acids at positions 39, 40, 41, 43, 79 to 82, 142, 143, 146, 166, or 185 in the amino acid sequence set forth in SEQ ID NO: 2.

3. The method for designing a mutant protein deamidase having modified substrate specificity or improved oxidative stability compared to the protein deamidase to be mutated according to claim 1, wherein step (A) identifies an amino acid in the amino acid sequence for a protein deamidase which corresponds to the amino acid at position 82 in the amino acid sequence set forth in SEQ ID NO: 2.

4. The method for designing a mutant protein deamidase having modified substrate specificity or improved oxidative stability compared to the protein deamidase to be mutated according to claim 1, wherein step (A) identifies one or more amino acids in the amino acid sequence for a protein deamidase which correspond to the amino acids at positions 35, 38, 40 to 43, 45, 46, 49, 80 to 84, 103 to 106, and 117 in the amino acid sequence set forth in SEQ ID NO: 2.

5. The method for designing a mutant protein deamidase having modified substrate specificity or improved oxidative stability compared to the protein deamidase to be mutated according to claim 1, wherein step (A) identifies an amino acid in the amino acid sequence for a protein deamidase which corresponds to the amino acid at position 84 in the amino acid sequence set forth in SEQ ID NO: 2.

6. The method for designing a mutant protein deamidase having modified substrate specificity or improved oxidative stability compared to the protein deamidase to be mutated according to claim 1, wherein identifying one or more amino acids in step (A) is performed by comparing the amino acid sequence of the protein deamidase and the amino acid sequence set forth in SEQ ID NO: 2 or by comparing the three-dimensional structure of the protein deamidase and the three-dimensional structure of the protein of SEQ ID NO: 2.

7. The method for designing a mutant protein deamidase having modified substrate specificity or improved oxidative stability compared to the protein deamidase to be mutated according to claim 1, wherein the one or more amino acids identified in step (A) are substituted by one or more amino acids having a different charge state.

8. The method for designing a mutant protein deamidase having modified substrate specificity or improved oxidative stability compared to the protein deamidase to be mutated according to claim 1, wherein the enzyme to be mutated is a wild-type enzyme.

9. The method for designing a mutant protein deamidase having modified substrate specificity or improved oxidative stability compared to the protein deamidase to be mutated according to claim 1, wherein the protein deamidase to be mutated is a protein deamidase derived from a microorganism.

10. The method for designing a mutant protein deamidase having modified substrate specificity or improved oxidative stability compared to the protein deamidase to be mutated according to claim 9, wherein the protein deamidase to be mutated is a protein glutaminase derived from a species of the genus *Chryseobacterium*.

11. The method for designing a mutant protein deamidase having modified substrate specificity or improved oxidative stability compared to the protein deamidase to be mutated according to claim 9, wherein the protein deamidase to be mutated is a protein glutaminase derived from *Chryseobacterium proteolyticum*.

12. The method for designing a mutant protein deamidase having modified substrate specificity or improved oxidative stability compared to the protein deamidase to be mutated according to claim 3, wherein the amino acid which corresponds to the amino acid at position 82 in the amino acid sequence set forth in SEQ ID NO: 2 is replaced with a Serine.

13. The method for designing a mutant protein deamidase having modified substrate specificity or improved oxidative stability compared to the protein deamidase to be mutated according to claim 5, wherein the amino acid which corresponds to the amino acid at position 84 in the amino acid sequence set forth in SEQ ID NO: 2 is replaced with an Aspartic Acid.

* * * * *